United States Patent
Zhang et al.

(10) Patent No.: US 9,434,695 B2
(45) Date of Patent: Sep. 6, 2016

(54) NITROGENOUS HETEROCYCLIC DERIVATIVES AND THEIR APPLICATION IN DRUGS

(71) Applicant: SUNSHINE LAKE PHARMA CO., LTD., Dongguan, Guangdong (CN)

(72) Inventors: Yingjun Zhang, Dongguan (CN); Jiancun Zhang, Dongguan (CN); Xiaojun Wang, Dongguan (CN); Runfeng Lin, Dongguan (CN); Shengtian Cao, Dongguan (CN); Zhaohe Wang, Dongguan (CN); Jing Li, Dongguan (CN)

(73) Assignee: SUNSHINE LAKE PHARMA CO., LTD, Dongguan, Guangdong (CN)

( * ) Notice: Subject to any disclaimer, the term of this patent is extended or adjusted under 35 U.S.C. 154(b) by 0 days.

(21) Appl. No.: 14/396,754

(22) PCT Filed: Jul. 18, 2013

(86) PCT No.: PCT/CN2013/000860
§ 371 (c)(1),
(2) Date: Oct. 24, 2014

(87) PCT Pub. No.: WO2014/012360
PCT Pub. Date: Jan. 23, 2014

(65) Prior Publication Data
US 2015/0087639 A1    Mar. 26, 2015

(30) Foreign Application Priority Data
Jul. 18, 2012 (CN) .......................... 2012 1 0250660

(51) Int. Cl.
| | | |
|---|---|---|
| C07D 239/36 | (2006.01) | |
| C07D 403/12 | (2006.01) | |
| C07D 401/12 | (2006.01) | |
| C07D 403/06 | (2006.01) | |
| C07D 405/12 | (2006.01) | |
| C07D 417/04 | (2006.01) | |
| C07D 498/04 | (2006.01) | |
| C07D 213/64 | (2006.01) | |

(52) U.S. Cl.
CPC ............ *C07D 239/36* (2013.01); *C07D 213/64* (2013.01); *C07D 401/12* (2013.01); *C07D 403/06* (2013.01); *C07D 403/12* (2013.01); *C07D 405/12* (2013.01); *C07D 417/04* (2013.01); *C07D 498/04* (2013.01)

(58) Field of Classification Search
CPC .. C07D 239/36; C07D 213/64; C07D 401/12; C07D 403/06; C07D 403/12; C07D 405/12; C07D 417/04; C07D 498/04
See application file for complete search history.

(56) References Cited

U.S. PATENT DOCUMENTS

| | | |
|---|---|---|
| 3,185,689 A | 5/1965 | Rusching et al. |
| 4,411,691 A | 10/1983 | Rohr et al. |
| 4,523,946 A | 6/1985 | Parg et al. |
| 4,990,512 A | 2/1991 | Perrior et al. |
| 5,079,251 A | 1/1992 | Fitzjohn |
| 5,104,878 A | 4/1992 | Whittle et al. |
| 5,127,935 A * | 7/1992 | Satow ............... A01N 43/54 504/168 |
| 5,149,810 A | 9/1992 | Perrior et al. |
| 5,470,975 A | 11/1995 | Atwal |
| 5,518,994 A | 5/1996 | Kawamura et al. |

(Continued)

FOREIGN PATENT DOCUMENTS

| | | |
|---|---|---|
| CA | 2045327 A1 | 1/1992 |
| CN | 1386737 A1 | 12/2002 |

(Continued)

OTHER PUBLICATIONS

B. Stanovinik et al., 91 Advances in Heterocyclic Chemistry, 1-134 (2006) (see pp. 67 et seq.).*

(Continued)

*Primary Examiner* — Alexander R Pagano
(74) *Attorney, Agent, or Firm* — Kam W. Law; Squire Patton Boggs (US) LLP

(57) ABSTRACT

The present invention relates to the field of medicine, provided herein are novel nitrogenous heterocyclic compounds, their preparation methods and their uses as drugs, especially for treatment and prevention of tissue fibrosis. Also provided herein are pharmaceutically acceptable compositions comprising the nitrogenous heterocyclic compounds and the uses of the compositions in the treatment of human or animal tissue fibrosis, especially for human or animal renal interstitial fibrosis, glomerular sclerosis, liver fibrosis, pulmonary fibrosis, peritoneal fibrosis, myocardial fibrosis, dermatofibrosis, postsurgical adhesion, benign prostatic hyperplasia, skeletal muscle fibrosis, scleroderma, multiple sclerosis, pancreatic fibrosis, cirrhosis, myosarcoma, neurofibroma, pulmonary interstitial fibrosis, diabetic nephropathy, alzheimer disease or vascular fibrosis.

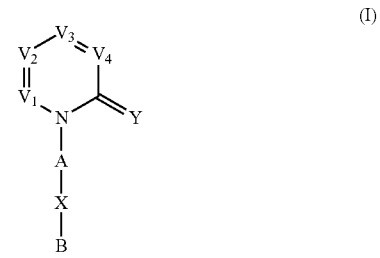

(I)

15 Claims, No Drawings

(56) References Cited

U.S. PATENT DOCUMENTS

| | | |
|---|---|---|
| 5,532,208 A | 7/1996 | Nagano et al. |
| 5,869,476 A | 2/1999 | Paik et al. |
| 5,877,121 A | 3/1999 | Andree et al. |
| 6,369,067 B1 | 4/2002 | Gurram et al. |
| 7,012,041 B2 | 3/2006 | Linker et al. |
| 7,183,287 B2 | 2/2007 | Durley |
| 7,732,456 B2 | 6/2010 | Otake et al. |
| 7,790,734 B2 | 9/2010 | Cao et al. |
| 7,790,736 B2 | 9/2010 | Feng et al. |
| 8,063,055 B2 | 11/2011 | Hu et al. |
| 8,084,465 B2 | 12/2011 | Yi |
| 8,158,643 B2 | 4/2012 | Andres-Gil et al. |
| 8,163,905 B2 | 4/2012 | Brough et al. |
| 8,198,276 B2 | 6/2012 | Liang |
| 8,304,413 B2 | 11/2012 | Kossen et al. |
| 8,324,230 B2 | 12/2012 | Selbo |
| 2004/0006062 A1 | 1/2004 | Smallheer et al. |
| 2005/0004134 A1 | 1/2005 | Tsutsumi et al. |
| 2005/0176775 A1 | 8/2005 | Devadas et al. |
| 2005/0256122 A1 | 11/2005 | Hepperle et al. |
| 2006/0199809 A1 | 9/2006 | Lu et al. |
| 2007/0088033 A1 | 4/2007 | Devadas et al. |
| 2007/0129379 A1 | 6/2007 | Naidu et al. |
| 2007/0161616 A1 | 7/2007 | Wagle et al. |
| 2007/0270446 A1 | 11/2007 | Marquis, Jr. et al. |
| 2008/0085884 A1 | 4/2008 | Armour et al. |
| 2009/0105267 A1 | 4/2009 | Cowart et al. |
| 2009/0137557 A1 | 5/2009 | Ku et al. |
| 2009/0221546 A1 | 9/2009 | Bigge et al. |
| 2009/0258911 A1 | 10/2009 | Tao et al. |
| 2009/0275751 A1 | 11/2009 | Nagato et al. |
| 2010/0184767 A1 | 7/2010 | Rohrig et al. |
| 2010/0190731 A1 | 7/2010 | Olgin et al. |
| 2010/0210637 A1 | 8/2010 | Ohtake et al. |
| 2010/0221211 A1 | 9/2010 | Furuyama et al. |
| 2010/0305067 A1 | 12/2010 | Haydon et al. |
| 2011/0003864 A1 | 1/2011 | Chen et al. |
| 2011/0160196 A1 | 6/2011 | Jia et al. |
| 2011/0189192 A1 | 8/2011 | Cooper et al. |
| 2011/0218515 A1 | 9/2011 | Olgin |
| 2012/0010185 A1 | 1/2012 | Stenkamp et al. |
| 2012/0028959 A1 | 2/2012 | Thunuguntla et al. |
| 2012/0088795 A1 | 4/2012 | Song et al. |
| 2012/0129859 A1 | 5/2012 | Hu et al. |
| 2012/0142688 A1 | 6/2012 | Hu et al. |
| 2012/0178733 A1 | 7/2012 | Zhu et al. |
| 2013/0157981 A1 | 6/2013 | Heckel et al. |
| 2013/0158053 A1 | 6/2013 | Selbo |

FOREIGN PATENT DOCUMENTS

| | | | |
|---|---|---|---|
| DE | 4343528 A1 | 6/1995 | |
| EP | 0481604 A1 | 4/1992 | |
| WO | WO 95/11235 A1 | 4/1995 | |
| WO | WO 96/08151 A1 | 3/1996 | |
| WO | WO 99/52878 A1 | 10/1999 | |
| WO | WO 2006/026926 A1 | 3/2006 | |
| WO | WO 2007/141200 A1 | 12/2007 | |
| WO | WO 2007/142217 A1 | 12/2007 | |
| WO | WO 2008/156607 A1 | 12/2008 | |
| WO | WO 2009085945 A1 * | 7/2009 | ........... C07D 413/04 |
| WO | WO 2010/142143 A1 | 12/2010 | |
| WO | WO 2011/109267 A1 | 9/2011 | |
| WO | WO 2012/011592 A1 | 1/2012 | |
| WO | WO 2013/086208 A1 | 6/2013 | |

OTHER PUBLICATIONS

B Testa et al., Prodrug Design in, 5 Encyclopedia of Pharmaceutical Technology, 3008-3014 (J. Swarbrick ed., 3rd ed., 2007).*
R.J. Kok, 25 Pharmaceutical Research, 2413-2415 (2008).*
Z. Ghiassi-Nejad et al. 2 Expert Review of Gastroenterology & Hepatology, 803-816 (2008).*
H. Girouard et al., 100 Journal of Applied Physiology, 328-335 (2006).*
R. S. Shah et al., 52 Biomedicine & Pharmacotherapy, 199-207 (2008).*
S. Yamada et al., 242 The Journal of Pharmacology and Experimental Therapeutics, 326-330 (1987).*
J. Kim et al., 150 Endocrinology, 3576-3583 (2009).*
J.D. Cashman et al., 171 Journal of Surgical Research, 495-503 (2011).*
S. Judge et al., 111 Pharmacology & Therapeutics, 224-259 (2006).*
V. Brinkmann et al., 9 Nature Reviews | Drug Discovery, 883-897 (2010).*
T. Yamamoto et al., 90 Proceedings of the National Academy of Sciences, 1814-1818 (1993).*
Y-M Sun et al., 433 Biochemical and Biophysical Research Communications, 359-361 (2013).*
A. Lim et al., 2014 International Journal of Nephrology and Renovascular Disease, 361-381 (2014).*
P.C. Seynaeve et al., Tumors of Muscular Origin in, Imaging of Soft Tissue Tumors, 293-310 (A.M. De Schepper ed., 2006).*
J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
C.J. Schaefer et al., 120 European Respiratory Reviews, 85-97 (2011).*
H. Oku et al., 590 European Journal of Pharmacology. 400-408 (2008).*
M. Stoker et al., 203 Nature, 1355-1357 (1964).*
M.J. Lehmann et al., 12 Gene Therapy, 446-451 (2005).*
K.C. Johnson et al., 111 Biotechnology and Bioengineering, 770-781 (2014).*
F. Zandi et al., 9 Proteomics, 2399-2407 (2009).*
D.A. Moshkov et al., 149 Bulletin of Experimental Biology and Medicine, 359-363 (2010).*
Eng. translation of the abstract of CN 1386737.
Eng_Abstract.
H. Schirok et al., J. Org. Chem., 70, 9463-9469 (2005).
W. Mederski et al., Bioorg. & Med. Chem., 14, 3763-3769 (2004).
J. Smallheer et al., Bioorg. & Med. Chem., 18, 2428-2433 (2008).
Q. Lou et al., Molecules, 17, 884-896 (2012).
ISR.
Written Opinion.
Kevin et al.; A versatile copper-catalyzed coupling reaction of pyridin-2(1H)-ones with aryl halides; Tetrahedron Letters, 2006, vol. 47, p. 7677-7680.
E. Hu et al., J. Med. Chem., 51, 3065-3068 (2008).
Po-Shih Wang et al., Tetrahedron, 2931-2939 (2005).
Chih-Kai Liang et al., Tetrahedron, 65, 1679-1688 (2009).
The extended European search report of EP2875001, Apr. 29, 2016.

* cited by examiner

NITROGENOUS HETEROCYCLIC DERIVATIVES AND THEIR APPLICATION IN DRUGS

CROSS-REFERENCE TO RELATED APPLICATIONS

This is a U.S. national stage application of the International Patent Application No. PCT/CN2013/000860, filed Jul. 18, 2013, which claims priority to Chinese Patent Application No. 201210250660.6, filed Jul. 18, 2012, both of which are incorporated herein by reference in their entirety.

FIELD OF THE INVENTION

The present invention relates to the field of medicine. Provided herein are novel nitrogenous heterocyclic compounds, their combinations, their methods of preparation and their uses as drugs, especially for treatment and prevention of tissue fibrosis.

BACKGROUND OF THE INVENTION

Slight fibrosis of organ or tissue be called fibrosis, severe fibrosis can cause damage of tissues leading to organ scarring. Tissue fibrosis is not only in lung and liver, but in all the organs and systems of the human body. A variety of factors (such as inflammation, immune response, poison, ischemia and changes of hemodynamics, and so on) cause parenchymal cellular damage. This leads to parenchymal cells inflammation, deformation, necrosis, and activates the corresponding macrophages to release cytokines and growth factors which in turn activate the resting extracellular martrix (ECM) to produce cells, and then transform the cells into myofibroblasts. Myofibroblasts proliferate and secrete cytokines which act on macrophages through paracrine. Myofibroblasts can synthesize a lot of collagen of ECM. ECM degradation is decreased at the same time causing organ and tissue fibrosis. Therefore, the occurrence and development of organ and tissue fibrosis is a result of the interactions between multiple factors, such as cell, cytokine and ECM. Cell produced by ECM is important for the formation of organ or tissue fibrosis. Therefore, one of the drug targets for treating organ and tissue fibrosis is the cell produced by ECM. Therapeutic goal can be achieved by inhibiting the cell proliferation, activation and inducing the cell apoptosis.

It is because each organ or tissue has different functions, morphologies and different main component cells, different organ or tissue fibrosis have commonness and individuality in the pathogenesises. Cells can be produced by ECM, while hepatic stellate cells are produced in liver, glomerular mesangial cells are produced in glomerulus, renal interstitial fibroblasts are produced in renal interstitium, lung fibroblasts are produced in lung, cardiac fibroblasts are produced in heart and peritoneal mesothelial cells are produced in peritoneal. Therefore, there are some differences in the pathogenesises and therapeutic targets of different organs or tissues fibrosis.

An anti-fibrotic drug named pirfenidone (PFD, 5-methyl-1-phenyl-2-(1H)-pyridone) was disclosed in patent EP1138329A. Experiments show that PFD could prevent ECM gathering, or even reverse it in animal experiments of renal fibrosis, pulmonary fibrosis, and in clinical trials of patients with specific lung fibrosis.

SUMMARY OF THE INVENTION

Provided herein are new compounds or pharmaceutical compositions that may be more effective to prevent or treat human or animal tissue fibrosis. In one aspect, provided herein are compounds having Formula (I) as shown below:

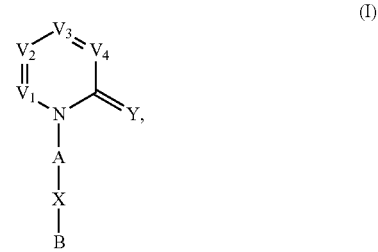

or a stereoisomer, a geometric isomer, a tautomer, an N-oxide, a hydrate, a solvate, a metabolite, a pharmaceutically acceptable salt or a prodrug thereof, wherein each $V_1$, $V_2$, $V_3$, $V_4$, A, B, X and Y is as defined herein.

In some embodiments, $V_1$ is N or $CR^1$, $V_2$ is N or $CR^2$, $V_3$ is N or $CR^3$, and $V_4$ is N or $CR^4$, wherein at most one of the $V_1$, $V_2$, $V_3$ and $V_4$ is N;

X is a bond, $NR^5$, O, S, $C_{1-10}$ alkylene, $C_{2-10}$ alkenylene, $C_{2-10}$ alkynylene, $-R^6-C(=Y)-$, $-R^6-C(=Y)-O-$, $-R^6-C(=Y)-N(R^5)-$, $-R^6-S(=O)_t-$, $-R^6-S(=O)_t-N(R^7)-$, or $-R^6-Y-$, wherein each t is 1 or 2;

Y is O or S;

A is heterocyclylene, carbocyclylene, fused bicyclylene, fused heterobicyclylene, spiro bicyclylene, spiro heterobicyclylene, arylene or heteroarylene;

B is alkoxy, hydroxy-substituted alkoxy, $-NR^7R^{7a}$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_t-$, $R^7S(=O)_t-$, $R^7-S(=O)_t-N(R^{7a})-$, $C_{4-12}$ carbocyclyl, $C_{4-12}$ cycloalkyl, heterocyclyl, aryl, heteroaryl, fused bicyclyl, fused heterobicyclyl, spiro bicyclyl, or spiro heterobicyclyl;

or A, X and B together form a group having Formula (II):

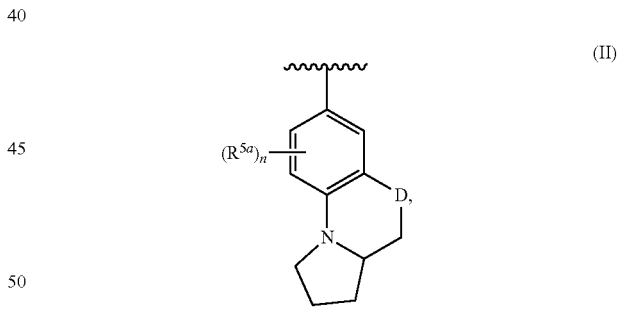

wherein D is $NR^5$, O, S, or $CR^7R^{7a}$;

$R^1$ is H, F, Cl, Br, I, cyano, hydroxy, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_t-$, $R^7S(=O)_t-$, $R^7S(=O)_tN(R^{7a})-$, $R^{7a}R^7N$-alkyl, $R^7S(=O)_t$-alkyl, $R^7R^{7a}N-C(=O)$-alkyl, $R^{7a}R^7N$-alkoxy, $R^7S(=O)_t$-alkoxy, $R^7R^{7a}N-C(=O)$-alkoxy, aliphatic, haloalkyl, alkoxy, hydroxyalkoxy, aminoalkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, cycloalkyloxy, arylalkoxy, arylalkylamino, heteroarylalkoxy, heteroarylalkylamino, heterocyclylalkylamino, cycloalkylamino, heterocyclylalkoxy, carbocyclylalkoxy, carbocyclylalkylamino, heterocyclyl(hydroxyalkoxy), carbocyclyl(hydroxyalkoxy), aryl(hydroxyalkoxy), aryloxyalkoxy, aryloxy, heteroaryloxy, heteroaryloxyalkoxy, heterocyclyloxyalkoxy, carbocyclyloxyalkoxy, heterocyclyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R^7$)—, fused heterobicyclyl-C(=O)N($R^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R^7$)—, spiro heterobicyclyl-C(=O)N($R^7$)—, heterocyclyl, cycloalkyl, aryl, heteroaryl, heterocyclyl aliphatic, cycloalkyl aliphatic, aryl aliphatic, heteroaryl aliphatic, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, or cycloalkyl-$(CH_2)_p$-G-$(CH_2)_m$—, wherein each G is O, S, $NR^5$, S(=O), S(=O)$_2$, C(=O), —C(=O)N($R^7$)—, —OC(=O)N($R^7$)—, —OC(=O)—, —N($R^7$)C(=O)N($R^7$)—, —($R^7$)N—S(=O)$_t$—, —OS(=O)$_t$—, or —OS(=O)$_t$N($R^7$)—; each t is 1 or 2; each p and m is independently 0, 1, 2, 3 or 4; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-$(CH_2)_m$— is optionally substituted by one or more F, Cl, Br, I, $C_{1-6}$ alkyl, $C_{2-6}$ alkynyl, $C_{1-6}$ alkoxy or cyano;

$R^2$ is H, F, Cl, Br, I, cyano, hydroxy, $R^{7a}R^7N$—, —C(=O)N$R^7R^{7a}$, —OC(=O)N$R^7R^{7a}$, —OC(=O)O$R^7$, —N($R^7$)C(=O)N$R^7R^{7a}$, —N($R^7$)C(=O)O$R^{7a}$, —N($R^7$)C(=O)—$R^{7a}$, $R^7R^{7a}N$—S(=O)$_t$—, $R^7S$(=O)$_t$—, $R^7S$(=O)$_t$N($R^{7a}$)—, $R^{7a}R^7N$-alkyl, $R^7S$(=O)$_t$-alkyl, $R^{7a}R^7N$—C(=O)-alkyl, $R^{7a}R^7N$-alkoxy, $R^7S$(=O)$_t$-alkoxy, $R^7R^{7a}N$—C(=O)-alkoxy, aliphatic, haloalkyl, alkoxy, hydroxyalkoxy, aminoalkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, arylalkoxy, arylalkylamino, heteroarylalkoxy, heteroarylalkylamino, heterocyclylalkylamino, cycloalkyloxy, cycloalkylamino, heterocyclylalkoxy, carbocyclylalkoxy, carbocyclylalkylamino, heterocyclyl(hydroxyalkoxy), carbocyclyl(hydroxyalkoxy), aryl(hydroxyalkoxy), aryloxyalkoxy, aryloxy, heteroaryloxy, heteroaryloxyalkoxy, heterocyclyloxyalkoxy, carbocyclyloxyalkoxy, heterocyclyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R^7$)—, fused heterobicyclyl-C(=O)N($R^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R^7$)—, spiro heterobicyclyl-C(=O)N($R^7$)—, heterocyclyl, cycloalkyl, aryl, $C_{1-4}$ heteroaryl, heterocyclyl aliphatic, cycloalkyl aliphatic, aryl aliphatic, heteroaryl aliphatic, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, or cycloalkyl-$(CH_2)_p$-G-$(CH_2)_m$—, wherein each G is O, S, $NR^5$, S(=O), S(=O)$_2$, C(=O), —C(=O)N($R^7$)—, —OC(=O)N($R^7$)—, —OC(=O)—, —N($R^7$)C(=O)N($R^7$)—, —($R^7$)N—S(=O)$_t$—, —OS(=O)$_t$—, or —OS(=O)$_t$N($R^7$)—; each t is 1 or 2; each p and m is independently 0, 1, 2, 3 or 4;

$R^3$ is H, F, Cl, I, cyano, $R^7R^{7a}N$—, —C(=O)N$R^7R^{7a}$, —OC(=O)N$R^7R^{7a}$, —OC(=O)O$R^7$, —N($R^7$)C(=O)N$R^7R^{7a}$, —N($R^7$)C(=O)O$R^{7a}$, —N($R^7$)C(=O)—$R^{7a}$, $R^7R^{7a}N$—S(=O)$_t$—, $R^7S$(=O)$_t$—, $R^7S$(=O)$_t$N($R^{7a}$)—, $R^{7a}R^7N$-alkyl, $R^7S$(=O)$_t$-alkyl, $R^{7a}R^7N$—C(=O)-alkyl, $R^{7a}R^7N$-alkoxy, $R^7S$(=O)$_t$-alkoxy, $R^7R^{7a}N$—C(=O)-alkoxy, aliphatic, $C_{2-10}$ haloalkyl, aryl-$C_{2-10}$ alkoxy, heteroaryl-$C_{3-10}$ alkoxy, cycloalkyl-$C_{2-10}$ alkoxy, fused bicyclyl-$C_{2-10}$ alkoxy, $C_{1-4}$ heteroaryl, substituted aryl, heterocyclyl, cycloalkyl, heterocyclyl aliphatic, cycloalkyl aliphatic, $C_{1-4}$ heteroaryl aliphatic, substituted aryl $C_{3-10}$ alkyl, heterocyclylalkyl, alkoxy, hydroxyalkoxy, aminoalkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, aryl-$C_{2-10}$ alkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, arylaminoalkoxy, aryloxy, heteroaryloxyalkoxy, heterocyclyloxyalkoxy, carbocyclyloxyalkoxy, heterocyclyloxy, cycloalkyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R^7$)—, fused heterobicyclyl-C(=O)N($R^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R^7$)—, spiro heterobicyclyl-C(=O)N($R^7$)—, aryl-(CH$_2$)$_p$-G-(CH$_2$)$_m$—, heteroaryl-(CH$_2$)$_p$-G-(CH$_2$)$_m$—, heterocyclyl-(CH$_2$)$_p$-G-(CH$_2$)$_m$—, or cycloalkyl-(CH$_2$)$_p$-G-(CH$_2$)$_m$—, wherein each G is O, S, NR$^5$, S(=O), S(=O)$_2$, C(=O), —C(=O)N($R^7$)—, —OC(=O)N($R^7$)—, —OC(=O)—, —N($R^7$)C(=O)N($R^7$)—, —($R^7$)N—S(=O)$_t$—, —OS(=O)$_t$—, or —OS(=O)$_t$N($R^7$)—; each t is 1 or 2; each p and m is independently 0, 1, 2, 3 or 4;

$R^4$ is H, F, I, cyano, hydroxy, $R^{7a}R^7$N—, —C(=O)NR$^7R^{7a}$, —OC(=O)NR$^7R^{7a}$, —OC(=O)OR$^7$, —N($R^7$)C(=O)NR$^7R^{7a}$, —N($R^7$)C(=O)OR$^{7a}$, —N($R^7$)C(=O)—$R^{7a}$, $R^7R^{7a}$N—S(=O)$_t$—, $R^7$S(=O)$_t$—, $R^7$S(=O)$_t$N($R^{7a}$)—, $R^{7a}R^7$N-alkyl, $R^7$S(=O)$_t$-alkyl, $R^7R^{7a}$N—C(=O)-alkyl, $R^{7a}R^7$N-alkoxy, $R^7$S(=O)$_t$-alkoxy, $R^7R^{7a}$N—C(=O)-alkoxy, aliphatic, haloalkyl, C$_{2-10}$ alkoxy, hydroxyalkoxy, aminoalkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, C$_{3-5}$ cycloalkyloxy, arylalkoxy, heteroarylalkoxy, heteroarylalkylamino, heterocyclylalkylamino, C$_{7-10}$ cycloalkoxy, cycloalkylamino, heterocyclylalkoxy, carbocyclylalkoxy, carbocyclylalkylamino, heterocyclyl(hydroxyalkoxy), carbocyclyl(hydroxyalkoxy), aryl(hydroxyalkoxy), aryloxyalkoxy, aryloxy, heteroaryloxy, heteroaryloxyalkoxy, heterocyclyloxyalkoxy, carbocyclyloxyalkoxy, heterocyclyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R^7$)—, fused heterobicyclyl-C(=O)N($R^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R^7$)—, spiro heterobicyclyl-C(=O)N($R^7$)—, heterocyclyl, cycloalkyl, aryl, heteroaryl, heterocyclyl aliphatic, cycloalkyl aliphatic, aryl C$_{2-10}$ aliphatic, heteroaryl aliphatic, aryl-(CH$_2$)$_p$-G-(CH$_2$)$_m$—, heteroaryl-(CH$_2$)$_p$-G-(CH$_2$)$_m$—, heterocyclyl-(CH$_2$)$_p$-G-(CH$_2$)$_m$—, or cycloalkyl-(CH$_2$)$_p$-G-(CH$_2$)$_m$—, wherein each G is O, S, NR$^5$, S(=O), S(=O)$_2$, C(=O), —C(=O)N($R^7$)—, —OC(=O)N($R^7$)—, —OC(=O)—, —N($R^7$)C(=O)N($R^7$)—, —($R^7$)N—S(=O)$_t$—, —OS(=O)$_t$—, or —OS(=O)$_t$N($R^7$)—; each t is 1 or 2; each p and m is independently 0, 1, 2, 3 or 4;

each $R^5$ is independently H, $R^7R^{7a}$NC(=O)—, $R^7$OC(=O)—, $R^7$C(=O)—, $R^7R^{7a}$NS(=O)—, $R^7$OS(=O)—, $R^7$S(=O)—, $R^7R^{7a}$NS(=O)$_2$—, $R^7$OS(=O)$_2$—, $R^7$S(=O)$_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;

each $R^{5a}$ is independently H, hydroxy, amino, F, Cl, Br, I, cyano, oxo (=O), $R^{7a}R^7$N—, —C(=O)NR$^7R^{7a}$, —OC(=O)NR$^7R^{7a}$, —OC(=O)OR$^7$, —N($R^7$)C(=O)NR$^7R^{7a}$, —N($R^7$)C(=O)OR$^{7a}$, —N($R^7$)C(=O)—$R^{7a}$, $R^7R^{7a}$N—S(=O)$_2$—, $R^7$S(=O)$_2$—, $R^7$S(=O)$_2$N($R^{7a}$)—, $R^{7a}R^7$N-alkyl, $R^7$S(=O)-alkyl, $R^7R^{7a}$N—C(=O)-alkyl, $R^{7a}R^7$N-alkoxy, $R^7$S(=O)-alkoxy, $R^7R^{7a}$N—C(=O)-alkoxy, aryl, heteroaryl, alkoxy, alkyl, alkenyl, alkynyl, heterocyclyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino or aryloxy;

each $R^6$ is independently a bond, C$_{1-10}$ alkylene, C$_{2-10}$ alkenylene, or C$_{2-10}$ alkynylene; and each $R^7$ and $R^{7a}$ is independently H, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring or a substituted or unsubstituted spiro bicyclic or fused bicyclic ring;

wherein each of NR$^5$, —$R^6$—C(=Y)—, —$R^6$—C(=Y)—O—, —$R^6$—C(=Y)—N($R^5$)—, —$R^6$—S(=O)$_t$—, —$R^6$—S(=O)$_t$—N($R^7$)—, —$R^6$—Y—, $R^{7a}R^7$N—, —C(=O)NR$^7R^{7a}$, —OC(=O)NR$^7R^{7a}$, —OC(=O)OR$^7$, —N($R^7$)C(=O)NR$^7R^{7a}$, —N($R^7$)C(=O)OR$^{7a}$, —N($R^7$)C(=O)—$R^{7a}$, $R^7R^{7a}$N—S(=O)$_t$—, $R^7$S(=O)$_t$—, $R^7$S(=O)$_t$N($R^{7a}$)—, $R^{7a}R^7$N-alkyl, $R^7$S(=O)$_t$-alkyl, $R^7R^{7a}$N—C(=O)—C$_{1-6}$ alkyl, $R^{7a}R^7$N—C$_{1-6}$ alkoxy, $R^7$S(=O)-alkoxy, $R^7R^{7a}$N—C(=O)-alkoxy, $R^7R^{7a}$NC(=O)—, $R^7$OC(=O)—, $R^7$C(=O)—, $R^7R^{7a}$NS(=O)—, $R^7$OS(=O)—, $R^7$S(=O)—, $R^7R^{7a}$NS(=O)$_2$—, $R^7$OS(=O)$_2$—, $R^7$S(=O)$_2$—, $R^{7a}R^7$N-aliphatic, aryl-(CH$_2$)$_p$-G-(CH$_2$)$_m$—, heteroaryl-(CH$_2$)$_p$-G-(CH$_2$)$_m$—, heterocyclyl-(CH$_2$)$_p$-G-(CH$_2$)$_m$—, cycloalkyl-(CH$_2$)$_p$-G-(CH$_2$)$_m$—, hydroxy-substituted C$_{1-6}$ alkyl-C(=O)—, C$_{1-6}$ alkyl-C(=O)—, C$_{1-6}$ alkyl-S(=O)—, C$_{1-6}$ alkyl-S(=O)$_2$—, hydroxy-substituted C$_{1-6}$ alkyl-S(=O)—, hydroxy-substituted C$_{1-6}$ alkyl-S(=O)$_2$—, carboxy C$_{1-6}$ alkoxy, haloalkyl, heterocyclylalkyl, heterocyclylalkoxy, heterocyclylalkylamino, heterocyclylamino, cycloalkyl, cycloalkylaliphatic, cycloalkylamino, cycloalkyloxyaliphatic, cycloalkylalkoxy, cycloalkylalkylamino, carbocyclylaliphatic, aralkyl, aryloxyalkyl, heteroaryloxyaliphatic, aliphatic, alkoxy, hydroxyalkoxy, aminoalkoxy, hydroxy-substituted C$_{1-6}$ alkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, arylalkoxy, arylalkylamino, heterocyclylalkoxy, carbocyclylalkoxy, heterocyclyl(hydroxyalkoxy), carbocyclyl(hydroxyalkoxy), aryl(hydroxyalkoxy), aryloxyalkoxy, heteroaryloxyalkoxy, aryloxy, arylamino, heterocyclyloxyalkoxy, carbocyclyloxyalkoxy, cycloalkyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N(R$^7$)—, fused heterobicyclyl-C(=O)N(R$^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N(R$^7$)—, spiro heterobicyclyl-C(=O)N(R$^7$)—, aryl, heteroaryl, arylaliphatic, heteroarylaliphatic, heteroaryloxy, heteroarylamino, heteroarylalkoxy, heteroarylalkylamino, haloaliphatic, hydroxyaliphatic, aminoaliphatic, alkoxyaliphatic, alkylaminoaliphatic, alkylthioaliphatic, cycloalkyl, heterocyclylaliphatic, aryloxyaliphatic, heterocyclyloxyaliphatic, cycloalkyloxyaliphatic, arylaminoaliphatic, heterocyclylaminoaliphatic, cycloalkylaminoaliphatic, heterocyclyl, carbocyclyl, heterocyclylene, carbocyclylene, fused bicyclylene, fused heterobicyclylene, spiro bicyclylene, spiro heterobicyclylene, arylene and heteroarylene is unsubstituted or substituted with at least one substituent wherein the substituent is haloalkyl, oxo (=O), hydroxy, amino, F, Cl, Br, I, cyano, $C_{1-10}$ alkoxy, $C_{1-10}$ alkylamino, $C_{1-10}$ alkylthio, $C_{1-10}$ alkyl, $C_{2-10}$ alkenyl, $C_{2-10}$ alkynyl, mercapto, nitro, $C_{6-10}$ aryl, $C_{1-9}$ heteroaryl, $C_{2-10}$ heterocyclyl, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy$C_{1-6}$ alkoxy.

In some embodiments, A is $C_{2-10}$ heterocyclylene, $C_{3-10}$ carbocyclylene, $C_{5-12}$ fused bicyclylene, $C_{5-12}$ fused heterobicyclylene, $C_{5-12}$ spiro bicyclylene, $C_{5-12}$ spiro heterobicyclylene, $C_{6-10}$ arylene, or $C_{1-9}$ heteroarylene.

In some embodiments, A is

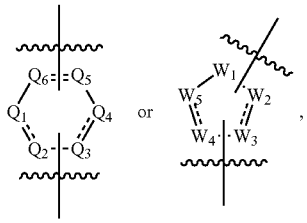

wherein each $Q_1$, $Q_2$, $Q_3$, $Q_4$, $Q_5$ and $Q_6$ is independently N, NR$^5$, O, S, CR$^7$R$^{7a}$ or CR$^8$, and at most four of the $Q_1$, $Q_2$, $Q_3$, $Q_4$, $Q_5$ and $Q_6$ are N or NR$^5$;

$W_1$ is NR$^5$, O, S, or CR$^7$R$^{7a}$; each $W_2$, $W_3$, $W_4$ and $W_5$ is independently N, NR$^5$, O, S, CR$^7$R$^{7a}$, or CR$^8$; and at most four of the $W_1$, $W_2$, $W_3$, $W_4$ and $W_5$ are N or NR$^5$; and each R$^8$ is independently H, hydroxy, amino, F, Cl, Br, I, cyano, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N-alkyl, R$^7$S(=O)-alkyl, R$^7$R$^{7a}$N—C(=O)-alkyl, R$^{7a}$R$^7$N-alkoxy, R$^7$S(=O)-alkoxy, R$^7$R$^{7a}$N—C(=O)-alkoxy, aryl, heteroaryl, alkoxy, alkyl, alkenyl, alkynyl, heterocyclyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino or aryloxy.

In some embodiments, A is

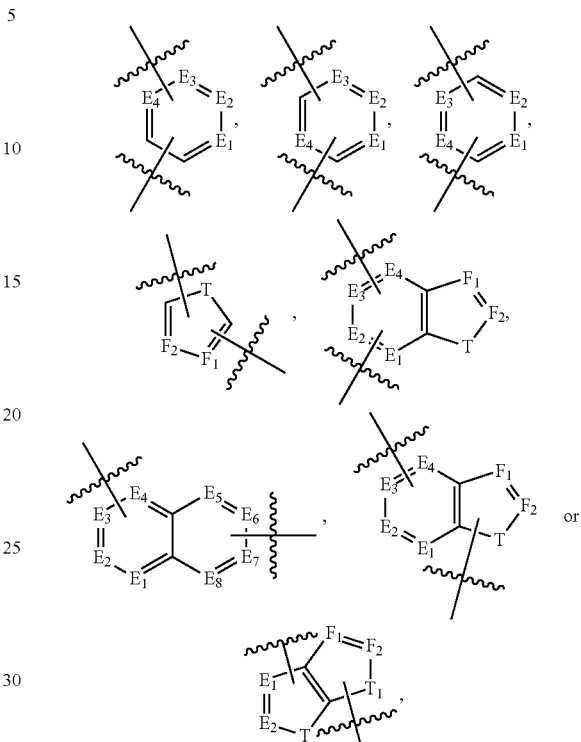

wherein each $E_1$, $E_2$, $E_3$, $E_4$, $E_5$, $E_6$, $E_7$, $E_8$, $F_1$ and $F_2$ is independently N or CR$^9$;

each T and T$_1$ is independently NR$^5$, O, S or CR$^9$R$^{9a}$; and each R$^9$ and R$^{9a}$ is independently H, hydroxy, amino, F, Cl, Br, I, cyano, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N—$C_{1-6}$ alkyl, R$^7$S(=O)—$C_{1-6}$ alkyl, R$^7$R$^{7a}$N—C(=O)—$C_{1-6}$ alkyl, R$^{7a}$R$^7$N—$C_{1-6}$ alkoxy, R$^7$S(=O)—$C_{1-6}$ alkoxy, R$^7$R$^{7a}$N—C(=O)—$C_{1-6}$ alkoxy, $C_{6-10}$ aryl, $C_{1-9}$ heteroaryl, $C_{1-6}$ alkoxy, $C_{1-6}$ alkyl, $C_{2-6}$ alkenyl, $C_{2-6}$ alkynyl, $C_{2-10}$ heterocyclyl, mercapto, nitro, $C_{6-10}$ aryl-$C_{1-6}$-alkyl, $C_{6-10}$ arylamino, $C_{1-9}$ heteroarylamino, $C_{6-10}$ aryl-$C_{1-6}$-alkylamino, $C_{1-9}$ heteroaryl-$C_{1-6}$-alkylamino, $C_{1-9}$ heteroaryloxy, $C_{1-9}$ heteroaryl-$C_{1-6}$-alkyl, $C_{6-10}$ aryl-$C_{1-6}$-alkoxy, $C_{1-9}$ heteroaryl-$C_{1-6}$-alkoxy, $C_{2-10}$ heterocyclyloxy, $C_{2-10}$ heterocyclyl-$C_{1-6}$-alkoxy, $C_{2-10}$ heterocyclylamino, $C_{2-10}$ heterocyclyl-$C_{1-6}$-alkylamino, or $C_{6-10}$ aryloxy.

In other embodiments, A is

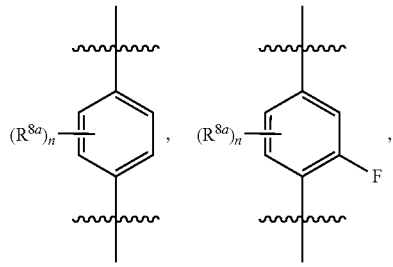

-continued

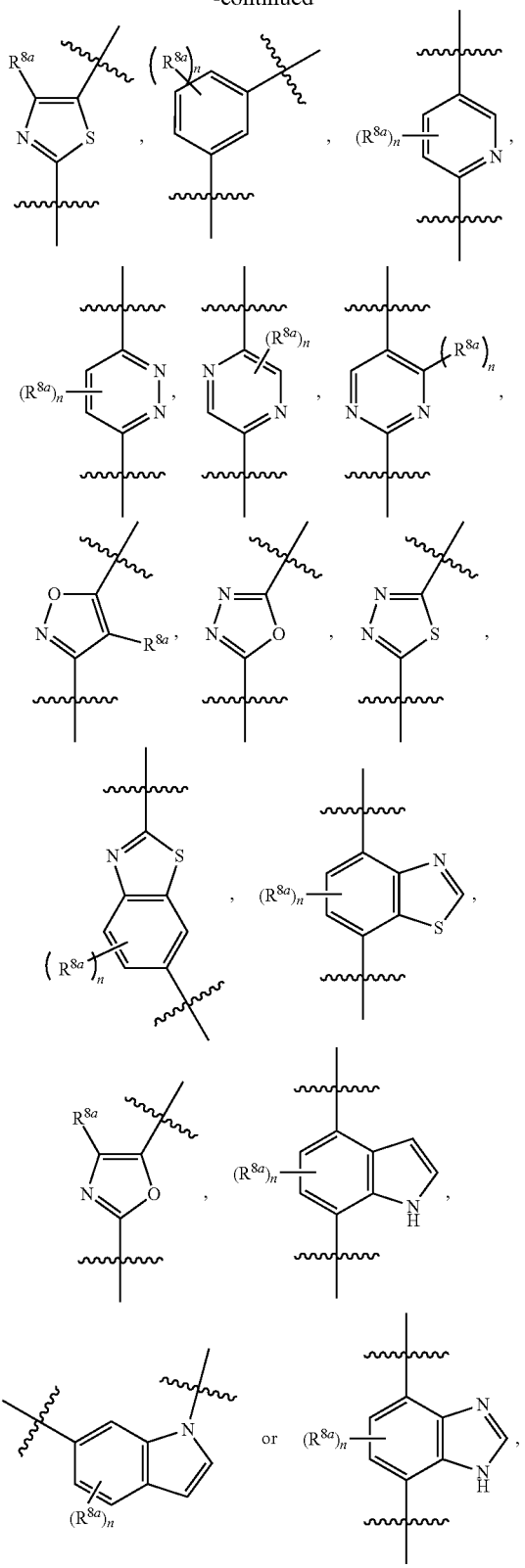

wherein each n is independently 0, 1, 2 or 3; and each $R^{8a}$ is independently H, hydroxy, amino, F, Cl, Br, I, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $R^7S(=O)_2-$, $R^7S(=O)_2N(R^{7a})-$, cyano, nitro, mercapto, $C_{1-4}$ alkyl, $C_{1-4}$ haloalkyl, $C_{1-4}$ alkoxy, $C_{1-4}$ alkylamino, $C_{1-4}$ alkylthio, $C_{6-10}$ aryl, or $C_{1-9}$ heteroaryl.

In some embodiments, B is $C_{1-6}$ alkoxy, hydroxy-substituted $C_{1-6}$ alkoxy, $-NR^7R^{7a}$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $R^7S(=O)_2-$, $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl, or $C_{5-12}$ spiro heterobicyclyl.

In some embodiments, $R^1$ is H, F, Cl, Br, I, cyano, hydroxy, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $R^7S(=O)_2-$, $R^7S(=O)_2N(R^{7a})-$, $R^{7a}R^7N-C_{1-6}$ alkyl, $R^7S(=O)-C_{1-6}$ alkyl, $R^7R^{7a}N-C(=O)-C_{1-6}$ alkyl, $R^{7a}R^7N-C_{1-6}$ alkoxy, $R^7S(=O)-C_{1-6}$ alkoxy, $R^7R^{7a}N-C(=O)-C_{1-6}$ alkoxy, $C_{1-6}$ aliphatic, $C_{1-6}$ alkoxy, $C_{1-6}$ hydroxyalkoxy, $C_{1-6}$ aminoalkoxy, hydroxy-substituted $C_{1-6}$ aminoalkoxy, $C_{1-6}$ haloalkoxy, amino-substituted $C_{1-6}$ haloalkoxy, $C_{1-6}$ alkylamino-$C_{1-6}$-haloalkoxy, hydroxy-substituted $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{3-10}$ cycloalkylamino, $C_{3-10}$ carbocyclyl-$C_{1-6}$-alkoxy, $C_{3-10}$ carbocyclyl-$C_{1-6}$-alkylamino, $C_{2-10}$ heterocyclyl($C_{1-6}$ hydroxyalkoxy), $C_{3-10}$ carbocyclyl($C_{1-6}$ hydroxyalkoxy), $C_{6-10}$ aryl($C_{1-6}$ hydroxyalkoxy), $C_{6-10}$ aryloxy-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{1-6}$ azidoalkoxy, $C_{5-12}$ fused bicyclyl, $C_{5-12}$ fused heterobicyclyl, $C_{5-12}$ fused bicyclyl-$C_{1-6}$-aliphatic, $C_{5-12}$ fused heterobicyclyl-$C_{1-6}$-aliphatic, $C_{5-12}$ fused bicycloxy, $C_{5-12}$ fused heterobicycloxy, $C_{5-12}$ fused bicyclylamino, $C_{5-12}$ fused heterobicyclylamino, $C_{5-12}$ fused bicyclyl-$C_{1-6}$-alkoxy, $C_{5-12}$ fused heterobicyclyl-$C_{1-6}$-alkoxy, $C_{5-12}$ fused bicyclyl-$C_{1-6}$-alkylamino, $C_{5-12}$ fused heterobicyclyl-$C_{1-6}$-alkylamino, $C_{5-12}$ fused bicycloxy-$C_{1-6}$-alkoxy, $C_{5-12}$ fused heterobicycloxy-$C_{1-6}$-alkoxy, $C_{5-12}$ fused bicyclylamino-$C_{1-6}$-alkoxy, $C_{5-12}$ fused heterobicyclylamino-$C_{1-6}$-alkoxy, $C_{5-12}$ fused bicyclyl-C(=O)-, $C_{5-12}$ fused bicyclyl-C(=O)O-, $C_{5-12}$ fused heterobicyclyl-C(=O)-, $C_{5-12}$ fused heterobicyclyl-C(=O)O-, $C_{5-12}$ fused bicyclylamino-C(=O)-, $C_{5-12}$ fused heterobicyclylamino-C(=O)-, $C_{5-12}$ fused bicyclyl-C(=O)N($R^7$)-, $C_{5-12}$ fused heterobicyclyl-C(=O)N($R^7$)-, $C_{5-12}$ spiro bicyclyl, $C_{5-12}$ spiro heterobicyclyl, $C_{5-12}$ spiro bicyclyl-$C_{1-6}$-aliphatic, $C_{5-12}$ spiro heterobicyclyl-$C_{1-6}$-aliphatic, $C_{5-12}$ spiro bicycloxy, $C_{5-12}$ spiro heterobicycloxy, $C_{5-12}$ spiro bicyclylamino, $C_{5-12}$ spiro heterobicyclylamino, $C_{5-12}$ spiro bicyclyl-$C_{1-6}$-alkoxy, $C_{5-12}$ spiro heterobicyclyl-$C_{1-6}$-alkoxy, $C_{5-12}$ spiro bicyclyl-$C_{1-6}$-alkylamino, $C_{5-12}$ spiro heterobicyclyl-$C_{1-6}$-alkylamino, $C_{5-12}$ spiro bicycloxy-$C_{1-6}$-alkoxy, $C_{5-12}$ spiro heterobicycloxy-$C_{1-6}$-alkoxy, $C_{5-12}$ spiro bicyclylamino-$C_{1-6}$-alkoxy, $C_{5-12}$ spiro heterobicyclylamino-$C_{1-6}$-alkoxy, $C_{5-12}$ spiro bicyclyl-C(=O)-, $C_{5-12}$ spiro bicyclyl-C(=O)O-, $C_{5-12}$ spiro heterobicyclyl-C(=O)-, $C_{5-12}$ spiro heterobicyclyl-C(=O)O-, $C_{5-12}$ spiro bicyclylamino-C(=O)-, $C_{5-12}$ spiro heterobicyclylamino-C(=O)-, $C_{5-12}$ spiro bicyclyl-C(=O)N($R^7$)-, $C_{5-12}$ spiro heterobicyclyl-C(=O)N($R^7$)-, $C_{2-10}$ heterocyclyl, $C_{3-10}$ cycloalkyl, $C_{6-10}$ aryl, $C_{1-9}$ heteroaryl, $C_{2-10}$ heterocyclyl-$C_{1-6}$-aliphatic, $C_{3-10}$ cycloalkyl-$C_{1-6}$-aliphatic, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-$(CH_2)_m$— is optionally substituted by one or more F, Cl, Br, I, $C_{1-6}$ alkyl, $C_{2-6}$ alkynyl, $C_{1-6}$ alkoxy or cyano;

$R^2$ is H, F, Cl, Br, I, cyano, hydroxy, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, $R^7R^{7a}N$—S(=O)$_2$—, $R^7S$(=O)$_2$—, $R^7S$(=O)$_2$N(R$^{7a}$)—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{1-6}$ aliphatic, $C_{1-6}$ alkoxy, $C_{1-6}$ hydroxyalkoxy, $C_{1-6}$ aminoalkoxy, hydroxy-substituted $C_{1-6}$ aminoalkoxy, $C_{1-6}$ haloalkoxy, amino-substituted $C_{1-6}$ haloalkoxy, $C_{1-6}$ alkylamino-$C_{1-6}$-haloalkoxy, hydroxy-substituted $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{3-10}$ cycloalkylamino, $C_{3-10}$ carbocyclyl-$C_{1-6}$-alkoxy, $C_{3-10}$ carbocyclyl-$C_{1-6}$-alkylamino, $C_{2-10}$ heterocyclyl($C_{1-6}$ hydroxyalkoxy), $C_{3-10}$ carbocyclyl($C_{1-6}$ hydroxyalkoxy), $C_{6-10}$ aryl($C_{1-6}$ hydroxyalkoxy), $C_{6-10}$ aryloxy-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{1-6}$ azidoalkoxy, $C_{5-12}$ fused bicyclyl, $C_{5-12}$ fused heterobicyclyl, $C_{5-12}$ fused bicyclyl-$C_{1-6}$-aliphatic, $C_{5-12}$ fused heterobicyclyl-$C_{1-6}$-aliphatic, $C_{5-12}$ fused bicycloxy, $C_{5-12}$ fused heterobicycloxy, $C_{5-12}$ fused bicyclylamino, $C_{5-12}$ fused heterobicyclylamino, $C_{5-12}$ fused bicyclyl-$C_{1-6}$-alkoxy, $C_{5-12}$ fused heterobicyclyl-$C_{1-6}$-alkoxy, $C_{5-12}$ fused bicyclyl-$C_{1-6}$-alkylamino, $C_{5-12}$ fused heterobicyclyl-$C_{1-6}$-alkylamino, $C_{5-12}$ fused bicycloxy-$C_{1-6}$-alkoxy, $C_{5-12}$ fused heterobicycloxy-$C_{1-6}$-alkoxy, $C_{5-12}$ fused bicyclylamino-$C_{1-6}$-alkoxy, $C_{5-12}$ fused heterobicyclylamino-$C_{1-6}$-alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)N(R$^7$)—, $C_{5-12}$ fused heterobicyclyl-C(=O)N(R$^7$)—, $C_{5-12}$ spiro bicyclyl, $C_{5-12}$ spiro heterobicyclyl, $C_{5-12}$ spiro bicyclyl-$C_{1-6}$-aliphatic, $C_{5-12}$ spiro heterobicyclyl-$C_{1-6}$-aliphatic, $C_{5-12}$ spiro bicycloxy, $C_{5-12}$ spiro heterobicycloxy, $C_{5-12}$ spiro bicyclylamino, $C_{5-12}$ spiro heterobicyclylamino, $C_{5-12}$ spiro bicyclyl-$C_{1-6}$-alkoxy, $C_{5-12}$ spiro heterobicyclyl-$C_{1-6}$-alkoxy, $C_{5-12}$ spiro bicyclyl-$C_{1-6}$-alkylamino, $C_{5-12}$ spiro heterobicyclyl-$C_{1-6}$-alkylamino, $C_{5-12}$ spiro bicycloxy-$C_{1-6}$-alkoxy, $C_{5-12}$ spiro heterobicycloxy-$C_{5-12}$-alkoxy, $C_{5-12}$ spiro bicyclylamino-$C_{1-6}$-alkoxy, $C_{5-12}$ spiro heterobicyclylamino-$C_{1-6}$-alkoxy, $C_{5-12}$ spiro bicyclyl-C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)N(R$^7$)—, $C_{5-12}$ spiro heterobicyclyl-C(=O)N(R$^7$)—, $C_{2-10}$ heterocyclyl, $C_{3-10}$ cycloalkyl, $C_{6-10}$ aryl, $C_{1-4}$ heteroaryl, $C_{2-10}$ heterocyclyl-$C_{1-6}$-aliphatic, $C_{3-10}$ cycloalkyl-$C_{1-6}$-aliphatic, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)$—, or $C_{3-10}$ cycloalkyl-$(CH_2)_p$-G-$(CH_2)$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4;

$R^3$ is H, F, Cl, I, cyano, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, $R^7R^{7a}N$—S(=O)$_2$—, $R^7S$(=O)$_2$—, $R^7S$(=O)$_2$N(R$^{7a}$)—, $R^{7a}R^7N$—$C_{1-6}$ alkyl, $R^7S$(=O)—$C_{1-6}$ alkyl, $R^7R^{7a}NT$-C(=O)—$C_{1-6}$ alkyl, $R^{7a}R^7N$—$C_{1-6}$ alkoxy, $R^7S$(=O)—$C_{1-6}$ alkoxy, $R^7R^{7a}NT$-C(=O)—$C_{1-6}$ alkoxy, $C_{1-6}$ aliphatic, $C_{2-10}$ haloalkyl, $C_{6-10}$ aryl-$C_{2-10}$-alkoxy, $C_{1-9}$ heteroaryl-$C_{3-6}$-alkoxy, $C_{3-10}$ cycloalkyl-$C_{2-10}$-alkoxy, $C_{5-10}$ fused bicyclyl-$C_{2-10}$-alkoxy, $C_{2-10}$ heterocyclyl, $C_{3-10}$ cycloalkyl, $C_{1-4}$ heteroaryl, substituted $C_{6-10}$ aryl, $C_{2-10}$ heterocyclyl-$C_{1-6}$-aliphatic, $C_{3-10}$ cycloalkyl-$C_{1-6}$-aliphatic, $C_{1-4}$ heteroaryl-$C_{1-6}$-aliphatic, $C_{1-9}$ heteroaryloxy-$C_{1-6}$-alkoxy, substituted $C_{6-10}$ aryl-$C_{3-6}$-alkyl, $C_{2-10}$ hetterocyclyl-$C_{1-6}$-alkyl, $C_{1-6}$ alkoxy, $C_{1-6}$ hydroxyalkoxy, $C_{1-6}$ aminoalkoxy, hydroxy-substituted $C_{1-6}$ aminoalkoxy, $C_{1-6}$ haloalkoxy, amino-substituted $C_{1-6}$ haloalkoxy, $C_{1-6}$ alkylamino-$C_{1-6}$-haloalkoxy, hydroxy-substituted $C_{1-6}$ haloalkoxy, $C_{1-6}$ alkylamino-$C_{1-6}$-alkoxy, $C_{1-6}$ alkoxy-$C_{1-6}$-alkoxy, $C_{6-10}$ aryl-$C_{2-10}$-alkoxy, $C_{2-10}$ heterocyclyl-$C_{1-6}$-alkoxy, $C_{3-10}$ carbocyclyl-$C_{1-6}$-alkoxy, $C_{2-10}$ heterocyclyl($C_{1-6}$ hydroxyalkoxy), $C_{3-10}$ carbocyclyl($C_{1-6}$ hydroxyalkoxy), $C_{6-10}$ aryl($C_{1-6}$ hydroxyalkoxy), $C_{6-10}$ aryloxy-$C_{1-6}$-alkoxy, $C_{6-10}$ arylamino-$C_{1-6}$-alkoxy, $C_{6-10}$ aryloxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{3-10}$ cycloalkyloxy, $C_{1-6}$ azidoalkoxy, $C_{5-12}$ fused bicyclyl, $C_{5-12}$ fused heterobicyclyl, $C_{5-12}$ fused bicyclyl-$C_{1-6}$-aliphatic, $C_{5-12}$ fused heterobicyclyl-$C_{1-6}$-aliphatic, $C_{5-12}$ fused bicycloxy, $C_{5-12}$ fused heterobicycloxy, $C_{5-12}$ fused bicyclylamino, $C_{5-12}$ fused heterobicyclylamino, $C_{5-12}$ fused bicyclyl-$C_{1-6}$-alkoxy, $C_{5-12}$ fused heterobicyclyl-$C_{1-6}$-alkoxy, $C_{5-12}$ fused bicyclyl-$C_{1-6}$-alkylamino, $C_{5-12}$ fused heterobicyclyl-$C_{1-6}$-alkylamino, $C_{5-12}$ fused bicycloxy-$C_{1-6}$-alkoxy, $C_{5-12}$ fused heterobicycloxy-$C_{1-6}$-alkoxy, $C_{5-12}$ fused bicyclylamino-$C_{1-6}$-alkoxy, $C_{5-12}$ fused heterobicyclylamino-$C_{1-6}$-alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)NR$^7$—, $C_{5-12}$ fused heterobicyclyl-C(=O)NR$^7$—, $C_{5-12}$ spiro bicyclyl, $C_{5-12}$ spiro heterobicyclyl, $C_{5-12}$ spiro bicyclyl-$C_{1-6}$-aliphatic, $C_{5-12}$ spiro heterobicyclyl-$C_{1-6}$-aliphatic, $C_{5-12}$ spiro bicycloxy, $C_{5-12}$ spiro heterobicycloxy, $C_{5-12}$ spiro bicyclylamino, $C_{5-12}$ spiro heterobicyclylamino, $C_{5-12}$ spiro bicyclyl-$C_{1-6}$-alkoxy, $C_{5-12}$ spiro heterobicyclyl-$C_{1-6}$-alkoxy, $C_{5-12}$ spiro bicyclyl-$C_{1-6}$-alkylamino, $C_{5-12}$ spiro heterobicyclyl-$C_{1-6}$-alkylamino, $C_{5-12}$ spiro bicycloxy-$C_{1-6}$-alkoxy, $C_{5-12}$ spiro heterobicycloxy-$C_{1-6}$-alkoxy, $C_{5-12}$ spiro bicyclylamino-$C_{1-6}$-alkoxy, $C_{5-12}$ spiro heterobicyclylamino-$C_{1-6}$-alkoxy, $C_{5-12}$ spiro bicyclyl-C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)NR$^7$—, $C_{5-12}$ spiro heterobicyclyl-C(=O)NR$^7$—, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)

NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4; and $R^4$ is H, F, I, cyano, hydroxy, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)—, $R^7S$(=O)—, $R^7S$(=O)N($R^{7a}$)—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{1-6}$ aliphatic, $C_{2-10}$ alkoxy, $C_{1-6}$ hydroxyalkoxy, $C_{1-6}$ aminoalkoxy, hydroxy-substituted $C_{1-6}$ aminoalkoxy, $C_{1-6}$ haloalkoxy, amino-substituted $C_{1-6}$ haloalkoxy, $C_{1-6}$ alkylamino-$C_{1-6}$-haloalkoxy, hydroxy-substituted $C_{1-6}$ haloalkoxy, $C_{1-6}$ alkylamino-$C_{1-6}$-alkoxy, $C_{1-6}$ alkoxy-$C_{1-6}$-alkoxy, $C_{3-5}$ cycloalkyloxy, $C_{6-10}$ aryl-$C_{1-6}$-alkoxy, $C_{1-9}$ heteroaryl-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{7-10}$ cycloalkyloxy, $C_{3-10}$ cycloalkylamino, $C_{3-10}$ carbocyclyl-$C_{1-6}$-alkoxy, $C_{3-10}$ carbocyclyl-$C_{1-6}$-alkylamino, $C_{2-10}$ heterocyclyl($C_{1-6}$ hydroxyalkoxy), $C_{3-10}$ carbocyclyl($C_{1-6}$ hydroxyalkoxy), $C_{6-10}$ aryl($C_{1-6}$ hydroxyalkoxy), $C_{6-10}$ aryloxy-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{1-6}$ azidoalkoxy, $C_{5-12}$ fused bicyclyl, $C_{5-12}$ fused heterobicyclyl, $C_{5-12}$ fused bicyclyl-$C_{1-6}$-aliphatic, $C_{5-12}$ fused heterobicyclyl-$C_{1-6}$-aliphatic, $C_{5-12}$ fused bicycloxy, $C_{5-12}$ fused heterobicycloxy, $C_{5-12}$ fused bicyclylamino, $C_{5-12}$ fused heterobicyclylamino, $C_{5-12}$ fused bicyclyl-$C_{1-6}$-alkoxy, $C_{5-12}$ fused heterobicyclyl-$C_{1-6}$-alkoxy, $C_{5-12}$ fused bicyclyl-$C_{1-6}$-alkylamino, $C_{5-12}$ fused heterobicyclyl-$C_{1-6}$-alkylamino, $C_{5-12}$ fused bicycloxy-$C_{1-6}$-alkoxy, $C_{5-12}$ fused heterobicycloxy-$C_{1-6}$-alkoxy, $C_{5-12}$ fused bicyclylamino-$C_{1-6}$-alkoxy, $C_{5-12}$ fused heterobicyclylamino-$C_{1-6}$-alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)$NR^7$—, $C_{5-12}$ fused heterobicyclyl-C(=O)$NR^7$—, $C_{5-12}$ spiro bicyclyl, $C_{5-12}$ spiro heterobicyclyl, $C_{5-12}$ spiro bicyclyl-$C_{1-6}$-aliphatic, $C_{5-12}$ spiro heterobicyclyl-$C_{1-6}$-aliphatic, $C_{5-12}$ spiro bicycloxy, $C_{5-12}$ spiro heterobicycloxy, $C_{5-12}$ spiro bicyclylamino, $C_{5-12}$ spiro heterobicyclylamino, $C_{5-12}$ spiro bicyclyl-$C_{1-6}$-alkoxy, $C_{5-12}$ spiro heterobicyclyl-$C_{1-6}$-alkoxy, $C_{5-12}$ spiro bicyclyl-$C_{1-6}$-alkylamino, $C_{5-12}$ spiro heterobicyclyl-$C_{1-6}$-alkylamino, $C_{5-12}$ spiro bicycloxy-$C_{1-6}$-alkoxy, $C_{5-12}$ spiro heterobicycloxy-$C_{1-6}$-alkoxy, $C_{5-12}$ spiro bicyclylamino-$C_{1-6}$-alkoxy, $C_{5-12}$ spiro heterobicyclylamino-$C_{1-6}$-alkoxy, $C_{5-12}$ spiro bicyclyl-C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)N($R^7$)—, $C_{5-12}$ spiro heterobicyclyl-C(=O)N($R^7$)—, $C_{2-10}$ heterocyclyl, $C_{3-10}$ cycloalkyl, $C_{6-10}$ aryl, $C_{1-9}$ heteroaryl, $C_{2-10}$ heterocyclyl-$C_{1-6}$-aliphatic, $C_{3-10}$ cycloalkyl-$C_{1-6}$-aliphatic, $C_{6-10}$ aryl-$C_{2-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4.

In some embodiments, each $R^5$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ aliphatic, $C_{1-6}$ haloaliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryloxy-$C_{1-6}$-aliphatic, $C_{2-10}$ heterocyclyloxy-$C_{1-6}$-aliphatic, $C_{3-10}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-10}$ cycloalkylamino-$C_{1-6}$-aliphatic, $C_{6-10}$ aryl, $C_{1-9}$ heteroaryl, $C_{2-10}$ heterocyclyl or $C_{3-10}$ carbocyclyl.

In some embodiments, each $R^{5a}$ is independently H, hydroxy, amino, F, Cl, Br, I, cyano, oxo (=O), $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2$N($R^{7a}$)—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{6-10}$ aryl, $C_{1-9}$ heteroaryl, $C_{1-6}$ alkoxy, $C_{1-6}$ alkyl, $C_{2-6}$ alkenyl, $C_{2-6}$ alkynyl, $C_{2-10}$ heterocyclyl, mercapto, nitro, $C_{6-10}$ aryl-$C_{1-6}$-alkyl, $C_{6-10}$ arylamino, $C_{1-9}$ heteroarylamino, $C_{6-10}$ aryl-$C_{1-6}$-alkylamino, $C_{1-9}$ heteroaryl-$C_{1-6}$-alkylamino, $C_{1-9}$ heteroaryloxy, $C_{1-9}$ heteroaryl-$C_{1-6}$-alkyl, $C_{6-10}$ aryl-$C_{1-6}$-alkoxy, $C_{1-9}$ heteroaryl-$C_{1-6}$-alkoxy, $C_{2-10}$ heterocyclyloxy, $C_{2-10}$ heterocyclyl-$C_{1-6}$-alkoxy, $C_{2-10}$ heterocyclylamino, $C_{2-10}$ heterocyclyl-$C_{1-6}$-alkylamino or $C_{6-10}$ aryloxy.

In some embodiments, each $R^7$ and $R^{7a}$ is independently H, $C_{1-6}$ aliphatic, $C_{1-6}$ haloaliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryloxy-$C_{1-6}$-aliphatic, $C_{2-10}$ heterocyclyloxy-$C_{1-6}$-aliphatic, $C_{3-10}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-10}$ cycloalkylamino-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted $C_{5-12}$ spiro bicyclic or $C_{5-12}$ fused bicyclic ring.

In some embodiments, N, $V_1$, $V_2$, $V_3$, $V_4$ and C(=Y) of Formula (I) define a group having Formula (III):

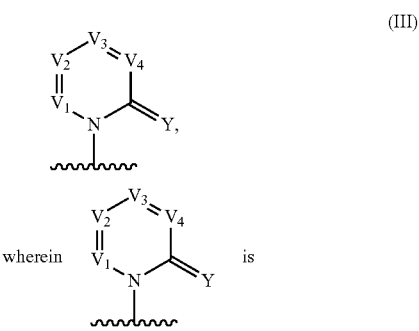

-continued

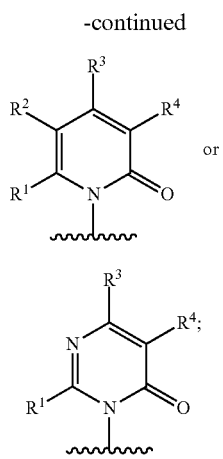

each R¹ is H, F, Cl, Br, I, cyano, hydroxy, $R^{7a}R^7N—$, $—C(=O)NR^7R^{7a}$, $—OC(=O)NR^7R^{7a}$, $—OC(=O)OR^7$, $—N(R^7)C(=O)NR^7R^{7a}$, $—N(R^7)C(=O)OR^{5a}$, $—N(R^7)C(=O)—R^{7a}$, $R^7R^{7a}N—S(=O)_2—$, $R^7S(=O)_2—$, $R^7S(=O)_2N(R^{7a})—$, $C_{1-6}$ aliphatic, $C_{1-6}$ haloalkyl, $C_{1-6}$ alkoxy, $C_{1-6}$ hydroxyalkoxy, $C_{1-6}$ amino alkoxy, $C_{1-6}$ halo alkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m—$, $C_{1-9}$ heteroaryl-$(CH_2)_p$-G-$(CH_2)_m—$, $C_{2-10}$ heterocyclyl-$(CH_2)_p$-G-$(CH_2)_m—$, or $C_{3-10}$ cycloalkyl-$(CH_2)_p$-G-$(CH_2)_m—$, wherein each G is O, S, $NR^5$, $S(=O)$, $S(=O)_2$, $C(=O)$, $—C(=O)NH—$, $—OC(=O)NH—$, $—OC(=O)—$, $—NHC(=O)NH—$, $—HN—S(=O)_t—$, $—OS(=O)_t—$, or $—OS(=O)_tNH—$; each t is 1 or 2; each p and m is independently 0, 1, 2, 3 or 4; or wherein each of the $C_{6-10}$ aryl-$(CH_2)_p$-G-$(CH_2)_m—$, $C_{1-9}$ heteroaryl-$(CH_2)_p$-G-$(CH_2)_m—$, $C_{2-10}$ heterocyclyl-$(CH_2)_p$-G-$(CH_2)_m—$, and $C_{3-10}$ cycloalkyl-$(CH_2)_p$-G-$(CH_2)_m—$ is optionally substituted by one or more F, Cl, Br, I, $C_{1-6}$ alkyl, $C_{2-6}$ alkynyl, $C_{1-6}$ alkoxy or cyano;

R² is H, F, Cl, Br, I, cyano, hydroxy, $R^{7a}R^7N—$, $—C(=O)NR^7R^{7a}$, $—OC(=O)NR^7R^{7a}$, $—OC(=O)OR^7$, $—N(R^7)C(=O)NR^7R^{7a}$, $—N(R^7)C(=O)OR^{5a}$, $—N(R^7)C(=O)—R^{7a}$, $R^7R^{7a}N—S(=O)_2—$, $R^7S(=O)_2—$, $R^7S(=O)_2N(R^{7a})—$, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-4}$ heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m—$, $C_{1-9}$ heteroaryl-$(CH_2)_p$-G-$(CH_2)_m—$, $C_{2-10}$ heterocyclyl-$(CH_2)_p$-G-$(CH_2)_m—$, or $C_{3-10}$ cycloalkyl-$(CH_2)_p$-G-$(CH_2)_m—$, wherein each G is O, S, $NR^5$, $S(=O)$, $S(=O)_2$, $C(=O)$, $—C(=O)NH—$, $—OC(=O)NH—$, $—OC(=O)—$, $—NHC(=O)NH—$, $—HN—S(=O)_t—$, $—OS(=O)_t—$, or $—OS(=O)_tNH—$; each t is 1 or 2; each p and m is independently 0, 1, 2, 3 or 4;

each R³ is H, F, Cl, I, cyano, $R^{7a}R^7N—$, $—C(=O)NR^7R^{7a}$, $—OC(=O)NR^7R^{7a}$, $—OC(=O)OR^7$, $—N(R^7)C(=O)NR^7R^{7a}$, $—N(R^7)C(=O)OR^{7a}$, $—N(R^7)C(=O)—R^{7a}$, $R^7R^{7a}N—S(=O)_2—$, $R^7S(=O)_2—$, $R^7S(=O)_2N(R^{7a})—$, $R^{7a}R^7N—C_{1-6}$ alkyl, $R^7S(=O)—C_{1-6}$ alkyl, $R^{7a}R^7N—C(=O)—C_{1-6}$ alkyl, $R^{7a}R^7N—C_{1-6}$ alkoxy, $R^7S(=O)—C_{1-6}$ alkoxy, $R^7R^{7a}N—C(=O)—C_{1-6}$ alkoxy, $C_{1-6}$ aliphatic, $C_{2-6}$ haloalkyl, $C_{6-10}$ aryl-$C_{2-6}$-alkoxy, $C_{1-9}$ heteroaryl-$C_{3-6}$-alkoxy, $C_{1-9}$ heteroaryloxy-$C_{1-6}$-alkoxy, $C_{3-10}$ cycloalkyl-$C_{2-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{1-4}$ heteroaryl, substituted $C_{6-10}$ aryl, $C_{1-4}$ heteroaryl-$C_{1-6}$-aliphatic, substituted $C_{6-10}$ aryl-$C_{3-6}$-alkyl, $C_{2-10}$ hetrocyclyl-$C_{1-6}$-alkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-haloalkoxy, $C_{1-6}$ alkylamino-$C_{1-6}$-alkoxy, $C_{1-6}$ alkoxy-$C_{1-6}$-alkoxy, $C_{6-10}$ aryl-$C_{2-10}$-alkoxy, $C_{2-10}$ heterocyclyl-$C_{1-6}$-alkoxy, $C_{3-10}$ carbocyclyl-$C_{1-6}$-alkoxy, $C_{2-10}$ heterocyclyloxy, $C_{3-10}$ cycloalkyloxy, $C_{6-10}$ aryl-$(CH_2)_p$-G-$(CH_2)_m—$, $C_{1-9}$ heteroaryl-$(CH_2)_p$-G-$(CH_2)_m—$, $C_{2-10}$ heterocyclyl-$(CH_2)_p$-G-$(CH_2)_m—$, or $C_{3-10}$ cycloalkyl-$(CH_2)_p$-G-$(CH_2)_m—$, wherein each G is O, S, $NR^5$, $S(=O)$, $S(=O)_2$, $C(=O)$, $—C(=O)NH—$, $—OC(=O)NH—$, $—OC(=O)—$, $—NHC(=O)NH—$, $—HN—S(=O)_t—$, $—OS(=O)_t—$, or $—OS(=O)_tNH—$; each t is 1 or 2; each p and m is independently 0, 1, 2, 3 or 4; and each R⁴ is H, F, I, cyano, hydroxy, $R^{7a}R^7N—$, $—C(=O)NR^7R^{7a}$, $—OC(=O)NR^7R^{7a}$, $—OC(=O)OR^7$, $—N(R^7)C(=O)NR^7R^{7a}$, $—N(R^7)C(=O)OR^{7a}$, $—N(R^7)C(=O)—R^{7a}$, $R^7R^{7a}N—S(=O)_2—$, $R^7S(=O)_2—$, $R^7S(=O)_2N(R^{7a})—$, $R^{7a}R^7N—C_{1-6}$ alkyl, $R^7S(=O)—C_{1-6}$ alkyl, $R^7R^{7a}N—C(=O)—C_{1-6}$ alkyl, $R^{7a}R^7N—C_{1-6}$ alkoxy, $R^7S(=O)—C_{1-6}$ alkoxy, $R^7R^{7a}N—C(=O)—C_{1-6}$ alkoxy, $C_{1-6}$ aliphatic, $C_{1-6}$ haloalkyl, $C_{2-10}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-5}$ cycloalkyloxy, $C_{6-10}$ aryl-$C_{1-6}$-alkoxy, $C_{1-9}$ heteroaryl-$C_{1-6}$-alkoxy, $C_{1-9}$ heteroaryloxy-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{3-10}$ cycloalkylamino, $C_{2-10}$ heterocyclyl-$C_{1-6}$-alkoxy, $C_{3-10}$ carbocyclyl-$C_{1-6}$-alkoxy, $C_{3-10}$ carbocyclyl-$C_{1-6}$-alkylamino, $C_{6-10}$ aryloxy, $C_{1-10}$ heteroaryloxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{2-6}$-aliphatic, $C_{1-9}$ heteroaryl-$C_{1-6}$-aliphatic, $C_{6-10}$ aryl-$(CH_2)_p$-G-$(CH_2)_m—$, $C_{1-9}$ heteroaryl-$(CH_2)_p$-G-$(CH_2)_m—$, $C_{2-10}$ heterocyclyl-$(CH_2)_p$-G-$(CH_2)_m—$, or $C_{3-10}$ cycloalkyl-$(CH_2)_p$-G-$(CH_2)_m—$, wherein each G is O, S, $NR^5$, $S(=O)$, $S(=O)_2$, $C(=O)$, $—C(=O)NH—$, $—OC(=O)NH—$, $—OC(=O)—$, $—NHC(=O)NH—$, $—HN—S(=O)_t—$, $—OS(=O)_t—$, or $—OS(=O)_tNH—$; each t is 1 or 2; each p and m is independently 0, 1, 2, 3 or 4.

In some embodiments,

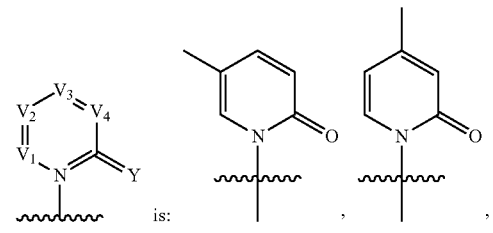

is:

-continued
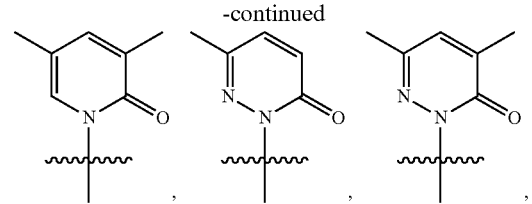
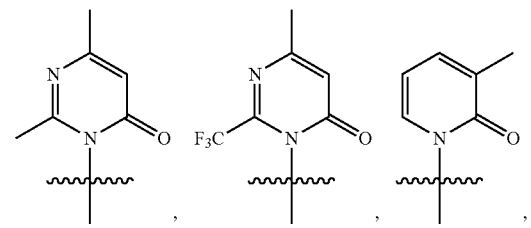
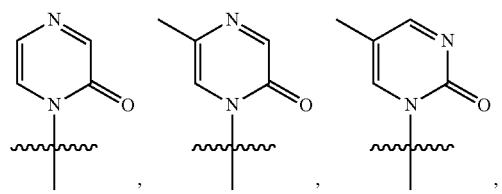
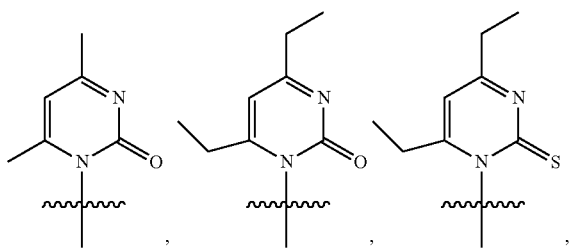
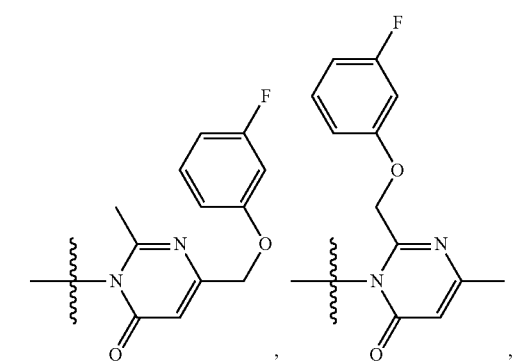
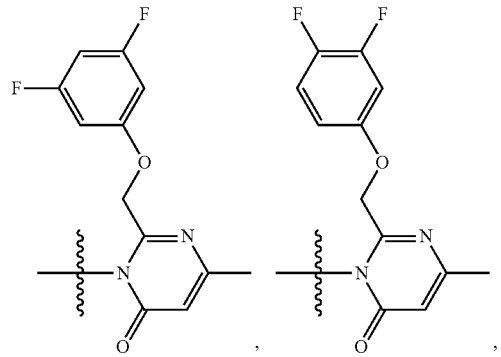
-continued
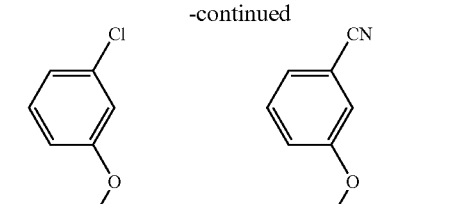
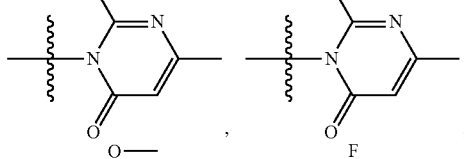
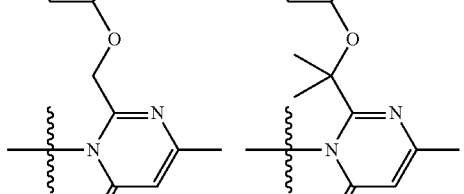
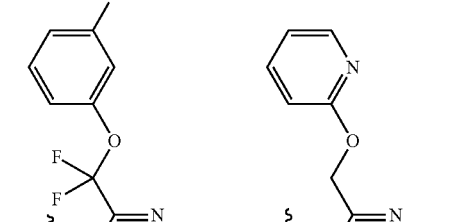
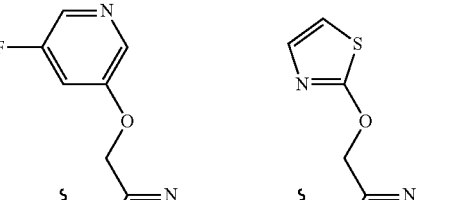
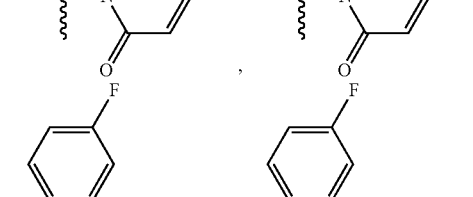
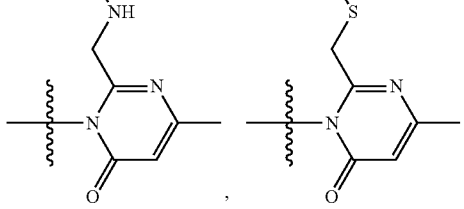

-continued

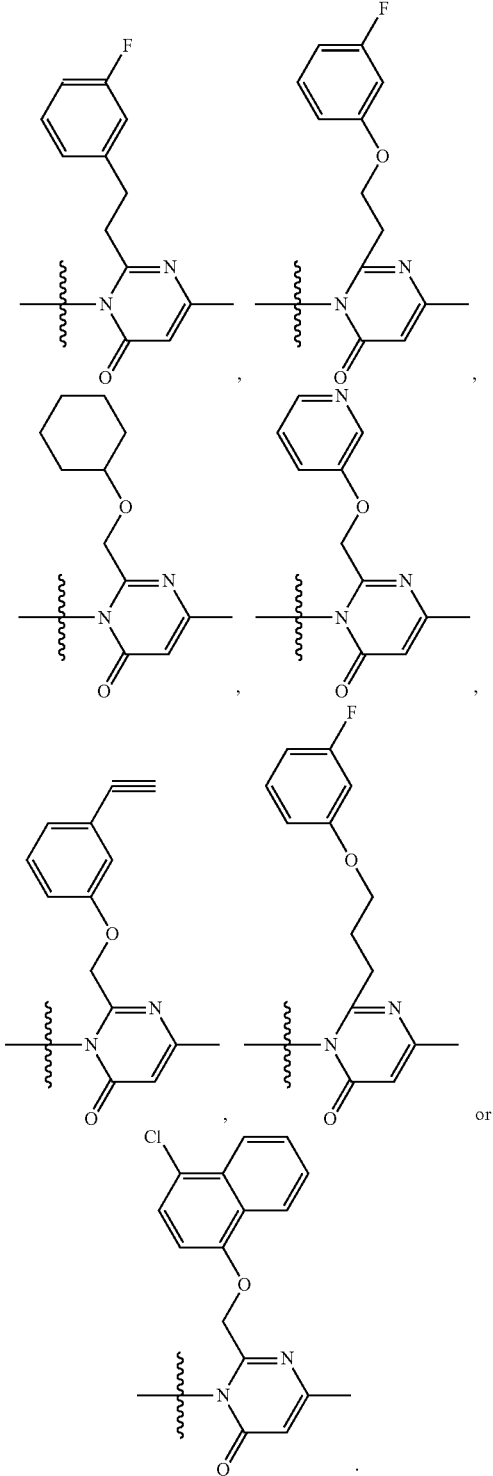

In some embodiments, A is:

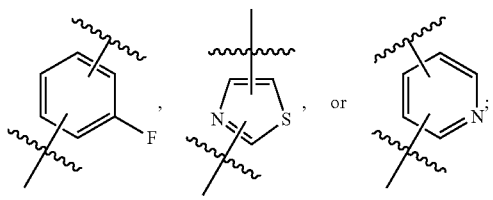

X is a bond, $NR^5$, O, S, $-(CH_2)_m-$, $-(CH_2)_m-C(=Y)-$, $-(CH_2)_m-C(=Y)-O-$, $-(CH_2)_m-C(=Y)-N(R^5)-$, $-(CH_2)_m-S(=O)_t-$, $-(CH_2)_m-S(=O)_t-N(R^7)-$, $-(CH_2)_m-Y-$, $-CH=CH-$, or $-C\equiv C-$, wherein each t is 1 or 2; each m is 0, 1, 2 or 3;

Y is O;

B is $-NR^7R^{7a}$, $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl, or $C_{5-12}$ spiro heterobicyclyl; wherein each of the $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl and $C_{5-12}$ spiro heterobicyclyl is optionally substituted by oxo (=O), hydroxy, amino, halo, cyano, $C_{6-10}$ aryl, $C_{1-9}$ heteroaryl, $C_{1-6}$ alkoxy, $C_{1-6}$ alkylamino, $C_{1-6}$ alkyl, $C_{2-6}$ alkenyl, $C_{2-6}$ alkynyl, $C_{2-10}$ heterocyclyl, mercapto, nitro, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy $C_{1-6}$ alkoxy;

$R^1$ is H, F, Cl, Br, I, cyano, hydroxy, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{5a}$, $-N(R^7)C(=O)R^{7a}$, $R^7R^{7a}N-S(=O)_2-$, $R^7S(=O)_2-$, $R^7S(=O)_2N(R^{7a})-$, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, or $C_{3-10}$ cycloalkyl-$(CH_2)_p$-G-$(CH_2)_m-$, wherein each G is O, S, $NR^5$, S(=O), S(=O)$_2$, C(=O), $-C(=O)NH-$, $-OC(=O)NH-$, $-OC(=O)-$, $-NHC(=O)NH-$, $-HN-S(=O)_t-$, $-OS(=O)_t-$, or $-OS(=O)_tNH-$; each t is 1 or 2; each p and m is independently 0, 1, 2, 3 or 4; or wherein each of the $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, and $C_{3-10}$ cycloalkyl-$(CH_2)_p$-G-$(CH_2)_m-$ is optionally substituted by one or more F, Cl, Br, I, methyl, ethyl, propyl, ethynyl, propynyl, butyryl, methoxy, ethoxy or cyano;

$R^2$ is H, F, Cl, Br, I, cyano, hydroxy, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{5a}$, $-N(R^7)C(=O)-R^{7a}$, $R^7R^{7a}N-S(=O)_2-$, $R^7S(=O)_2-$, $R^7S(=O)_2N(R^{7a})-$, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-4}$ heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, or $C_{3-10}$ cycloalkyl-$(CH_2)_p$-G-$(CH_2)_m-$, wherein each G is O, S, $NR^5$, S(=O), S(=O)$_2$, C(=O), $-C(=O)NH-$, $-OC(=O)NH-$, —OC(═O)—, —NHC(═O)NH—, —HN—S(═O)$_t$—, —OS(═O)$_t$—, or —OS(═O)$_t$NH—; each t is 1 or 2; each p and m is independently 0, 1, 2, 3 or 4;

$R^3$ is H, F, Cl, I, cyano, $R^{7a}R^7N$—, —C(═O)NR$^7$R$^{7a}$, —OC(═O)NR$^7$R$^{7a}$, —OC(═O)OR$^7$, —N(R$^7$)C(═O) NR$^7$R$^{7a}$, —N(R$^7$)C(═O)OR$^{7a}$, —N(R$^7$)C(═O)—R$^{7a}$, $R^7R^{7a}N$—S(═O)$_2$—, R$^7$S(═O)$_2$—, R$^7$S(═O)$_2$N(R$^{7a}$)—, $R^{7a}R^7N$—C$_{1-6}$ alkyl, R$^7$S(═O)—C$_{1-6}$ alkyl, R$^7$R$^{7a}$N—C (═O)—C$_{1-6}$ alkyl, R$^{7a}$R$^7$N—C$_{1-6}$ alkoxy, R$^7$S(═O)—C$_{1-6}$ alkoxy, R$^7$R$^{7a}$N—C(═O)—C$_{1-6}$ alkoxy, C$_{1-6}$ aliphatic, C$_{2-6}$ haloalkyl, C$_{6-10}$ aryl-C$_{2-6}$-alkoxy, C$_{1-9}$ heteroaryl-C$_{3-6}$-alkoxy, C$_{1-9}$ heteroaryloxy-C$_{1-6}$-alkoxy, C$_{3-10}$ cycloalkyl-C$_{2-6}$-alkoxy, C$_{2-10}$ heterocyclyl, C$_{3-10}$ cycloalkyl, C$_{2-10}$ heterocyclyl-C$_{1-6}$-aliphatic, C$_{3-10}$ cycloalkyl-C$_{1-6}$-aliphatic, C$_{1-4}$ heteroaryl, substituted C$_{6-10}$ aryl, C$_{1-4}$ heteroaryl-C$_{1-6}$-aliphatic, substituted C$_{6-10}$ aryl-C$_{3-6}$-alkyl, C$_{2-10}$ heterocyclyl-C$_{1-6}$-alkyl, C$_{1-6}$ alkoxy, C$_{1-6}$ hydroxyalkoxy, C$_{1-6}$ aminoalkoxy, C$_{1-6}$ haloalkoxy, C$_{1-6}$ alkylamino-C$_{1-6}$-haloalkoxy, C$_{1-6}$ alkylamino-C$_{1-6}$-alkoxy, C$_{1-6}$ alkoxy-C$_{1-6}$-alkoxy, C$_{6-10}$ aryl-C$_{2-10}$-alkoxy, C$_{2-10}$ heterocyclyl-C$_{1-6}$-alkoxy, C$_{3-10}$ carbocyclyl-C$_{1-6}$-alkoxy, C$_{2-10}$ heterocyclyloxy, C$_{3-10}$ cycloalkyloxy, C$_{6-10}$ aryl-(CH$_2$)$_p$-G-(CH$_2$)$_m$—, C$_{1-9}$ heteroaryl-(CH$_2$)$_p$-G-(CH$_2$)$_m$—, C$_{2-10}$ heterocyclyl-(CH$_2$)$_p$-G-(CH$_2$)$_m$—, or C$_{3-10}$ cycloalkyl-(CH$_2$)$_p$-G-(CH$_2$)$_m$—, wherein each G is O, S, NR$^5$, S(═O), S(═O)$_2$, C(═O), —C(═O)NH—, —OC(═O)NH—, —OC(═O)—, —NHC(═O) NH—, —HN—S(═O)$_t$—, —OS(═O)$_t$—, or —OS (═O)$_t$NH—; each t is 1 or 2; each p and m is independently 0, 1, 2, 3 or 4;

$R^4$ is H, F, I, cyano, hydroxy, R$^{7a}$R$^7$N—, —C(═O) NR$^7$R$^{7a}$, —OC(═O)NR$^7$R$^{7a}$, —OC(═O)OR$^7$, —N(R$^7$)C (═O)NR$^7$R$^{7a}$, —N(R$^7$)C(═O)OR$^{7a}$, —N(R$^7$)C(═O)—R$^{7a}$, R$^7$R$^{7a}$N—S(═O)$_2$—, R$^7$S(═O)$_2$—, R$^7$S(═O)$_2$N (R$^{7a}$)—, R$^{7a}$R$^7$N—C$_{1-6}$ alkyl, R$^7$S(═O)—C$_{1-6}$ alkyl, R$^7$R$^{7a}$N—C(═O)—C$_{1-6}$ alkyl, R$^{7a}$R$^7$N—C$_{1-6}$ alkoxy, R$^7$S (═O)—C$_{1-6}$ alkoxy, R$^7$R$^{7a}$N—C(═O)—C$_{1-6}$ alkoxy, C$_{1-6}$ aliphatic, C$_{1-6}$ haloalkyl, C$_{2-10}$ alkoxy, C$_{1-6}$ hydroxyalkoxy, C$_{1-6}$ aminoalkoxy, C$_{1-6}$ haloalkoxy, C$_{1-6}$ alkylamino-C$_{1-6}$-alkoxy, C$_{1-6}$ alkoxy-C$_{1-6}$-alkoxy, C$_{3-5}$ cycloalkyloxy, C$_{6-10}$ aryl-C$_{1-6}$-alkoxy, C$_{1-9}$ heteroaryl-C$_{1-6}$-alkoxy, C$_{1-9}$ heteroaryloxy-C$_{1-6}$-alkoxy, C$_{1-9}$ heteroaryl-C$_{1-6}$-alkylamino, C$_{2-10}$ heterocyclyl-C$_{1-6}$-alkoxy, C$_{2-10}$ heterocyclyl-C$_{1-6}$-alkylamino, C$_{3-10}$ cycloalkylamino, C$_{2-10}$ heterocyclyl-C$_{1-6}$-alkoxy, C$_{3-10}$ carbocyclyl-C$_{1-6}$-alkoxy, C$_{3-10}$ carbocyclyl-C$_{1-6}$-alkylamino, C$_{6-10}$ aryloxy, C$_{1-10}$ heteroaryloxy, C$_{2-10}$ heterocyclyl, C$_{3-10}$ cycloalkyl, C$_{2-10}$ heterocyclyl-C$_{1-6}$-aliphatic, C$_{3-10}$ cycloalkyl-C$_{1-6}$-aliphatic, C$_{6-10}$ aryl, C$_{1-9}$ heteroaryl, C$_{6-10}$ aryl-C$_{2-6}$-aliphatic, C$_{1-9}$ heteroaryl-C$_{1-6}$-aliphatic, C$_{6-10}$ aryl-(CH$_2$)$_p$-G-(CH$_2$)$_m$—, C$_{1-9}$ heteroaryl-(CH$_2$)$_p$-G-(CH$_2$)$_m$—, C$_{2-10}$ heterocyclyl-(CH$_2$)$_p$-G-(CH$_2$)$_m$—, or C$_{3-10}$ cycloalkyl-(CH$_2$)$_p$-G-(CH$_2$)$_m$—, wherein each G is O, S, NR$^5$, S(═O), S(═O)$_2$, C(═O), —C(═O) NH—, —OC(═O)NH—, —OC(═O)—, —NHC(═O) NH—, —HN—S(═O)$_t$—, —OS(═O)$_t$—, or —OS (═O)$_t$NH—; each t is 1 or 2; each p and m is independently 0, 1, 2, 3 or 4;

each R$^5$ is independently H, R$^7$R$^{7a}$NC(═O)—, R$^7$OC (═O)—, R$^7$C(═O)—, R$^7$R$^{7a}$NS(═O)—, R$^7$OS(═O)—, R$^7$S(═O)—, R$^7$R$^{7a}$NS(═O)$_2$—, R$^7$OS(═O)$_2$—, R$^7$ S(═O)$_2$—, C$_{1-3}$ alkyl, C$_{1-3}$ haloalkyl, C$_{1-3}$ hydroxyalkyl, C$_{1-3}$ aminoalkyl, C$_{1-3}$ alkoxy-C$_{1-3}$-alkyl, C$_{1-3}$ alkylamino-C$_{1-3}$-alkyl, C$_{1-3}$ alkylthio-C$_{1-3}$-alkyl, C$_{6-10}$ aryl-C$_{1-3}$-alkyl, C$_{1-9}$ heteroaryl-C$_{1-3}$-alkyl, C$_{2-10}$ heterocyclyl-C$_{1-3}$-alkyl, C$_{3-10}$ cycloalkyl-C$_{1-3}$-alkyl, C$_{6-10}$ aryl, C$_{1-9}$ heteroaryl, C$_{2-10}$ heterocyclyl or C$_{3-10}$ carbocyclyl; and each R$^7$ and R$^{7a}$ is independently H, C$_{1-6}$ aliphatic, C$_{1-6}$ haloaliphatic, C$_{1-6}$ hydroxyaliphatic, C$_{1-6}$ aminoaliphatic, C$_{1-6}$ alkoxy-C$_{1-6}$-aliphatic, C$_{1-6}$ alkylamino-C$_{1-6}$-aliphatic, C$_{1-6}$ alkylthio-C$_{1-6}$-aliphatic, C$_{6-10}$ aryl-C$_{1-6}$-aliphatic, C$_{1-9}$ heteroaryl-C$_{1-6}$-aliphatic, C$_{2-10}$ heterocyclyl-C$_{1-6}$-aliphatic, C$_{3-10}$ cycloalkyl-C$_{1-6}$-aliphatic, C$_{6-10}$ aryl, C$_{1-9}$ heteroaryl, C$_{2-10}$ heterocyclyl or C$_{3-10}$ carbocyclyl; with the proviso that where R$^7$ and R$^{7a}$ are bonded to the same nitrogen atom, R$^7$ and R$^{7a}$, together with the nitrogen atom they are attached to, optionally form a substituted or unsubstituted 3-8 membered ring.

In some embodiments, A, X and B define a group having Formula (II) is:

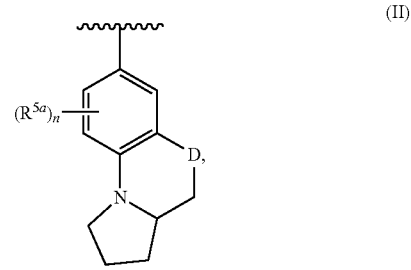

(II)

wherein D is O; n is 0, 1 or 2; and each R$^{5a}$ is independently H, hydroxy, amino, F, Cl, Br, I, R$^{7a}$R$^7$N—, —C(═O)NR$^7$R$^{7a}$, —OC(═O)NR$^7$R$^{7a}$, —OC (═O)OR$^7$, —N(R$^7$)C(═O)NR$^7$R$^{7a}$, —N(R$^7$)C(═O)OR$^{7a}$, —N(R$^7$)C(═O)—R$^{7a}$, R$^7$R$^{7a}$N—S(═O)$_2$—, R$^7$S(═O)$_2$—, R$^7$S(═O)$_2$N(R$^{7a}$)—, cyano, nitro, mercapto, C$_{1-4}$ alkyl, C$_{1-4}$ alkoxy, C$_{1-4}$ alkylamino, C$_{1-4}$ alkylthio, C$_{6-10}$ aryl, or C$_{1-9}$ heteroaryl.

In some embodiments, Formula (IV) is

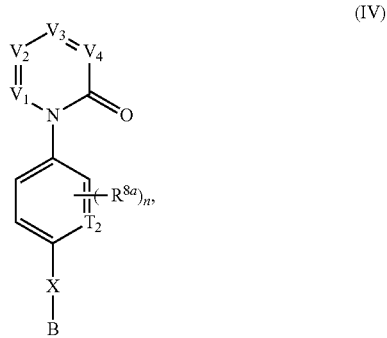

(IV)

wherein V$_1$ is N or CR$^1$, V$_2$ is N or CR$^2$, V$_3$ is N or CR$^3$, and V$_4$ is N or CR$^4$, wherein at most one of the V$_1$, V$_2$, V$_3$ and V$_4$ is N;

T$_2$ is N or CR$^{10}$;

X is a bond, NR$^5$, O, S, —(CH$_2$)$_m$—, —(CH$_2$)$_m$—Y—, —C(═O)—, —C(═O)NH—, —CH═CH—, or —C≡C—, wherein each m is independently 0, 1, 2 or 3;

B is —NR$^7$R$^{7a}$, C$_{4-12}$ carbocyclyl, C$_{4-12}$ cycloalkyl, C$_{2-10}$ heterocyclyl, C$_{6-10}$ aryl, C$_{1-9}$ heteroaryl, C$_{5-12}$ fused bicyclyl, C$_{5-12}$ fused heterobicyclyl, C$_{5-12}$ spiro bicyclyl, or C$_{5-12}$ spiro heterobicyclyl; wherein each of the C$_{4-12}$ carbocyclyl, C$_{4-12}$ cycloalkyl, C$_{2-10}$ heterocyclyl, C$_{6-10}$ aryl, C$_{1-9}$ heteroaryl, C$_{5-12}$ fused bicyclyl, C$_{5-12}$ fused heterobicyclyl, C$_{5-12}$ spiro bicyclyl and C$_{5-12}$ spiro heterobicyclyl is optionally substituted by oxo (═O), hydroxy, amino, halo, cyano, C$_{6-10}$ aryl, C$_{1-9}$ heteroaryl, C$_{1-6}$ alkoxy, C$_{1-6}$ alkylamino, C$_{1-6}$ alkyl, C$_{2-6}$ alkenyl, C$_{2-6}$ alkynyl, C$_{2-10}$ heterocyclyl, mercapto, nitro, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy $C_{1-6}$ alkoxy;

$R^1$ is H, F, Cl, Br, I, cyano, hydroxy, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{5a}$, —N($R^7$)C(=O)—$R^{7a}$, $R^7R^{7a}N$—S(=O)$_2$—, $R^7S$(=O)$_2$—, $R^7S$(=O)$_2N(R^{7a})$—, $C_{1-6}$ aliphatic, $C_{1-6}$ haloalkyl, $C_{1-6}$ alkoxy, $C_{1-6}$ hydroxyalkoxy, $C_{1-6}$ amino alkoxy, $C_{1-6}$ halo alkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{1-6}$-aliphatic, $C_{1-9}$ heteroaryl-$C_{1-6}$-aliphatic, $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, or $C_{3-10}$ cycloalkyl-(CH$_2$)$_p$-G-(CH$_2$)$_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4; or wherein each of the $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, and $C_{3-10}$ cycloalkyl-(CH$_2$)$_p$-G-(CH$_2$)$_m$— is optionally substituted by one or more F, Cl, Br, I, methyl, ethyl, propyl, ethynyl, propynyl, butyryl, methoxy, ethoxy or cyano;

$R^2$ is H, F, Cl, Br, I, cyano, hydroxy, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{5a}$, —N($R^7$)C(=O)—$R^{7a}$, $R^7R^{7a}N$—S(=O)$_2$—, $R^7S$(=O)$_2$—, $R^7S$(=O)$_2N(R^{7a})$—, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-4}$ heteroaryl, $C_{6-10}$ aryl-$C_{1-6}$-aliphatic, $C_{1-9}$ heteroaryl-$C_{1-6}$-aliphatic, $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, or $C_{3-10}$ cycloalkyl-(CH$_2$)$_p$-G-(CH$_2$)$_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4;

$R^3$ is H, F, Cl, I, cyano, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2N(R^{7a})$—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{1-6}$ aliphatic, $C_{2-6}$ haloalkyl, $C_{6-10}$ aryl-$C_{2-6}$-alkoxy, $C_{1-9}$ heteroaryl-$C_{3-6}$-alkoxy, $C_{1-9}$ heteroaryloxy-$C_{1-6}$-alkoxy, $C_{3-10}$ cycloalkyl-$C_{2-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{1-4}$ heteroaryl, substituted $C_{6-10}$ aryl, $C_{1-4}$ heteroaryl-$C_{1-6}$-aliphatic, substituted $C_{6-10}$ aryl-$C_{3-6}$-alkyl, $C_{2-10}$ heterocyclyl-$C_{1-6}$-alkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-haloalkoxy, $C_{1-6}$ alkylamino-$C_{1-6}$-alkoxy, $C_{1-6}$ alkoxy-$C_{1-6}$-alkoxy, $C_{6-10}$ aryl-$C_{2-10}$-alkoxy, $C_{2-10}$ heterocyclyl-$C_{1-6}$-alkoxy, $C_{3-10}$ carbocyclyl-$C_{1-6}$-alkoxy, $C_{2-10}$ heterocyclyloxy, $C_{3-10}$ cycloalkyloxy, $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, or $C_{3-10}$ cycloalkyl-(CH$_2$)$_p$-G-(CH$_2$)$_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4;

$R^4$ is H, F, I, cyano, hydroxy, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2N(R^{7a})$—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{1-6}$ aliphatic, $C_{1-6}$ haloalkyl, $C_{2-10}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-5}$ cycloalkyloxy, $C_{6-10}$ aryl-$C_{1-6}$-alkoxy, $C_{1-9}$ heteroaryl-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{3-10}$ cycloalkylamino, $C_{2-10}$ heterocyclyl-$C_{1-6}$-alkoxy, $C_{3-10}$ carbocyclyl-$C_{1-6}$-alkoxy, $C_{3-10}$ carbocyclyl-$C_{1-6}$-alkylamino, $C_{6-10}$ aryloxy, $C_{1-10}$ heteroaryloxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{2-6}$-aliphatic, $C_{1-9}$ heteroaryl-$C_{1-6}$-aliphatic, $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, or $C_{3-10}$ cycloalkyl-(CH$_2$)$_p$-G-(CH$_2$)$_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4;

each $R^5$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl-$C_{1-3}$-alkyl, $C_{2-10}$ heterocyclyl-$C_{1-3}$-alkyl, $C_{3-10}$ cycloalkyl-$C_{1-3}$-alkyl, $C_{6-10}$ aryl, $C_{1-9}$ heteroaryl, $C_{2-10}$ heterocyclyl or $C_{3-10}$ carbocyclyl;

each $R^7$ and $R^{7a}$ is independently H, $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring;

each $R^{8a}$ is independently H, hydroxy, amino, F, Cl, Br, I, —N(CH$_3$)$_2$, —C(=O)NH—$C_{1-4}$ alkyl, —OC(=O)NH—$C_{1-4}$ alkyl, —OC(=O)O—$C_{1-4}$ alkyl, —NHC(=O)NH—$C_{1-4}$ alkyl, —NHC(=O)O—$C_{1-4}$ alkyl, —NHC(=O)—$C_{1-4}$ alkyl, $C_{1-4}$ alkyl-NH—S(=O)$_2$—, $C_{1-4}$ alkyl-S(=O)$_2$—, $C_{1-4}$ alkyl-S(=O)$_2$NH—, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl;
n is 0, 1, 2 or 3; and
each $R^{10}$ is independently H, hydroxy, amino, F, Cl, Br, I, cyano, nitro, mercapto, $C_{1-4}$ alkyl, trifluoromethyl, $C_{1-4}$ alkoxy, $C_{1-4}$ alkylamino, or $C_{1-4}$ alkylthio.
In some embodiments, B is —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$,
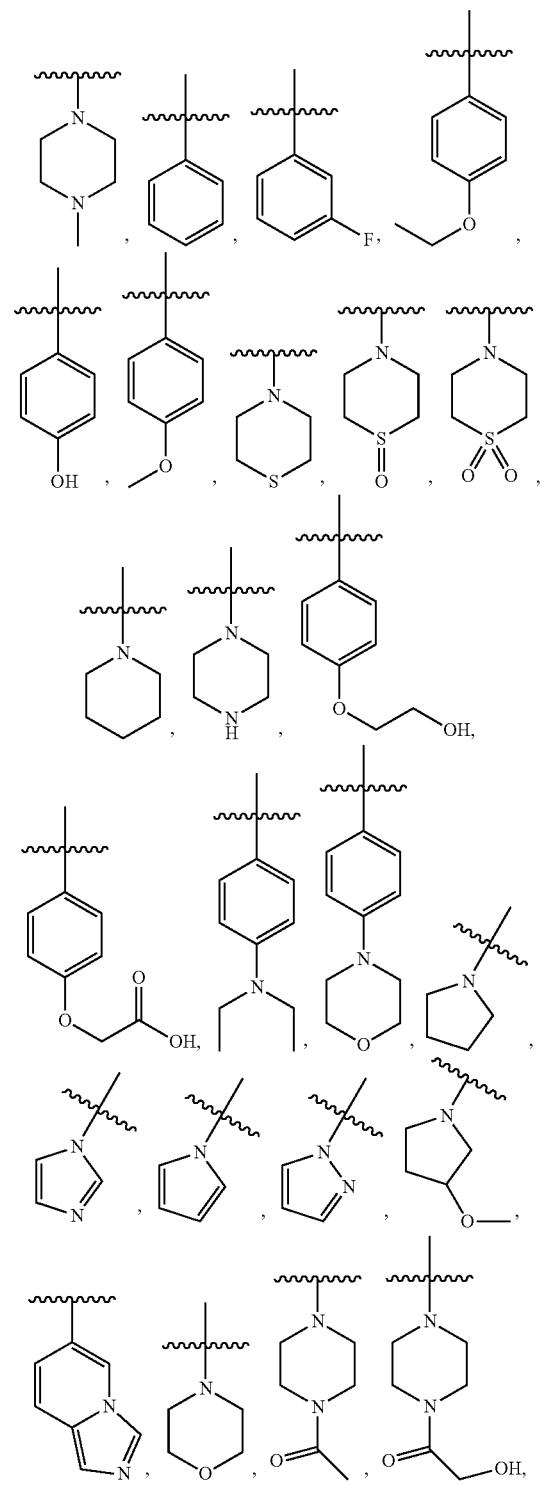
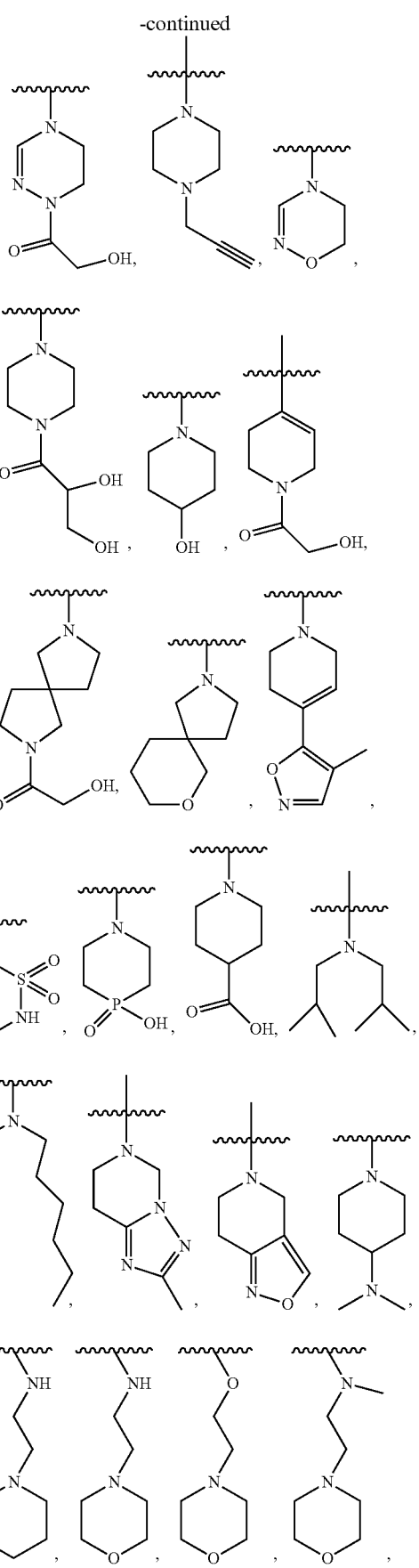

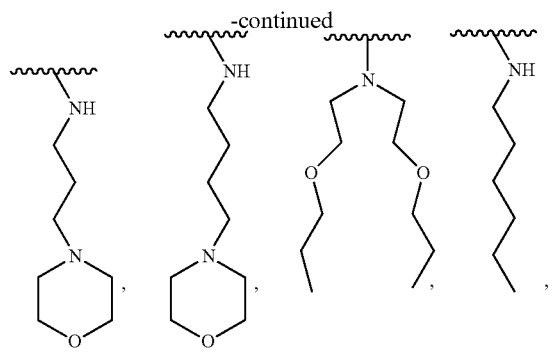
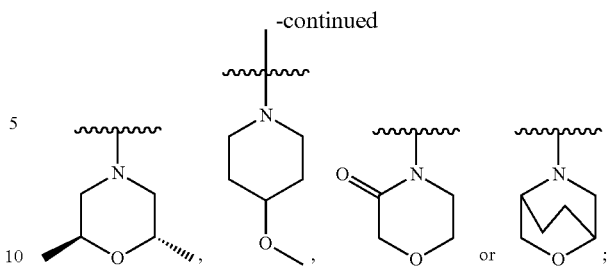

R[1] is H, F, Cl, Br, I, cyano, hydroxy, —N(CH$_3$)$_2$, —C(═O)NH—C$_{1-4}$ alkyl, —OC(═O)NH—C$_{1-4}$ alkyl, —OC(═O)O—C$_{1-4}$ alkyl, —NHC(═O)NH—C$_{1-4}$ alkyl, —NHC(═O)O—C$_{1-4}$ alkyl, —NHC(═O)—C$_{1-4}$ alkyl, C$_{1-4}$ alkyl-NH—S(═O)$_2$—, C$_{1-4}$ alkyl-S(═O)$_2$—, C$_{1-4}$ alkyl-S(═O)$_2$NH—, methyl, ethyl, propyl, isopropyl, butyl, ter-butyl, trifluoromethyl, phenyl-(CH$_2$)$_p$-G-(CH$_2$)$_m$—, (fluoro-substituted phenyl)-(CH$_2$)$_p$-G-(CH$_2$)$_m$—, thiazolyl-(CH$_2$)$_p$-G-(CH$_2$)$_m$—, pyridyl-(CH$_2$)$_p$-G-(CH$_2$)$_m$—, phenylethyl, cyclohexyl-(CH$_2$)$_p$-G-(CH$_2$)$_m$—, naphthyl-(CH$_2$)$_p$-G-(CH$_2$)$_m$—, or morpholinyl-(CH$_2$)$_p$-G-(CH$_2$)$_m$—, wherein each G is O, S, NR$^5$, S(═O), S(═O)$_2$, C(═O), —C(═O)NH—, —OC(═O)NH—, —OC(═O)—, —NHC(═O)NH—, —HN—S(═O)$_t$—, —OS(═O)$_t$—, or —OS(═O)$_t$NH—; each t is 1 or 2; each p and m is independently 0, 1, 2, 3 or 4; or wherein each of the phenyl-(CH$_2$)$_p$-G-(CH$_2$)$_m$—, (fluoro-substituted phenyl)-(CH$_2$)$_p$-G-(CH$_2$)$_m$—, thiazolyl-(CH$_2$)$_p$-G-(CH$_2$)$_m$—, pyridyl-(CH$_2$)$_p$-G-(CH$_2$)$_m$—, phenylethyl, cyclohexyl-(CH$_2$)$_p$-G-(CH$_2$)$_m$—, naphthyl-(CH$_2$)$_p$-G-(CH$_2$)$_m$—, and morpholinyl-(CH$_2$)$_p$-G-(CH$_2$)$_m$— is optionally substituted by one or more F, Cl, Br, I, methyl, ethyl, propyl, ethynyl, propynyl, butyryl, methoxy, ethoxy or cyano;

R[2] is H, F, Cl, Br, I, cyano, hydroxy, —N(CH$_3$)$_2$, —C(═O)NH—C$_{1-4}$ alkyl, —OC(═O)NH—C$_{1-4}$ alkyl, —OC(═O)O—C$_{1-4}$ alkyl, —NHC(═O)NH—C$_{1-4}$ alkyl, —NHC(═O)O—C$_{1-4}$ alkyl, —NHC(═O)—C$_{1-4}$ alkyl, C$_{1-4}$ alkyl-NH—S(═O)$_2$—, C$_{1-4}$ alkyl-S(═O)$_2$—, C$_{1-4}$ alkyl-S(═O)$_2$NH—, methyl, ethyl, propyl, isopropyl, butyl, ter-butyl, trifluoromethyl, phenyl-(CH$_2$)$_p$-G-(CH$_2$)$_m$—, (fluoro-substituted phenyl)-(CH$_2$)$_p$-G-(CH$_2$)$_m$—, thiazolyl-(CH$_2$)$_p$-G-(CH$_2$)$_m$—, or morpholinyl-(CH$_2$)$_p$-G-(CH$_2$)$_m$—, wherein each G is O, S, NR$^5$, S(═O), S(═O)$_2$, C(═O), —C(═O)NH—, —OC(═O)NH—, —OC(═O)—, —NHC(═O)NH—, —HN—S(═O)$_t$—, —OS(═O)$_t$—, or —OS(═O)$_t$NH—; each t is 1 or 2; each p and m is independently 0, 1, 2, 3 or 4;

R[3] is H, F, Cl, I, cyano, hydroxy, —N(CH$_3$)$_2$, —C(═O)NH—C$_{1-4}$ alkyl, —OC(═O)NH—C$_{1-4}$ alkyl, —OC(═O)O—C$_{1-4}$ alkyl, —NHC(═O)NH—C$_{1-4}$ alkyl, —NHC(═O)O—C$_{1-4}$ alkyl, —NHC(═O)—C$_{1-4}$ alkyl, C$_{1-4}$ alkyl-NH—S(═O)$_2$—, C$_{1-4}$ alkyl-S(═O)$_2$—, C$_{1-4}$ alkyl-S(═O)$_2$NH—, methyl, ethyl, propyl, isopropyl, butyl, ter-butyl, phenyl-(CH$_2$)$_p$-G-(CH$_2$)$_m$—, (fluoro-substituted phenyl)-(CH$_2$)$_p$-G-(CH$_2$)$_m$—, thiazolyl-(CH$_2$)$_p$-G-(CH$_2$)$_m$—, or morpholinyl-(CH$_2$)$_p$-G-(CH$_2$)$_m$—, wherein each G is O, S, NR$^5$, S(═O), S(═O)$_2$, C(═O), —C(═O)NH—, —OC(═O)NH—, —OC(═O)—, —NHC(═O)NH—, —HN—S(═O)$_t$—, —OS(═O)$_t$—, or —OS(═O)$_t$NH—; each t is 1 or 2; each p and m is independently 0, 1, 2, 3 or 4;

R[4] is H, F, I, cyano, hydroxy, —N(CH$_3$)$_2$, —C(═O)NH—C$_{1-4}$ alkyl, —OC(═O)NH—C$_{1-4}$ alkyl, —OC(═O)O—C$_{1-4}$ alkyl, —NHC(═O)NH—C$_{1-4}$ alkyl, —NHC(═O)O—C$_{1-4}$ alkyl, —NHC(═O)—C$_{1-4}$ alkyl, C$_{1-4}$ alkyl-NH—S(═O)$_2$—, C$_{1-4}$ alkyl-S(═O)$_2$—, C$_{1-4}$ alkyl-S(═O)$_2$NH—, methyl, ethyl, propyl, isopropyl, butyl, ter-butyl, trifluoromethyl, phenyl-(CH$_2$)$_p$-G-(CH$_2$)$_m$—, (fluoro-substituted phenyl)-(CH₂)ₚ-G-(CH₂)ₘ—, thiazolyl-(CH₂)ₚ-G-(CH₂)ₘ—, or morpholinyl-(CH₂)ₚ-G-(CH₂)ₘ—, wherein each G is O, S, NR⁵, S(=O), S(=O)₂, C(=O), —C(=O)NH—, —OC(=O)NH—, —OC(=O)—, —NHC(=O)NH—, —HN—S(=O)ₜ—, —OS(=O)ₜ—, or —OS(=O)ₜNH—; each t is 1 or 2; each p and m is independently 0, 1, 2, 3 or 4;

each $R^5$ is independently H, $C_{1-3}$ alkyl, phenyl, benzyl, pyridyl or morpholino methyl;

each $R^{8a}$ is independently H, hydroxy, amino, F, Cl, Br, I, —N(CH₃)₂, —C(=O)NH—$C_{1-4}$ alkyl, —OC(=O)NH—$C_{1-4}$ alkyl, —OC(=O)O—$C_{1-4}$ alkyl, —NHC(=O)NH—$C_{1-4}$ alkyl, —NHC(=O)O—$C_{1-4}$ alkyl, —NHC(=O)—$C_{1-4}$ alkyl, $C_{1-4}$ alkyl-NH—S(=O)₂—, $C_{1-4}$ alkyl-S(=O)₂—, $C_{1-4}$ alkyl-S(=O)₂NH—, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl;

n is 0, 1, 2, or 3; and each $R^{10}$ is independently H, hydroxy, amino, F, Cl, Br, I, cyano, nitro, mercapto, $C_{1-4}$ alkyl, trifluoromethyl, $C_{1-4}$ alkoxy, $C_{1-4}$ alkylamino, or $C_{1-4}$ alkylthio.

In some embodiments, Formula (V) is

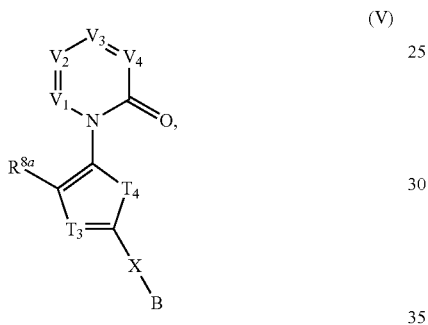

(V)

wherein $V_1$ is N or $CR^1$, $V_2$ is N or $CR^2$, $V_3$ is N or $CR^3$, and $V_4$ is N or $CR^4$, wherein at most one of the $V_1$, $V_2$, $V_3$ and $V_4$ is N;

$T_3$ is N or $CR^{10}$;

$T_4$ is $NR^5$, O, S or $CR^{11}R^{11a}$;

X is a bond, NR⁵, O, S, —(CH₂)ₘ—, —(CH₂)ₘ—Y—, —C(=O)—, —C(=O)NH—, —CH=CH—, or —C≡C—, wherein each m is independently 0, 1, 2 or 3;

B is —N(CH₃)₂, —N(CH₂CH₃)₂, —N(CH₂CH₂CH₃)₂, —N(CH₂CH₂CH₂CH₃)₂,

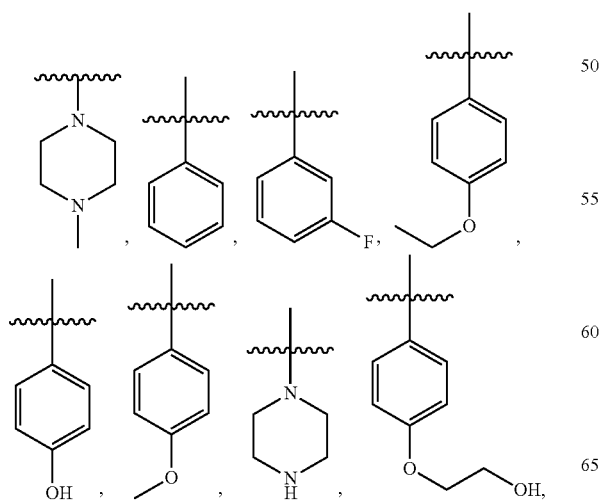

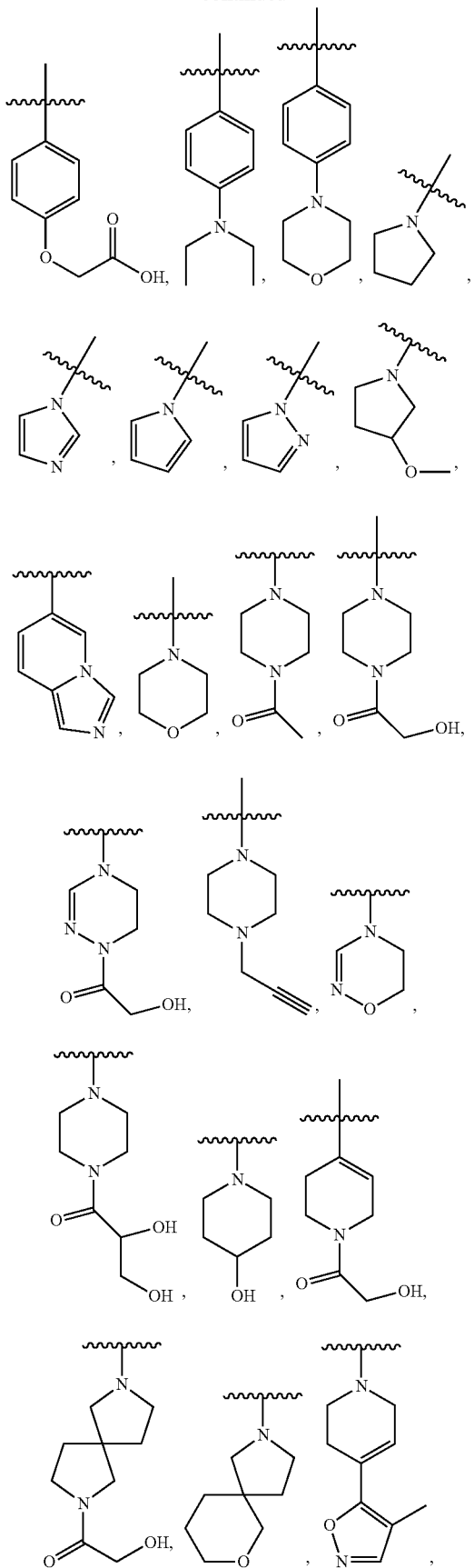

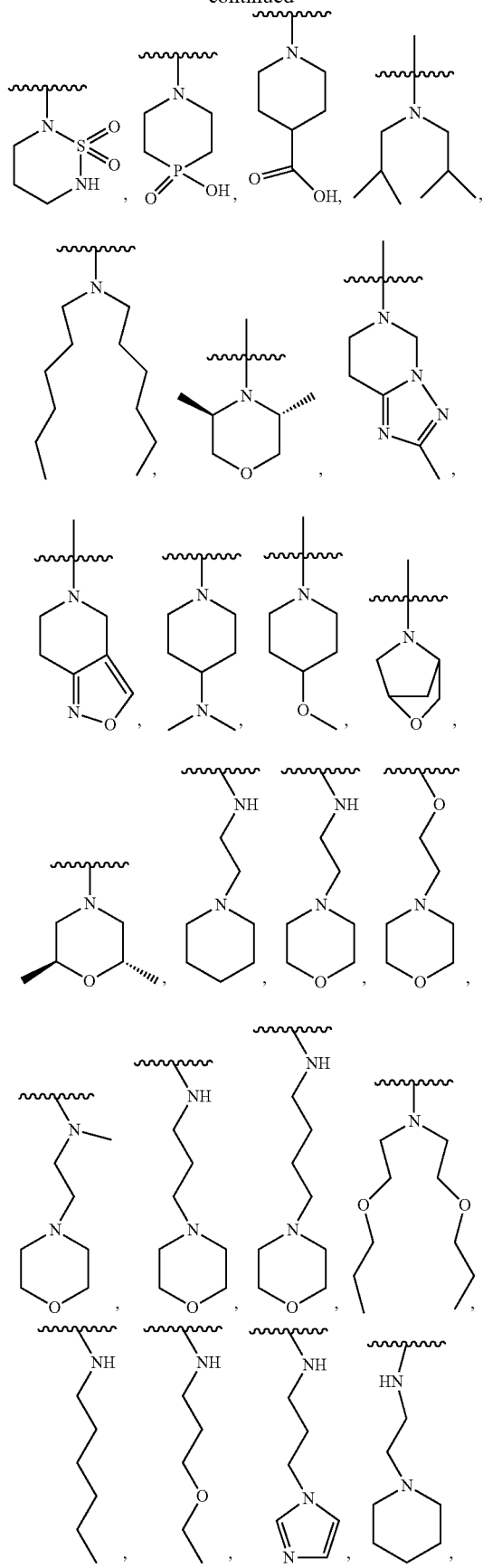

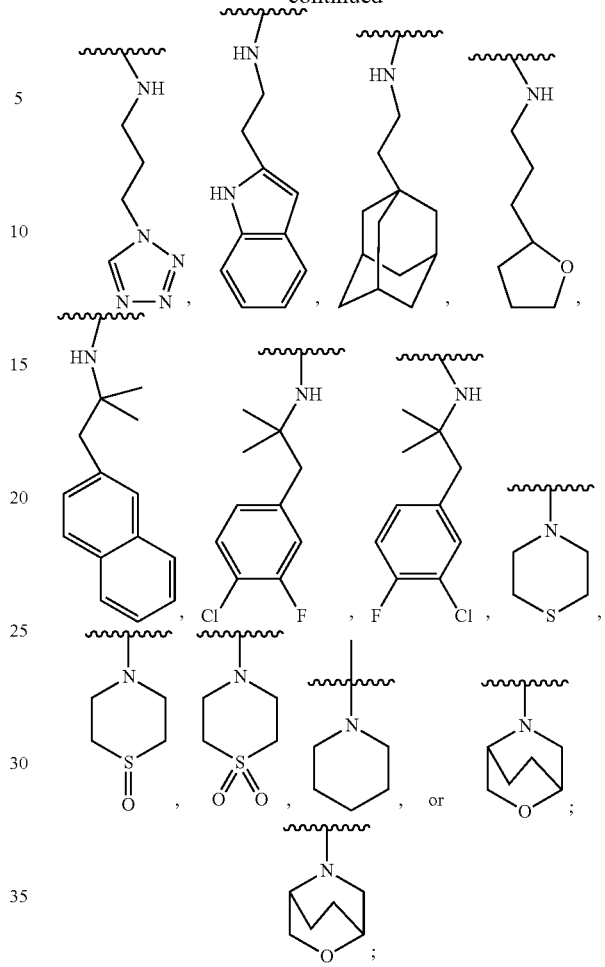

R[1] is H, F, Cl, Br, I, cyano, hydroxy, —N(CH$_3$)$_2$, —C(=O)NH—C$_{1-4}$ alkyl, —OC(=O)NH—C$_{1-4}$ alkyl, —OC(=O)O—C$_{1-4}$ alkyl, —NHC(=O)NH—C$_{1-4}$ alkyl, —NHC(=O)O—C$_{1-4}$ alkyl, —NHC(=O)—C$_{1-4}$ alkyl, C$_{1-4}$ alkyl-NH—S(=O)$_2$—, C$_{1-4}$ alkyl-S(=O)$_2$—, C$_{1-4}$ alkyl-S(=O)$_2$NH—, methyl, ethyl, propyl, isopropyl, butyl, ter-butyl, trifluoromethyl, or C$_{6-10}$ aryl-(CH$_2$)$_p$-G-(CH$_2$)$_m$—, wherein G is O, S, NR$^5$, S(=O), S(=O)$_2$, or C(=O); each p and m is independently 0, 1, 2 or 3; or wherein C$_{6-10}$ aryl-(CH$_2$)$_p$-G-(CH$_2$)$_m$— is optionally substituted by one or more F, Cl, Br, I, methyl, ethyl, propyl, ethynyl, propynyl, butyryl, methoxy, ethoxy or cyano;

R[2] is H, F, Cl, Br, I, cyano, hydroxy, —N(CH$_3$)$_2$, —C(=O)NH—C$_{1-4}$ alkyl, —OC(=O)NH—C$_{1-4}$ alkyl, —OC(=O)O—C$_{1-4}$ alkyl, —NHC(=O)NH—C$_{1-4}$ alkyl, —NHC(=O)O—C$_{1-4}$ alkyl, —NHC(=O)—C$_{1-4}$ alkyl, C$_{1-4}$ alkyl-NH—S(=O)$_2$—, C$_{1-4}$ alkyl-S(=O)$_2$—, C$_{1-4}$ alkyl-S(=O)$_2$NH—, methyl, ethyl, propyl, isopropyl, butyl, ter-butyl, trifluoromethyl, or C$_{6-10}$ aryl-(CH$_2$)$_p$-G-(CH$_2$)$_m$—, wherein G is O, S, NR$^5$, S(=O), S(=O)$_2$, or C(=O); each p and m is independently 0, 1, 2 or 3;

R[3] is H, F, Cl, I, cyano, hydroxy, —N(CH$_3$)$_2$, —C(=O)NH—C$_{1-4}$ alkyl, —OC(=O)NH—C$_{1-4}$ alkyl, —OC(=O)O—C$_{1-4}$ alkyl, —NHC(=O)NH—C$_{1-4}$ alkyl, —NHC(=O)O—C$_{1-4}$ alkyl, —NHC(=O)—C$_{1-4}$ alkyl, C$_{1-4}$ alkyl-NH—S(=O)$_2$—, C$_{1-4}$ alkyl-S(=O)$_2$—, C$_{1-4}$ alkyl-S(=O)$_2$NH—, methyl, ethyl, propyl, isopropyl, butyl, ter-butyl, or C$_{6-10}$ aryl-$(CH_2)_p$-G-$(CH_2)_m$—, wherein G is O, S, $NR^5$, S(=O), S(=O)$_2$, or C(=O); each p and m is independently 0, 1, 2 or 3;

$R^4$ is H, F, I, cyano, hydroxy, —$N(CH_3)_2$, —C(=O)NH—$C_{1-4}$ alkyl, —OC(=O)NH—$C_{1-4}$ alkyl, —OC(=O)O—$C_{1-4}$ alkyl, —NHC(=O)NH—$C_{1-4}$ alkyl, —NHC(=O)O—$C_{1-4}$ alkyl, —NHC(=O)—$C_{1-4}$ alkyl, $C_{1-4}$ alkyl-NH—S(=O)$_2$—, $C_{1-4}$ alkyl-S(=O)$_2$—, $C_{1-4}$ alkyl-S(=O)$_2$NH—, methyl, ethyl, propyl, isopropyl, butyl, ter-butyl, trifluoromethyl, or $C_{6-10}$ aryl-$(CH_2)_p$-G-$(CH_2)_m$—, wherein G is O, S, $NR^5$, S(=O), S(=O)$_2$, or C(=O); each p and m is independently 0, 1, 2 or 3;

each $R^5$ is independently H, $C_{1-4}$ alkyl, phenyl, benzyl, pyridyl or morpholino methyl; and each $R^{8a}$, $R^{10}$, $R^{11}$, and $R^{11a}$ is independently H, hydroxy, amino, F, Cl, Br, I, —$N(CH_3)_2$, —C(=O)NH—$C_{1-4}$ alkyl, —OC(=O)NH—$C_{1-4}$ alkyl, —OC(=O)O—$C_{1-4}$ alkyl, —NHC(=O)NH—$C_{1-4}$ alkyl, —NHC(=O)O—$C_{1-4}$ alkyl, —NHC(=O)—$C_{1-4}$ alkyl, $C_{1-4}$ alkyl-NH—S(=O)$_2$—, $C_{1-4}$ alkyl-S(=O)$_2$—, $C_{1-4}$ alkyl-S(=O)$_2$NH—, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl.

In some embodiments, Formula (VI) is

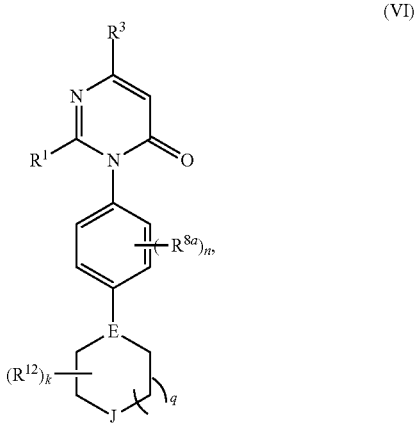

(VI)

wherein E is N or $CR^{10}$;
J is O, S, S(=O), S(=O)$_2$, $NR^{13}$ or $CR^{14}R^{14a}$;
k is 0, 1, 2, 3 or 4;
q is 0, 1 or 2;
$R^1$ is H, F, Cl, Br, I, cyano, hydroxy, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$C_{1-6}$ alkyl, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O)NH—, —OC(=O)— or —NHC(=O)NH—; each p and m is independently 0, 1, 2 or 3; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, $C_{6-10}$ aryl-$C_{1-6}$ alkyl, and $C_{3-10}$ cycloalkyl-$(CH_2)_p$-G-$(CH_2)_m$— is optionally substituted by one or more F, Cl, Br, I, methyl, ethyl, propyl, ethynyl, propynyl, butyryl, methoxy, ethoxy, or cyano;

$R^3$ is H, F, Cl, I, cyano, hydroxy, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O) NH—, —OC(=O)— or —NHC(=O)NH—; each p and m is independently 0, 1, 2 or 3;

each $R^5$ is independently H, $R^7R^{7a}NC(=O)$—, $R^7OC(=O)$—, $R^7C(=O)$—, $C_{1-3}$ alkyl, $C_{1-3}$ haloalkyl, $C_{1-3}$ hydroxyalkyl, $C_{1-3}$ amino alkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl-$C_{1-3}$-alkyl, $C_{2-10}$ heterocyclyl-$C_{1-3}$-alkyl, $C_{3-10}$ cycloalkyl-$C_{1-3}$-alkyl, $C_{6-10}$ aryl, $C_{1-9}$ heteroaryl, $C_{2-10}$ heterocyclyl or $C_{3-10}$ carbocyclyl;

each $R^{8a}$ is independently H, hydroxy, amino, F, Cl, Br, I, —$N(CH_3)_2$, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl;

n is 0, 1, 2 or 3;

each $R^{10}$ is independently H, hydroxy, amino, F, Cl, Br, I, cyano, nitro, mercapto, $C_{1-4}$ alkyl, trifluoromethyl, $C_{1-4}$ alkoxy, $C_{1-4}$ alkylamino, or $C_{1-4}$ alkylthio;

each $R^{12}$ is oxo (=O), hydroxy, amino, halo, cyano, $C_{1-10}$ alkoxy, $C_{1-10}$ alkylamino, $C_{1-10}$ alkylthio, $C_{1-10}$ alkyl, $C_{2-10}$ alkenyl, $C_{2-10}$ alkynyl, mercapto, nitro, $C_{6-10}$ aryl, $C_{1-9}$ heteroaryl, $C_{2-10}$ heterocyclyl, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy $C_{1-6}$ alkoxy;

$R^{13}$ is H, $C_{1-4}$ alkyl, $C_{2-4}$ alkynyl, $C_{1-4}$ alkoxy, hydroxy-substituted $C_{1-4}$ alkoxy, $C_{1-4}$ carboxyalkoxy, $C_{1-4}$ alkylcarbonyl or hydroxy-substituted $C_{1-4}$ alkylcarbony; and each $R^{14}$ and $R^{14a}$ is independently H, hydroxy, carboxy, $C_{1-4}$ alkyl, $C_{1-4}$ alkoxy or $C_{1-4}$ alkylamino.

In some embodiments, $R^1$ is independently H, F, Cl, Br, I, cyano, hydroxy, methyl, ethyl, propyl, isopropyl, butyl, ter-butyl, $C_{6-8}$ aryl-$(CH_2)_p$-G-$(CH_2)_m$— or $C_{4-6}$ heteroaryl-$(CH_2)_p$-G-$(CH_2)_m$—, wherein each G is $NR^5$, O or S, each p and m is independently 0, 1, 2 or 3; or wherein each of the $C_{6-8}$ aryl-$(CH_2)_p$-G-$(CH_2)_m$— and $C_{4-6}$ heteroaryl-$(CH_2)_p$-G-$(CH_2)_m$— is optionally substituted by one or more F, Cl, Br, methyl, ethyl, propyl, ethynyl, propynyl, butyryl, methoxy, or cyano; and $R^3$ is independently H, F, Cl, I, cyano, hydroxy, methyl, ethyl, propyl, isopropyl, butyl, ter-butyl, $C_{6-8}$ aryl-$(CH_2)_p$-G-$(CH_2)_m$— or $C_{4-6}$ heteroaryl-$(CH_2)_p$-G-$(CH_2)_m$—, wherein each G is O or S, each p and m is independently 0, 1, 2 or 3.

In some embodiments, Formula (VII) is

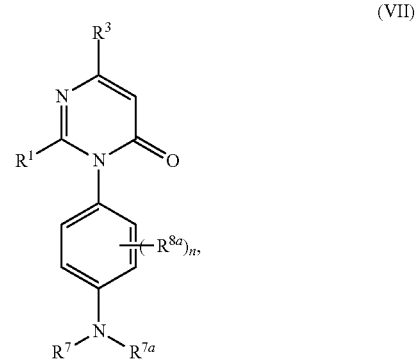

(VII)

wherein $R^1$ is H, F, Cl, Br, I, cyano, hydroxy, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O)NH—, —OC(=O)— or —NHC(=O)NH—; each p and m is independently 0, 1, 2 or 3; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-$(CH_2)_m$— is optionally substituted by one or more F, Cl, Br, I, methyl, ethyl, propyl, cyano, ethynyl, methoxy, ethoxy, or propynyl;

$R^3$ is H, F, Cl, I, cyano, hydroxy, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O)NH—, —OC(=O)— or —NHC(=O)NH—; each p and m is independently 0, 1, 2 or 3;

each $R^5$ is independently H, $R^7R^{7a}NC(=O)$—, $R^7OC(=O)$—, $R^7C(=O)$—, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl-$C_{1-3}$-alkyl, $C_{2-10}$ heterocyclyl-$C_{1-3}$-alkyl, $C_{3-10}$ cycloalkyl-$C_{1-3}$-alkyl, $C_{6-10}$ aryl, $C_{1-9}$ heteroaryl, $C_{2-10}$ heterocyclyl or $C_{3-10}$ carbocyclyl;

each $R^7$ is independently H, $C_{1-6}$ alkyl, $C_{1-6}$ haloaliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{10}$ heteroaryl, $C_{2-10}$ heterocyclyl or $C_{3-10}$ carbocyclyl;

each $R^{7a}$ is independently $C_{1-6}$ alkyl, $C_{1-6}$ haloaliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring;

each $R^{8a}$ is independently H, hydroxy, amino, F, Cl, Br, I, —$N(CH_3)_2$, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl; and n is 0, 1, 2 or 3.

In some embodiments, each $R^7$ is independently H, $C_{1-6}$ alkyl, $C_{1-4}$ alkoxy-$C_{1-6}$-alkyl,

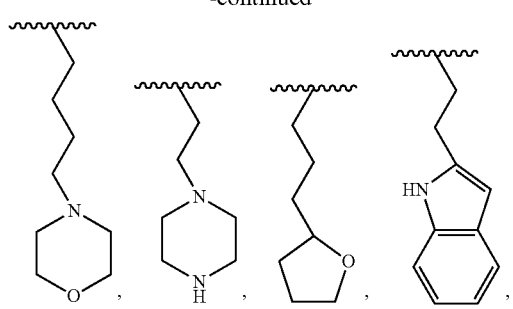

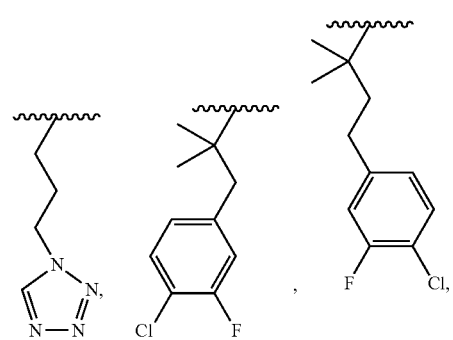

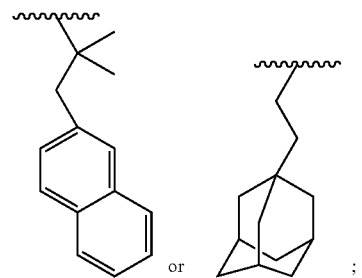

each $R^{7a}$ is independently $C_{1-6}$ alkyl, $C_{1-4}$ alkoxy-$C_{1-6}$-alkyl,

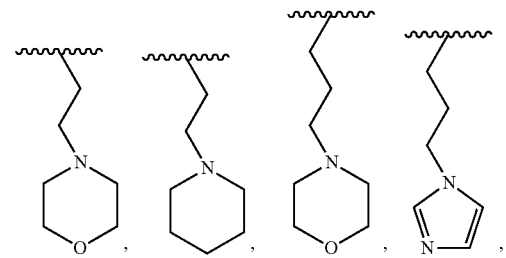

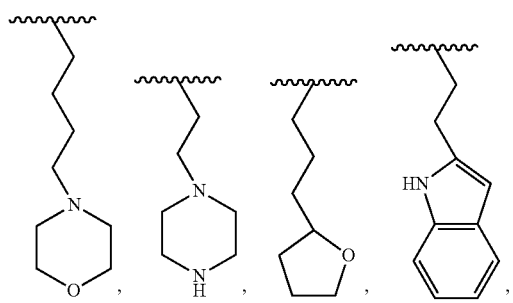

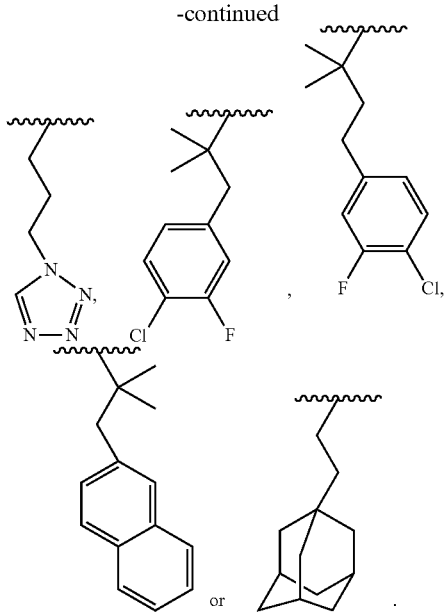

In one aspect, provided herein are pharmaceutical compositions comprising a compound disclosed herein, or a stereoisomer, geometric isomer, tautomer, nitrogen oxide, hydrate, solvate, metabolite, pharmaceutically acceptable salt or prodrug thereof; and an optionally pharmaceutically acceptable carrier, excipient, diluent, adjuvant, vehicle or a combination thereof.

In another aspect, provided herein are methods for protecting, managing, treating or lessening the severity of tissue or organ fibrotic diseases in a patient, which comprises administering a pharmaceutically effective amount of the pharmaceutical composition disclosed herein to the patient.

In one aspect, provided herein are methods for protecting, managing, treating or lessening the severity of tissue or organ fibrotic diseases in a patient, which comprises administering a pharmaceutically effective amount of the compound disclosed herein to the patient.

In another aspect, provided herein is use of the compound disclosed herein in the manufacture of a medicament for preventing, managing, treating or lessening the severity of a tissue or organ fibrotic disease in a patient.

In one aspect, provided herein is use of the pharmaceutical composition disclosed herein in the manufacture of a medicament for preventing, managing, treating or lessening the severity of a tissue or organ fibrotic disease in a patient.

In another aspect, provided herein is use of the compound or pharmaceutical composition disclosed herein for preventing, managing, treating or lessening the severity of a tissue or organ fibrotic disease in human or animal, which comprises administering a pharmaceutically effective amount of the (a) compound or pharmaceutical composition disclosed herein to the patient.

In some embodiments, the tissue or organ fibrosis disorder is renal interstitial fibrosis, glomerulosclerosis, liver fibrosis, pulmonary fibrosis, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis. In other embodiments, post-surgery adhesions is the scar healing.

In another aspect, provided herein include methods of preparing, methods of separating, and methods of purifying compounds of Formula (I), (IV), (V), (VI) or (VII).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and *the Handbook of Chemistry and Physics*, 75$^{th}$ Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, Inc., New York: 2007, all of which are incorporated herein by reference in their entireties.

As described herein, compounds may optionally be substituted with one or more substituents, such as those illustrated above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure may be substituted with more than one substituent selected from a specified group, the substituent may be either the same or different at each position. Wherein the substituents include, but are not limited to, hydroxy, amino, halo, cyano, aryl, heteroaryl, alkoxy, alkylamino, alkylthio, alkyl, haloalkyl, alkenly, alkynyl, heterocyclyl, thiol, nitro, aryloxy, heteroaryloxy, oxo (O═), carboxy, hydroxy-substituted alkoxy, hydroxy-substituted alkyl-C(═O)—, alkyl-C (═O)—, alkyl-S(═O)—, alkyl-S(═O)$_2$—, hydroxy-substituted alkyl-S(═O)—, hydroxy-substituted alkyl-S(═O)$_2$—, carboxyalkoxy, and the like.

The term "aliphatic" or "aliphatic group" refers to a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms. In yet other embodiments, aliphatic groups contain 1-4 carbon atoms and in yet other embodiments, aliphatic groups contain 1-3 carbon atoms. Suitable aliphatic groups include, but are not limited to, linear or branched, substituted or unsubstituted alkyl, alkenyl, or alkynyl groups, such as methyl, ethyl, propyl, isopropyl, butyl, tert-butyl, hexyl, isobutyl, sec-butyl, ethenyl, and the like.

The term "haloaliphatic" refers to an aliphatic group substituted by one or more of the same or different halogen atoms, wherein the aliphatic group is as defined herein, halogen atoms refer to F, Cl, Br or I. Some non-limiting examples include trifluoromethyl, trifluoroethyl, chloromethyl, 2-chloroethylene, and the like.

The term "hydroxyaliphatic" refers to an aliphatic group substituted by one or more hydroxy groups, wherein the aliphatic group is as defined herein. Some non-limiting examples include hydroxyethyl, 2-hydroxypropyl, hydroxymethyl, and the like.

The term "aminoaliphatic" refers to an aliphatic group substituted by one or more amino groups, wherein the aliphatic group is as defined herein. Some non-limiting examples include aminomethyl, 2-aminoethyl, 2-aminoisopropyl, and the like.

The term "alkyl" refers to a saturated linear or branched-chain monovalent hydrocarbon radical of 1-20 carbon atoms, 1-10 carbon atoms, 1-6 carbon atoms, 1-4 carbon atoms, or 1-3 carbon atoms, wherein the alkyl radical may be optionally substituted independently with one or more substituents described below. Further examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like. The terms "alkyl" and the prefix "alk-" are inclusive of both straight chain and branched saturated carbon chain. The term "alkylene", as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkylene" refers to alkyl system having two connection points connected to the rest of the molecule, wherein alkyl radical is as defined herein.

The term "alkenyl" refers to a linear or branched-chain monovalent hydrocarbon radical of 2-12 carbon atoms, 2-8 carbon atoms, 2-6 carbon atoms, or 2-4 carbon atoms, with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Some non-limiting examples include ethenyl or vinyl (—CH═$CH_2$), allyl (—$CH_2$CH═$CH_2$), and the like.

The term "alkenylene" refers to alkenyl system having two connection points connected to the rest of the molecule, wherein alkenyl radical is as defined herein.

The term "alkynyl" refers to a linear or branched-chain monovalent hydrocarbon radical of 2-12 carbon atoms, 2-8 carbon atoms, 2-6 carbon atoms, or 2-4 carbon atoms, with at least one site of unsaturation, i.e., a carbon-carbon, sp triple bond, wherein the alkynyl radical may be optionally substituted independently with one or more substituents described herein. Some non-limiting examples include ethynyl (—C≡CH), 2-propynyl (—$CH_2$C≡CH), and the like.

The term "alkynylene" refers to alkynyl system having two connection points connected to the rest of the molecule, wherein alkynyl radical is as defined herein.

The term "hydroxy-substituted alkyl" refers to an alkyl group substituted with one or more hydroxy groups, wherein the alkyl group is as defined herein. Some non-limiting examples include hydroxymethyl, hydroxyethyl, 1,2-dihydroxyethyl, and the like.

The term "carboxy-substituted alkyl" refers to an alkyl group substituted with one or more carboxy groups, wherein the alkyl group is as defined herein. Some non-limiting examples include carboxymethyl, carboxyethyl, and the like.

The term "cycloaliphatic", "carbocycle", "carbocyclyl" or "cycloalkyl" refers to a monovalent or multivalent, non-aromatic, saturated or partially unsaturated ring, and not containing heteroatoms, having 3 to 12 carbon atoms as a monocyclic ring or 7 to 12 carbon atoms as a bicyclic ring or a tricyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system. Some non-limiting examples of cycloaliphatic groups include cycloalkyl, cycloalkenyl, and cycloalkynyl. Further examples of cycloaliphatic groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantyl, and the like. And "cycloaliphatic", "carbocycle", "carbocyclyl", or "cycloalkyl" may be substituted or unsubstituted, wherein the substituent may be, but is not limited to, hydroxy, amino, halo, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted —C(═O)—, alkyl-C(═O)—, alkyl-S(═O)—, alkyl-S(═O)$_2$—, hydroxy-substituted alkyl-S(═O)—, hydroxy-substituted alkyl-S(═O)$_2$—, carboxyalkoxy, and the like.

The term "carbocyclylene" refers to carbocyclyl system having two connection points connected to the rest of the molecule, wherein carbocyclyl radical is as defined herein.

The term "carbocyclyl (hydroxyalkoxy)" refers to a hydroxyalkoxy group substituted with one or more carbocyclyl groups, wherein the carbocyclyl group and hydroxyalkoxy group are as defined herein. Some non-limiting examples include cyclopropyl hydroxymethyl, cyclopropyl hydroxyethyl, cyclopropyl hydroxypropyl, cyclohexyl hydroxypropyl, cyclohexyl hydroxymethyl, and the like.

The term "cycloalkyloxy" or "carbocyclyloxy" refers to an optionally substituted cycloalkyl radical or carbocyclyl radical, as defined hererin, attached to an oxygen atom, which is connected to the rest of the molecule. Some non-limiting examples include cyclopropyloxy, cyclopentyloxy, cyclohexyloxy, hydroxy-substituted cyclopropyloxy, and the like.

The term "cycloalkylamino" refers to an amino group substituted with one or two cycloalkyl groups, wherein the cycloalkyl group is as defined herein. Some non-limiting examples include cyclopropylamino, cyclopentylamino, cyclohexylamino, hydroxy-substituted cyclopropylamino, dicyclohexylamino, dicyclopropylamino, and the like.

The term "carbocyclyloxyalkoxy" refers to an alkoxy group substituted with one or more carbocyclyloxy groups, wherein the alkoxy group and carbocyclyloxy group are as defined herein. Some non-limiting examples include cyclopropyloxymethoxy, cyclopropyloxyethoxy, cyclopentyloxyethoxy, cyclohexyloxyethoxy, cyclohexenyl-3-oxyethoxy, and the like.

The term "cycloalkyloxyaliphatic" refers to an aliphatic group substituted with one or more cycloalkyloxy groups, wherein the aliphatic group and cycloalkyloxy group are as defined herein. Some non-limiting examples include cyclopropyloxymethyl, cyclopropyloxyethyl, cyclopentyloxymethyl, cyclopentyloxyethyl, cyclohexyloxyethyl, halocyclopropyloxyethyl, and the like.

The term "cycloalkylaminoaliphatic" refers to an aliphatic group substituted with one or more cycloalkylamino groups, wherein the aliphatic group and cycloalkylamino group are as defined herein. Some non-limiting examples include cyclopropylaminomethyl, cyclopropylaminoethyl, cyclopentylaminomethyl, cyclopentylaminoethyl, cyclohexylaminoethyl, halocyclopropylaminoethyl, and the like.

The term "cycloalkylaliphatic" or "carbocyclylaliphatic" refers to an aliphatic group substituted with one or more cycloalkyl groups or carbocyclyl groups, wherein the carbocyclyl group, cycloalkyl group and aliphatic group are as defined herein. Some non-limiting examples include cyclopropylmethyl, cyclopropylethyl, cyclopropylpropyl, cyclopentylmethyl, cyclohexylethyl, and the like.

The term "cycloalkylalkoxy" ("carbocyclylalkoxy") refers to an alkoxy group substituted with one or more cycloalkyl groups or carbocyclyl groups, wherein the carbocyclyl group, cycloalkyl group and alkoxy group are as defined herein. Some non-limiting examples include cyclopropylmethoxy, cyclopropylethoxy, cyclopentylethoxy, cyclohexylethoxy, cyclohexylmethoxy, cyclopropylpropoxy, and the like.

The term "cycloalkylalkylamino" ("carbocyclylalkylamino") refers to an alkylamino group substituted with one or more cycloalkyl groups or carbocyclyl groups, wherein the carbocyclyl group, cycloalkyl group and alkylamino group are as defined herein. Some non-limiting examples include cyclopropylmethylamino, cyclopropylethylamino, cyclopentylethylamino, cyclohexylethylamino, cyclohexylmethylamino, cyclopropylpropylamino, and the like.

The term "heterocycle", "heterocyclyl", "heterocycloaliphatic", or "heterocyclic" as used interchangeably herein refers to a monocyclic, bicyclic, or tricyclic ring system in which one or more ring members are an independently selected heteroatom and that is completely saturated or that contains one or more units of unsaturation, but not aromatic having a single point of attachment to the rest of the molecule. One or more ring atoms are optionally substituted independently with one or more substituents described herein. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or $SO_2$, PO or $PO_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or $SO_2$, PO or $PO_2$).

The heterocyclyl may be a carbon radical or heteroatom radical. "Heterocyclyl" also includes radicals where heterocycle radicals are fused with a saturated, partially unsaturated ring, or heterocyclic ring. Some non-limiting examples of heterocyclic rings include pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, piperidinyl, homopiperidinyl, epoxypropyl, azepanyl, oxepanyl, thiepanyl, 4-methoxy-piperidin-1-yl, 1,2,3,6-tetrahydropyridin-1-yl, oxazepinyl, diazepinyl, thiazepinyl, pyrrolin-1-yl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydrothienyl, pyrazolidinylimidazolinyl, imidazolidinyl, 1,2,3,4-tetrahydroisoquinolinyl, 1,2,6-thiadiazane-1-1-dioxo-2-yl, 4-hydroxy-1,4-azaphosphine-4-oxid-1-yl, 2-hydroxy-1-(piperazin-1-yl)ethanon-4-yl, 2-hydroxy-1-(5,6-dihydro-1,2,4-triazin-1(4H)-yl)ethanon-4-yl, 5,6-dihydro-4H-1,2,4-oxadiazin-4-yl, 2-hydroxy-1-(5,6-dihydropyridin-1(2H)-yl)ethanon-4-yl, 3-azabicyco[3.1.0]hexanyl, 3-azabicyclo[4.1.0]heptanyl, azabicyclo[2.2.2]hexanyl, 2-methyl-5,6,7,8-tetrahydro-[1,2,4]triazolo[1,5-c]pyrimidin-6-yl, 4,5,6,7-tetrahydroisoxazol[4,3-c]pyridin-5-yl, 3H-indolyl-2-oxo-5-azabicyclo[2.2.1]heptan-5-yl, 2-oxo-5-azabicyclo[2.2.2]octan-5-yl, quinolizinyl and N-pyridyl urea. Some non-limiting examples of a heterocyclic ring include 1,1-dioxo-thiomorpholinyl and heterocyclic group wherein 2 carbon atoms on the ring are substituted with oxo (=O) moieties are pyrimidindionyl. The heterocyclic group herein may be substituted or unsubstituted, wherein the substituent may be, but is not limited to, oxo (=O), hydroxy, amino, halo, cyano, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "heterocyclylene" refers to heterocyclyl system having two connection points connected to the rest of the molecule, wherein heterocyclyl radical is as defined herein.

The term "heterocyclylalkyl" refers to heterocyclic-substituted alkyl radical. The term "heterocyclylalkoxy" refers to heterocyclic-substituted alkoxy radical wherein oxygen atom serves as the attaching point to the rest of the molecule. The term "heterocyclylalkylamino" refers to heterocyclic-substituted alkylamino radical wherein nitrogen atom serves as the attaching point to the rest of the molecule. Some non-limiting examples of heterocyclyl, alkyl, alkoxy and alkylamino include pyrrol-2-ylmethyl, morpholin-4-ylethyl, morpholin-4-ylethoxy, piperazin-4-ylethoxy, piperidin-4-ylethylamino, and the like.

The term "heterocyclylaliphatic" refers to heterocyclic-substituted aliphatic group, wherein the heterocyclic radical and aliphatic group are as defined herein. Some non-limiting examples include pyrrol-2-ylmethyl, piperidin-2-ylethyl, piperazin-2-ylethyl, piperidin-2-ylmethyl, and the like.

The term "heterocyclyloxy" refers to optionally substituted heterocyclyl radical, as defined herein, connected to an oxygen atom, and the oxygen atom serves as the attaching point to the rest of the molecule. Some non-limiting examples include pyrrol-2-yloxy, pyrrol-3-yloxy, piperidin-2-yloxy, piperidin-3-yloxy, piperazin-2-yloxy, piperidin-4-yloxy, and the like.

The term "heterocyclylamino" refers to an amino group substituted with one or two heterocyclyl groups, wherein the heterocyclyl group is as defined herein. Some non-limiting examples include pyrrol-2-ylamino, pyrrol-3-ylamino, piperidin-2-ylamino, piperidin-3-ylamino, piperidin-4-ylamino, piperazin-2-ylamino, dipyrrol-2-ylamino, and the like.

The term "heterocyclyloxyalkoxy" refers to an alkoxy radical substituted with one or more heterocyclyloxy groups, wherein the alkoxy radical and heterocyclyloxy group are as defined herein. Some non-limiting examples include pyrrol-2-yloxymethoxy, pyrrol-3-yloxyethoxy, piperidin-2-yloxyethoxy, piperidin-3-yloxyethoxy, piperazin-2-yloxyethoxy, piperidin-4-yloxyethoxy, and the like.

The term "heterocyclyloxyaliphatic" refers to an aliphatic group substituted with one or more heterocyclyloxy groups, wherein the aliphatic group and heterocyclyloxy group are as defined herein. Some non-limiting examples include pyrrol-2-yloxymethyl, piperazin-3-yloxyethyl, piperazin-2-yloxyethyl, morpholin-2-yloxymethyl, piperidin-2-yloxyethyl, and the like.

The term "heterocyclylaminoaliphatic" refers to an aliphatic group substituted with one or more heterocyclylamino groups, wherein the aliphatic group and heterocyclylamino group are as defined herein. Some non-limiting examples include pyrrol-2-ylaminomethyl, piperazin-3-lyamino ethyl, piperazin-2-lyamino ethyl, piperidin-2-lyaminoethyl, morpholin-2-lyaminomethyl, and the like.

The term "heterocyclyl(hydroxyalkoxy)" refers to a hydroxyalkoxy group substituted with one or more heterocyclyl groups, wherein the heterocyclyl group and hydroxyalkoxy group are as defined herein. Some non-limiting examples include pyrrol-2-ylhydroxymethoxy and morpholin-4-ylhydroxymethoxy.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to F, Cl, Br or I.

The term "unsaturated" refers to a moiety having one or more units of unsaturation.

The term "alkoxy" refers to an alkyl group, as previously defined, attached to the principal carbon chain through an oxygen ("alkoxy") atom. Some non-limiting examples include methoxy, ethoxy, propoxy, butoxy, and the like. And the alkoxy defined above may be substituted or unsubstituted, wherein the substituent may be, but is not limited to, hydroxy, amino, halo, cyano, alkoxy, alkyl, alkenyl, alkynyl, thiol, nitro, and the like.

The term "hydroxy-substituted alkoxy" or "hydroxyalkoxy" refers to an alkoxy group substituted with one or more hydroxy groups, wherein the alkoxy group is as defined above. Some non-limiting examples include hydroxymethoxy, 2-hydroxyethoxy, 2-hydroxypropoxy, 2-hydroxyisopropoxy, and the like.

The term "aminoalkoxy" refers to an alkoxy group substituted with one or more amino groups, wherein the alkoxy group is as defined above. Some non-limiting examples include aminomethoxy, 2-aminoethoxy, 2-aminopropoxy, 2-aminoisopropoxy, and the like.

The term "hydroxy-substituted aminoalkoxy" refers to an aminoalkoxy group substituted with one or more hydroxy groups, wherein the aminoalkoxy group is as defined above. Some non-limiting examples include hydroxyaminomethoxy, 2-hydroxy-2-aminoethoxy, and the like.

The term "azidoalkoxy" refers to an alkoxy group substituted with one or more azido groups, wherein the alkoxy group is as defined above. Some non-limiting examples include 2-azidoethoxy, 3-azidopropoxy, 2-azidopropoxy, and the like.

The term "alkoxyalkoxy" refers to an alkoxy group substituted with one or more alkoxy groups, wherein the alkoxy group is as defined above. Some non-limiting examples include methoxymethoxy, methoxyethoxy, ethoxymethoxy, ethoxyethoxy, ethoxypropoxy, and the like.

The term "alkoxyaliphatic" refers to an aliphatic group substituted with one or more alkoxy groups, wherein the aliphatic group and alkoxy group are as defined herein. Some non-limiting examples include methoxymethyl, ethoxymethyl, ethoxyethyl, ethoxypropenyl, and the like.

The term "alkylaminoaliphatic" refers to an aliphatic group substituted with one or more alkylamino groups, wherein the aliphatic group and alkylamino group are as defined herein. Some non-limiting examples include dimethylaminoethyl, methylaminoethyl, diethylaminomethyl, diethylaminoethyl, and the like.

The term "alkylthioaliphatic" refers to an aliphatic group substituted with one or more alkylthio groups, wherein the aliphatic group and alkylthio group are as defined herein. Some non-limiting examples include methylthioethyl, methylthiopropyl, ethylthioethyl, methylthiopropenyl, and the like.

The term "haloalkyl", "haloalkenyl" or "haloalkoxy" refers to an alkyl group, alkenyl group or alkoxy group substituted with one or more halogen atoms. Some non-limiting examples include trifluoromethyl, 2-chloro-ethenyl, trifluoromethoxy, and the like.

The term "amino-substituted haloalkoxy" refers to a haloalkoxy group substituted with one or more amino groups, wherein the haloalkoxy is as defined herein. Some non-limiting examples include 3-amino-2-chloropropoxy, and the like.

The term "alkylaminoalkoxy" refers to an alkoxy group substituted with one or more alkylamino groups, wherein the alkoxy group and alkylamino group are as defined herein. Some non-limiting examples include 3-methylamino-2-propoxy, and the like.

The term "alkylaminohaloalkoxy" refers to a haloalkoxy group substituted with one or more alkylamino groups, wherein the haloalkoxy group and alkylamino group are as defined herein. Some non-limiting examples include 3-methylamino-2-chloropropoxy, and the like.

The term "hydroxy-substituted haloalkoxy" refers to a haloalkoxy group substituted with one or more hydroxy groups, wherein the haloalkoxy is as defined herein. Some non-limiting examples include 3-hydroxy-2-fluoropropoxy, hydroxymethyl trifluoromethoxy, and the like.

The term "aryl" used alone or as part of a larger moiety as in "aralkyl", "arylalkoxy" or "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl, and anthracene. And the aryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "fluorophenyl" or "fluoro-substituted phenyl" refers to a phenyl group substituted with one or more fluorine atoms.

The term "arylene" refers to aryl system having two connection points connected to the rest of the molecule, wherein aryl radical is as defined herein.

The term "arylaliphatic" refers to an aliphatic group substituted with one or more aryl groups, wherein the aliphatic group and the aryl group are as defined herein. Some non-limiting examples include phenylethyl, phenylmethyl, (p-tolyl)ethyl, styryl, and the like.

The term "aryloxy" refers to optionally substituted aryl radicals, as defined herein, attached to an oxygen atom, wherein the oxygen atom serves as the attaching point to the rest of the molecule. Wherein the aryl radical is as defined herein. Some non-limiting examples include phenyloxy, methylphenyloxy, ethylphenyloxy, and the like.

The term "arylamino" refers to an amino group substituted with one or two aryl groups, wherein the aryl group is as defined herein. Some non-limiting examples include phenylamino, (p-fluorophenyl)amino, diphenylamino, ditolylamino, (di-p-tolyl)amino, and the like.

The term "aryloxyalkoxy" refers to an alkoxy group substituted with one or more aryloxy groups, wherein the alkoxy group and the aryloxy group are as defined herein. Such examples include phenyloxymethoxy, phenyloxyethoxy, phenyloxypropoxy, and the like.

The term "heteroaryloxyalkoxy" refers to an alkoxy group substituted with one or more heteroaryloxy groups, wherein the alkoxy group and the heteroaryloxy group are as defined herein. Some non-limiting examples include pyridyloxymethoxy, pyrimidinyloxyethoxy, thiazoloxypropoxy, and the like.

The term "aryloxyaliphatic" refers to an aliphatic group substituted with one or more aryloxy groups, wherein the aryloxy group and the aliphatic group are as defined herein. Some non-limiting examples include phenyloxymethyl, phenyloxyethyl, phenyloxypropyl, and the like.

The term "heteroaryloxyaliphatic" refers to an aliphatic group may be substituted with one or more heteroaryloxy groups, wherein the heteroaryloxy group and the aliphatic group are as defined herein. Some non-limiting examples include furanyloxymethyl, pyrimidinyloxyethyl, and the like.

The term "arylaminoaliphatic" refers to an aliphatic group substituted with one or more arylamino groups, wherein the arylamino group and the aliphatic group are as defined herein. Some non-limiting examples include phenylaminomethyl, phenylaminoethyl, tolylaminoethyl, phenylaminopropyl, phenylaminoallyl, and the like.

The term "aryl(hydroxyalkoxy)" refers to a hydroxyalkoxy group substituted with one or more aryl groups, wherein the aryl group and the hydroxyalkoxy group are as defined herein. Some non-limiting examples include phenylhydroxymethyl, phenylhydroxyethyl, (p-tolyl)hydroxyethyl, and the like.

The term "arylalkoxy" refers to an alkoxy group substituted with one or more aryl groups, wherein the aryl group and the alkoxy group are as defined herein. Some non-limiting examples include phenylmethoxy, phenylethoxy, (p-tolyl)methoxy, phenylpropoxy, and the like. The aryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C (=O)—, alkyl-C(=O)—, alkyl-S(=O)—, alkyl-S (=O)$_2$—, hydroxy-substituted alkyl-S(=O)—, hydroxy-substituted alkyl-S(=O)$_2$—, carboxyalkoxy, and the like.

The term "arylalkylamino" refers to an alkylamino group substituted with one or more aryl groups, wherein the aryl group and the alkylamino group are as defined herein. Some non-limiting examples include phenylmethylamino, phenylethylamino, phenylpropylamino, (p-tolyl)methylamino, and the like.

The term "heteroaryl" used alone or as part of a larger moiety as in "heteroaralkyl" or "heteroarylalkoxy" refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic". And the heteroaryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C (=O)—, alkyl-C(=O), alkyl-S(=O)—, alkyl-S(=O)$_2$—, hydroxy-substituted alkyl-S(=O)—, hydroxy-substituted alkyl-S(=O)$_2$—, carboxyalkoxy, and the like.

Some non-limiting examples of suitable heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazol-5-yl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, 2-pyrazinyl, 1,3,5-triazinyl, benzo[d]thiazol-2-yl, imidazo[1, 5-a]pyridyl and the following bicycles include: benzimidazolyl, benzofuryl, benzothiophenyl, benzothiazolyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl).

The term "heteroarylene" refers to heteroaryl system having two connection points connected to the rest of the molecule, wherein heteroaryl radical is as defined herein.

The term "heteroaryloxy" refers to optionally substituted aryl radicals, as defined herein, attached to an oxygen atom, wherein the oxygen atom serves as the attaching point to the rest of the molecule. Some non-limiting examples include pyrid-2-yloxy, thiazol-2-yloxy, imidazol-2-yloxy, pyrimidin-2-yloxy, and the like.

The term "heteroaryloxyaliphatic" refers to an aliphatic group substituted with one or more heteroaryloxy groups, wherein the aliphatic group and the heteroaryloxy group are as defined herein. Some non-limiting examples include pyrid-2-yloxyethyl, thiazol-2-yloxymethyl, imidazol-2-yloxyethyl, pyrimidin-2-yloxypropyl, and the like. The term "sulfonyl", whether used alone or linked to other terms such as alkylsulfonyl, refers to respectively divalent radicals —SO$_2$—. The term "alkylsulfonyl", refers to a sulfonyl radical substituted with an alkyl radical, forming an alkylsulfonyl (—SO$_2$CH$_3$).

The term "sulfamyl", "aminosulfonyl" or "sulfonamidyl" refers to a sulfonyl radical substituted with an amine radical, forming a sulfonamide (—SO$_2$NH$_2$).

The term "carboxy" or "carboxyl", whether used alone or with other terms, such as "carboxyalkyl", refers to —CO$_2$H. The term "carbonyl", whether used alone or with other terms, such as "aminocarbonyl" or "carbonyloxy", refers to —(C=O)—.

The term "carboxyalkoxy" refers to an alkoxy group substituted with one or more carboxy groups, wherein the alkoxy group and the carboxy group are as defined herein. Some non-limiting examples include carboxymethoxy, carboxyethoxy, and the like.

The term "alkylcarbonyl" refers to optionally substituted alkyl connected to a carbonyl radical, and the carbonyl radical connected to the rest of the molecule, wherein alkyl is as defined above. Some non-limiting examples include methylcarbonyl, ethylcarbonyl, and the like.

The term "hydroxyalkylcarbonyl" refers to hydroxy-substituted alkyl connected to a carbonyl radical, and the carbonyl radical connected to the rest of the molecule, wherein alkyl is as defined above. Some non-limiting examples include hydroxymethylcarbonyl, 1,2-dihydroxyethylcarbonyl, and the like.

The term "aralkyl" or "arylalkyl" refers to aryl-substituted alkyl radicals. In some embodiments, aralkyl radicals are "lower aralkyl" radicals having aryl radicals attached to alkyl radicals having one to six carbon atoms. In other embodiments, aralkyl radicals are "phenylalkylenyl" attached to alkyl portions having one to three carbon atoms. Some non-limiting examples of such radicals include benzyl, diphenylmethyl and phenylethyl. The aryl in said aralkyl can be additionally substituted with halo, alkyl, alkoxy, haloalkyl or haloalkoxy.

The term "alkylthio" refers to radicals containing a linear or branched alkyl radical, of one to ten carbon atoms, attached to a divalent sulfur atom. In other embodiments, alkylthio radicals are lower alkylthio radicals having one to three carbon atoms. Some non-limiting examples of "alkylthio" include methylthio (CH$_3$S—).

The term "haloalkylthio" refers to radicals containing a haloalkyl radical, of one to ten carbon atoms, attached to a divalent sulfur atom. In other embodiments, haloalkylthio radicals are lower haloalkylthio radicals having one to three carbon atoms. Some non-limiting examples of "haloalkylthio" include trifluoromethylthio.

The term "alkylamino" refers to "N-alkylamino" and "N,N-dialkylamino" where amino groups are independently substituted with one alkyl radical or with two alkyl radicals, respectively. In other embodiments, alkylamino radicals are "lower alkylamino" radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals include mono or dialkylamino such as N-methylamino, N-ethylamino, N,N-dimethylamino, N,N-diethylamino, and the like.

The term "alkylaminohaloalkoxy" refers to a haloalkoxy group substituted with one or more alkylamino groups, wherein the haloalkoxy group and the alkylamino group are as defined herein. Some non-limiting examples include methylaminodifluoromethoxy, ethylaminotrifluoromethoxy, and the like.

The term "heteroarylamino" refers to amino groups substituted with one or two heteroaryl radicals, wherein the heteroaryl radical is as defined herein. Some non-limiting examples of heteroarylamino include N-thienylamino, and the like. In other embodiments, the "heteroarylamino" radicals include substituted on the heteroaryl ring portion of the radical.

The term "heteroarylaliphatic" refers to aliphatic groups substituted with one or more heteroaryl radicals, wherein the heteroaryl radical and the aliphatic group are as defined herein. Some non-limiting examples of heteroarylaliphatic include thiophen-2-ylpropenyl, pyridin-4-ylethyl, imidazol-2-methyl, furan-2-ethyl, indole-3-methyl, and the like.

The term "heteroarylalkyl" refers to alkyl groups substituted with one or more heteroaryl radicals, wherein the heteroaryl radical and the alkyl group are as defined herein. Some non-limiting examples of heteroarylalkyl include imidazol-2-methyl, furan-2-ethyl, indole-3-methyl, and the like.

The term "heteroarylalkylamino" refers to nitrogen-containing heteroarylalkyl radicals attached through a nitrogen atom to other radicals, wherein the heteroarylalkyl radicals is as defined herein. Some non-limiting examples of heteroarylalkylamino include pyridin-2-methylamino, thiazol-2-ethylamino, imidazol-2-ethylamino, pyrimidin-2-propylamino, pyrimidin-2-methylamino, and the like.

The term "aminoalkyl" refers to a linear or branched alkyl radical having one to ten carbon atoms, substituted with one or more amino radicals. In some embodiments, aminoalkyl radicals are "lower aminoalkyl" radicals having one to six carbon atoms and one or more amino radicals. Some non-limiting examples of such radicals include aminomethyl, aminoethyl, aminopropyl, aminobutyl or aminohexyl.

The term "alkylaminoalkyl" refers to alkyl radicals substituted with alkylamino radicals. In some embodiments, alkylaminoalkyl radicals are "lower alkylaminoalkyl" radicals having alkyl radicals of one to six carbon atoms. In other embodiments, alkylaminoalkyl radicals are lower alkylaminoalkyl radicals having alkyl radicals of one to three carbon atoms. Some non-limiting examples of suitable alkylaminoalkyl radicals include mono or dialkyl substituted, such as N-methylaminomethyl, N,N-dimethyl-aminoethyl, N,N-diethylaminomethyl, and the like.

The term "alkylaminoalkoxy" refers to alkoxy radicals substituted with alkylamino radicals. Some non-limiting examples of suitable alkylaminoalkoxy radicals include mono or dialkyl substituted, such as N-methylaminoethoxy, N,N-dimethylaminoethoxy, N,N-diethylaminoethoxy, and the like.

The term "alkylaminoalkoxyalkoxy" refers to alkoxy radicals substituted with alkylaminoalkoxy radicals. Some non-limiting examples of suitable alkylaminoalkoxyalkoxy radicals include mono or dialkyl substituted, such as N-methylaminomethoxyethoxy, N-methylaminoethoxyethoxy, N,N-dimethylaminoethoxyethoxy, N,N-diethylaminomethoxymethoxy, and the like.

The term "carboxyalkyl" refers to a linear or branched alkyl radical having one to about ten carbon atoms, substituted with one or more carboxy radicals. Some non-limiting examples of such radicals include carboxymethyl, carboxypropyl, and the like.

The term "heteroarylalkoxy" refers to oxy-containing heteroarylalkyl radicals attached through an oxygen atom to other radicals, wherein the heteroarylalkyl radical is as defined herein. Some non-limiting examples of such radicals include pyridin-2-ylmethoxy, thiazol-2-ylethoxy, imidazol-2-ylethoxy, pyrimidin-2-ylpropoxy, pyrimidin-2-ylmethoxy, and the like.

The term "cycloalkylalkyl" refers to cycloalkyl-substituted alkyl radicals. Some non-limiting examples of such radicals include cyclohexylmethyl. The cycloalkyl in the radicals may be additionally substituted with halo, alkyl, alkoxy or hydroxy.

The term "fused bicyclic", "fused cyclic", "fused bicyclyl" or "fused cyclyl" refers to saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon). Each cyclic ring in the fused bicyclyl can be either a carbocyclic or a heteroalicyclic. Some non-limiting examples of fused bicyclic ring system include hexahydro-furo[3,2-b]furan, 2,3,3a,4,7,7a-hexahydro-1H-indene, 7-azabicyclo[2.3.0]heptane, fused bicyclo[3.3.0]octane, fused bicyclo[3.1.0]hexane, 1,2,3,4,4a,5,8,8a-octahydro-naphthalene, and the like. And the fused bicyclyl defined herein may be substituted or unsubstituted, wherein the substituents include, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "fused bicyclylene" refers to fused bicyclyl system having two connection points connected to the rest of the molecule, wherein fused bicyclyl radical is as defined herein.

The term "fused heterobicyclyl" refers to saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon). Wherein at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, SO$_2$, PO or PO$_2$. Some non-limiting examples of fused heterobicyclic ring system include hexahydro-furo[3,2-b]furan, 7-azabicyclo[2.3.0]heptane, and the like. And the fused heterobicyclyl defined herein may be substituted or unsubstituted, wherein the substituents include, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "fused heterobicyclylene" refers to fused heterobicyclyl system having two connection points connected to the rest of the molecule, wherein fused heterobicyclyl radical is as defined herein.

The term "fused bicyclylaliphatic" refers to aliphatic groups substituted with one or more fused bicyclyl groups, wherein the aliphatic group and the fused bicyclyl group are as defined herein. Some non-limiting examples include 1,2,3,4,4a,5,8,8a-octahydro-naphthylethyl, 1,2,3,4,4a,5,8,8a-octahydro-naphthylmethyl, 1,2,3,4,4a,5,8,8a-octahydro-naphthylpropyl, fused bicyclo[3.3.0]octylmethyl, fused bicyclo[3.1.0]hexylethyl, and the like.

The term "fused heterobicyclylaliphatic" refers to aliphatic groups substituted with one or more fused heterobicyclyl groups, wherein the aliphatic group and the fused heterobicyclyl group are as defined herein. Some non-limiting examples include hexahydro-furo[3,2-b]furan-2-ylethyl, hexahydro-furo[3,2-b]furan-2-ylmethyl, 7-azabicyclo[2.3.0]hept-2-ylmethyl, 7-azabicyclo[2.3.0]hept-2-ylethyl, 7-azabicyclo[2.3.0]hept-4-ylmethyl, and the like.

The term "fused bicycloxy" refers to optionally substituted fused bicyclyl radicals, as defined herein, oxy-containing fused bicyclyl radicals attached through an oxygen atom to other radicals, wherein the fused bicyclyl radical is as defined herein. Some non-limiting examples include 1,2,3,4,4a,5,8,8a-octahydro-naphthyloxy, fused bicyclo[3.3.0]oct-2-yloxy, fused bicyclo[3.1.0]hex-2-yloxy, and the like.

The term "fused heterobicycloxy" refers to optionally substituted fused heterobicyclyl radicals, as defined herein, oxy-containing fused heterobicyclyl radicals attached through an oxygen atom to other radicals. Some non-limiting examples include hexahydro-furo[3,2-b]furan-2-yloxy, 7-azabicyclo[2.3.0]hept-2-yloxy, 7-azabicyclo[2.3.0]hept-4-yloxy, and the like.

The term "fused bicyclylamino" refers to an amino group substituted with one or two fused bicyclyl groups, wherein the fused bicyclyl group is as defined herein. Some non-limiting examples include 1,2,3,4,4a,5,8,8a-octahydro-naphthylamino, di(1,2,3,4,4a,5,8,8a-octahydro-naphthyl)amino, fused bicyclo[3.3.0]octylamino, fused bicyclo[3.1.0]hexylamino, and the like.

The term "fused heterobicyclylamino" refers to an amino group substituted with one or two fused heterobicyclyl groups, wherein the fused heterobicyclyl group is as defined herein. Some non-limiting examples include hexahydro-furo[3,2-b]furan-2-ylamino, 7-azabicyclo[2.3.0]hept-2-ylamino, 7-azabicyclo[2.3.0]hept-4-ylamino, and the like.

The term "fused bicyclylalkylamino" refers to alkylamino groups substituted with one or more fused bicyclyl groups, wherein the fused bicyclyl group is as defined herein. Some non-limiting examples include 1,2,3,4,4a,5,8,8a-octahydro-naphthylmethylamino, di(1,2,3,4,4a,5,8,8a-octahydro-naphthyl)methylamino, fused bicyclo[3.3.0]octylmethylamino, fused bicyclo[3.1.0]hexylmethylamino, and the like.

The term "fused heterobicyclylalkyamino" refers to alkylamino groups substituted with one or more fused heterobicyclyl groups, wherein the fused heterobicyclyl group is as defined herein. Some non-limiting examples include hexahydro-furo[3,2-b]furan-2-ylmethylamino, 7-azabicyclo[2.3.0]hept-2-ylmethylamino, 7-azabicyclo[2.3.0]hept-4-ylmethylamino, and the like.

The term "fused bicyclylalkoxy" refers to alkoxy groups substituted with one or more fused bicyclyl groups, wherein the fused bicyclyl group is as defined herein. Some non-limiting examples include 1,2,3,4,4a,5,8,8a-octahydro-naphthylmethoxy, 1,2,3,4,4a,5,8,8a-octahydro-naphthylethoxy, fused bicyclo[3.3.0]octylethoxy, fused bicyclo[3.1.0]hexylpropoxy, and the like.

The term "fused heterobicyclylalkoxy" refers to alkoxy groups substituted with one or more fused heterobicyclyl groups, wherein the fused heterobicyclyl group is as defined herein. Some non-limiting examples include hexahydro-furo[3,2-b]furan-2-ylpropoxy, 7-azabicyclo[2.2.1]hept-2-ylethoxy, 7-azabicyclo[2.3.0]hept-4-ylpropoxy, hexahydro-furo[3,2-b]furan-2-ylethoxy, 7-azabicyclo[2.3.0]hept-4-ylpropoxy, 7-azabicyclo[2.3.0]hept-4-ylethoxy, and the like.

The term "fused bicycloxyalkoxy" refers to alkoxy groups substituted with one or more fused bicycloxy groups, wherein the alkoxy group and the fused bicycloxy group are as defined herein. Some non-limiting examples include 1,2,3,4,4a,5,8,8a-octahydro-naphthyloxymethoxy, 1,2,3,4,4a,5,8,8a-octahydro-naphthyloxymethoxy, 1,2,3,4,4a,5,8,8a-octahydronaphthyloxyethoxy, fused bicyclo[3.3.0]oct-2-yloxyethoxy, fused bicyclo[3.1.0]hex-2-yloxypropoxy, and the like.

The term "fused heterobicycloxyalkoxy" refers to alkoxy groups substituted with one or more fused heterobicycloxy groups, wherein the alkoxy group and the fused heterobicyclyl group are as defined herein. Some non-limiting examples include hexahydro-furo[3,2-b]furan-2-yloxypropoxy, 7-azabicyclo[2.2.1]hept-2-yloxyethoxy, 7-azabicyclo[2.3.0]hept-4-yloxypropoxy, hexahydro-furo[3,2-b]furan-2-yloxyethoxy, 7-azabicyclo[2.3.0]hept-2-yloxypropoxy, 7-azabicyclo[2.3.0]hept-4-yloxyethoxy, and the like.

The term "fused bicyclylaminoalkoxy" refers to alkoxy groups substituted with one or more fused bicyclylamino groups, wherein the alkoxy group and the fused bicyclylamino group are as defined herein. Some non-limiting examples include 1,2,3,4,4a,5,8,8a-octahydro-naphthylamino ethoxy, 1,2,3,4,4a,5,8,8a-octahydro-naphthylaminopropoxy, di(1,2,3,4,4a,5,8,8a-octahydro-naphthyl)aminopropoxy, fused bicyclo[3.3.0]oct-2-ylaminoethoxy, fused bicyclo[3.1.0]hex-2-ylaminopropoxy, and the like.

The term "fused heterobicyclylaminoalkoxy" refers to alkoxy groups substituted with one or more fused heterobicyclylamino groups, wherein the alkoxy group and the fused heterobicyclylamino group are as defined herein. Some non-limiting examples include 7-azabicyclo[2.2.1]hept-2-ylamino ethoxy, 7-azabicyclo[2.3.0]hept-4-ylaminopropoxy, hexahydro-furo[3,2-b]furan-2-ylamino ethoxy, hexahydro-furo[3,2-b]furan-2-ylaminopropoxy, hexahydro-furo[3,2-b]furan-2-ylaminomethoxy, and the like.

The term "spirocyclyl", "spirocyclic", "spiro bicyclyl" or "spiro bicyclic" refers to a ring originating from a particular annular carbon of another ring. For example, as depicted below, a saturated bridged ring system (ring B and B') is termed as "fused bicyclic", whereas ring A and ring B share an atom between the two saturated ring system, which terms as a "spirocyclyl" or "spiro bicyclyl". Each cyclic ring in the spirocyclyl or spiro bicyclyl can be either a carbocyclic or a heteroalicyclic. Some non-limiting examples include 2,7-diaza-spiro[4.4]non-2-yl, 7-oxo-2-azaspiro[4.5]dec2-yl, 4-azaspiro[2.4]hept-5-yl, 4-oxaspiro[2.4]hept-5-yl, 5-azaspiro[2.4]hept5-yl, spiro[2.4]heptyl, spiro[4.4]nonyl, 7-hydroxy-5-azaspiro[2.4]hept-5-yl, and the like. The spirocyclyl or spiro bicyclyl can be optionally substituted, wherein the substituents can be, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

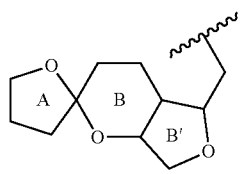

The term "spiro bicyclylene" refers to spiro bicyclyl system having two connection points connected to the rest of the molecule, wherein spiro bicyclyl radical is as defined herein.

The term "spiro heterobicyclyl" refers to a ring originating from a particular annular carbon of another ring. For example, as depicted above, a saturated bridged ring system (ring B and B') is termed as "fused bicyclic", whereas ring A and ring B share an carbon atom between the two saturated ring system, which terms as a "spirocyclyl" or "spiro bicyclyl". Wherein at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, SO$_2$, PO or PO$_2$. Some non-limiting examples of spiro heterobicyclic ring system include 4-azaspiro[2.4]hept-5-yl, 4-oxaspiro[2.4]hept-5-yl, 5-azaspiro[2.4]hept-5-yl, 7-hydroxy-5-azaspiro[2.4]hept-5-yl, and the like. And the spiro heterobicyclyl defined herein may be substituted or unsubstituted, wherein the substituents include, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "spiro heterobicyclylene" refers to spiro heterobicyclyl system having two connection points connected to the rest of the molecule, wherein spiro heterobicyclyl radical is as defined herein.

The term "spiro bicyclylaliphatic" refers to aliphatic groups substituted with one or more spiro bicyclyl groups, wherein the aliphatic group and the spiro bicyclyl group are as defined herein. Some non-limiting examples include spiro [2.4]heptylmethyl, spiro[2.4]heptylethyl, spiro[2.4]heptylpropyl, spiro[4.4]nonylmethyl, spiro[4.4]nonylethyl, 4-azaspiro[2.4]hept-5-yl-methyl, 4-azaspiro[2.4]hept-5-yl-ethyl, 4-oxaspiro[2.4]hept-5-yl-ethyl, 5-azaspiro[2.4]hept-5-yl-propyl, 7-hydroxy-5-azaspiro[2.4]hept-5-yl-propyl, and the like.

The term "spiro heterobicyclylaliphatic" refers to aliphatic groups substituted with one or more spiro heterobicyclyl groups, wherein the aliphatic group and the fused heterobicyclyl group are as defined herein. Some non-limiting examples include 4-azaspiro[2.4]hept-5-yl-methyl, 4-azaspiro[2.4]hept-5-yl-ethyl, 4-oxaspiro[2.4]hept-5-yl-ethyl, 5-azaspiro[2.4]hept-5-yl-propyl, 7-hydroxy-5-azaspiro[2.4]hept-5-yl-propyl, and the like.

The term "spiro bicycloxy" refers to optionally substituted spiro bicyclyl radicals, as defined herein, oxy-containing spiro bicyclyl radicals attached through an oxygen atom to other radicals, wherein the spiro bicyclyl radical is as defined herein. Some non-limiting examples include spiro[2.4]heptyl-2-oxy, spiro[2.4]heptyl-3-oxy, spiro[2.4]heptyl-4-oxy, spiro[4.4]nonyl-2-oxy, spiro[4.4]nonyl-4-oxy, 4-azaspiro[2.4]hept-5-oxy, and the like.

The term "spiro heterobicycloxy" refers to optionally substituted spiro heterobicyclyl radicals, as defined herein, oxy-containing spiro heterobicyclyl radicals attached through an oxygen atom to other radicals. Some non-limiting examples include 4-azaspiro[2.4]hept-5-yloxy, 4-oxaspiro[2.4]hept-5-yloxy, 5-azaspiro[2.4]hept-5-yloxy, and the like.

The term "spiro bicyclylamino" refers to an amino group substituted with one or two spiro bicyclyl groups, wherein the spiro bicyclyl group is as defined herein. Some non-limiting examples include spiro[2.4]heptyl-2-amino, spiro[2.4]heptyl-3-amino, spiro[2.4]heptyl-4-amino, spiro[4.4]nonyl-2-amino, spiro[4.4]nonyl-4-amino, 4-azaspiro[2.4]hept-5-amino, and the like.

The term "spiro heterobicyclylamino" refers to an amino group substituted with one or two spiro heterobicyclyl groups, wherein the spiro heterobicyclyl group is as defined herein. Some non-limiting examples include 4-azaspiro[2.4]hept-5-ylamino, 4-oxaspiro[2.4]hept-2-ylamino, 4-oxaspiro[2.4]hept-5-ylamino, 5-azaspiro[2.4]hept-5-ylamino, and the like.

The term "spiro bicyclylalkoxy" refers to alkoxy groups substituted with one or more spiro bicyclyl groups, wherein the spiro bicyclyl group is as defined herein. Some non-limiting examples include spiro[2.4]heptyl-2-methoxy, spiro[2.4]heptyl-3-ethoxy, spiro[2.4]heptyl-4-ethoxy, spiro[4.4]nonyl-2-methoxy, spiro[4.4]nonyl-4-propoxy, 4-azaspiro[2.4]hept-5-methoxy, and the like.

The term "spiro heterobicyclylalkoxy" refers to alkoxy groups substituted with one or more spiro heterobicyclyl groups, wherein the spiro heterobicyclyl group is as defined herein. Some non-limiting examples include 4-azaspiro[2.4]hept-5-yl-methoxy, 4-azaspiro[2.4]hept-2-yl-ethoxy, 4-oxaspiro[2.4]hept-5-yl-ethoxy, 5-azaspiro[2.4]hept-5-yl-propoxy, and the like.

The term "spiro bicyclylalkyamino" refers to alkylamino groups substituted with one or more spiro bicyclyl groups, wherein the spiro bicyclyl group is as defined herein. Some non-limiting examples include spiro[2.4]heptyl-2-methylamino, spiro[2.4]heptyl-3-ethylamino, spiro[2.4]heptyl-4-ethylamino, spiro[4.4]nonyl-2-methylamino, spiro[4.4]nonyl-4-propylamino, 4-azaspiro[2.4]hept-5-methylamino, and the like.

The term "spiro heterobicyclylalkyamino" refers to alkylamino groups substituted with one or more spiro heterobicyclyl groups, wherein the spiro heterobicyclyl group is as defined herein. Some non-limiting examples include 4-azaspiro[2.4]hept-5-yl-methylamino, 4-azaspiro[2.4]hept-2-yl-ethylamino, 4-oxaspiro[2.4]hept-5-yl-ethylamino, 5-azaspiro[2.4]hept-5-yl-propylamino, and the like.

The term "spiro bicycloxyalkoxy" refers to alkoxy groups substituted with one or more spiro bicycloxy groups, wherein the alkoxy group and the spiro bicyclyl group are as defined herein. Some non-limiting examples include spiro[2.4]heptyl-2-oxyethoxy, spiro[2.4]heptyl-3-oxypropoxy, spiro[2.4]heptyl-4-oxypropoxy, spiro[4.4]nonyl-2-oxyethoxy, spiro[4.4]nonyl-4-oxypropoxy, 4-azaspiro[2.4]hept-5-oxypropoxy, and the like.

The term "spiro heterobicycloxyalkoxy" refers to alkoxy groupsn substituted with one or more spiro heterobicycloxy groups, wherein the alkoxy group and the spiro heterobicyclyl group are as defined herein. Some non-limiting examples include 4-azaspiro[2.4]hept-5-yloxyethoxy, 4-oxaspiro[2.4]hept-5-yloxyethoxy, 5-azaspiro[2.4]hept-5-yloxyethoxy, 4-azaspiro[2.4]hept-5-yloxypropoxy, 4-oxaspiro[2.4]hept-5-yloxypropoxy, 5-azaspiro[2.4]hept-5-yloxypropoxy, and the like.

The term "spiro bicyclylaminoalkoxy" refers to alkoxy groups substituted with one or more spiro bicyclylamino groups, wherein the alkoxy group and the spiro bicyclylamino group are as defined herein. Some non-limiting examples include spiro[2.4]heptyl-2-aminoethoxy, spiro[2.4]heptyl-3-aminopropoxy, spiro[2.4]heptyl-4-aminoethoxy, spiro[4.4]nonyl-2-aminoethoxy, spiro[4.4]nonyl-4-aminopropoxy, 4-azaspiro[2.4]hept-5-aminopropoxy, and the like.

The term "spiro heterobicyclylaminoalkoxy" refers to alkoxy groups substituted with one or more spiro heterobicyclylamino groups, wherein the alkoxy group and the spiro heterobicyclylamino group are as defined herein. Some non-limiting examples include 4-azaspiro[2.4]hept-5-ylamino ethoxy, 4-oxaspiro[2.4]hept-2-ylaminopropoxy, 4-oxaspiro[2.4]hept-5-ylaminoethoxy, 5-azaspiro[2.4]hept-5-ylaminopropoxy, and the like.

As described herein, a bond drawn from a substituent to the center of one ring within a ring system (as shown below) represents substitution of the substituent at any substitutable position on the ring A and ring B. For example, Figure a represents possible substitution in any of the positions on the A ring and B ring shown in Figure b.

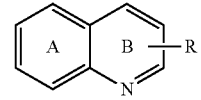

Figure a

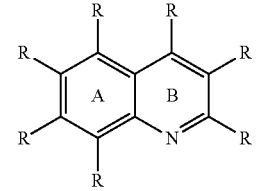

Figure b

As described herein, a dot line drawn together with a bond within a ring system (as shown in Figure c) represents either a double bond or a single bond. For example, structure in Figure c represents any structures selected from Figure d.

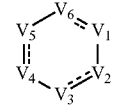

Figure c

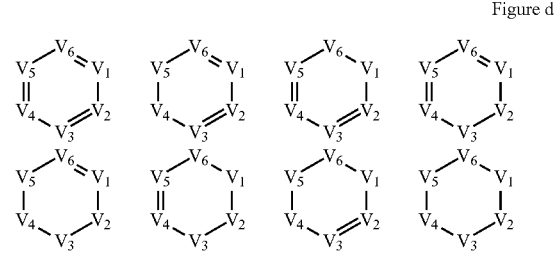

Figure d

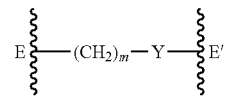

Figure e

As described herein, two attaching points either E or E', within a ring system (as shown in Figure e), attach to the rest of the molecule, e.g., E and E' may be used interchangeably with each other.

Unless otherwise stated, structures depicted herein are also meant to include all isomeric (e.g., enantiomeric, diastereomeric, and geometric (or conformational)) forms of the structure, for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" refers to a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., *Pro-drugs as Novel Delivery Systems*, Vol. 14, A.C.S. Symposium Series; Roche et al., ed., *Bioreversible Carriers in Drug Design*, American Pharmaceutical Association and Pergamon Press, 1987; Rautio et al., Prodrugs: Design and Clinical Applications, *Nature Reviews Drug Discovery*, 2008, 7, 255-270, and Hecker et al., Prodrugs of Phosphates and Phosphonates, *J. Med. Chem.*, 2008, 51, 2328-2345, all of which are incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow Parker et al., McGraw-Hill Dictionary of Chemical Terms (1984) McGraw-Hill Book Company, New York and Eliel et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in *J. Pharmacol Sci*, 1977, 66, 1-19, which is incorporated herein by reference. Some non-limiting examples of pharmaceutically acceptable salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, malic acid salts, 2-hydracrylic acid salt, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (Boc), benzyloxycarbonyl (Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group"" refers to a substituent of the carboxy group that blocks or protects the carboxy functionality. Some non-limiting examples of common carboxy-protecting groups include —CH₂CH₂SO₂Ph, cyanoethyl, 2-(tri-methylsilyl)ethyl, 2-(trimethylsilyl)ethoxymethyl, 2-(p-toluenesulfonyl)ethyl, 2-(p-nitrophenylsulfonyl)ethyl, 2-(diphenyl phosphino)-ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

DESCRIPTION OF COMPOUNDS OF THE INVENTION

Provided herein are new compounds or pharmaceutical compositions that may be more effective to prevent or treat human or animal tissue fibrosis. In one aspect, provided herein are compounds having Formula (I) as shown below:

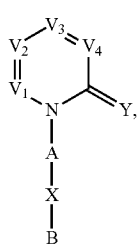

(I)

or a stereoisomer, a geometric isomer, a tautomer, an N-oxide, a hydrate, a solvate, a metabolite, a pharmaceutically acceptable salt or a prodrug thereof, wherein each $V_1, V_2, V_3, V_4, A, B, X$ and $Y$ is as defined herein.

In some embodiments, $V_1$ is N or $CR^1$, $V_2$ is N or $CR^2$, $V_3$ is N or $CR^3$ and $V_4$ is N or $CR^4$, wherein at most one of the $V_1$, $V_2$, $V_3$ and $V_4$ is N;

X is a bond, $NR^5$, O, S, $C_{1\text{-}10}$ alkylene, $C_{2\text{-}10}$ alkenylene, $C_{2\text{-}10}$ alkynylene, —$R^6$—C(=Y)—, —$R^6$—C(=Y)—O—, —$R^6$—C(=Y)—N($R^5$)—, —$R^6$—S(=O)$_t$—, —$R^6$—S(=O)$_t$—N($R^7$)—, or —$R^6$—Y—, wherein each t is 1 or 2;
Y is O or S;

A is heterocyclylene, carbocyclylene, fused bicyclylene, fused heterobicyclylene, spiro bicyclylene, spiro heterobicyclylene, arylene and heteroarylene;

B is alkoxy, hydroxy-substituted alkoxy, —$NR^7R^{7a}$, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}$N—S(=O)$_t$—, $R^7$S(=O)$_t$—, $R^7$S(=O)$_t$N($R^{7a}$)—, $C_{4\text{-}12}$ carbocyclyl, $C_{4\text{-}12}$ cycloalkyl, heterocyclyl, aryl, heteroaryl, fused bicyclyl, fused heterobicyclyl, spiro bicyclyl, or spiro heterobicyclyl;

or A, X and B together form a group having Formula (II):

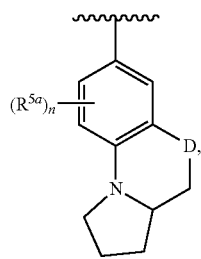

(II)

wherein D is $NR^5$, O, S, or $CR^7R^{7a}$;

$R^1$ is H, F, Cl, Br, I, cyano, hydroxy, $R^{7a}R^7$N—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}$N—S(=O)$_t$—, $R^7$S(=O)$_t$—, $R^7$S(=O)$_t$N($R^{7a}$)—, $R^{7a}R^7$N-alkyl, $R^7$S(=O)$_t$-alkyl, $R^7R^{7a}$N—C(=O)-alkyl, $R^{7a}R^7$N-alkoxy, $R^7$S(=O)$_t$-alkoxy, $R^7R^{7a}$N—C(=O)-alkoxy, aliphatic, haloalkyl, alkoxy, hydroxyalkoxy, aminoalkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, cycloalkyloxy, arylalkoxy, arylalkylamino, heteroarylalkoxy, heteroarylalkylamino, heterocyclylalkylamino, cycloalkylamino, heterocyclylalkoxy, carbocyclylalkoxy, carbocyclylalkylamino, heterocyclyl(hydroxyalkoxy), carbocyclyl(hydroxyalkoxy), aryl(hydroxyalkoxy), aryloxyalkoxy, aryloxy, heteroaryloxy, heteroaryloxyalkoxy, heterocyclyloxyalkoxy, carbocyclyloxyalkoxy, heterocyclyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R^7$)—, fused heterobicyclyl-C(=O)N($R^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R^7$)—, spiro heterobicyclyl-C(=O)N($R^7$)—, heterocyclyl, cycloalkyl, aryl, heteroaryl, heterocyclyl aliphatic, cycloalkyl aliphatic, aryl aliphatic, heteroaryl aliphatic, aryl-(CH₂)$_p$-G-(CH₂)$_m$—, heteroaryl-(CH₂)$_p$-G-(CH₂)$_m$—, heterocyclyl-(CH₂)$_p$-G-(CH₂)$_m$—, or cycloalkyl-(CH₂)$_p$-G-(CH₂)$_m$—, wherein each G is O, S, $NR^5$, S(=O), S(=O)₂, C(=O), —C(=O)N($R^7$)—, —OC(=O)N($R^7$)—, —OC(=O)—, —N($R^7$)C(=O)N($R^7$)—, —($R^7$)N—S(=O)$_t$—, —OS(=O)$_t$—, or —OS(=O)$_t$N($R^7$)—; each t is 1 or 2; each p and m is independently 0, 1, 2, 3 or 4; or wherein each of the $C_{6\text{-}10}$ aryl-(CH₂)$_p$-G-(CH₂)$_m$—, $C_{1\text{-}9}$ heteroaryl-(CH₂)$_p$-G-(CH₂)$_m$—, $C_{2\text{-}10}$ heterocyclyl-(CH₂)$_p$-G-(CH₂)$_m$—, and $C_{3\text{-}10}$ cycloalkyl-(CH₂)$_p$-G-(CH₂)$_m$— is optionally substituted by one or more F, Cl, Br, I, $C_{1\text{-}6}$ alkyl, $C_{2\text{-}6}$ alkynyl, $C_{1\text{-}6}$ alkoxy or cyano;

$R^2$ is H, F, Cl, Br, I, cyano, hydroxy, $R^{7a}R^7$N—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}$N—S(=O)$_t$—, $R^7$S(=O)$_t$—, $R^7$S(=O)$_t$N($R^{7a}$)—, $R^{7a}R^7$N-alkyl, $R^7$S(=O)$_t$-alkyl, $R^7R^{7a}$N—C(=O)-alkyl, $R^{7a}R^7$N-alkoxy, $R^7$S(=O)$_t$-alkoxy, $R^7R^{7a}$N—C(=O)-alkoxy, aliphatic, haloalkyl, alkoxy, hydroxyalkoxy, aminoalkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, arylalkoxy, arylalkylamino, heteroarylalkoxy, heteroarylalkylamino, heterocyclylalkylamino, cycloalkyloxy, cycloalkylamino, heterocyclylalkoxy, carbocyclylalkoxy, carbocyclylalkylamino, heterocyclyl(hydroxyalkoxy), carbocyclyl(hydroxyalkoxy), aryl(hydroxyalkoxy), aryloxyalkoxy, aryloxy, heteroaryloxy, heteroaryloxyalkoxy, heterocyclyloxyalkoxy, carbocyclyloxyalkoxy, heterocyclyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R^7$)—, fused heterobicyclyl-C(=O)N($R^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R^7$)—, spiro heterobicyclyl-C(=O)N($R^7$)—, heterocyclyl, cycloalkyl, aryl, $C_{1-4}$ heteroaryl, heterocyclyl aliphatic, cycloalkyl aliphatic, aryl aliphatic, heteroaryl aliphatic, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, or cycloalkyl-$(CH_2)_p$-G-$(CH_2)_m$—, wherein each G is O, S, $NR^5$, S(=O), S(=O)$_2$, C(=O), —C(=O)N($R^7$)—, —OC(=O)N($R^7$)—, —OC(=O)—, —N($R^7$)C(=O)N($R^7$)—, —($R^7$)N—S(=O)$_t$—, —OS(=O)$_t$—, or —OS(=O)$_t$N($R^7$)—; each t is 1 or 2; each p and m is independently 0, 1, 2, 3 or 4;

$R^3$ is H, F, Cl, I, cyano, $R^7R^{7a}N$—, —C(=O)N$R^7R^{7a}$, —OC(=O)N$R^7R^{7a}$, —OC(=O)O$R^7$, —N($R^7$)C(=O)N$R^7R^{7a}$, —N($R^7$)C(=O)O$R^{7a}$, —N($R^7$)C(=O)—$R^{7a}$, $R^7R^{7a}N$—S(=O)$_t$—, $R^7$S(=O)$_t$—, $R^7$S(=O)$_t$N($R^{7a}$)—, $R^{7a}R^7N$-alkyl, $R^7$S(=O)$_t$-alkyl, $R^7R^{7a}N$—C(=O)-alkyl, $R^{7a}R^7N$-alkoxy, $R^7$S(=O)$_t$-alkoxy, $R^7R^{7a}N$—C(=O)-alkoxy, aliphatic, haloalkyl, aryl-$C_{2-10}$ alkoxy, heteroaryl-$C_{3-10}$ alkoxy, cycloalkyl-$C_{2-10}$ alkoxy, fused bicyclyl-$C_{2-10}$ alkoxy, $C_{1-4}$ heteroaryl, substituted aryl, heterocyclyl, cycloalkyl, heterocyclyl aliphatic, cycloalkyl aliphatic, $C_{1-4}$ heteroaryl aliphatic, substituted aryl $C_{3-10}$ alkyl, heterocyclylalkyl, alkoxy, hydroxyalkoxy, aminoalkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, aryl-$C_{2-10}$ alkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, arylaminoalkoxy, aryloxy, heteroaryloxyalkoxy, heterocyclyloxyalkoxy, carbocyclyloxyalkoxy, heterocyclyloxy, cycloalkyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R^7$)—, fused heterobicyclyl-C(=O)N($R^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R^7$)—, spiro heterobicyclyl-C(=O)N($R^7$)—, heterocyclyl, cycloalkyl, aryl, heteroaryl, heterocyclyl aliphatic, cycloalkyl aliphatic, aryl $C_{2-10}$ aliphatic, heteroaryl aliphatic, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, or cycloalkyl-$(CH_2)_p$-G-$(CH_2)_m$—, wherein each G is O, S, $NR^5$, S(=O), S(=O)$_2$, C(=O), —C(=O)N($R^7$)—, —OC(=O)N($R^7$)—, —OC(=O)—, —N($R^7$)C(=O)N($R^7$)—, —($R^7$)N—S(=O)$_t$—, —OS(=O)$_t$—, or —OS(=O)$_t$N($R^7$)—; each t is 1 or 2; each p and m is independently 0, 1, 2, 3 or 4;

$R^4$ is H, F, I, cyano, hydroxy, $R^{7a}R^7N$—, —C(=O)N$R^7R^{7a}$, —OC(=O)N$R^7R^{7a}$, —OC(=O)O$R^7$, —N($R^7$)C(=O)N$R^7R^{7a}$, —N($R^7$)C(=O)O$R^{7a}$, —N($R^7$)C(=O)—$R^{7a}$, $R^7R^{7a}N$—S(=O)$_t$—, $R^7$S(=O)$_t$—, $R^7$S(=O)$_t$N($R^{7a}$)—, $R^{7a}R^7N$-alkyl, $R^7$S(=O)$_t$-alkyl, $R^7R^{7a}N$—C(=O)-alkyl, $R^{7a}R^7N$-alkoxy, $R^7$S(=O)$_t$-alkoxy, $R^7R^{7a}N$—C(=O)-alkoxy, aliphatic, haloalkyl, $C_{2-10}$ alkoxy, hydroxyalkoxy, aminoalkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, $C_{3-5}$ cycloalkyloxy, arylalkoxy, heteroarylalkoxy, heteroarylalkylamino, heterocyclylalkylamino, $C_{7-10}$ cycloalkoxy, cycloalkylamino, heterocyclylalkoxy, carbocyclylalkoxy, carbocyclylalkylamino, heterocyclyl(hydroxyalkoxy), carbocyclyl(hydroxyalkoxy), aryl(hydroxyalkoxy), aryloxyalkoxy, aryloxy, heteroaryloxy, heteroaryloxyalkoxy, heterocyclyloxyalkoxy, carbocyclyloxyalkoxy, heterocyclyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R^7$)—, fused heterobicyclyl-C(=O)N($R^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R^7$)—, spiro heterobicyclyl-C(=O)N($R^7$)—, heterocyclyl, cycloalkyl, aryl, heteroaryl, heterocyclyl aliphatic, cycloalkyl aliphatic, aryl $C_{2-10}$ aliphatic, heteroaryl aliphatic, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, or cycloalkyl-$(CH_2)_p$-G-

(CH$_2$)$_m$—, wherein each G is O, S, NR$^5$, S(=O), S(=O)$_2$, C(=O), —C(=O)N(R$^7$)—, —OC(=O)N(R$^7$)—, —OC(=O)—, —N(R$^7$)C(=O)N(R$^7$)—, —(R$^7$)N—S(=O)$_t$—, —OS(=O)$_t$—, or —OS(=O)$_t$N(R$^7$)—; each t is 1 or 2; each p and m is independently 0, 1, 2, 3 or 4;

each R$^5$ is independently H, R$^7$R$^{7a}$NC(=O)—, R$^7$OC(=O)—, R$^7$C(=O)—, R$^7$R$^{7a}$NS(=O)—, R$^7$OS(=O)—, R$^7$S(=O)—, R$^7$R$^{7a}$NS(=O)$_2$—, R$^7$OS(=O)$_2$—, R$^7$S(=O)$_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;

each R$^{5a}$ is independently H, hydroxy, amino, F, Cl, Br, I, cyano, oxo (=O), R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N-alkyl, R$^7$S(=O)-alkyl, R$^7$R$^{7a}$N—C(=O)-alkyl, R$^{7a}$R$^7$N-alkoxy, R$^7$S(=O)-alkoxy, R$^7$R$^{7a}$N—C(=O)-alkoxy, aryl, heteroaryl, alkoxy, alkyl, alkenyl, alkynyl, heterocyclyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylalkyl, heterocyclylamino, heterocyclylalkylamino or aryloxy;

each R$^6$ is independently a bond, C$_{1-10}$ alkylene, C$_{2-10}$ alkenylene, or C$_{2-10}$ alkynylene; and each R$^7$ and R$^{7a}$ is independently H, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; with the proviso that where R$^7$ and R$^{7a}$ are bonded to the same nitrogen atom, R$^7$ and R$^{7a}$, together with the nitrogen atom they are attached to, optionally form a substituted or unsubstituted 3-8 membered ring or a substituted or unsubstituted spiro bicyclic or fused bicyclic ring;

wherein each of NR$^5$, —R$^6$—C(=Y)—, —R$^6$—C(=Y)—O—, —R$^6$—C(=Y)—N(R$^5$)—, —R$^6$—S(=O)$_t$—, —R$^6$—S(=O)$_t$—N(R$^7$)—, —R$^6$—Y—, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_t$—, R$^7$S(=O)$_t$—, R$^7$S(=O)$_t$N(R$^{7a}$)—, R$^{7a}$R$^7$N-alkyl, R$^7$S(=O)$_t$-alkyl, R$^7$R$^{7a}$N—C(=O)—C$_{1-6}$ alkyl, R$^{7a}$R$^7$N—C$_{1-6}$ alkoxy, R$^7$S(=O)-alkoxy, R$^7$R$^{7a}$N—C(=O)-alkoxy, R$^7$R$^{7a}$NC(=O)—, R$^7$OC(=O)—, R$^7$C(=O)—, R$^7$R$^{7a}$NS(=O)—, R$^7$OS(=O)—, R$^7$S(=O)—, R$^7$R$^{7a}$NS(=O)$_2$—, R$^7$OS(=O)$_2$—, R$^7$S(=O)$_2$—, R$^{7a}$R$^7$N-aliphatic, aryl-(CH$_2$)$_p$-G-(CH$_2$)$_m$—, heteroaryl-(CH$_2$)$_p$-G-(CH$_2$)$_m$—, heterocyclyl-(CH$_2$)$_p$-G-(CH$_2$)$_m$—, cycloalkyl-(CH$_2$)$_p$-G-(CH$_2$)$_m$—, hydroxy-substituted C$_{1-6}$ alkyl-C(=O)—, C$_{1-6}$ alkyl-C(=O)—, C$_{1-6}$ alkyl-S(=O)—, C$_{1-6}$ alkyl-S(=O)$_2$—, hydroxy-substituted C$_{1-6}$ alkyl-S(=O)—, hydroxy-substituted C$_{1-6}$ alkyl-S(=O)$_2$—, carboxy C$_{1-6}$ alkoxy, haloalkyl, heterocyclylalkyl, heterocyclylalkoxy, heterocyclylalkylamino, heterocyclylamino, cycloalkyl, cycloalkylaliphatic, cycloalkylamino, cycloalkyloxyaliphatic, cycloalkylalkoxy, cycloalkylalkylamino, carbocyclylaliphatic, aralkyl, aryloxyalkyl, heteroaryloxyaliphatic, aliphatic, alkoxy, hydroxyalkoxy, aminoalkoxy, hydroxy-substituted C$_{1-6}$ alkoxy, hydroxy-substituted aminoalkoxy, haloalkoxy, amino-substituted haloalkoxy, alkylaminohaloalkoxy, hydroxy-substituted haloalkoxy, alkylaminoalkoxy, alkoxyalkoxy, arylalkoxy, arylalkylamino, heterocyclylalkoxy, carbocyclylalkoxy, heterocyclyl(hydroxyalkoxy), carbocyclyl(hydroxyalkoxy), aryl(hydroxyalkoxy), aryloxyalkoxy, heteroaryloxyalkoxy, aryloxy, arylamino, heterocyclyloxyalkoxy, carbocyclyloxyalkoxy, cycloalkyloxy, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N(R$^7$)—, fused heterobicyclyl-C(=O)N(R$^7$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N(R$^7$)—, spiro heterobicyclyl-C(=O)N(R$^7$)—, aryl, heteroaryl, arylaliphatic, heteroarylaliphatic, heteroaryloxy, heteroarylamino, heteroarylalkoxy, heteroarylalkylamino, haloaliphatic, hydroxyaliphatic, aminoaliphatic, alkoxyaliphatic, alkylaminoaliphatic, alkylthioaliphatic, cycloalkyl, heterocyclylaliphatic, aryloxyaliphatic, heterocyclyloxyaliphatic, cycloalkyloxyaliphatic, arylaminoaliphatic, heterocyclylaminoaliphatic, cycloalkylaminoaliphatic, heterocyclyl, carbocyclyl, heterocyclylene, carbocyclylene, fused bicyclylene, fused heterobicyclylene, spiro bicyclylene, spiro heterobicyclylene, arylene and heteroarylene is unsubstituted or substituted with at least one substituent wherein the substituent is haloalkyl, oxo (=O), hydroxy, amino, F, Cl, Br, I, cyano, C$_{1-10}$ alkoxy, C$_{1-10}$ alkylamino, C$_{1-10}$ alkylthio, C$_{1-10}$ alkyl, C$_{2-10}$ alkenyl, C$_{2-10}$ alkynyl, mercapto, nitro, C$_{6-10}$ aryl, C$_{1-9}$ heteroaryl, C$_{2-10}$ heterocyclyl, C$_{6-10}$ aryloxy, carboxy, hydroxy-substituted C$_{1-6}$ alkoxy, hydroxy-substituted C$_{1-6}$ alkyl-C(=O)—, C$_{1-6}$ alkyl-C(=O)—, C$_{1-6}$ alkyl-S(=O)—, C$_{1-6}$ alkyl-S(=O)$_2$—, hydroxy-substituted C$_{1-6}$ alkyl-S(=O)—, hydroxy-substituted C$_{1-6}$ alkyl-S(=O)$_2$—, or carboxyC$_{1-6}$ alkoxy.

In some embodiments, A is C$_{2-10}$ heterocyclylene, C$_{3-10}$ carbocyclylene, C$_{5-12}$ fused bicyclylene, C$_{5-12}$ fused heterobicyclylene, C$_{5-12}$ spiro bicyclylene, C$_{5-12}$ spiro heterobicyclylene, C$_{6-10}$ arylene, and C$_{1-9}$ heteroarylene.

In some embodiments, A is

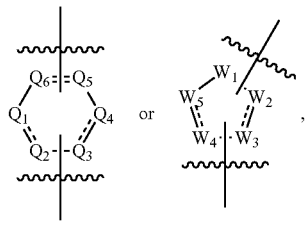

wherein each Q$_1$, Q$_2$, Q$_3$, Q$_4$, Q$_5$ and Q$_6$ is independently N, NR$^5$, O, S, CR$^7$R$^{7a}$ or CR$^8$, and at most four of the Q$_1$, Q$_2$, Q$_3$, Q$_4$, Q$_5$ and Q$_6$ are N or NR$^5$;

$W_1$ is $NR^5$, O, S, or $CR^7R^{7a}$, each $W_2$, $W_3$, $W_4$ and $W_5$ is independently N, $NR^5$, O, S, $CR^7R^{7a}$, or $CR^8$, and at most four of the $W_1$, $W_2$, $W_3$, $W_4$ and $W_5$ are N or $NR^5$; and each $R^8$ is independently H, hydroxy, amino, F, Cl, Br, I, cyano, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $R^7S(=O)_2-$, $R^7S(=O)_2N(R^{7a})-$, $R^{7a}R^7N$-alkyl, $R^7S(=O)$-alkyl, $R^7R^{7a}N-C(=O)$-alkyl, $R^7R^{7a}N$-alkoxy, $R^7S(=O)$-alkoxy, $R^7R^{7a}N-C(=O)$-alkoxy, aryl, heteroaryl, alkoxy, alkyl, alkenyl, alkynyl, heterocyclyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino or aryloxy.

In some embodiments, A is

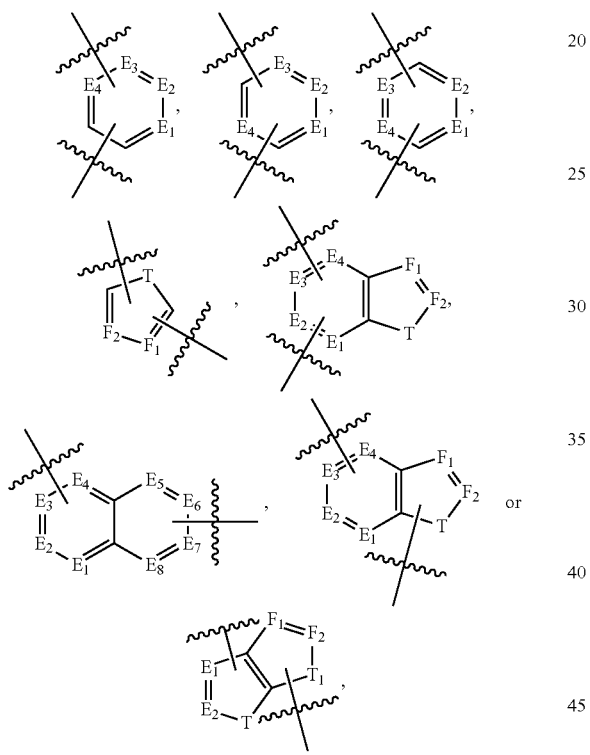

wherein each $E_1$, $E_2$, $E_3$, $E_4$, $E_5$, $E_6$, $E_7$, $E_8$, $F_1$ and $F_2$ is independently N or $CR^9$;

each T and $T_1$ is independently $NR^5$, O, S or $CR^9R^{9a}$; and each $R^9$ and $R^{9a}$ is independently H, hydroxy, amino, F, Cl, Br, I, cyano, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $R^7S(=O)_2-$, $R^7S(=O)_2N(R^{7a})-$, $R^{7a}R^7N-C_{1-6}$ alkyl, $R^7S(=O)-C_{1-6}$ alkyl, $R^7R^{7a}N-C(=O)-C_{1-6}$ alkyl, $R^{7a}R^7N-C_{1-6}$ alkoxy, $R^7S(=O)-C_{1-6}$ alkoxy, $R^7R^{7a}N-C(=O)-C_{1-6}$ alkoxy, $C_{6-10}$ aryl, $C_{1-9}$ heteroaryl, $C_{1-6}$ alkoxy, $C_{1-6}$ alkyl, $C_{2-6}$ alkenyl, $C_{2-6}$ alkynyl, $C_{2-10}$ heterocyclyl, mercapto, nitro, $C_{6-10}$ aryl-$C_{1-6}$-alkyl, $C_{6-10}$ arylamino, $C_{1-9}$ heteroarylamino, $C_{6-10}$ aryl-$C_{1-6}$-alkylamino, $C_{1-9}$ heteroaryl-$C_{1-6}$-alkylamino, $C_{1-9}$ heteroaryloxy, $C_{1-9}$ heteroaryl-$C_{1-6}$-alkyl, $C_{6-10}$ aryl-$C_{1-6}$-alkoxy, $C_{1-9}$ heteroaryl-$C_{1-6}$-alkoxy, $C_{2-10}$ heterocyclyloxy, $C_{2-10}$ heterocyclyl-$C_{1-6}$-alkoxy, $C_{2-10}$ heterocyclylamino, $C_{2-10}$ heterocyclyl-$C_{1-6}$-alkylamino, or $C_{6-10}$ aryloxy.

In other embodiments, A is

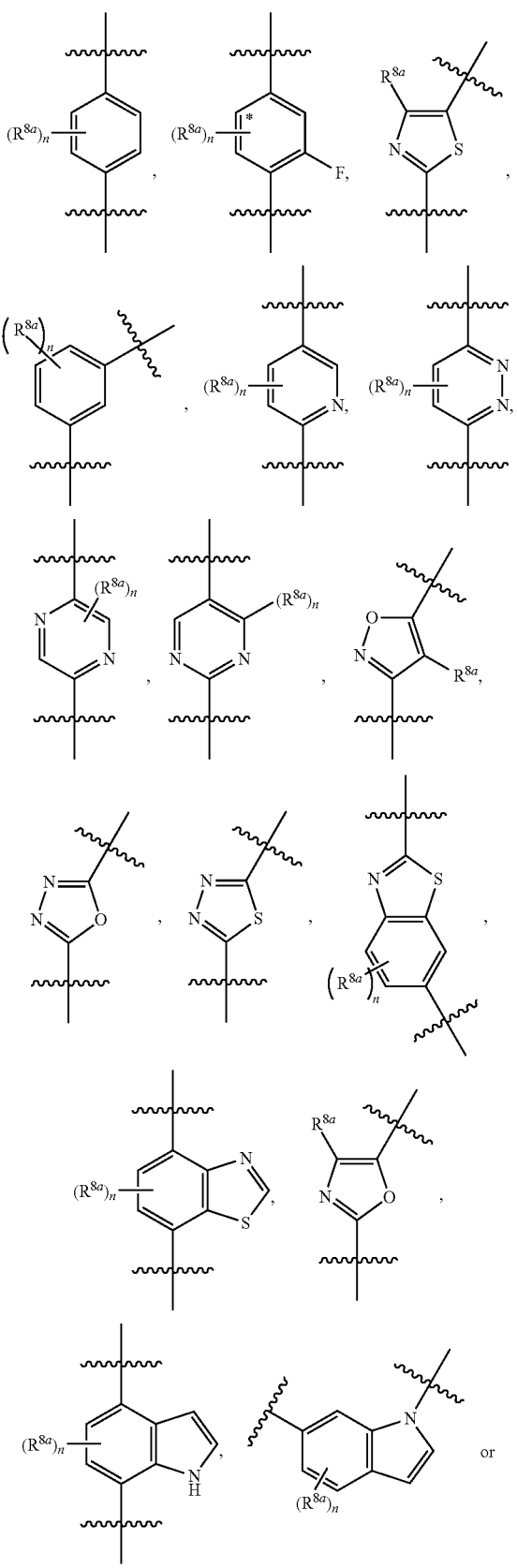

-continued

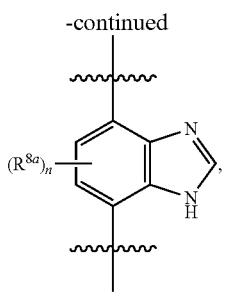

$(R^{8a})_n$ wherein each n is independently 0, 1, 2 or 3; and
each $R^{8a}$ is independently H, hydroxy, amino, F, Cl, Br, I, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2N(R^{7a})$—, cyano, nitro, mercapto, $C_{1-4}$ alkyl, $C_{1-4}$ haloalkyl, $C_{1-4}$ alkoxy, $C_{1-4}$ alkylamino, $C_{1-4}$ alkylthio, $C_{6-10}$ aryl, or $C_{1-9}$ heteroaryl.

In some embodiments, B is $C_{1-6}$ alkoxy, hydroxy-substituted $C_{1-6}$ alkoxy, —$NR^7R^{7a}$, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl, or $C_{5-12}$ spiro heterobicyclyl.

In some embodiments, $R^1$ is H, F, Cl, Br, I, cyano, hydroxy, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2N(R^{7a})$—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{1-6}$ aliphatic, $C_{1-6}$ alkoxy, $C_{1-6}$ hydroxyalkoxy, $C_{1-6}$ aminoalkoxy, hydroxy-substituted $C_{1-6}$ aminoalkoxy, $C_{1-6}$ haloalkoxy, amino-substituted $C_{1-6}$ haloalkoxy, $C_{1-6}$ alkylamino-$C_{1-6}$-haloalkoxy, hydroxy-substituted $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{3-10}$ cycloalkylamino, $C_{3-10}$ carbocyclyl-$C_{1-6}$-alkoxy, $C_{3-10}$ carbocyclyl-$C_{1-6}$-alkylamino, $C_{2-10}$ heterocyclyl($C_{1-6}$ hydroxyalkoxy), $C_{3-10}$ carbocyclyl($C_{1-6}$ hydroxyalkoxy), $C_{6-10}$ aryl($C_{1-6}$ hydroxyalkoxy), $C_{6-10}$ aryloxy-$C_{1-6}$-alkoxy, $C_{6-10}$ aryloxy, $C_{1-9}$ heteroaryloxy, $C_{1-6}$ heteroaryloxy-$C_{1-6}$-alkoxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{1-6}$ azidoalkoxy, $C_{5-12}$ fused bicyclyl, $C_{5-12}$ fused heterobicyclyl, $C_{5-12}$ fused bicyclyl-$C_{1-6}$-aliphatic, $C_{5-12}$ fused heterobicyclyl-$C_{1-6}$-aliphatic, $C_{5-12}$ fused bicycloxy, $C_{5-12}$ fused heterobicycloxy, $C_{5-12}$ fused bicyclylamino, $C_{5-12}$ fused heterobicyclylamino, $C_{5-12}$ fused bicyclyl-$C_{1-6}$-alkoxy, $C_{5-12}$ fused heterobicyclyl-$C_{1-6}$-alkoxy, $C_{5-12}$ fused bicyclyl-$C_{1-6}$-alkylamino, $C_{5-12}$ fused heterobicyclyl-$C_{1-6}$-alkylamino, $C_{5-12}$ fused bicycloxy-$C_{1-6}$-alkoxy, $C_{5-12}$ fused heterobicycloxy-$C_{1-6}$-alkoxy, $C_{5-12}$ fused bicyclylamino-$C_{1-6}$-alkoxy, $C_{5-12}$ fused heterobicyclylamino-$C_{1-6}$-alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)N($R^7$)—, $C_{5-12}$ fused heterobicyclyl-C(=O)N($R^7$)—, $C_{5-12}$ spiro bicyclyl, $C_{5-12}$ spiro heterobicyclyl, $C_{5-12}$ spiro bicyclyl-$C_{1-6}$-aliphatic, $C_{5-12}$ spiro heterobicyclyl-$C_{1-6}$-aliphatic, $C_{5-12}$ spiro bicycloxy, $C_{5-12}$ spiro heterobicycloxy, $C_{5-12}$ spiro bicyclylamino, $C_{5-12}$ spiro heterobicyclylamino, $C_{5-12}$ spiro bicyclyl-$C_{1-6}$-alkoxy, $C_{5-12}$ spiro heterobicyclyl-$C_{1-6}$-alkoxy, $C_{5-12}$ spiro bicyclyl-$C_{1-6}$-alkylamino, $C_{5-12}$ spiro heterobicyclyl-$C_{1-6}$-alkylamino, $C_{5-12}$ spiro bicycloxy-$C_{1-6}$-alkoxy, $C_{5-12}$ spiro heterobicycloxy-$C_{1-6}$-alkoxy, $C_{5-12}$ spiro bicyclylamino-$C_{1-6}$-alkoxy, $C_{5-12}$ spiro heterobicyclylamino-$C_{1-6}$-alkoxy, $C_{5-12}$ spiro bicyclyl-C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)N($R^7$)—, $C_{5-12}$ spiro heterobicyclyl-C(=O)N($R^7$)—, $C_{2-10}$ heterocyclyl, $C_{3-10}$ cycloalkyl, $C_{6-10}$ aryl, $C_{1-9}$ heteroaryl, $C_{2-10}$ heterocyclyl-$C_{1-6}$-aliphatic, $C_{3-10}$ cycloalkyl-$C_{1-6}$-aliphatic, $C_{6-10}$ aryl-$C_{1-6}$-aliphatic, $C_{1-9}$ heteroaryl-$C_{1-6}$-aliphatic, $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, or $C_{3-10}$ cycloalkyl-(CH$_2$)$_p$-G-(CH$_2$)$_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4; or wherein each of the $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, and $C_{3-10}$ cycloalkyl-(CH$_2$)$_p$-G-(CH$_2$)$_m$— is optionally substituted by one or more F, Cl, Br, I, $C_{1-6}$ alkyl, $C_{2-6}$ alkynyl, $C_{1-6}$ alkoxy or cyano;

$R^2$ is H, F, Cl, Br, I, cyano, hydroxy, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2N(R^{7a})$—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{1-6}$ aliphatic, $C_{1-6}$ alkoxy, $C_{1-6}$ hydroxyalkoxy, $C_{1-6}$ aminoalkoxy, hydroxy-substituted $C_{1-6}$ aminoalkoxy, $C_{1-6}$ haloalkoxy, amino-substituted $C_{1-6}$ haloalkoxy, $C_{1-6}$ alkylamino-$C_{1-6}$-haloalkoxy, hydroxy-substituted $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{3-10}$ cycloalkylamino, $C_{3-10}$ carbocyclyl-$C_{1-6}$-alkoxy, $C_{3-10}$ carbocyclyl-$C_{1-6}$-alkylamino, $C_{2-10}$ heterocyclyl($C_{1-6}$ hydroxyalkoxy), $C_{3-10}$ carbocyclyl($C_{1-6}$ hydroxyalkoxy), $C_{6-10}$ aryl($C_{1-6}$ hydroxyalkoxy), $C_{6-10}$ aryloxy-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{1-6}$ azidoalkoxy, $C_{5-12}$ fused bicyclyl, $C_{5-12}$ fused heterobicyclyl, $C_{5-12}$ fused bicyclyl-$C_{1-6}$-aliphatic, $C_{5-12}$ fused heterobicyclyl-$C_{1-6}$-aliphatic, $C_{5-12}$ fused bicycloxy, $C_{5-12}$ fused heterobicycloxy, $C_{5-12}$ fused bicyclylamino, $C_{5-12}$ fused heterobicyclylamino, $C_{5-12}$ fused bicyclyl-$C_{1-6}$-alkoxy, $C_{5-12}$ fused heterobicyclyl-$C_{1-6}$-alkoxy, $C_{5-12}$ fused bicyclyl-$C_{1-6}$-alkylamino, $C_{5-12}$ fused heterobicyclyl-$C_{1-6}$-alkylamino, $C_{5-12}$ fused bicycloxy-$C_{1-6}$-alkoxy, $C_{5-12}$ fused heterobicycloxy-$C_{1-6}$-alkoxy, $C_{5-12}$ fused bicyclylamino-$C_{1-6}$-alkoxy, $C_{5-12}$ fused heterobicyclylamino-$C_{1-6}$-alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)N($R^7$)—, $C_{5-12}$ fused heterobicyclyl-C(=O)N($R^7$)—, $C_{5-12}$ spiro bicyclyl, $C_{5-12}$ spiro heterobicyclyl, $C_{5-12}$ spiro bicyclyl-$C_{1-6}$-aliphatic, $C_{5-12}$ spiro heterobicyclyl-$C_{1-6}$-aliphatic, $C_{5-12}$ spiro bicycloxy, $C_{5-12}$ spiro heterobicycloxy, $C_{5-12}$ spiro bicyclylamino, $C_{5-12}$ spiro heterobicyclylamino, $C_{5-12}$ spiro bicyclyl-$C_{1-6}$-alkoxy, $C_{5-12}$ spiro heterobicyclyl-$C_{1-6}$-alkoxy, $C_{5-12}$ spiro bicyclyl-$C_{1-6}$-alkylamino, $C_{5-12}$ spiro heterobicyclyl-$C_{1-6}$-alkylamino, $C_{5-12}$ spiro bicycloxy-$C_{1-6}$-alkoxy, $C_{5-12}$ spiro heterobicycloxy-$C_{5-12}$-alkoxy, $C_{5-12}$ spiro bicyclylamino-$C_{1-6}$-alkoxy, $C_{5-12}$ spiro heterobicyclylamino-$C_{1-6}$-alkoxy, $C_{5-12}$ spiro bicyclyl-C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)N($R^7$)—, $C_{5-12}$ spiro heterobicyclyl-C(=O)N($R^7$)—, $C_{2-10}$ heterocyclyl, $C_{3-10}$ cycloalkyl, $C_{6-10}$ aryl, $C_{1-4}$ heteroaryl, $C_{2-10}$ heterocyclyl-$C_{1-6}$-aliphatic, $C_{3-10}$ cycloalkyl-$C_{1-6}$-aliphatic, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4;

$R^3$ is H, F, Cl, I, cyano, $R^{7a}R^7N$—, —C(=O)N$R^7R^{7a}$, —OC(=O)N$R^7R^{7a}$, —OC(=O)O$R^7$, —N($R^7$)C(=O)N$R^7R^{7a}$, —N($R^7$)C(=O)O$R^{7a}$, —N($R^7$)C(=O)—$R^{7a}$, $R^7R^{7a}N$—S(=O)$_2$—, $R^7$S(=O)$_2$—, $R^7$S(=O)$_2$N($R^{7a}$)—, $R^{7a}R^7N$—$C_{1-6}$ alkyl, $R^7$S(=O)—$C_{1-6}$ alkyl, $R^7R^{7a}N$—C(=O)—$C_{1-6}$ alkyl, $R^{7a}R^7N$—$C_{1-6}$ alkoxy, $R^7$S(=O)—$C_{1-6}$ alkoxy, $R^7R^{7a}N$—C(=O)—$C_{1-6}$ alkoxy, $C_{1-6}$ aliphatic, $C_{2-10}$ haloalkyl, $C_{6-10}$ aryl-$C_{2-10}$-alkoxy, $C_{1-9}$ heteroaryl-$C_{3-6}$-alkoxy, $C_{3-10}$ cycloalkyl-$C_{2-10}$-alkoxy, $C_{5-10}$ fused bicyclyl-$C_{2-10}$-alkoxy, $C_{2-10}$ heterocyclyl, $C_{3-10}$ cycloalkyl, $C_{1-4}$ heteroaryl, substituted $C_{6-10}$ aryl, $C_{2-10}$ heterocyclyl-$C_{1-6}$-aliphatic, $C_{3-10}$ cycloalkyl-$C_{1-6}$-aliphatic, $C_{1-4}$ heteroaryl-$C_{1-6}$-aliphatic, $C_{1-9}$ heteroaryloxy-$C_{1-6}$-alkoxy, substituted $C_{6-10}$ aryl-$C_{3-6}$-alkyl, $C_{2-10}$ hetrerocyclyl-$C_{1-6}$-alkyl, $C_{1-6}$ alkyl, $C_{1-6}$ hydroxyalkoxy, $C_{1-6}$ aminoalkoxy, hydroxy-substituted $C_{1-6}$ aminoalkoxy, $C_{1-6}$ haloalkoxy, amino-substituted $C_{1-6}$ haloalkoxy, $C_{1-6}$ alkylamino-$C_{1-6}$-haloalkoxy, hydroxy-substituted $C_{1-6}$ haloalkoxy, $C_{1-6}$ alkylamino-$C_{1-6}$-alkoxy, $C_{1-6}$ alkoxy-$C_{1-6}$-alkoxy, $C_{6-10}$ aryl-$C_{2-10}$-alkoxy, $C_{2-10}$ heterocyclyl-$C_{1-6}$-alkoxy, $C_{3-10}$ carbocyclyl-$C_{1-6}$-alkoxy, $C_{2-10}$ heterocyclyl($C_{1-6}$ hydroxyalkoxy), $C_{3-10}$ carbocyclyl($C_{1-6}$ hydroxyalkoxy), $C_{6-10}$ aryl($C_{1-6}$ hydroxyalkoxy), $C_{6-10}$ aryloxy-$C_{1-6}$-alkoxy, $C_{6-10}$ arylamino-$C_{1-6}$-alkoxy, $C_{6-10}$ aryloxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{3-10}$ cycloalkyloxy, $C_{1-6}$ azidoalkoxy, $C_{5-12}$ fused bicyclyl, $C_{5-12}$ fused heterobicyclyl, $C_{5-12}$ fused bicyclyl-$C_{1-6}$-aliphatic, $C_{5-12}$ fused heterobicyclyl-$C_{1-6}$-aliphatic, $C_{5-12}$ fused bicycloxy, $C_{5-12}$ fused heterobicycloxy, $C_{5-12}$ fused bicyclylamino, $C_{5-12}$ fused heterobicyclylamino, $C_{5-12}$ fused bicyclyl-$C_{1-6}$-alkoxy, $C_{5-12}$ fused heterobicyclyl-$C_{1-6}$-alkoxy, $C_{5-12}$ fused bicyclyl-$C_{1-6}$-alkylamino, $C_{5-12}$ fused heterobicyclyl-$C_{1-6}$-alkylamino, $C_{5-12}$ fused bicycloxy-$C_{1-6}$-alkoxy, $C_{5-12}$ fused heterobicycloxy-$C_{1-6}$-alkoxy, $C_{5-12}$ fused bicyclylamino-$C_{1-6}$-alkoxy, $C_{5-12}$ fused heterobicyclylamino-$C_{1-6}$-alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)N$R^7$—, $C_{5-12}$ fused heterobicyclyl-C(=O)N$R^7$—, $C_{5-12}$ spiro bicyclyl, $C_{5-12}$ spiro heterobicyclyl, $C_{5-12}$ spiro bicyclyl-$C_{1-6}$-aliphatic, $C_{5-12}$ spiro heterobicyclyl-$C_{1-6}$-aliphatic, $C_{5-12}$ spiro bicycloxy, $C_{5-12}$ spiro heterobicycloxy, $C_{5-12}$ spiro bicyclylamino, $C_{5-12}$ spiro heterobicyclylamino, $C_{5-12}$ spiro bicyclyl-$C_{1-6}$-alkoxy, $C_{5-12}$ spiro heterobicyclyl-$C_{1-6}$-alkoxy, $C_{5-12}$ spiro bicyclyl-$C_{1-6}$-alkylamino, $C_{5-12}$ spiro heterobicyclyl-$C_{1-6}$-alkylamino, $C_{5-12}$ spiro bicycloxy-$C_{1-6}$-alkoxy, $C_{5-12}$ spiro heterobicycloxy-$C_{1-6}$-alkoxy, $C_{5-12}$ spiro bicyclylamino-$C_{1-6}$-alkoxy, $C_{5-12}$ spiro heterobicyclylamino-$C_{1-6}$-alkoxy, $C_{5-12}$ spiro bicyclyl-C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)N$R^7$—, $C_{5-12}$ spiro heterobicyclyl-C(=O)N$R^7$—, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4; and $R^4$ is H, F, I, cyano, hydroxy, $R^{7a}R^7N$—, —C(=O)N$R^7R^{7a}$, —OC(=O)N$R^7R^{7a}$, —OC(=O)O$R^7$, —N($R^7$)C(=O)N$R^7R^{7a}$, —N($R^7$)C(=O)O$R^{7a}$, —N($R^7$)C(=O)—$R^{7a}$, $R^7R^{7a}N$—S(=O)—, $R^7$S(=O)—, $R^7$S(=O)N($R^{7a}$)—$R^{7a}R^7N$—$C_{1-6}$ alkyl, $R^7$S(=O)—$C_{1-6}$ alkyl, $R^7R^{7a}N$—C(=O)—$C_{1-6}$ alkyl, $R^{7a}R^7N$—$C_{1-6}$ alkoxy, $R^7$S(=O)—$C_{1-6}$ alkoxy, $R^7R^{7a}N$—C(=O)—$C_{1-6}$ alkoxy, $C_{1-6}$ aliphatic, $C_{2-10}$ alkoxy, $C_{1-6}$ hydroxyalkoxy, $C_{1-6}$ aminoalkoxy, hydroxy-substituted $C_{1-6}$ aminoalkoxy, $C_{1-6}$ haloalkoxy, amino-substituted $C_{1-6}$ haloalkoxy, $C_{1-6}$ alkylamino-$C_{1-6}$-haloalkoxy, hydroxy-substituted $C_{1-6}$ haloalkoxy, $C_{1-6}$ alkylamino-$C_{1-6}$-alkoxy, $C_{1-6}$ alkoxy-$C_{1-6}$-alkoxy, $C_{3-5}$ cycloalkyloxy, $C_{6-10}$ aryl-$C_{1-6}$-alkoxy, $C_{1-9}$ heteroaryl-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{7-10}$ cycloalkyloxy, $C_{3-10}$ cycloalkylamino, $C_{3-10}$ carbocyclyl-$C_{1-6}$-alkoxy, $C_{3-10}$ carbocyclyl-$C_{1-6}$-alkylamino, $C_{2-10}$ heterocyclyl($C_{1-6}$ hydroxyalkoxy), $C_{3-10}$ carbocyclyl($C_{1-6}$ hydroxyalkoxy), $C_{6-10}$ aryl($C_{1-6}$ hydroxyalkoxy), $C_{6-10}$ aryloxy-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{1-6}$ azidoalkoxy, $C_{5-12}$ fused bicyclyl, $C_{5-12}$ fused heterobicyclyl, $C_{5-12}$ fused bicyclyl-$C_{1-6}$-aliphatic, $C_{5-12}$ fused heterobicyclyl-$C_{1-6}$-aliphatic, $C_{5-12}$ fused bicycloxy, $C_{5-12}$ fused heterobicycloxy, $C_{5-12}$ fused bicyclylamino, $C_{5-12}$ fused heterobicyclylamino, $C_{5-12}$ fused bicyclyl-$C_{1-6}$-alkoxy, $C_{5-12}$ fused heterobicyclyl-$C_{1-6}$-alkoxy, $C_{5-12}$ fused bicyclyl-$C_{1-6}$-alkylamino, $C_{5-12}$ fused heterobicyclyl-$C_{1-6}$-alkylamino, $C_{5-12}$ fused bicycloxy-$C_{1-6}$-alkoxy, $C_{5-12}$ fused heterobicycloxy-$C_{1-6}$-alkoxy, $C_{5-12}$ fused bicyclylamino-$C_{1-6}$-alkoxy, $C_{5-12}$ fused heterobicyclylamino-$C_{1-6}$-alkoxy, $C_{5-12}$ fused bicyclyl-C(=O)—, $C_{5-12}$ fused bicyclyl-C(=O)O—, $C_{5-12}$ fused heterobicyclyl-C(=O)—, $C_{5-12}$ fused heterobicyclyl-C(=O)O—, $C_{5-12}$ fused bicyclylamino-C(=O)—, $C_{5-12}$ fused heterobicyclylamino-C(=O)—, $C_{5-12}$ fused bicyclyl-C(=O)N$R^7$—, $C_{5-12}$ fused heterobicyclyl-C(=O)N$R^7$—, $C_{5-12}$ spiro bicyclyl, $C_{5-12}$ spiro heterobicyclyl, $C_{5-12}$ spiro bicyclyl-$C_{1-6}$-aliphatic, $C_{5-12}$ spiro heterobicyclyl-$C_{1-6}$-aliphatic, $C_{5-12}$ spiro bicycloxy, $C_{5-12}$ spiro heterobicycloxy, $C_{5-12}$ spiro bicyclylamino, $C_{5-12}$ spiro heterobicyclylamino, $C_{5-12}$ spiro bicyclyl-$C_{1-6}$-alkoxy, $C_{5-12}$ spiro heterobicyclyl-$C_{1-6}$-alkoxy, $C_{5-12}$ spiro bicyclyl-$C_{1-6}$-alkylamino, $C_{5-12}$ spiro heterobicyclyl-$C_{1-6}$-alkylamino, $C_{5-12}$ spiro bicycloxy-$C_{1-6}$-alkoxy, $C_{5-12}$ spiro heterobicycloxy-$C_{1-6}$-alkoxy, $C_{5-12}$ spiro bicyclylamino-$C_{1-6}$-alkoxy, $C_{5-12}$ spiro heterobicyclylamino-$C_{1-6}$-alkoxy, $C_{5-12}$ spiro bicyclyl-C(=O)—, $C_{5-12}$ spiro bicyclyl-C(=O)O—, $C_{5-12}$ spiro heterobicyclyl-C(=O)—, $C_{5-12}$ spiro heterobicyclyl-C(=O)O—, $C_{5-12}$ spiro bicyclylamino-C(=O)—, $C_{5-12}$ spiro heterobicyclylamino-C(=O)—, $C_{5-12}$ spiro bicyclyl-C(=O)N($R^7$)—, $C_{5-12}$ spiro heterobicyclyl-C(=O)N($R^7$)—, $C_{2-10}$ heterocyclyl, $C_{3-10}$ cycloalkyl, $C_{6-10}$ aryl, $C_{1-9}$ heteroaryl, $C_{2-10}$ heterocyclyl-$C_{1-6}$-aliphatic, $C_{3-10}$ cycloalkyl-$C_{1-6}$-aliphatic, $C_{6-10}$ aryl-$C_{2-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4.

In some embodiments, each $R^5$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-6}$ aliphatic, $C_{1-6}$ halo aliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryloxy-$C_{1-6}$-aliphatic, $C_{2-10}$ heterocyclyloxy-$C_{1-6}$-aliphatic, $C_{3-10}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-10}$ cycloalkylamino-$C_{1-6}$-aliphatic, $C_{6-10}$ aryl, $C_{1-9}$ heteroaryl, $C_{2-10}$ heterocyclyl or $C_{3-10}$ carbocyclyl.

In some embodiments, each $R^{5a}$ is independently H, hydroxy, amino, F, Cl, Br, I, cyano, oxo (=O), $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S(=O)_2$—, $R^7S(=O)_2N(R^{7a})$—, $R^{7a}R^7N$—$C_{1-6}$ alkyl, $R^7S(=O)$—$C_{1-6}$ alkyl, $R^7R^{7a}N$—C(=O)—$C_{1-6}$ alkyl, $R^{7a}R^7N$—$C_{1-6}$ alkoxy, $R^7S(=O)$—$C_{1-6}$ alkoxy, $R^7R^{7a}N$—C(=O)—$C_{1-6}$ alkoxy, $C_{6-10}$ aryl, $C_{1-9}$ heteroaryl, $C_{1-6}$ alkoxy, $C_{1-6}$ alkyl, $C_{2-6}$ alkenyl, $C_{2-6}$ alkynyl, $C_{2-10}$ heterocyclyl, mercapto, nitro, $C_{6-10}$ aryl-$C_{1-6}$-alkyl, $C_{6-10}$ arylamino, $C_{1-9}$ heteroarylamino, $C_{6-10}$ aryl-$C_{1-6}$-alkylamino, $C_{1-9}$ heteroaryl-$C_{1-6}$-alkylamino, $C_{1-9}$ heteroaryloxy, $C_{1-9}$ heteroaryl-$C_{1-6}$-alkyl, $C_{6-10}$ aryl-$C_{1-6}$-alkoxy, $C_{1-9}$ heteroaryl-$C_{1-6}$-alkoxy, $C_{2-10}$ heterocyclyloxy, $C_{2-10}$ heterocyclyl-$C_{1-6}$-alkoxy, $C_{2-10}$ heterocyclylamino, $C_{2-10}$ heterocyclyl-$C_{1-6}$-alkylamino or $C_{6-10}$ aryloxy.

In some embodiments, each $R^7$ and $R^{7a}$ is independently H, $C_{1-6}$ aliphatic, $C_{1-6}$ halo aliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryloxy-$C_{1-6}$-aliphatic, $C_{2-10}$ heterocyclyloxy-$C_{1-6}$-aliphatic, $C_{3-10}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-10}$ cycloalkylamino-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted $C_{5-12}$ spiro bicyclic or $C_{5-12}$ fused bicyclic ring.

In some embodiments, N, $V_1$, $V_2$, $V_3$, $V_4$ and C(=Y) of Formula (I) define a group having Formula (III):

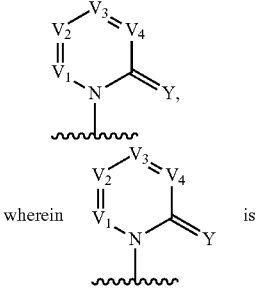

(III)

wherein 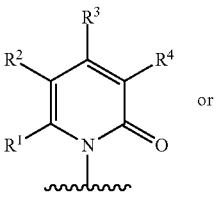 is

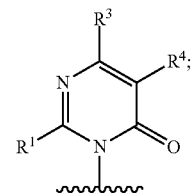

(IIIa)

or (IIIb)

each $R^1$ is H, F, Cl, Br, I, cyano, hydroxy, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{5a}$, —N($R^7$)C(=O)—$R^{7a}$, $R^7R^{7a}N$—S(=O)$_2$—, $R^7S(=O)_2$—, $R^7S(=O)_2N(R^{7a})$—, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-$(CH_2)_m$— is optionally substituted by one or more F, Cl, Br, I, $C_{1-6}$ alkyl, $C_{2-6}$ alkynyl, $C_{1-6}$ alkoxy or cyano;

$R^2$ is H, F, Cl, Br, I, cyano, hydroxy, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{5a}$, —N($R^7$)C(=O)—$R^{7a}$, $R^7R^{7a}N$—S(=O)$_2$—, $R^7S(=O)_2$—, $R^7S(=O)_2N(R^{7a})$—, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$- alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-4}$ heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4;

each $R^3$ is H, F, Cl, I, cyano, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2N$($R^{7a}$)—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{1-6}$ aliphatic, $C_{2-6}$ haloalkyl, $C_{6-10}$ aryl-$C_{2-6}$-alkoxy, $C_{1-9}$ heteroaryl-$C_{3-6}$-alkoxy, $C_{1-9}$ heteroaryloxy-$C_{1-6}$-alkoxy, $C_{3-10}$ cycloalkyl-$C_{2-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{1-4}$ heteroaryl, substituted $C_{6-10}$ aryl, $C_{1-4}$ heteroaryl-$C_{1-6}$-aliphatic, substituted $C_{6-10}$ aryl-$C_{3-6}$-alkyl, $C_{2-10}$ hetrerocyclyl-$C_{1-6}$-alkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-haloalkoxy, $C_{1-6}$ alkylamino-$C_{1-6}$-alkoxy, $C_{1-6}$ alkoxy-$C_{1-6}$-alkoxy, $C_{6-10}$ aryl-$C_{2-10}$-alkoxy, $C_{2-10}$ heterocyclyl-$C_{1-6}$-alkoxy, $C_{3-10}$ carbocyclyl-$C_{1-6}$-alkoxy, $C_{2-10}$ heterocyclyloxy, $C_{3-10}$ cycloalkyloxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4; and each $R^4$ is H, F, I, cyano, hydroxy, $R^{7a}R^7N$—, —C(=O)$NR^7R^{7a}$, —OC(=O)$NR^7R^{7a}$, —OC(=O)$OR^7$, —N($R^7$)C(=O)$NR^7R^{7a}$, —N($R^7$)C(=O)$OR^{7a}$, —N($R^7$)C(=O)—$R^{7a}$, $R^7R^{7a}N$—S(=O)$_2$—, $R^7S$(=O)$_2$—, $R^7S$(=O)$_2N$($R^{7a}$)—, $R^{7a}R^7N$—$C_{1-6}$ alkyl, $R^7S$(=O)—$C_{1-6}$ alkyl, $R^7R^{7a}N$—C(=O)—$C_{1-6}$ alkyl, $R^{7a}R^7N$—$C_{1-6}$ alkoxy, $R^7S$(=O)—$C_{1-6}$ alkoxy, $R^7R^{7a}N$—C(=O)—$C_{1-6}$ alkoxy, $C_{1-6}$ aliphatic, $C_{1-6}$ haloalkyl, $C_{2-10}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-5}$ cycloalkyloxy, $C_{6-10}$ aryl-$C_{1-6}$-alkoxy, $C_{1-9}$ heteroaryl-$C_{1-6}$-alkoxy, $C_{1-9}$ heteroaryloxy-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{3-10}$ cycloalkylamino, $C_{2-10}$ heterocyclyl-$C_{1-6}$-alkoxy, $C_{3-10}$ carbocyclyl-$C_{1-6}$-alkoxy, $C_{3-10}$ carbocyclyl-$C_{1-6}$-alkylamino, $C_{6-10}$ aryloxy, $C_{1-10}$ heteroaryloxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{2-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4.

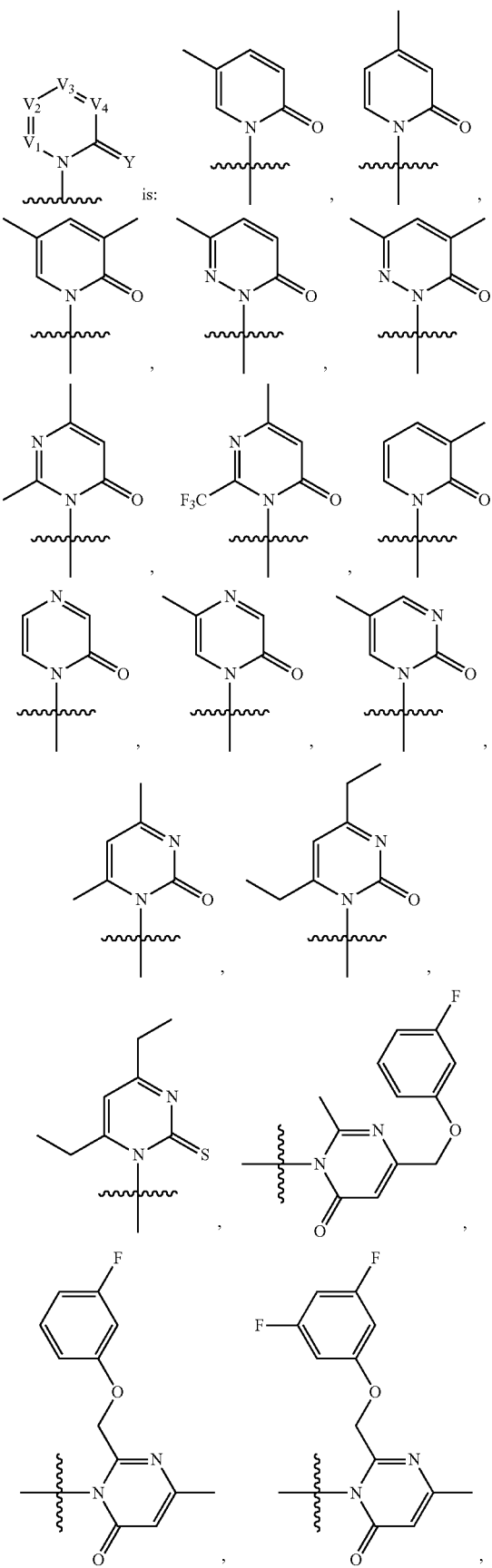

is:

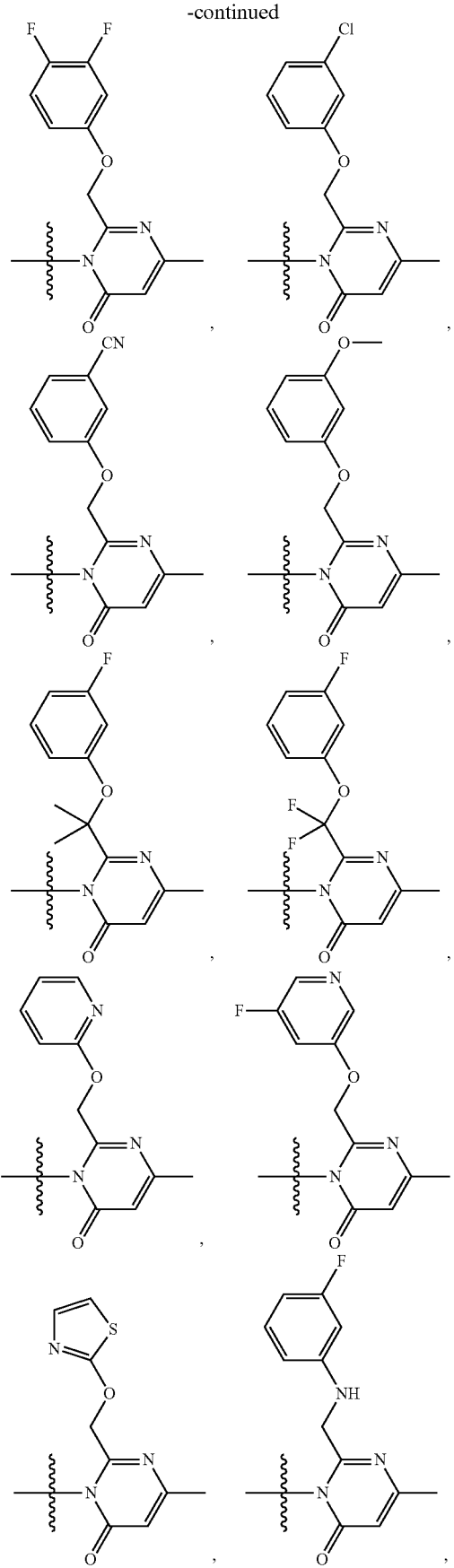
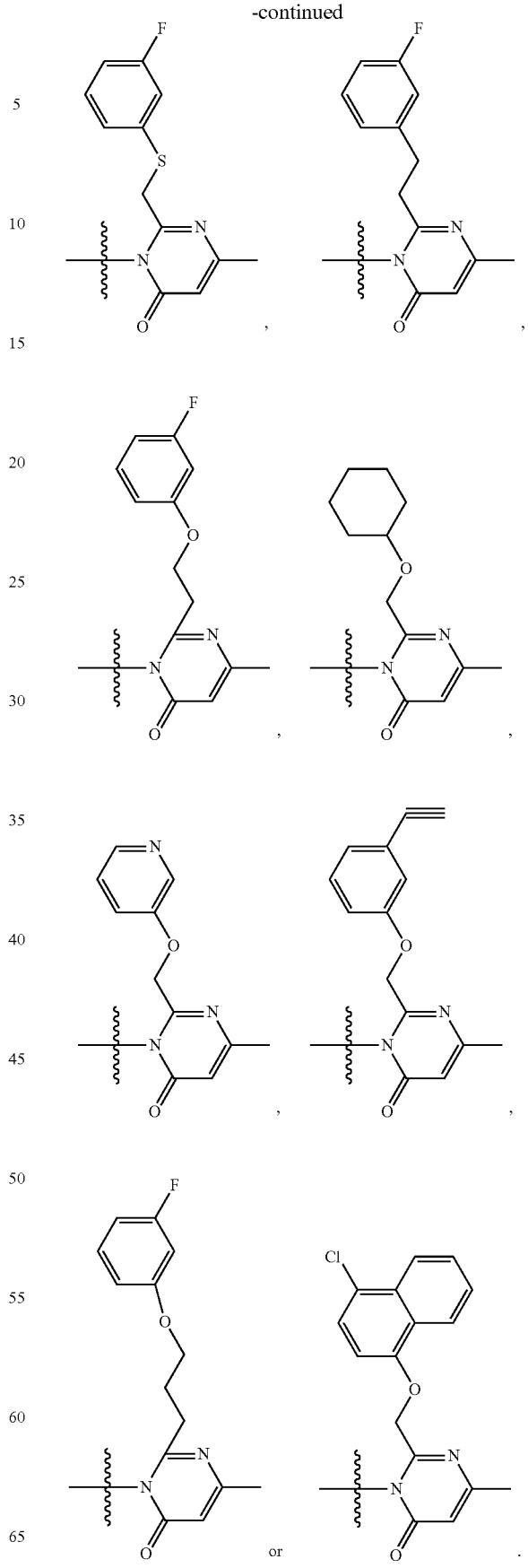

In some embodiments,
In some embodiments, A is:

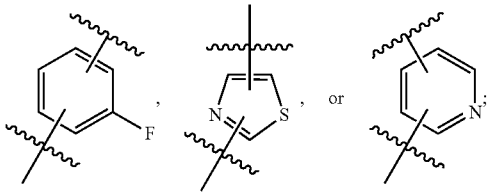

X is a bond, $NR^5$, O, S, $-(CH_2)_m-$, $-(CH_2)_m-C(=Y)-$, $-(CH_2)_m-C(=Y)-O-$, $-(CH_2)_m-C(=Y)-N(R^5)-$, $-(CH_2)_m-S(=O)_t-$, $-(CH_2)_m-S(=O)_t-N(R^7)-$, $-(CH_2)_m-Y-$, $-CH=CH-$, or $-C\equiv C-$, wherein each t is 1 or 2; each m is 0, 1, 2 or 3; Y is O;

B is $-NR^7R^{7a}$, $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl, or $C_{5-12}$ spiro heterobicyclyl; wherein each of the $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl and $C_{5-12}$ spiro heterobicyclyl is optionally substituted by oxo (=O), hydroxy, amino, halo, cyano, $C_{6-10}$ aryl, $C_{1-9}$ heteroaryl, $C_{1-6}$ alkoxy, $C_{1-6}$ alkylamino, $C_{1-6}$ alkyl, $C_{2-6}$ alkenyl, $C_{2-6}$ alkynyl, $C_{2-10}$ heterocyclyl, mercapto, nitro, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy $C_{1-6}$ alkoxy;

$R^1$ is H, F, Cl, Br, I, cyano, hydroxy, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{5a}$, $-N(R^7)C(=O)-R^{7a}$, $R^7R^{7a}N-S(=O)_2-$, $R^7S(=O)_2-$, $R^7S(=O)_2N(R^{7a})-$, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, or $C_{3-10}$ cycloalkyl-$(CH_2)_p$-G-$(CH_2)_m-$, wherein each G is O, S, $NR^5$, S(=O), S(=O)$_2$, C(=O), $-C(=O)NH-$, $-OC(=O)NH-$, $-OC(=O)-$, $-NHC(=O)NH-$, $-HN-S(=O)_t-$, $-OS(=O)_t-$, or $-OS(=O)_tNH-$; each t is 1 or 2; each p and m is independently 0, 1, 2, 3 or 4; or wherein each of the $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, and $C_{3-10}$ cycloalkyl-$(CH_2)_p$-G-$(CH_2)_m-$ is optionally substituted by one or more F, Cl, Br, I, methyl, ethyl, propyl, ethynyl, propynyl, butyryl, methoxy, ethoxy or cyano;

$R^2$ is H, F, Cl, Br, I, cyano, hydroxy, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{5a}$, $-N(R^7)C(=O)-R^{7a}$, $R^7R^{7a}N-S(=O)_2-$, $R^7S(=O)_2-$, $R^7S(=O)_2N(R^{7a})-$, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-4}$ heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, or $C_{3-10}$ cycloalkyl-$(CH_2)_p$-G-$(CH_2)_m-$, wherein each G is O, S, $NR^5$, S(=O), S(=O)$_2$, C(=O), $-C(=O)NH-$, $-OC(=O)NH-$, $-OC(=O)-$, $-NHC(=O)NH-$, $-HN-S(=O)_t-$, $-OS(=O)_t-$, or $-OS(=O)_tNH-$; each t is 1 or 2; each p and m is independently 0, 1, 2, 3 or 4;

$R^3$ is H, F, Cl, I, cyano, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $R^7S(=O)_2-$, $R^7S(=O)_2N(R^{7a})-$, $R^{7a}R^7N-C_{1-6}$ alkyl, $R^7S(=O)-C_{1-6}$ alkyl, $R^7R^{7a}N-C(=O)-C_{1-6}$ alkyl, $R^{7a}R^7N-C_{1-6}$ alkoxy, $R^7S(=O)-C_{1-6}$ alkoxy, $R^7R^{7a}N-C(=O)-C_{1-6}$ alkoxy, $C_{1-6}$ aliphatic, $C_{2-6}$ haloalkyl, $C_{6-10}$ aryl-$C_{2-6}$-alkoxy, $C_{1-9}$ heteroaryl-$C_{3-6}$-alkoxy, $C_{1-9}$ heteroaryloxy-$C_{1-6}$-alkoxy, $C_{3-10}$ cycloalkyl-$C_{2-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{1-4}$ heteroaryl, substituted $C_{6-10}$ aryl, $C_{1-4}$ heteroaryl-$C_{1-6}$-aliphatic, substituted $C_{6-10}$ aryl-$C_{3-6}$-alkyl, $C_{2-10}$ heterocyclyl-$C_{1-6}$-alkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-haloalkoxy, $C_{1-6}$ alkylamino-$C_{1-6}$-alkoxy, $C_{1-6}$ alkoxy-$C_{1-6}$-alkoxy, $C_{6-10}$ aryl-$C_{2-10}$-alkoxy, $C_{2-10}$ heterocyclyl-$C_{1-6}$-alkoxy, $C_{3-10}$ carbocyclyl-$C_{1-6}$-alkoxy, $C_{2-10}$ heterocyclyloxy, $C_{3-10}$ cycloalkyloxy, $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, or $C_{3-10}$ cycloalkyl-$(CH_2)_p$-G-$(CH_2)_m-$, wherein each G is O, S, $NR^5$, S(=O), S(=O)$_2$, C(=O), $-C(=O)NH-$, $-OC(=O)NH-$, $-OC(=O)-$, $-NHC(=O)NH-$, $-HN-S(=O)_t-$, $-OS(=O)_t-$, or $-OS(=O)_tNH-$; each t is 1 or 2; each p and m is independently 0, 1, 2, 3 or 4;

$R^4$ is H, F, I, cyano, hydroxy, $R^{7a}R^7N-$, $-C(=O)NR^7R^{7a}$, $-OC(=O)NR^7R^{7a}$, $-OC(=O)OR^7$, $-N(R^7)C(=O)NR^7R^{7a}$, $-N(R^7)C(=O)OR^{7a}$, $-N(R^7)C(=O)-R^{7a}$, $R^7R^{7a}N-S(=O)_2-$, $R^7S(=O)_2-$, $R^7S(=O)_2N(R^{7a})-$, $R^{7a}R^7N-C_{1-6}$ alkyl, $R^7S(=O)-C_{1-6}$ alkyl, $R^7R^{7a}N-C(=O)-C_{1-6}$ alkyl, $R^{7a}R^7N-C_{1-6}$ alkoxy, $R^7S(=O)-C_{1-6}$ alkoxy, $R^7R^{7a}N-C(=O)-C_{1-6}$ alkoxy, $C_{1-6}$ aliphatic, $C_{1-6}$ haloalkyl, $C_{2-10}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-5}$ cycloalkyloxy, $C_{6-10}$ aryl-$C_{1-6}$-alkoxy, $C_{1-9}$ heteroaryl-$C_{1-6}$-alkoxy, $C_{1-9}$ heteroaryloxy-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{3-10}$ cycloalkylamino, $C_{2-10}$ heterocyclyl-$C_{1-6}$-alkoxy, $C_{3-10}$ carbocyclyl-$C_{1-6}$-alkoxy, $C_{3-10}$ carbocyclyl-$C_{1-6}$-alkylamino, $C_{6-10}$ aryloxy, $C_{1-10}$ heteroaryloxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{2-6}$-aliphatic, $C_{1-9}$ heteroaryl-$C_{1-6}$-aliphatic, $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, or $C_{3-10}$ cycloalkyl-$(CH_2)_p$-G-$(CH_2)_m-$, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4;

each $R^5$ is independently H, $R^7R^{7a}NC(=O)$—, $R^7OC(=O)$—, $R^7C(=O)$—, $R^7R^{7a}NS(=O)$—, $R^7OS(=O)$—, $R^7S(=O)$—, $R^7R^{7a}NS(=O)_2$—, $R^7OS(=O)_2$—, $R^7S(=O)_2$—, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl-$C_{1-3}$-alkyl, $C_{2-10}$ heterocyclyl-$C_{1-3}$-alkyl, $C_{3-10}$ cycloalkyl-$C_{1-3}$-alkyl, $C_{6-10}$ aryl, $C_{1-9}$ heteroaryl, $C_{2-10}$ heterocyclyl or $C_{3-10}$ carbocyclyl; and each $R^7$ and $R^{7a}$ is independently H, $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring.

In some embodiments, A, X and B define a group having Formula (II):

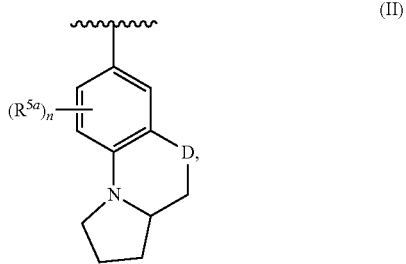

(II)

wherein D is O; n is 0, 1 or 2; and each $R^{5a}$ is independently H, hydroxy, amino, F, Cl, Br, I, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, cyano, nitro, mercapto, $C_{1-4}$ alkyl, $C_{1-4}$ alkoxy, $C_{1-4}$ alkylamino, $C_{1-4}$ alkylthio, $C_{6-10}$ aryl, or $C_{1-9}$ heteroaryl.

In some embodiments, Formula (IV) is

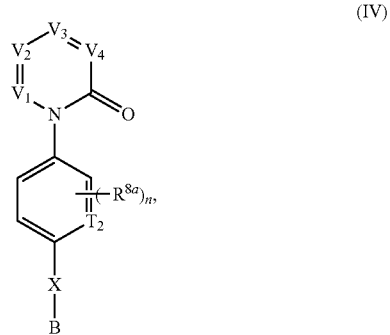

(IV)

wherein $V_1$ is N or CR$^1$, $V_2$ is N or CR$^2$, $V_3$ is N or CR$^3$, and $V_4$ is N or CR$^4$, wherein at most one of the $V_1$, $V_2$, $V_3$ and $V_4$ is N;

$T_2$ is N or CR$^{10}$;

X is a bond, NR$^5$, O, S, —(CH$_2$)$_m$—, —(CH$_2$)$_m$—Y—, —C(=O)—, —C(=O)NH—, —CH=CH—, or C≡C—, wherein each m is independently 0, 1, 2 or 3;

B is —NR$^7$R$^{7a}$, $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl, or $C_{5-12}$ spiro heterobicyclyl; wherein each of the $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl and $C_{5-12}$ spiro heterobicyclyl is optionally substituted by oxo (=O), hydroxy, amino, halo, cyano, $C_{6-10}$ aryl, $C_{1-9}$ heteroaryl, $C_{1-6}$ alkoxy, $C_{1-6}$ alkylamino, $C_{1-6}$ alkyl, $C_{2-6}$ alkenyl, $C_{2-6}$ alkynyl, $C_{2-10}$ heterocyclyl, mercapto, nitro, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S=O)$_2$—, hydroxy-substituted $C_{1-6}$ alkyl-S(=O)—, hydroxy-substituted $C_{1-6}$ alkyl-S(=O)$_2$—, or carboxy $C_{1-6}$ alkoxy;

$R^1$ is H, F, Cl, Br, I, cyano, hydroxy, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{5a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{1-6}$-aliphatic, $C_{1-9}$ heteroaryl-$C_{1-6}$-aliphatic, $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, or $C_{3-10}$ cycloalkyl-(CH$_2$)$_p$-G-(CH$_2$)$_m$—, wherein each G is O, S, NR$^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4; or wherein each of the $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, and $C_{3-10}$ cycloalkyl-(CH$_2$)$_p$-G-(CH$_2$)$_m$— is optionally substituted by one or more F, Cl, Br, I, methyl, ethyl, propyl, ethynyl, propynyl, butyryl, methoxy, ethoxy or cyano;

$R^2$ is H, F, Cl, Br, I, cyano, hydroxy, $R^{7a}R^7N$—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{5a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-4}$ heteroaryl, $C_{6-10}$ aryl-$C_{1-6}$-aliphatic, $C_{1-9}$ heteroaryl-$C_{1-6}$-aliphatic, $C_{6-10}$ aryl-(CH$_2$)$_p$-G-(CH$_2$)$_m$—, $C_{1-9}$ heteroaryl-(CH$_2$)$_p$-G-(CH$_2$)$_m$—, $C_{2-10}$ heterocyclyl-(CH$_2$)$_p$-G-(CH$_2$)$_m$—, or $C_{3-10}$ cycloalkyl-(CH$_2$)$_p$-G-(CH$_2$)$_m$—, wherein each G is O, S, NR$^5$, S(=O), S(=O)$_2$, C(=O), —C(=O)NH—, —OC(=O)NH—, —OC(=O)—, —NHC(=O)NH—, —HN—

S(=O)$_t$—, —OS(=O)$_t$—, or —OS(=O)$_t$NH—; each t is 1 or 2; each p and m is independently 0, 1, 2, 3 or 4;

R$^3$ is H, F, Cl, I, cyano, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^{7a}$R$^7$N—C$_{1-6}$ alkyl, R$^7$S(=O)—C$_{1-6}$ alkyl, R$^7$R$^{7a}$N—C(=O)—C$_{1-6}$ alkyl, R$^{7a}$R$^7$N—C$_{1-6}$ alkoxy, R$^7$S(=O)—C$_{1-6}$ alkoxy, R$^7$R$^{7a}$N—C(=O)—C$_{1-6}$ alkoxy, C$_{1-6}$ aliphatic, C$_{2-6}$ haloalkyl, C$_{6-10}$ aryl-C$_{2-6}$-alkoxy, C$_{1-9}$ heteroaryl-C$_{3-6}$-alkoxy, C$_{1-9}$ heteroaryloxy-C$_{1-6}$-alkoxy, C$_{3-10}$ cycloalkyl-C$_{2-6}$-alkoxy, C$_{2-10}$ heterocyclyl, C$_{3-10}$ cycloalkyl, C$_{2-10}$ heterocyclyl-C$_{1-6}$-aliphatic, C$_{3-10}$ cycloalkyl-C$_{1-6}$-aliphatic, C$_{1-4}$ heteroaryl, substituted C$_{6-10}$ aryl, C$_{1-4}$ heteroaryl-C$_{1-6}$-aliphatic, substituted C$_{6-10}$ aryl-C$_{3-6}$-alkyl, C$_{2-10}$ heterocyclyl-C$_{1-6}$-alkyl, C$_{1-6}$ alkoxy, C$_{1-6}$ hydroxyalkoxy, C$_{1-6}$ aminoalkoxy, C$_{1-6}$ haloalkoxy, C$_{1-6}$ alkylamino-C$_{1-6}$-haloalkoxy, C$_{1-6}$ alkylamino-C$_{1-6}$-alkoxy, C$_{1-6}$ alkoxy-C$_{1-6}$-alkoxy, C$_{6-10}$ aryl-C$_{2-10}$-alkoxy, C$_{2-10}$ heterocyclyl-C$_{1-6}$-alkoxy, C$_{3-10}$ carbocyclyl-C$_{1-6}$-alkoxy, C$_{2-10}$ heterocyclyloxy, C$_{3-10}$ cycloalkyloxy, C$_{6-10}$ aryl-(CH$_2$)$_p$-G-(CH$_2$)$_m$—, C$_{1-9}$ heteroaryl-(CH$_2$)$_p$-G-(CH$_2$)$_m$—, C$_{2-10}$ heterocyclyl-(CH$_2$)$_p$-G-(CH$_2$)$_m$—, or C$_{3-10}$ cycloalkyl-(CH$_2$)$_p$-G-(CH$_2$)$_m$—, wherein each G is O, S, NR$^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4;

R$^4$ is H, F, I, cyano, hydroxy, R$^{7a}$R$^7$N—, —C(=O)NR$^7$R$^{7a}$, —OC(=O)NR$^7$R$^{7a}$, —OC(=O)OR$^7$, —N(R$^7$)C(=O)NR$^7$R$^{7a}$, —N(R$^7$)C(=O)OR$^{7a}$, —N(R$^7$)C(=O)—R$^{7a}$, R$^7$R$^{7a}$N—S(=O)$_2$—, R$^7$S(=O)$_2$—, R$^7$S(=O)$_2$N(R$^{7a}$)—, R$^7$R$^{7a}$N—C$_{1-6}$ alkyl, R$^7$S(=O)—C$_{1-6}$ alkyl, R$^7$R$^{7a}$N—C(=O)—C$_{1-6}$ alkyl, R$^{7a}$R$^7$N—C$_{1-6}$ alkoxy, R$^7$S(=O)—C$_{1-6}$ alkoxy, R$^7$R$^{7a}$N—C(=O)—C$_{1-6}$ alkoxy, C$_{1-6}$ aliphatic, C$_{1-6}$ haloalkyl, C$_{2-10}$ alkoxy, C$_{1-6}$ hydroxyalkoxy, C$_{1-6}$ aminoalkoxy, C$_{1-6}$ haloalkoxy, C$_{1-6}$ alkylamino-C$_{1-6}$-alkoxy, C$_{1-6}$ alkoxy-C$_{1-6}$-alkoxy, C$_{3-5}$ cycloalkyloxy, C$_{6-10}$ aryl-C$_{1-6}$-alkoxy, C$_{1-9}$ heteroaryl-C$_{1-6}$-alkoxy, C$_{1-9}$ heteroaryloxy-C$_{1-6}$-alkoxy, C$_{1-9}$ heteroaryl-C$_{1-6}$-alkylamino, C$_{2-10}$ heterocyclyl-C$_{1-6}$-alkoxy, C$_{2-10}$ heterocyclyl-C$_{1-6}$-alkylamino, C$_{3-10}$ cycloalkylamino, C$_{2-10}$ heterocyclyl-C$_{1-6}$-alkoxy, C$_{3-10}$ carbocyclyl-C$_{1-6}$-alkoxy, C$_{3-10}$ carbocyclyl-C$_{1-6}$-alkylamino, C$_{6-10}$ aryloxy, C$_{1-10}$ heteroaryloxy, C$_{2-10}$ heterocyclyl, C$_{3-10}$ cycloalkyl, C$_{2-10}$ heterocyclyl-C$_{1-6}$-aliphatic, C$_{3-10}$ cycloalkyl-C$_{1-6}$-aliphatic, C$_{6-10}$ aryl, C$_{1-9}$ heteroaryl, C$_{6-10}$ aryl-C$_{2-6}$-aliphatic, C$_{1-9}$ heteroaryl-C$_{1-6}$-aliphatic, C$_{6-10}$ aryl-(CH$_2$)$_p$-G-(CH$_2$)$_m$—, C$_{1-9}$ heteroaryl-(CH$_2$)$_p$-G-(CH$_2$)$_m$—, C$_{2-10}$ heterocyclyl-(CH$_2$)$_p$-G-(CH$_2$)$_m$—, or C$_{3-10}$ cycloalkyl-(CH$_2$)$_p$-G-(CH$_2$)$_m$—, wherein each G is O, S, NR$^5$, S(=O), S(=O)$_2$, C(=O), —C(=O)NH—, —OC(=O)NH—, —OC(=O)—, —NHC(=O)NH—, —HN—S(=O)$_t$—, —OS(=O)$_t$—, or —OS(=O)$_t$NH—; each t is 1 or 2; each p and m is independently 0, 1, 2, 3 or 4;

each R$^5$ is independently H, R$^7$R$^{7a}$NC(=O)—, R$^7$OC(=O)—, R$^7$C(=O)—, R$^7$R$^{7a}$NS(=O)—, R$^7$OS(=O)—, R$^7$S(=O)—, R$^7$R$^{7a}$NS(=O)$_2$—, R$^7$OS(=O)$_2$—, R$^7$S(=O)$_2$—, C$_{1-3}$ alkyl, C$_{1-3}$ haloalkyl, C$_{1-3}$ hydroxyalkyl, C$_{1-3}$ aminoalkyl, C$_{1-3}$ alkoxy-C$_{1-3}$-alkyl, C$_{1-3}$ alkylamino-C$_{1-3}$-alkyl, C$_{1-3}$ alkylthio-C$_{1-3}$-alkyl, C$_{6-10}$ aryl-C$_{1-3}$-alkyl, C$_{1-9}$ heteroaryl-C$_{1-3}$-alkyl, C$_{2-10}$ heterocyclyl-C$_{1-3}$-alkyl, C$_{3-10}$ cycloalkyl-C$_{1-3}$-alkyl, C$_{6-10}$ aryl, C$_{1-9}$ heteroaryl, C$_{2-10}$ heterocyclyl or C$_{3-10}$ carbocyclyl;

each R$^7$ and R$^{7a}$ is independently H, C$_{1-6}$ aliphatic, C$_{1-6}$ haloaliphatic, C$_{1-6}$ hydroxyaliphatic, C$_{1-6}$ aminoaliphatic, C$_{1-6}$ alkoxy-C$_{1-6}$-aliphatic, C$_{1-6}$ alkylamino-C$_{1-6}$-aliphatic, C$_{1-6}$ alkylthio-C$_{1-6}$-aliphatic, C$_{6-10}$ aryl-C$_{1-6}$-aliphatic, C$_{1-9}$ heteroaryl-C$_{1-6}$-aliphatic, C$_{2-10}$ heterocyclyl-C$_{1-6}$-aliphatic, C$_{3-10}$ cycloalkyl-C$_{1-6}$-aliphatic, C$_{6-10}$ aryl, C$_{1-9}$ heteroaryl, C$_{2-10}$ heterocyclyl or C$_{3-10}$ carbocyclyl; with the proviso that where R$^7$ and R$^{7a}$ are bonded to the same nitrogen atom, R$^7$ and R$^{7a}$, together with the nitrogen atom they are attached to, optionally form a substituted or unsubstituted 3-8 membered ring;

each R$^{8a}$ is independently H, hydroxy, amino, F, Cl, Br, I, —N(CH$_3$)$_2$, —C(=O)NH—C$_{1-4}$ alkyl, —OC(=O)NH—C$_{1-4}$ alkyl, —OC(=O)O—C$_{1-4}$ alkyl, —NHC(=O)NH—C$_{1-4}$ alkyl, —NHC(=O)O—C$_{1-4}$ alkyl, —NHC(=O)—C$_{1-4}$ alkyl, C$_{1-4}$ alkyl-NH—S(=O)$_2$—, C$_{1-4}$ alkyl-S(=O)$_2$—, C$_{1-4}$ alkyl-S(=O)$_2$NH—, cyano, nitro, mercapto, C$_{1-4}$ alkyl, trifluoromethyl, C$_{1-4}$ alkoxy, C$_{1-4}$ alkylamino, C$_{1-4}$ alkylthio, C$_{6-10}$ aryl, C$_{6-10}$ aryl-C$_{1-4}$-alkyl or C$_{1-9}$ heteroaryl;

n is 0, 1, 2 or 3; and each R$^{10}$ is independently H, hydroxy, amino, F, Cl, Br, I, cyano, nitro, mercapto, C$_{1-4}$ alkyl, trifluoromethyl, C$_{1-4}$ alkoxy, C$_{1-4}$ alkylamino, or C$_{1-4}$ alkylthio.

In some embodiments, B is —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$,

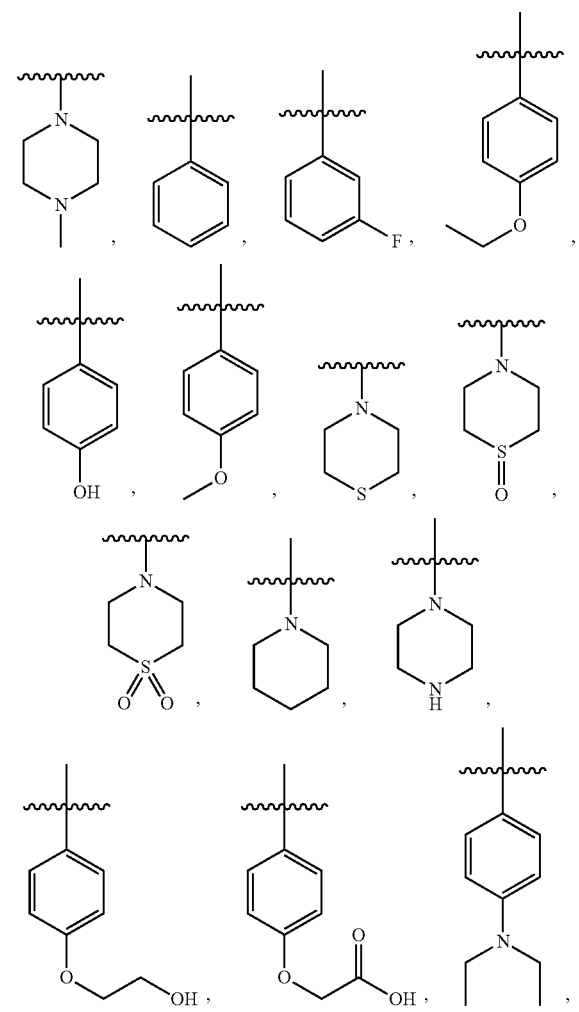

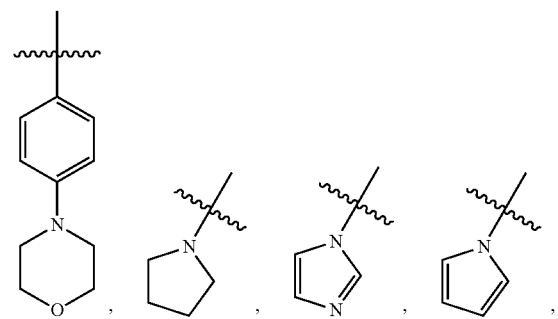
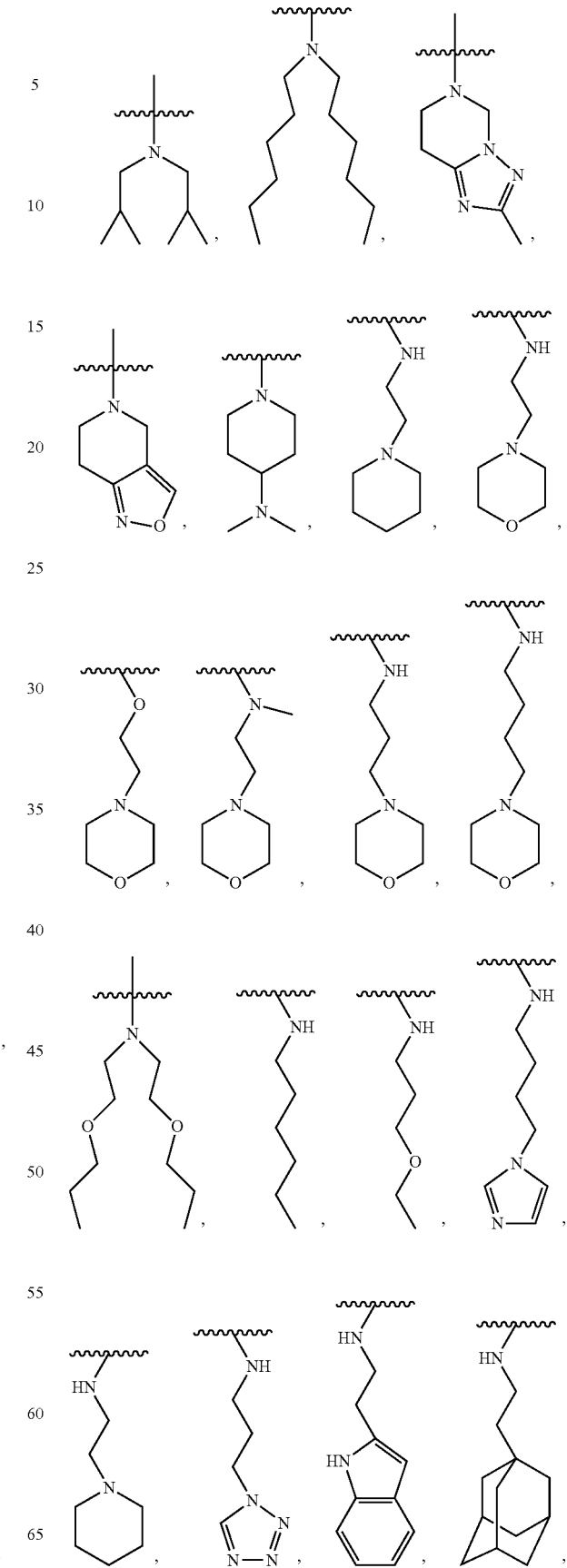

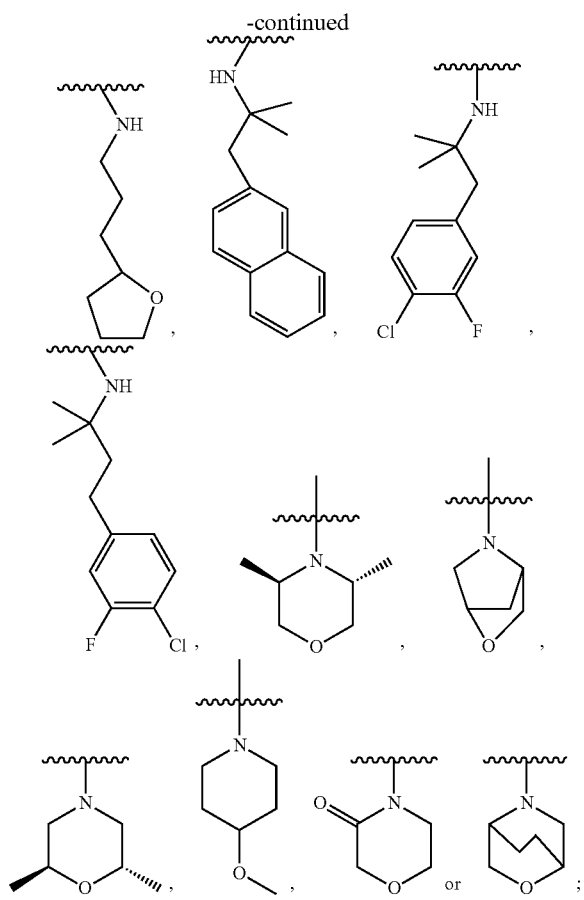

R¹ is H, F, Cl, Br, I, cyano, hydroxy, —N(CH₃)₂, —C(=O)NH—C₁₋₄ alkyl, —OC(=O)NH—C₁₋₄ alkyl, —OC(=O)O—C₁₋₄ alkyl, —NHC(=O)NH—C₁₋₄ alkyl, —NHC(=O)O—C₁₋₄ alkyl, —NHC(=O)—C₁₋₄ alkyl, C₁₋₄ alkyl-NH—S(=O)₂—, C₁₋₄ alkyl-S(=O)₂—, C₁₋₄ alkyl-S(=O)₂NH—, methyl, ethyl, propyl, isopropyl, butyl, ter-butyl, trifluoromethyl, phenyl-(CH₂)ₚ-G-(CH₂)ₘ—, (fluoro-substituted phenyl)-(CH₂)ₚ-G-(CH₂)ₘ—, thiazolyl-(CH₂)ₚ-G-(CH₂)ₘ—, pyridyl-(CH₂)ₚ-G-(CH₂)ₘ—, phenylethyl, cyclohexyl-(CH₂)ₚ-G-(CH₂)ₘ—, naphthyl-(CH₂)ₚ-G-(CH₂)ₘ—, or morpholinyl-(CH₂)ₚ-G-(CH₂)ₘ—, wherein each G is O, S, NR⁵, S(=O), S(=O)₂, C(=O), —C(=O)NH—, —OC(=O)NH—, —OC(=O)—, —NHC(=O)NH—, —HN—S(=O)ₜ—, —OS(=O)ₜ—, or —OS(=O)ₜNH—; each t is 1 or 2; each p and m is independently 0, 1, 2, 3 or 4; or wherein each of the phenyl-(CH₂)ₚ-G-(CH₂)ₘ—, (fluoro-substituted phenyl)-(CH₂)ₚ-G-(CH₂)ₘ—, thiazolyl-(CH₂)ₚ-G-(CH₂)ₘ—, pyridyl-(CH₂)ₚ-G-(CH₂)ₘ—, phenylethyl, cyclohexyl-(CH₂)ₚ-G-(CH₂)ₘ—, naphthyl-(CH₂)ₚ-G-(CH₂)ₘ—, and morpholinyl-(CH₂)ₚ-G-(CH₂)ₘ— is optionally substituted by one or more F, Cl, Br, I, methyl, ethyl, propyl, ethynyl, propynyl, butyryl, methoxy, ethoxy or cyano;

R² is H, F, Cl, Br, I, cyano, hydroxy, —N(CH₃)₂, —C(=O)NH—C₁₋₄ alkyl, —OC(=O)NH—C₁₋₄ alkyl, —OC(=O)O—C₁₋₄ alkyl, —NHC(=O)NH—C₁₋₄ alkyl, —NHC(=O)O—C₁₋₄ alkyl, —NHC(=O)—C₁₋₄ alkyl, C₁₋₄ alkyl-NH—S(=O)₂—, C₁₋₄ alkyl-S(=O)₂—, C₁₋₄ alkyl-S(=O)₂NH—, methyl, ethyl, propyl, isopropyl, butyl, ter-butyl, trifluoromethyl, phenyl-(CH₂)ₚ-G-(CH₂)ₘ—, (fluoro-substituted phenyl)-(CH₂)ₚ-G-(CH₂)ₘ—, thiazolyl-(CH₂)ₚ-G-(CH₂)ₘ—, or morpholinyl-(CH₂)ₚ-G-(CH₂)ₘ—, wherein each G is O, S, NR⁵, S(=O), S(=O)₂, C(=O), —C(=O)NH—, —OC(=O)NH—, —OC(=O)—, —NHC(=O)NH—, —HN—S(=O)ₜ—, —OS(=O)ₜ—, or —OS(=O)ₜNH—; each t is 1 or 2; each p and m is independently 0, 1, 2, 3 or 4;

R³ is H, F, Cl, I, cyano, hydroxy, —N(CH₃)₂, —C(=O)NH—C₁₋₄ alkyl, —OC(=O)NH—C₁₋₄ alkyl, —OC(=O)O—C₁₋₄ alkyl, —NHC(=O)NH—C₁₋₄ alkyl, —NHC(=O)O—C₁₋₄ alkyl, —NHC(=O)—C₁₋₄ alkyl, C₁₋₄ alkyl-NH—S(=O)₂—, C₁₋₄ alkyl-S(=O)₂—, C₁₋₄ alkyl-S(=O)₂NH—, methyl, ethyl, propyl, isopropyl, butyl, ter-butyl, phenyl-(CH₂)ₚ-G-(CH₂)ₘ—, (fluoro-substituted phenyl)-(CH₂)ₚ-G-(CH₂)ₘ—, thiazolyl-(CH₂)ₚ-G-(CH₂)ₘ—, or morpholinyl-(CH₂)ₚ-G-(CH₂)ₘ—, wherein each G is O, S, NR⁵, S(=O), S(=O)₂, C(=O), —C(=O)NH—, —OC(=O)NH—, —OC(=O)—, —NHC(=O)NH—, —HN—S(=O)ₜ—, —OS(=O)ₜ—, or —OS(=O)ₜNH—; each t is 1 or 2; each p and m is independently 0, 1, 2, 3 or 4;

R⁴ is H, F, I, cyano, hydroxy, —N(CH₃)₂, —C(=O)NH—C₁₋₄ alkyl, —OC(=O)NH—C₁₋₄ alkyl, —OC(=O)O—C₁₋₄ alkyl, —NHC(=O)NH—C₁₋₄ alkyl, —NHC(=O)O—C₁₋₄ alkyl, —NHC(=O)—C₁₋₄ alkyl, C₁₋₄ alkyl-NH—S(=O)₂—, C₁₋₄ alkyl-S(=O)₂—, C₁₋₄ alkyl-S(=O)₂NH—, methyl, ethyl, propyl, isopropyl, butyl, ter-butyl, trifluoromethyl, phenyl-(CH₂)ₚ-G-(CH₂)ₘ—, (fluoro-substituted phenyl)-(CH₂)ₚ-G-(CH₂)ₘ—, thiazolyl-(CH₂)ₚ-G-(CH₂)ₘ—, or morpholinyl-(CH₂)ₚ-G-(CH₂)ₘ—, wherein each G is O, S, NR⁵, S(=O), S(=O)₂, C(=O), —C(=O)NH—, —OC(=O)NH—, —OC(=O)—, —NHC(=O)NH—, —HN—S(=O)ₜ—, —OS(=O)ₜ—, or —OS(=O)ₜNH—; each t is 1 or 2; each p and m is independently 0, 1, 2, 3 or 4;

each R⁵ is independently H, C₁₋₃ alkyl, phenyl, benzyl, pyridyl or morpholino methyl;

each R⁸ᵃ is independently H, hydroxy, amino, F, Cl, Br, I, —N(CH₃)₂, —C(=O)NH—C₁₋₄ alkyl, —OC(=O)NH—C₁₋₄ alkyl, —OC(=O)O—C₁₋₄ alkyl, —NHC(=O)NH—C₁₋₄ alkyl, —NHC(=O)O—C₁₋₄ alkyl, —NHC(=O)—C₁₋₄ alkyl, C₁₋₄ alkyl-NH—S(=O)₂—, C₁₋₄ alkyl-S(=O)₂—, C₁₋₄ alkyl-S(=O)₂NH—, cyano, nitro, mercapto, C₁₋₄ alkyl, trifluoromethyl, C₁₋₄ alkoxy, C₁₋₄ alkylamino, C₁₋₄ alkylthio, C₆₋₁₀ aryl, C₆₋₁₀ aryl-C₁₋₄-alkyl or C₁₋₉ heteroaryl;

n is 0, 1, 2, or 3; and each R¹⁰ is independently H, hydroxy, amino, F, Cl, Br, I, cyano, nitro, mercapto, C₁₋₄ alkyl, trifluoromethyl, C₁₋₄ alkoxy, C₁₋₄ alkylamino, or C₁₋₄ alkylthio.

In some embodiments, Formula (V) is

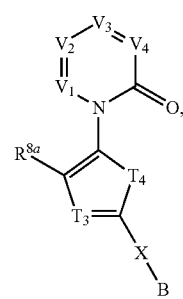

(V)

wherein V₁ is N or CR¹, V₂ is N or CR², V₃ is N or CR³, and V₄ is N or CR⁴, wherein at most one of the V₁, V₂, V₃ and V₄ is N;

$T_3$ is N or $CR^{10}$;
$T_4$ is $NR^5$, O, S or $CR^{11}R^{11a}$;
X is a bond, $NR^5$, O, S, $-(CH_2)_m-$, $-(CH_2)_m-Y-$, $-C(=O)-$, $-C(=O)NH-$, $-CH=CH-$, or $-C\equiv C-$, wherein each m is independently 0, 1, 2 or 3;
B is $-N(CH_3)_2$, $-N(CH_2CH_3)_2$, $-N(CH_2CH_2CH_3)_2$, $-N(CH_2CH_2CH_2CH_3)_2$,
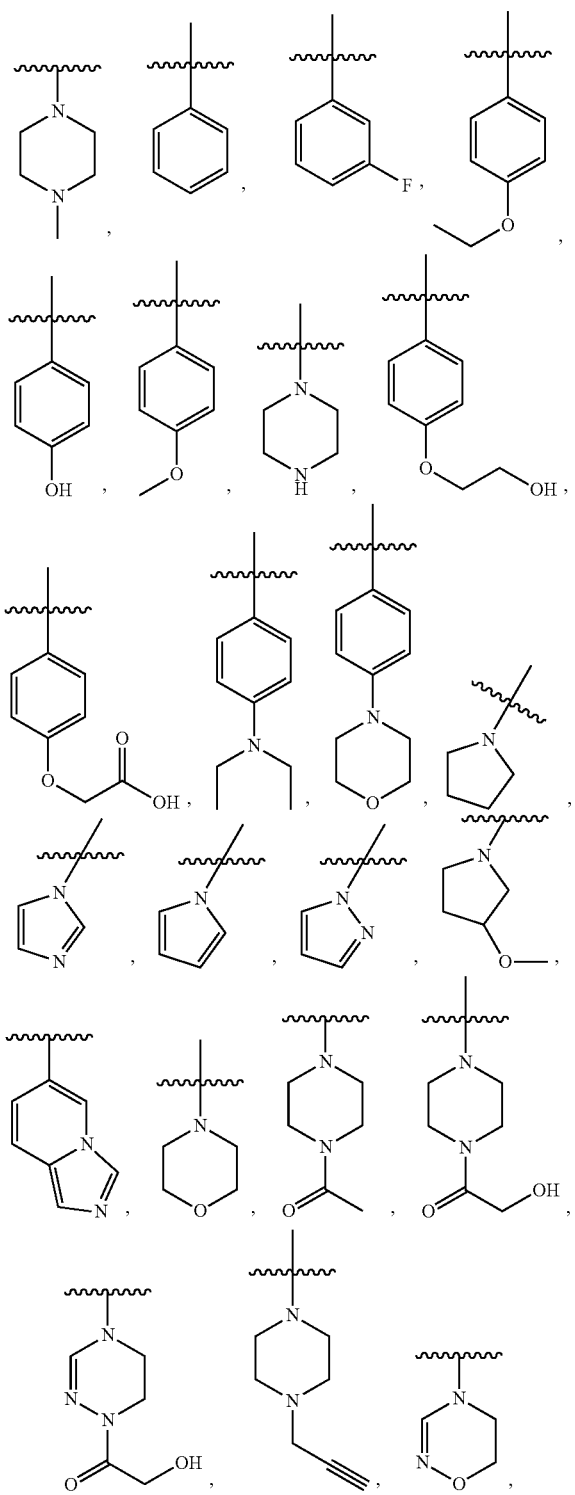
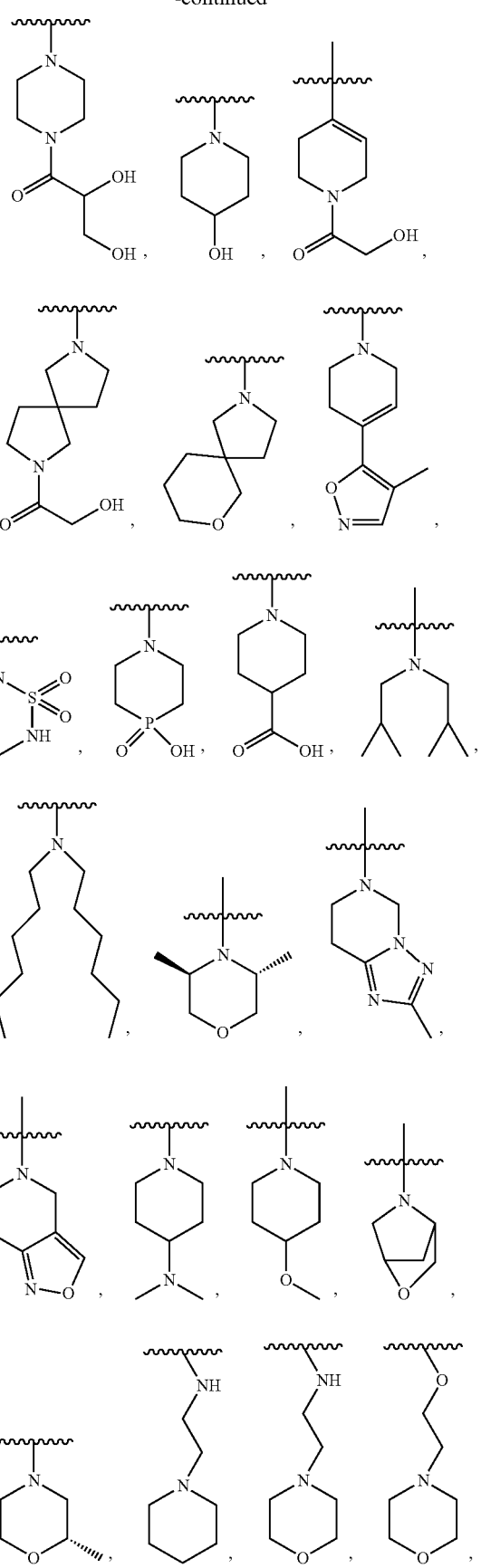
-continued

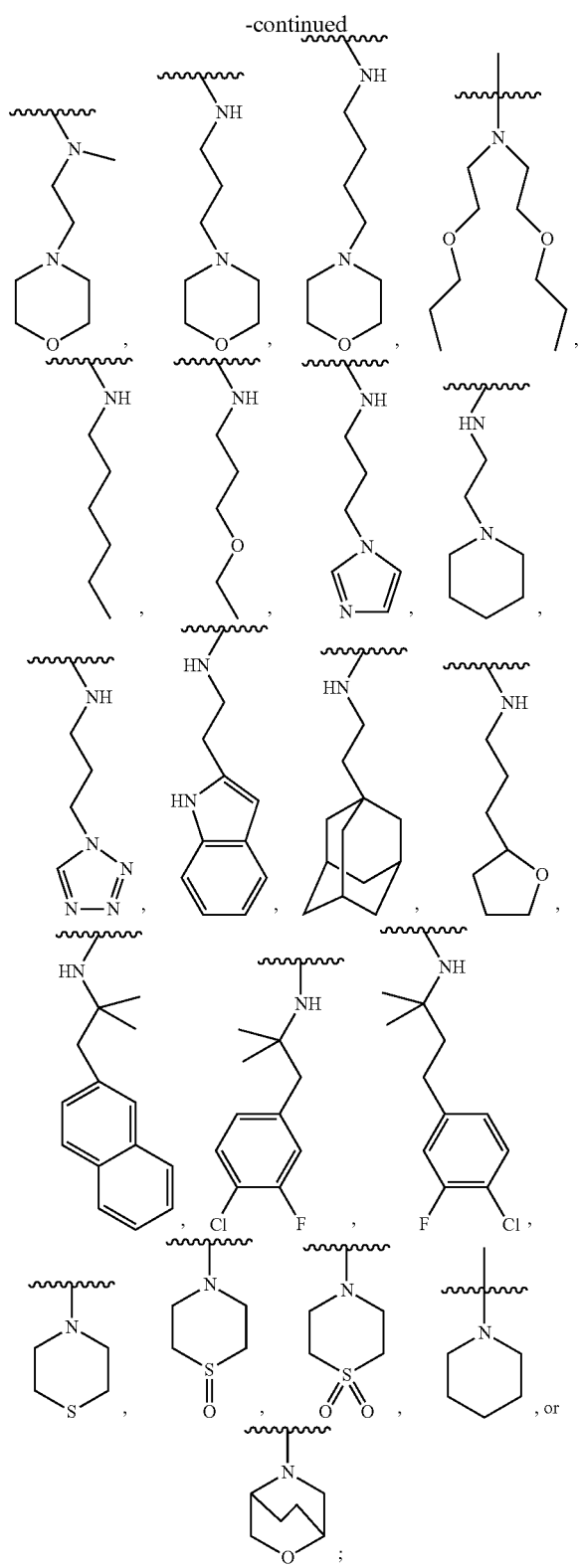

$R^1$ is H, F, Cl, Br, I, cyano, hydroxy, —N(CH$_3$)$_2$, —C(=O)NH—C$_{1-4}$ alkyl, —OC(=O)NH—C$_{1-4}$ alkyl, —OC(=O)O—C$_{1-4}$ alkyl, —NHC(=O)NH—C$_{1-4}$ alkyl, —NHC(=O)O—C$_{1-4}$ alkyl, —NHC(=O)—C$_{1-4}$ alkyl, C$_{1-4}$ alkyl-NH—S(=O)$_2$—, C$_{1-4}$ alkyl-S(=O)$_2$—, C$_{1-4}$ alkyl-S(=O)$_2$NH—, methyl, ethyl, propyl, isopropyl, butyl, ter-butyl, trifluoromethyl, or C$_{6-10}$ aryl-(CH$_2$)$_p$-G-(CH$_2$)$_m$—, wherein G is O, S, NR$^5$, S(=O), S(=O)$_2$, or C(=O); each p and m is independently 0, 1, 2 or 3; or wherein C$_{6-10}$ aryl-(CH$_2$)$_p$-G-(CH$_2$)$_m$— is optionally substituted by one or more F, Cl, Br, I, methyl, ethyl, propyl, ethynyl, propynyl, butyryl, methoxy, ethoxy or cyano;

$R^2$ is H, F, Cl, Br, I, cyano, hydroxy, —N(CH$_3$)$_2$, —C(=O)NH—C$_{1-4}$ alkyl, —OC(=O)NH—C$_{1-4}$ alkyl, —OC(=O)O—C$_{1-4}$ alkyl, —NHC(=O)NH—C$_{1-4}$ alkyl, —NHC(=O)O—C$_{1-4}$ alkyl, —NHC(=O)—C$_{1-4}$ alkyl, C$_{1-4}$ alkyl-NH—S(=O)$_2$—, C$_{1-4}$ alkyl-S(=O)$_2$—, C$_{1-4}$ alkyl-S(=O)$_2$NH—, methyl, ethyl, propyl, isopropyl, butyl, ter-butyl, trifluoromethyl, or C$_{6-10}$ aryl-(CH$_2$)$_p$-G-(CH$_2$)$_m$—, wherein G is O, S, NR$^5$, S(=O), S(=O)$_2$, or C(=O); each p and m is independently 0, 1, 2 or 3;

$R^3$ is H, F, Cl, I, cyano, hydroxy, —N(CH$_3$)$_2$, —C(=O)NH—C$_{1-4}$ alkyl, —OC(=O)NH—C$_{1-4}$ alkyl, —OC(=O)O—C$_{1-4}$ alkyl, —NHC(=O)NH—C$_{1-4}$ alkyl, —NHC(=O)O—C$_{1-4}$ alkyl, —NHC(=O)—C$_{1-4}$ alkyl, C$_{1-4}$ alkyl-NH—S(=O)$_2$—, C$_{1-4}$ alkyl-S(=O)$_2$—, C$_{1-4}$ alkyl-S(=O)$_2$NH—, methyl, ethyl, propyl, isopropyl, butyl, ter-butyl, or C$_{6-10}$ aryl-(CH$_2$)$_p$-G-(CH$_2$)$_m$—, wherein G is O, S, NR$^5$, S(=O), S(=O)$_2$, or C(=O); each p and m is independently 0, 1, 2 or 3;

$R^4$ is H, F, I, cyano, hydroxy, —N(CH$_3$)$_2$, —C(=O)NH—C$_{1-4}$ alkyl, —OC(=O)NH—C$_{1-4}$ alkyl, —OC(=O)O—C$_{1-4}$ alkyl, —NHC(=O)NH—C$_{1-4}$ alkyl, —NHC(=O)O—C$_{1-4}$ alkyl, —NHC(=O)—C$_{1-4}$ alkyl, C$_{1-4}$ alkyl-NH—S(=O)$_2$—, C$_{1-4}$ alkyl-S(=O)$_2$—, C$_{1-4}$ alkyl-S(=O)$_2$NH—, methyl, ethyl, propyl, isopropyl, butyl, ter-butyl, trifluoromethyl, or C$_{6-10}$ aryl-(CH$_2$)$_p$-G-(CH$_2$)$_m$—, wherein G is O, S, NR$^5$, S(=O), S(=O)$_2$, or C(=O); each p and m is independently 0, 1, 2 or 3;

each $R^5$ is independently H, C$_{1-4}$ alkyl, phenyl, benzyl, pyridyl or morpholino methyl; and each $R^{8a}$, $R^{10}$, $R^{11}$, and $R^{11a}$ is independently H, hydroxy, amino, F, Cl, Br, I, —N(CH$_3$)$_2$, —C(=O)NH—C$_{1-4}$ alkyl, —OC(=O)NH—C$_{1-4}$ alkyl, —OC(=O)O—C$_{1-4}$ alkyl, —NHC(=O)NH—C$_{1-4}$ alkyl, —NHC(=O)O—C$_{1-4}$ alkyl, —NHC(=O)—C$_{1-4}$ alkyl, C$_{1-4}$ alkyl-NH—S(=O)$_2$—, C$_{1-4}$ alkyl-S(=O)$_2$—, C$_{1-4}$ alkyl-S(=O)$_2$NH—, cyano, nitro, mercapto, C$_{1-4}$ alkyl, trifluoromethyl, C$_{1-4}$ alkoxy, C$_{1-4}$ alkylamino, C$_{1-4}$ alkylthio, C$_{6-10}$ aryl, C$_{6-10}$ aryl-C$_{1-4}$-alkyl or C$_{1-9}$ heteroaryl.

In some embodiments, Formula (VI) is

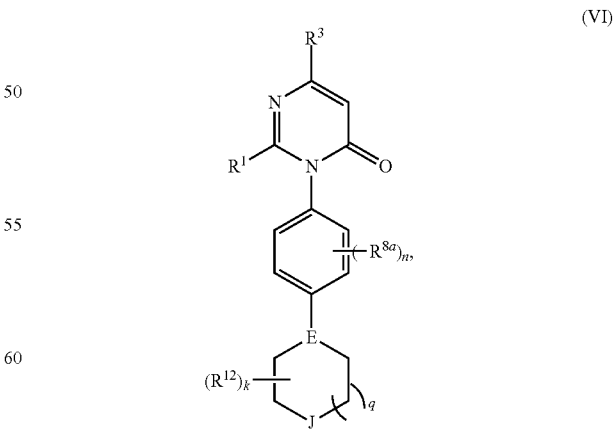

(VI)

wherein E is N or CR$^{10}$;
J is O, S, S(=O), S(=O)$_2$, NR$^{13}$ or CR$^{14}$R$^{14a}$;
k is 0, 1, 2, 3 or 4;
q is 0, 1 or 2;

$R^1$ is H, F, Cl, Br, I, cyano, hydroxy, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$C_{1-6}$ alkyl, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O)NH—, —OC(=O)— or —NHC(=O)NH—; each p and m is independently 0, 1, 2 or 3; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, $C_{6-10}$ aryl-$C_{1-6}$ alkyl, and $C_{3-10}$ cycloalkyl-$(CH_2)_p$-G-$(CH_2)_m$— is optionally substituted by one or more F, Cl, Br, I, methyl, ethyl, propyl, ethynyl, propynyl, butyryl, methoxy, ethoxy, or cyano;

$R^3$ is H, F, Cl, I, cyano, hydroxy, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O)NH—, —OC(=O)— or —NHC(=O)NH—; each p and m is independently 0, 1, 2 or 3;

each $R^5$ is independently H, $R^7R^{7a}NC(=O)$—, $R^7OC(=O)$—, $R^7C(=O)$—, $C_{1-3}$ alkyl, $C_{1-3}$ haloalkyl, $C_{1-3}$ hydroxyalkyl, $C_{1-3}$ amino alkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl-$C_{1-3}$-alkyl, $C_{2-10}$ heterocyclyl-$C_{1-3}$-alkyl, $C_{3-10}$ cycloalkyl-$C_{1-3}$-alkyl, $C_{6-10}$ aryl, $C_{1-9}$ heteroaryl, $C_{2-10}$ heterocyclyl or $C_{3-10}$ carbocyclyl;

each $R^{8a}$ is independently H, hydroxy, amino, F, Cl, Br, I, —N(CH_3)_2, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl;

n is 0, 1, 2 or 3;

$R^{10}$ is independently H, hydroxy, amino, F, Cl, Br, I, cyano, nitro, mercapto, $C_{1-4}$ alkyl, trifluoromethyl, $C_{1-4}$ alkoxy, $C_{1-4}$ alkylamino, or $C_{1-4}$ alkylthio;

each $R^{12}$ is oxo (=O), hydroxy, amino, halo, cyano, $C_{1-10}$ alkoxy, $C_{1-10}$ alkylamino, $C_{1-10}$ alkylthio, $C_{1-10}$ alkyl, $C_{2-10}$ alkenyl, $C_{2-10}$ alkynyl, mercapto, nitro, $C_{6-10}$ aryl, $C_{1-9}$ heteroaryl, $C_{2-10}$ heterocyclyl, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)_2—, hydroxy-substituted $C_{1-6}$ alkyl-S(=O)—, hydroxy-substituted $C_{1-6}$ alkyl-S(=O)_2—, or carboxy $C_{1-6}$ alkoxy;

$R^{13}$ is H, $C_{1-4}$ alkyl, $C_{2-4}$ alkynyl, $C_{1-4}$ alkoxy, hydroxy-substituted $C_{1-4}$ alkoxy, $C_{1-4}$ carboxyalkoxy, $C_{1-4}$ alkylcarbonyl or hydroxy-substituted $C_{1-4}$ alkylcarbony; and each $R^{14}$ and $R^{14a}$ is independently H, hydroxy, carboxy, $C_{1-4}$ alkyl, $C_{1-4}$ alkoxy or $C_{1-4}$ alkylamino.

In some embodiments, $R^1$ is independently H, F, Cl, Br, I, cyano, hydroxy, methyl, ethyl, propyl, isopropyl, butyl, ter-butyl, $C_{6-8}$ aryl-$(CH_2)_p$-G-$(CH_2)_m$— or $C_{4-6}$ heteroaryl-$(CH_2)_p$-G-$(CH_2)_m$—, wherein each G is $NR^5$, O or S, each p and m is independently 0, 1, 2 or 3; or wherein each of the $C_{6-8}$ aryl-$(CH_2)_p$-G-$(CH_2)_m$— and $C_{4-6}$ heteroaryl-$(CH_2)_p$-G-$(CH_2)_m$— is optionally substituted by one or more F, Cl, Br, methyl, ethyl, propyl, ethynyl, propynyl, butynyl, methoxy, or cyano; and $R^3$ is independently H, F, Cl, I, cyano, hydroxy, methyl, ethyl, propyl, isopropyl, butyl, ter-butyl, $C_{6-8}$ aryl-$(CH_2)_p$-G-$(CH_2)_m$— or $C_{4-6}$ heteroaryl-$(CH_2)_p$-G-$(CH_2)_m$—, wherein each G is O or S, each p and m is independently 0, 1, 2 or 3.

In some embodiments, Formula (VII) is

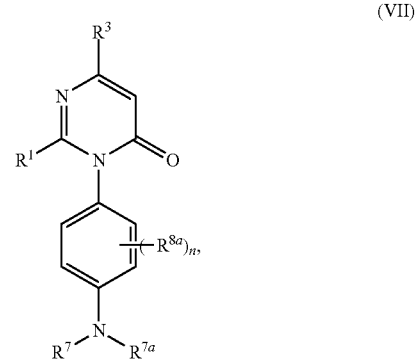

(VII)

wherein $R^1$ is H, F, Cl, Br, I, cyano, hydroxy, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O)NH—, —OC(=O)— or —NHC(=O)NH—; each p and m is independently 0, 1, 2 or 3; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-$(CH_2)_m$— is optionally substituted by one or more F, Cl, Br, I, methyl, ethyl, propyl, cyano, ethynyl, methoxy, ethoxy, or propynyl;

$R^3$ is H, F, Cl, I, cyano, hydroxy, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O)NH—, —OC(=O)— or —NHC(=O)NH—; each p and m is independently 0, 1, 2 or 3;

each $R^5$ is independently H, $R^7R^{7a}NC(=O)$—, $R^7OC(=O)$—, $R^7C(=O)$—, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl-$C_{1-3}$-alkyl, $C_{2-10}$ heterocyclyl-$C_{1-3}$-alkyl, $C_{3-10}$ cycloalkyl-$C_{1-3}$-alkyl, $C_{6-10}$ aryl, $C_{1-9}$ heteroaryl, $C_{2-10}$ heterocyclyl or $C_{3-10}$ carbocyclyl;

each $R^7$ is independently H, $C_{1-6}$ alkyl, $C_{1-6}$ haloaliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-19}$ carbocyclyl;

each $R^{7a}$ is independently $C_{1-6}$ alkyl, $C_{1-6}$ haloaliphatic, $C_{1-6}$ hydroxyaliphatic, $C_{1-6}$ amino aliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-19}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring;

each $R^{8a}$ is independently H, hydroxy, amino, F, Cl, Br, I, —N(CH_3)_2, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl, $C_{6-10}$ aryl-$C_{1-4}$-alkyl or $C_{1-9}$ heteroaryl; and n is 0, 1, 2 or 3.

In some embodiments, each $R^7$ is independently H, $C_{1-6}$ alkyl, $C_{1-4}$ alkoxy-$C_{1-6}$-alkyl,

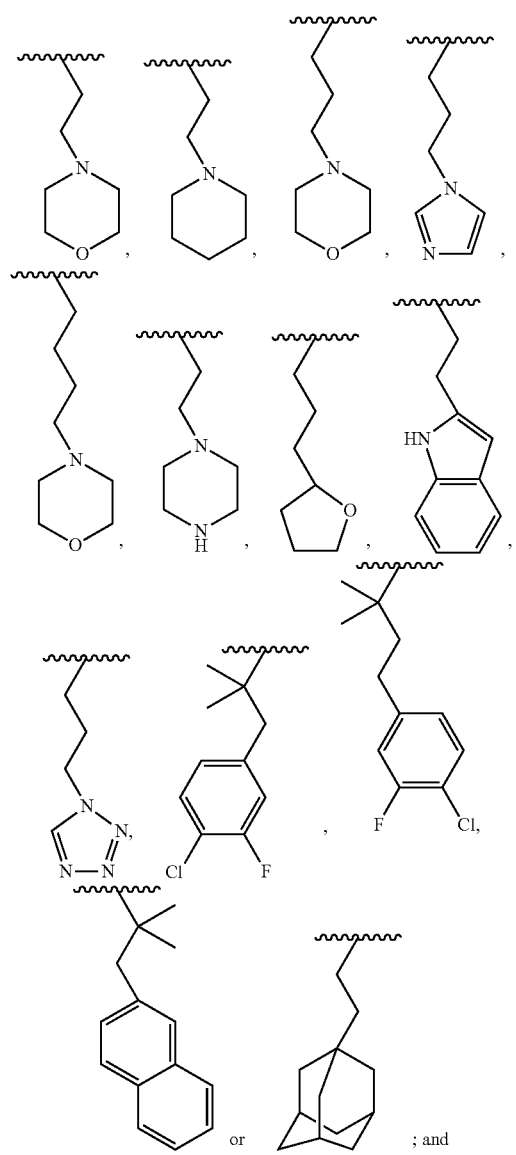

; and each $R^{7a}$ is independently $C_{1-6}$ alkyl, $C_{1-4}$ alkoxy-$C_{1-6}$-alkyl,

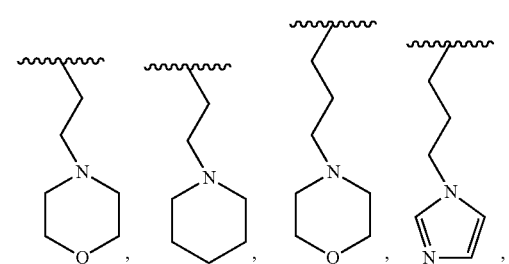

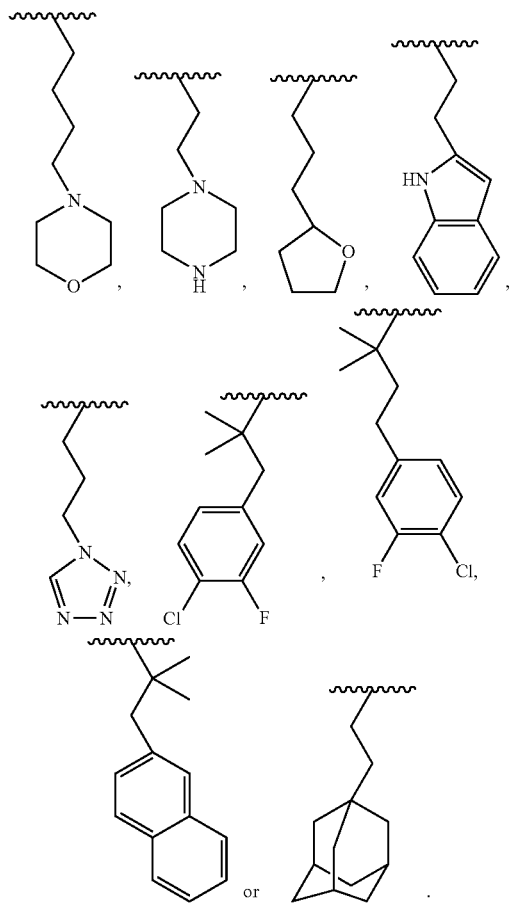

In another aspect, provided herein are one of the compounds as follows, or a stereoisomer, geometric isomer, tautomer, nitrogen oxide, hydrate, solvate, or pharmaceutically acceptable salt thereof, and not limited to:

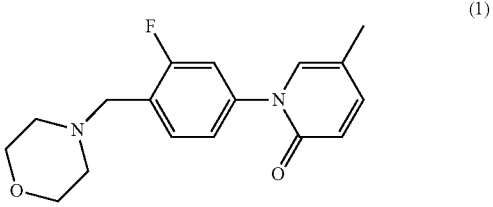

(1)

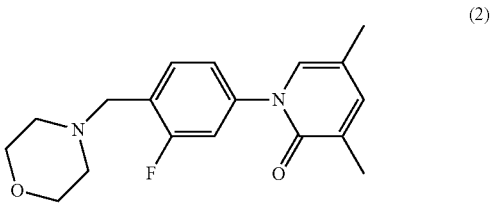

(2)

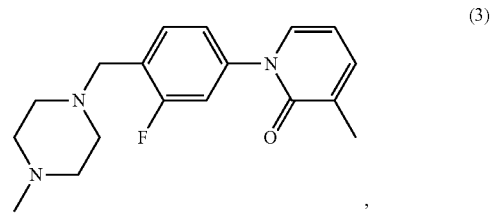

(3)

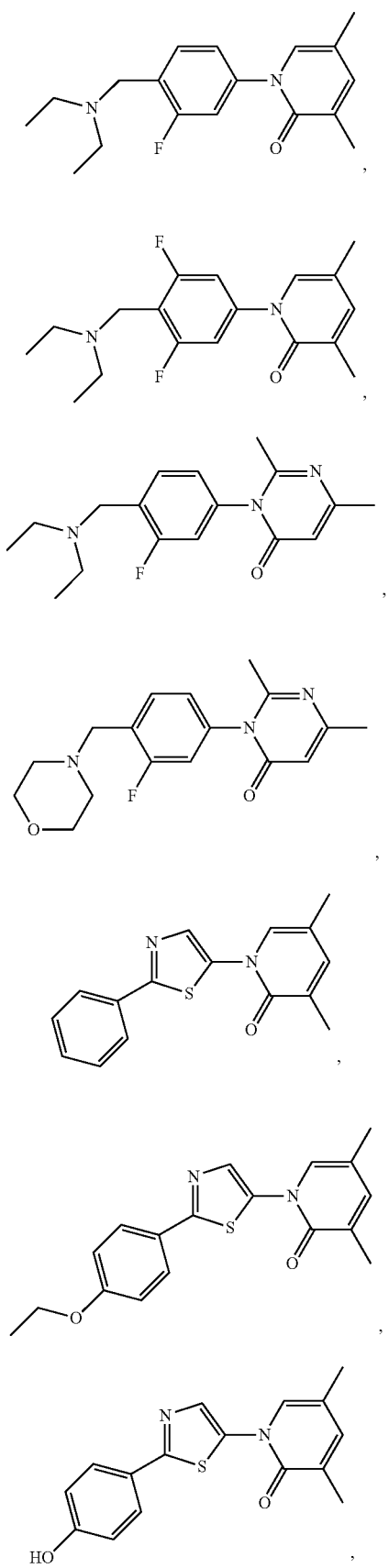
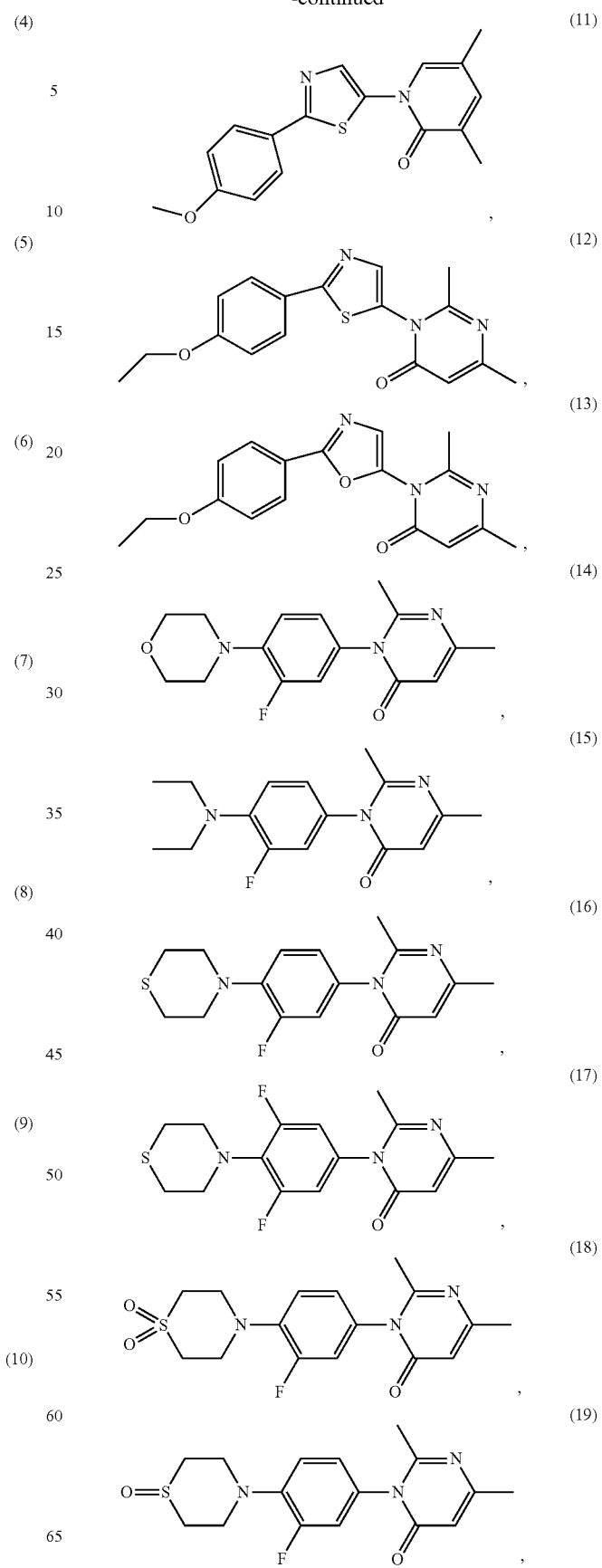

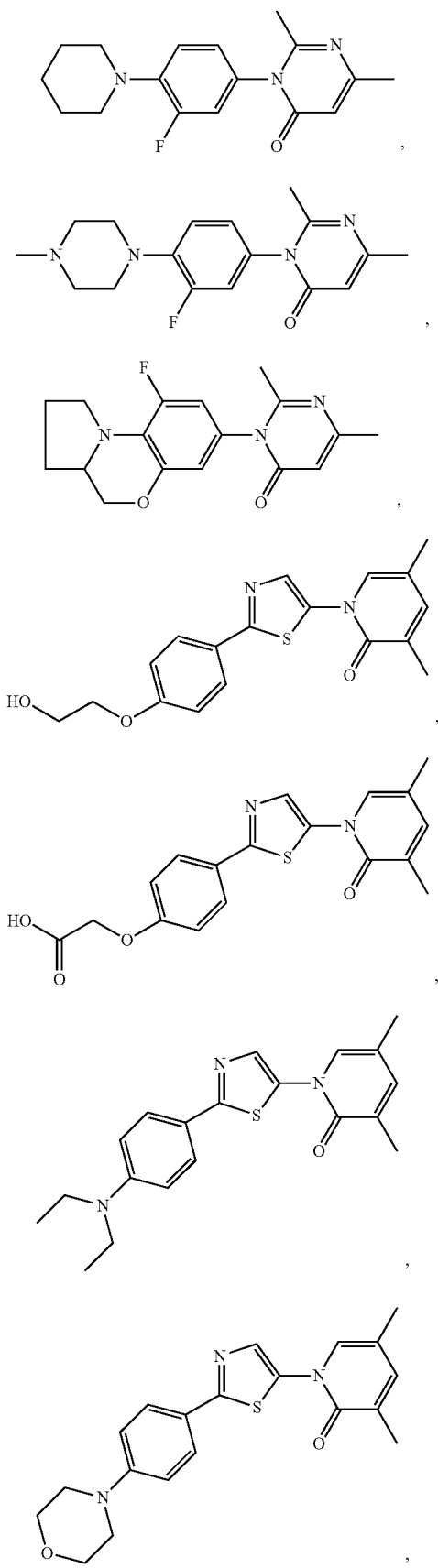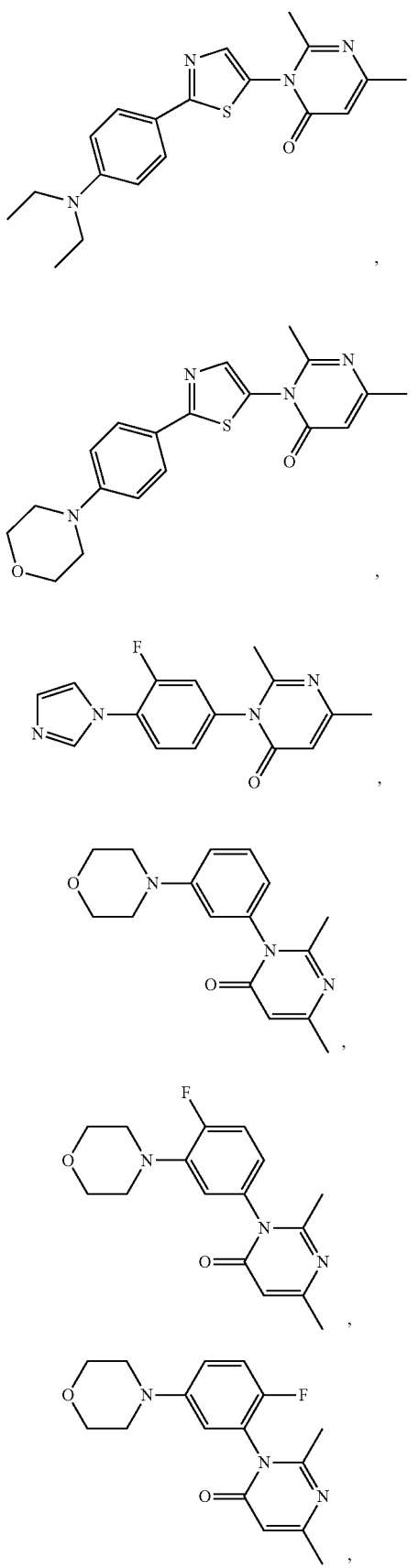

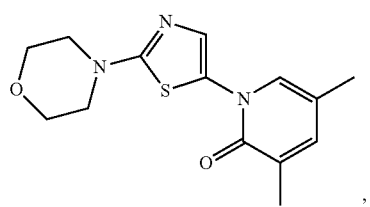
(33)
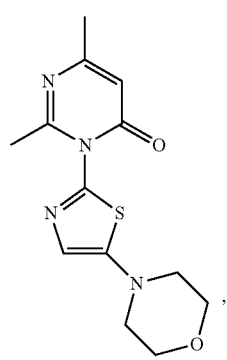
(34)
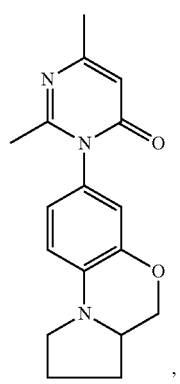
(35)
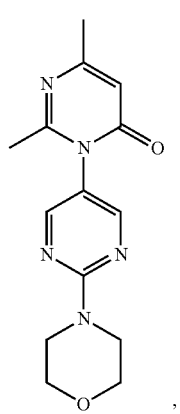
(36)
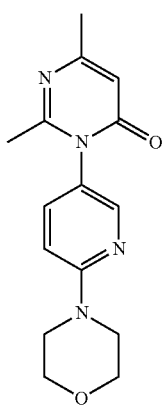
(37)
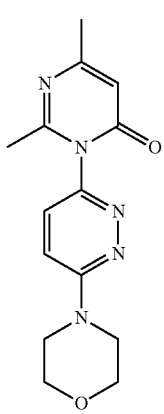
(38)
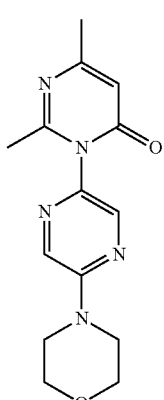
(39)
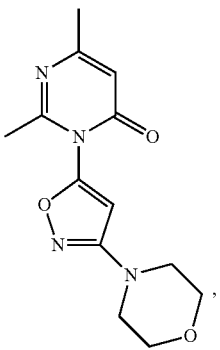
(40)

(41)
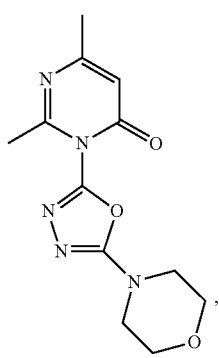
(42)
(43)
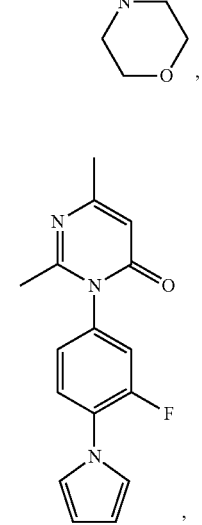
(44)
(45)
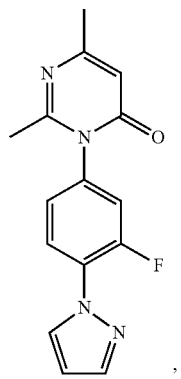
(46)
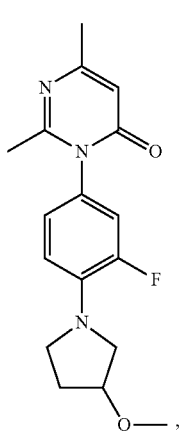
(47)
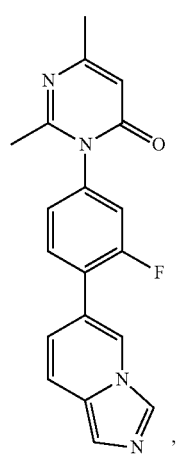

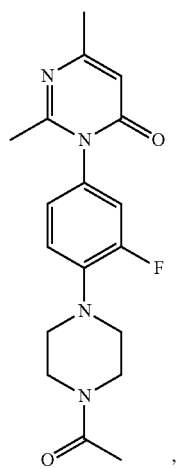 (48)
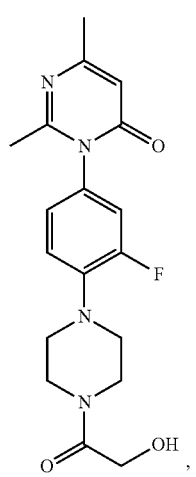 (49)
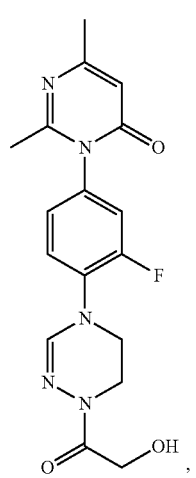 (50)
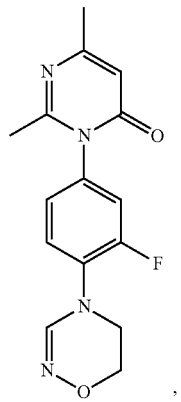 (51)
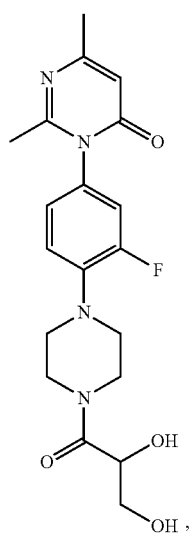 (52)
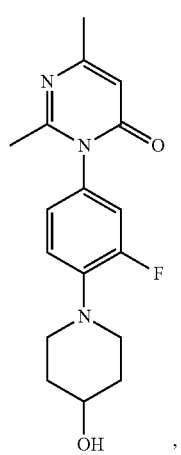 (53)

-continued
(54)
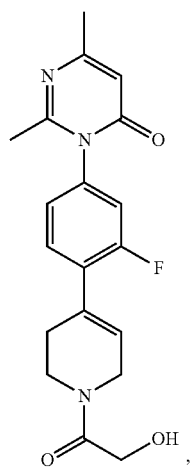
(55)
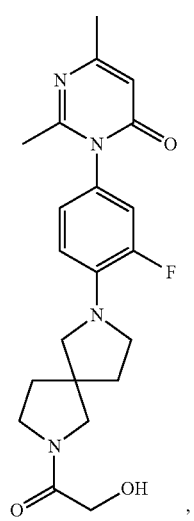
(56)
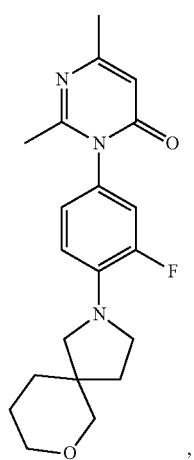
-continued
(57)
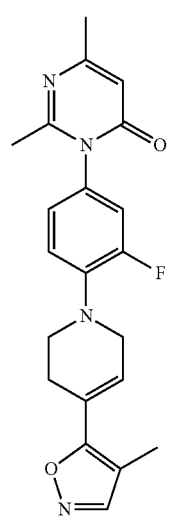
(58)
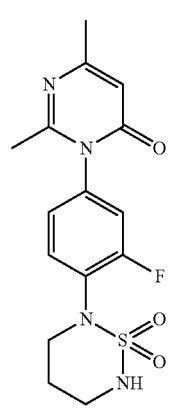
(59)
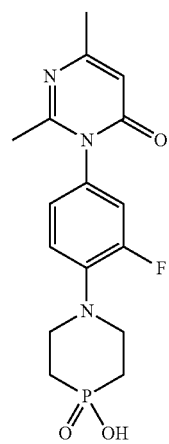

-continued
(60) 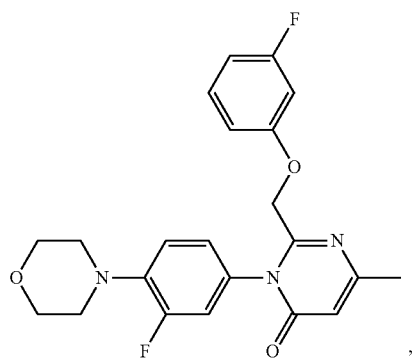
(61) 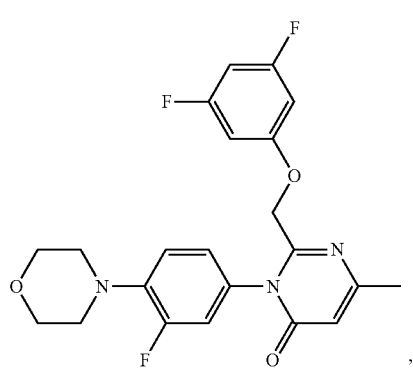
(62) 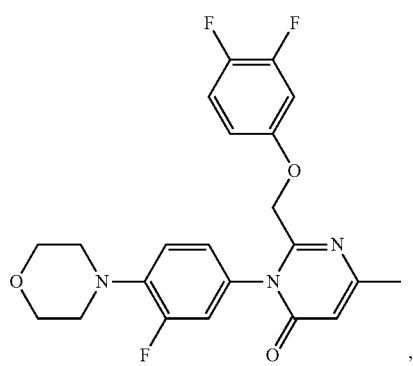
(63) 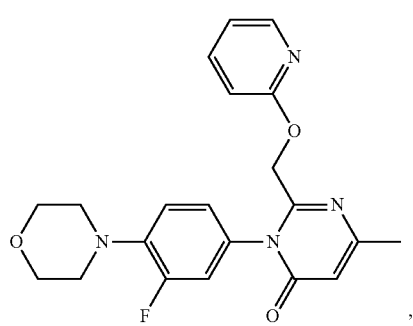
-continued
(64) 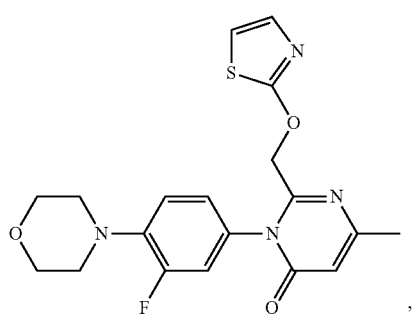
(65) 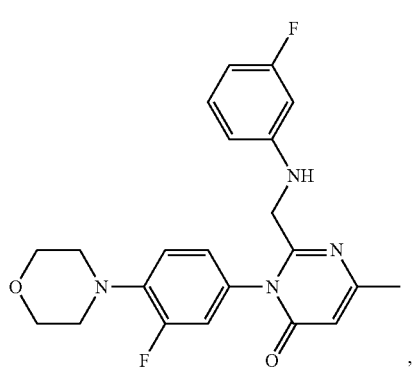
(66) 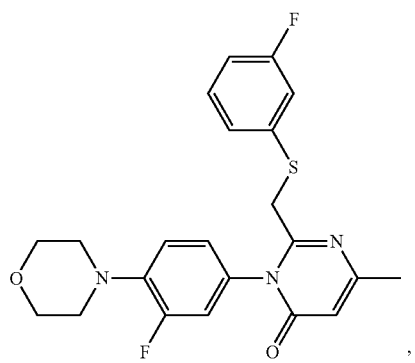
(67) 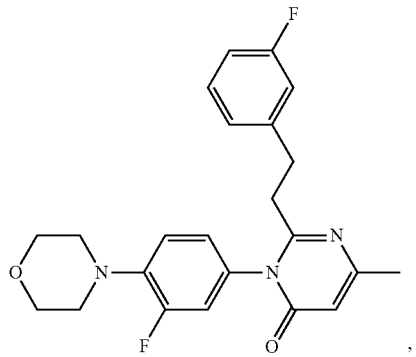

(68) 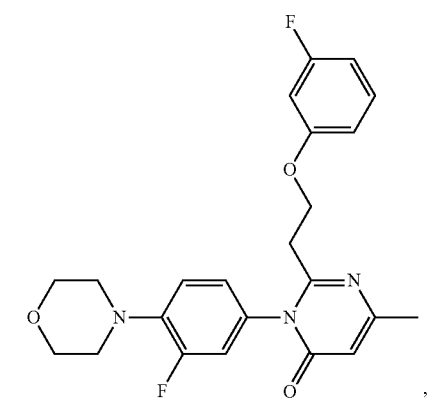
(69) 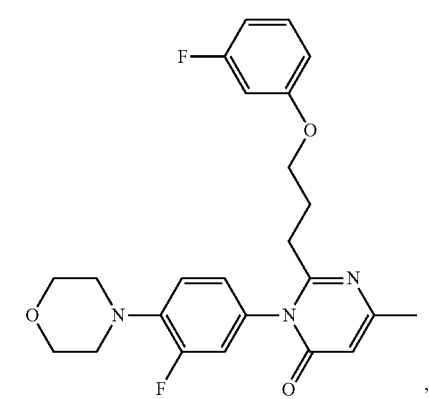
(70) 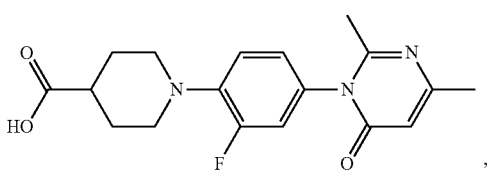
(71) 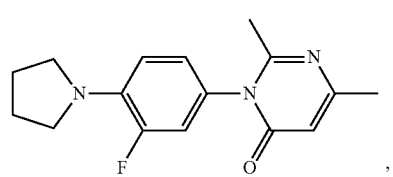
(72) 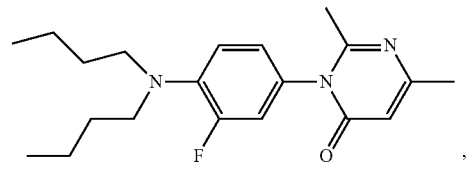
(73) 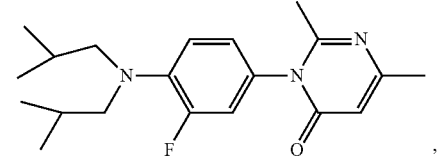
(74) 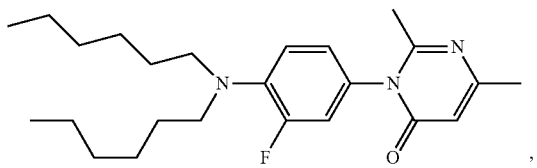
(75) 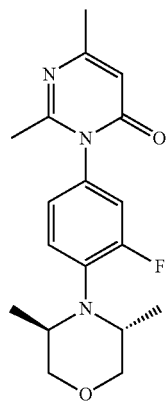
(76) 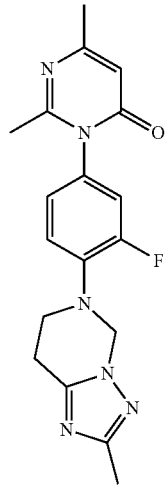
(77) 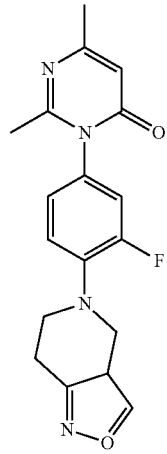

(78)
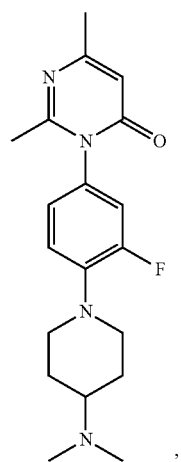
(79)
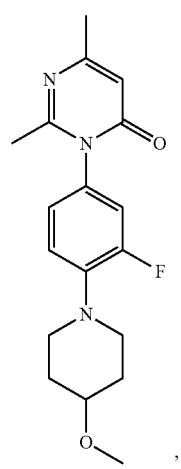
(80)
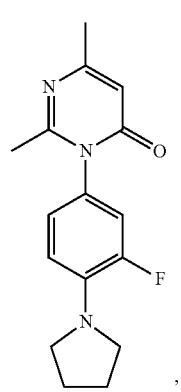
(81)
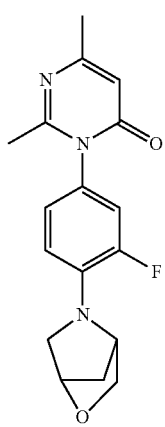
(82)
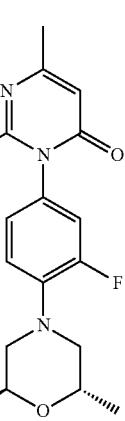
(83)
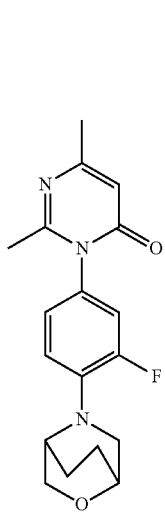

(84)
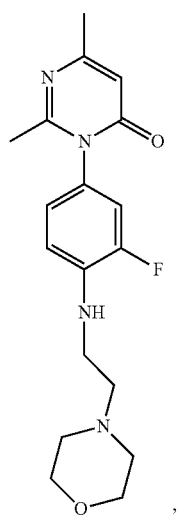
(85)
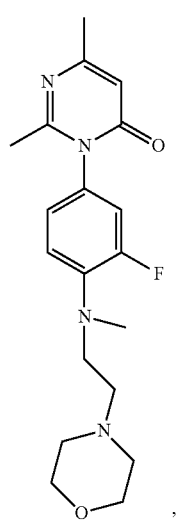
(86)
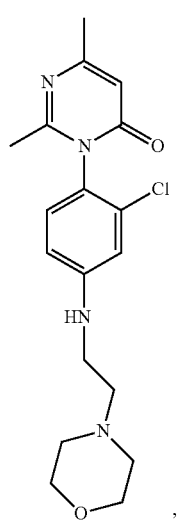
(87)
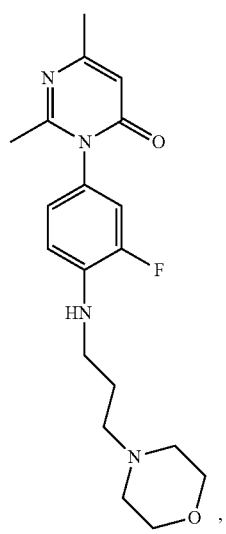
(88)
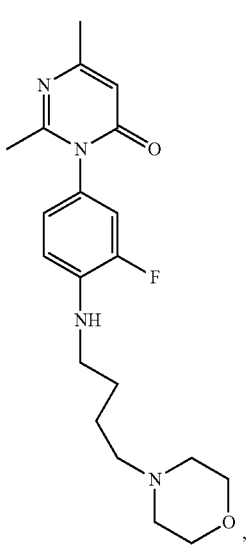
(89)
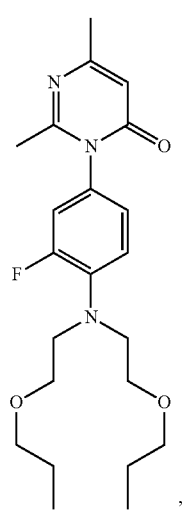

(90)
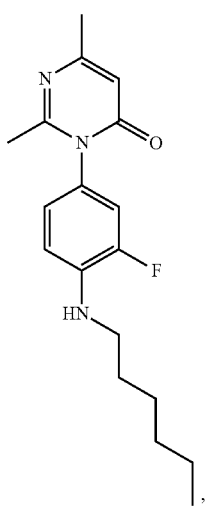
(91)
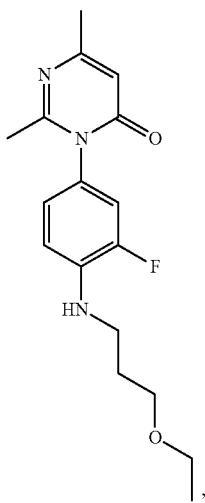
(92)
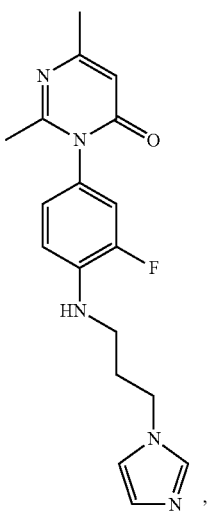
(93)
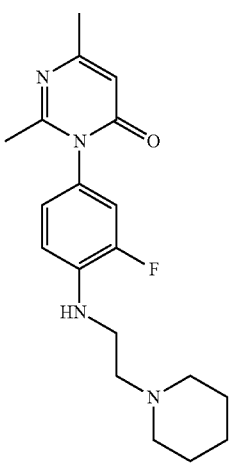
(94)
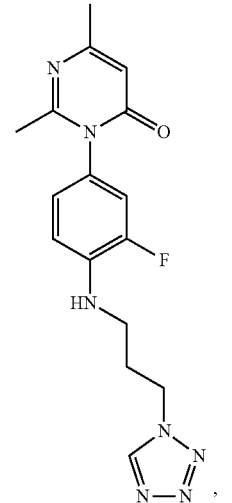
(95)
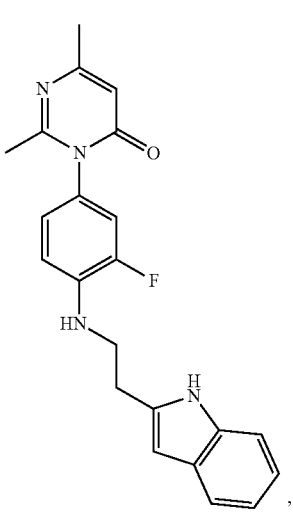

(96) 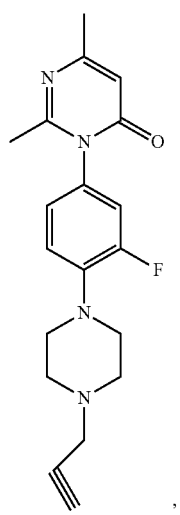
(97) 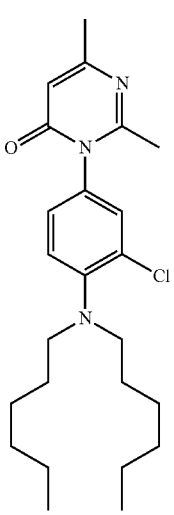
(98) 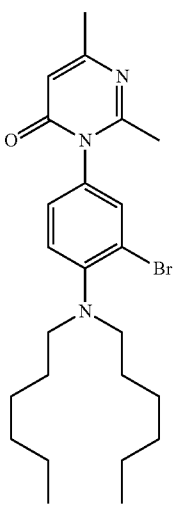
(99) 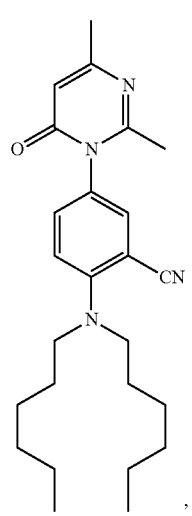
(100) 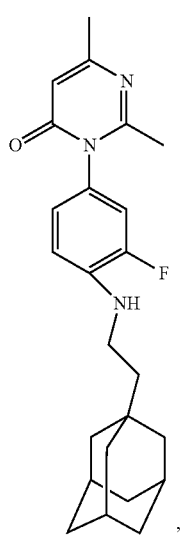
(101) 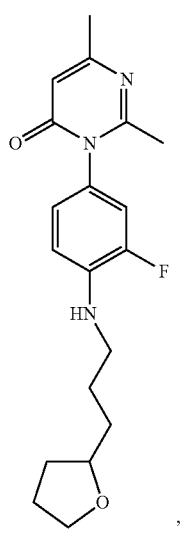

-continued
(102)
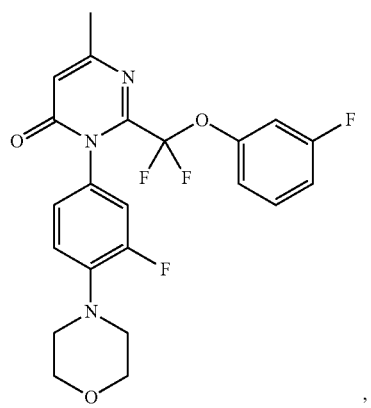
(103)
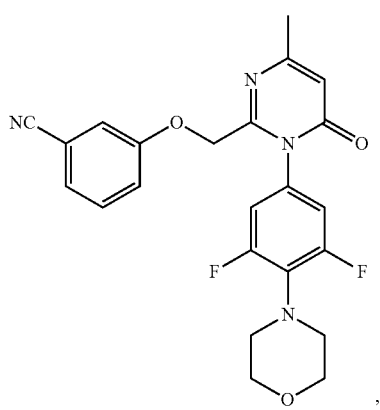
(104)
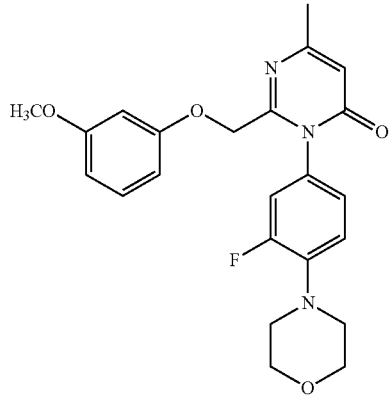
-continued
(105)
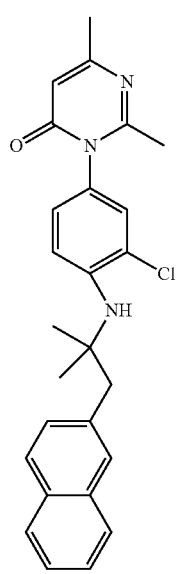
(106)
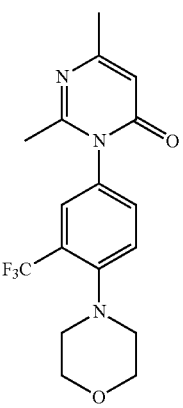
(107)

(108)
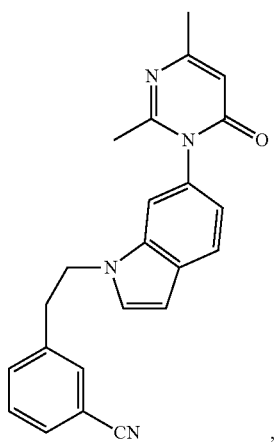
(109)
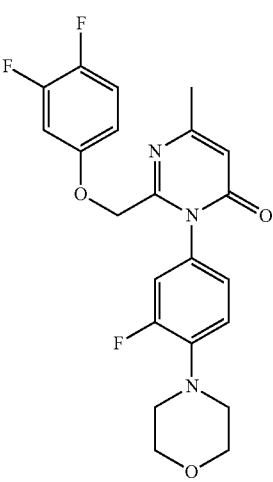
(110)
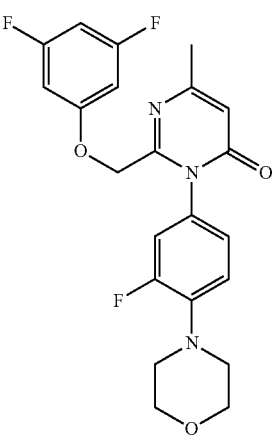
(111)
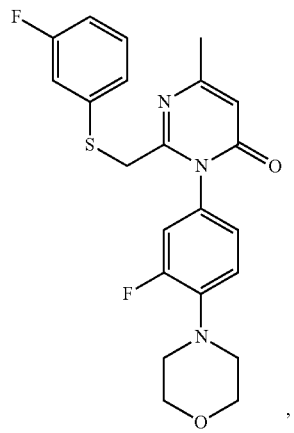
(112)
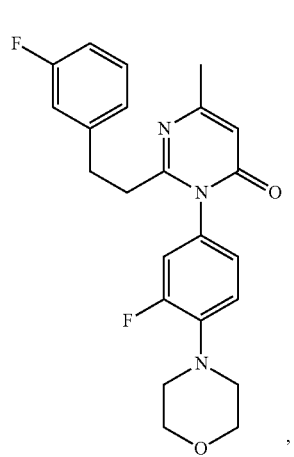
(113)
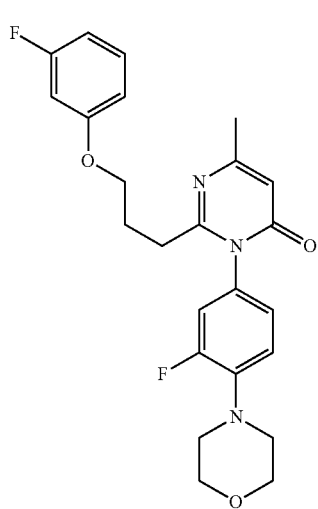

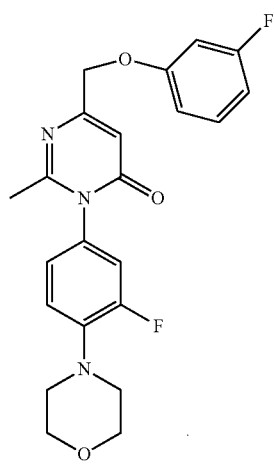
(114)
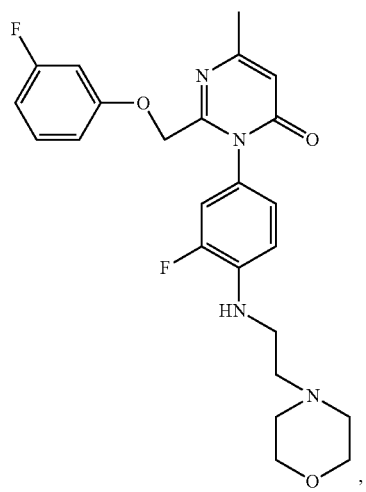
(117)
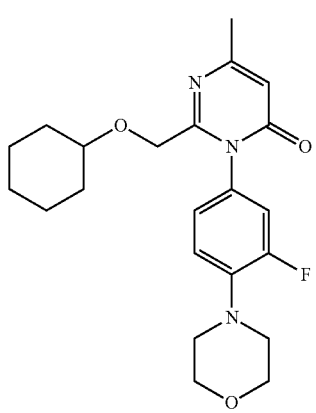
(118)
(115)
(116)
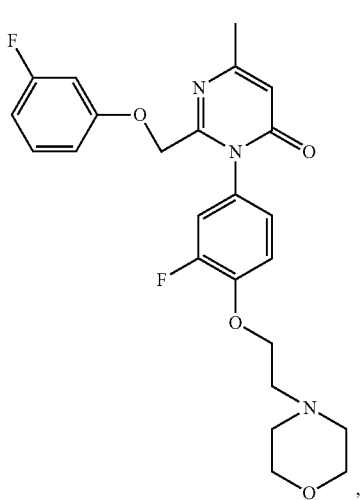
(119)

(120) 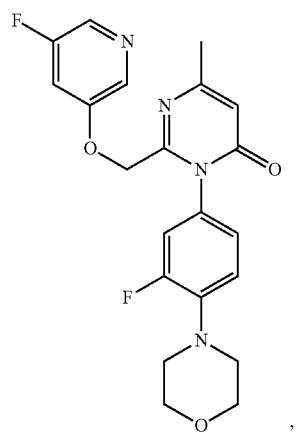
(121) 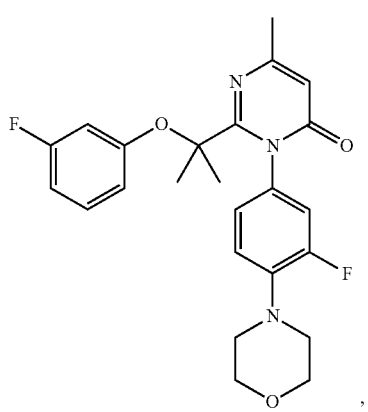
(122) 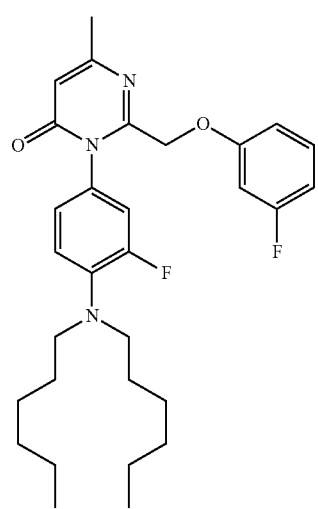
(123) 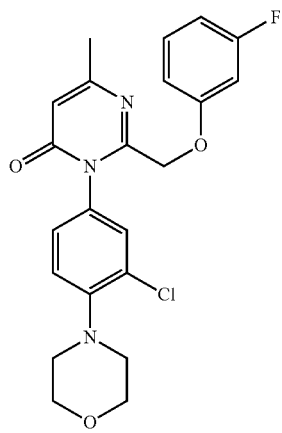
(124) 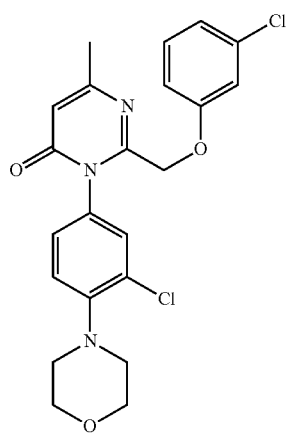
(125) 

(126) 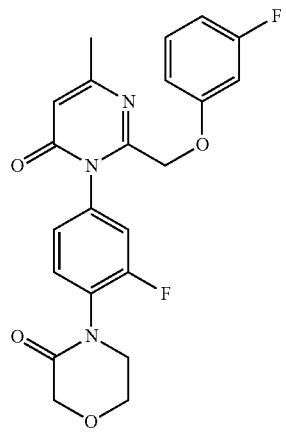
(127) 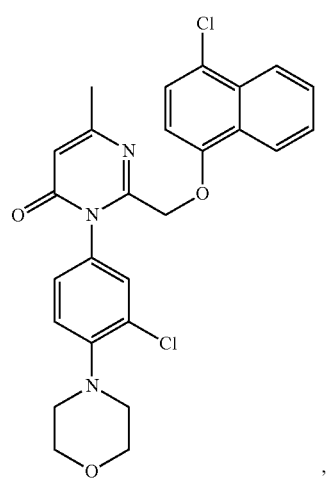
(128) 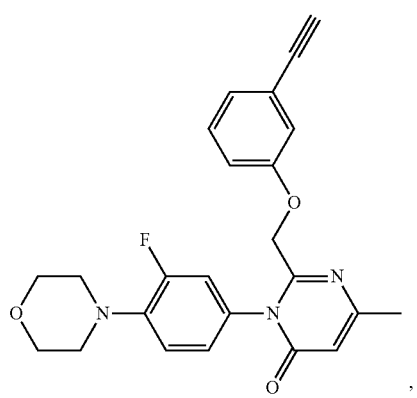
(129) 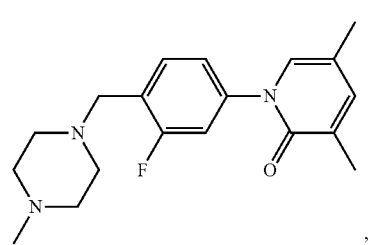
(130) 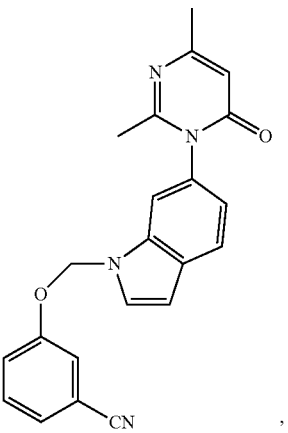
(131) 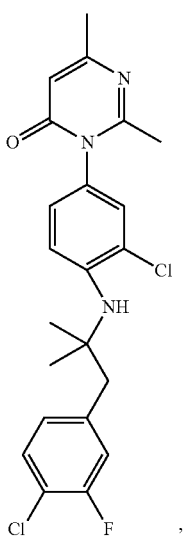
, or
(132) 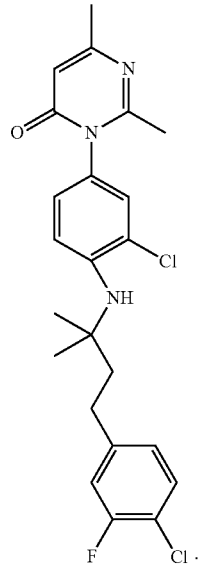
Provided herein includes the use of a compound disclosed herein, or a pharmaceutically acceptable salt thereof, in the manufacture of a medicament for treating the severity of tissue or organ fibrosis in a patient, including those described herein. Provided herein is a pharmaceutical composition comprising a therapeutically effective amount of a compound of Formula (I), (V), (VI), (VII) or (IV) in association with at least one pharmaceutically acceptable carrier, excipient, diluent, adjuvant or vehicle.

Provided herein are pharmaceutical compositions comprising a compound disclosed herein, or a stereoisomer, geometric isomer, tautomer, nitrogen oxide, hydrate, solvate, metabolite, pharmaceutically acceptable salt or prodrug thereof; and an optionally pharmaceutically acceptable carrier, excipient, diluent, adjuvant, vehicle or a combination thereof.

Also provided herein is a method of treating the severity of tissue or organ fibrosis in a patient or susceptible to such fibrosis, the method comprising treating the subject with a therapeutically effective amount of a compound of Formula (I), (V), (VI), (VII) or (IV).

Provided herein, the tissue or organ fibrosis disorder is renal interstitial fibrosis, glomerulosclerosis, liver fibrosis, pulmonary fibrosis, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis. In other embodiments, post-surgery adhesions is the scar healing.

Unless otherwise stated, all stereoisomers, geometric isomers, tautomers, nitrogen oxides, hydrates, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a Formulation, and/or the mammal being treated therewith.

The compounds disclosed herein also include salts of such compounds which are not necessarily pharmaceutically acceptable salts, and which may be useful as intermediates for preparing and/or purifying compounds of Formula (I), (V), (VI), (VII) or (IV) and/or for separating enantiomers of compounds of Formula (I), (V), (VI), (VII) or (IV).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Some non-limiting examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

Composition, Formulations and Administration of Compounds of the Invention

According to another aspect, the invention features pharmaceutical compositions that include a compound of Formula (I), (V), (VI), (VII) or (IV), a compound listed herein, or a compound named in Examples 1-72, and a pharmaceutically acceptable carrier, adjuvant, or vehicle. The amount of the compound in the compositions disclosed herein is such that is effective to detectably treat or lessen the severity of a tissue or organ fibrotic disease in a patient.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Troy et al., *Remington: The Science and Practice of Pharmacy,* 21st ed., 2005, Lippincott Williams & Wilkins, Philadelphia and Swarbrick et al., Encyclopedia of Pharmaceutical Technology, eds., 1988-1999, Marcel Dekker, New York, all of which are herein incorporated by reference in their entireties, are disclosed various carriers used in Formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be administered orally, parenterally, by inhalation spray, topically, rectally, nasally, buccally, vaginally or via an implanted reservoir. The pharmaceutically acceptable compositions disclosed herein include orally administered in any orally acceptable dosage form including, but not limited to, capsules, tablets, pills, powders, granules, aqueous suspensions or solutions.

The compositions disclosed herein can be orally administered in the following dosage forms: tablets, pellets, capsules, dispensable powders, particles or suspensions, syrup, and elixirs. Alternatively, the compositions disclosed herein can be for external use in the form of ointment, gel, or medicated patch; or they can be administered parenterally in the form of sterile injectable solution or suspension.

The compounds disclosed herein may be administered parenterally or intraperitoneally. The compounds disclosed herein (as free bases or pharmaceutically acceptable salt) may be formulated into solutions or suspensions in water suitably mixed with surfactant (e.g. hydroxypropyl cellulose, polyvinyl pyrrolidone). Dispersion can also be prepared from a mixture of the active compounds in glycerin, liquid, polyethylene glycol and oil. In the normal condition of storage and usage, these preparations may contain preservatives to prevent the growth of microorganisms.

The pharmaceutical forms suitable for injection include sterile water or dispersion and sterile powder (used for the temporary preparation of sterile injectable solutions or dispersions). In all the cases, these forms must be sterile, and they must be fluidic to allow their discharge from the injection syringe. These forms must be stable in the condition of production and storage, and they must prevent from the pollution of microorganisms (such as bacteria and fungi). The carriers may be solvents or dispersion media, including, for example, water, alcohols (such as glycerin, propylene glycol and liquid polyethylene glycol), plant oil and combinations thereof.

The compounds disclosed herein can be administered in a local rather than systemic manner, for example, via injection of the compound directly into organ, often in a depot or sustained release formulation. Furthermore, the pharmaceutical composition comprising a compound disclosed herein can be administered in a targeted drug delivery system, for example, in a liposome coated with organ-specific antibody. The liposomes may be targeted to and taken up selectively by the organ. In addition, the pharmaceutical compositions comprising a compound disclosed herein may be provided in the form of a rapid release formulation, in the form of an extended release formulation, or in the form of an intermediate release formulation.

For administration by inhalation, the compounds disclosed herein may be in a form as an aerosol, a mist or a powder. The pharmaceutical compositions comprising a compound disclosed herein may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a value to deliver a metered amount. Capsules and cartridges, such as, by way of example only, gelatin for use in an inhaler or insufflators maybe formulated containing a powder mix of the compound disclosed herein and a suitable powder base such as lactose or starch.

The compounds disclosed herein may also be formulated in rectal compositions such as enemas, rectal gels, rectal foams, rectal aerosol, suppositories, jelly suppositories, or retention enemas, containing conventional suppository bases such as cocoa butter or other glycerides, as well as any synthetic polymers suitable for preparing suppository bases such as polyvinylpyrrolidone, PEG, and the like. In suppository forms of the compositions, a low-melting wax such as, but not limited to, a mixture of fatty acid glycerides, optionally in combination with cocoa butter is first melted.

Additionally, the compound disclosed herein may be used in combination with other agents of treating fibrosis, such as, but not limited to, ivacaftor, roflumilast, pirfenidone, miglustat, losartan, ACTIMMUNE® (interferon gamma-1B), dornase alfa, VELDONA® (interferon alfa), ataluren, cortical hormone, methotrexate, tacrolimus and combinations thereof.

The pharmaceutical compositions disclosed herein may be formulated in conventional manner using one or more physiologically acceptable carriers comprising excipients and auxiliaries which facilitate processing of the active compounds into preparations which may be used pharmaceutically. Proper formulation is dependent upon the route of administration chosen. Any of the well-known techniques, carriers, and excipients may be used as suitable and as understood in the art. The pharmaceutical compositions comprising a compound disclosed herein may be manufactured in a conventional manner, such as, by way of example, by means of conventional mixing, dissolving, granulating, dragee-making, levigating, emulsifying, encapsulating, entrapping, or compression processes.

The pharmaceutical compositions disclosed herein include at least one pharmaceutically acceptable carrier, diluent or excipient and a compound disclosed herein as an active ingredient in free-acid or free-base form, or in a pharmaceutically acceptable salt form. In addition, the pharmaceutical compositions disclosed herein include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions contain other therapeutically valuable substances.

Methods for the preparation of the pharmaceutical compositions disclosed herein include formulating the compounds disclosed herein with one or more inert, pharmaceutically acceptable excipients or carriers to form a solid, semi-solid or liquid. Some non-limiting examples of solid compositions include powders, tablets, dispersible granules, capsules, cachets, and suppositories. Some non-limiting examples of liquid compositions include solutions in which a compound is dissolved, emulsions comprising a compound, or a solution containing liposomes, micelles, or nanoparticles comprising a compound as disclosed herein. Some non-limiting examples of semi-solid compositions include gels, suspensions and creams. The compositions may be in liquid solutions or suspensions, solid forms suitable for solution or suspension in a liquid prior to use, or as emulsions. The pharmaceutical compositions disclosed herein may also contain minor amounts of nontoxic, auxiliary substances, such as wetting or emulsifying agents, pH buffering agents, and so forth.

The compounds disclosed herein are preferably formulated in dosage unit form for ease of administration and uniformity of dosage. The expression "dosage unit form" refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The effective dose of the active ingredients used may vary with the compound used, the administration mode and the severity of the disease to be treated. However, typically, a desirable result can be achieved when the compound disclosed herein is administered at a dose of about 0.25-1000 mg/kg animal body weight per day. More preferably, it is administered in 2-4 separated dosages per day, or in the form of slow release. For most of the large mammals, the total dose per day is about 1-100 mg/kg, more preferably about 2-80 mg/kg. The dosage form suitable for inner use comprises about 0.25-500 mg active compound sufficiently mixed with a solid or liquid pharmaceutically acceptable carrier. The dosage may be adjusted to provide the best treatment response. In addition, upon urgent requirement of the condition to be treated, several separate dosages per day may be administered, or the dosage may be reduced in proportion.

The selective biological properties of the compounds may be enhanced through being modified by additional appropriate functional groups. Such modification is known in the field herein and includes the modification of penetrate to biological cavities (such as blood, lymphatic system, central nervous system), improves oral effectiveness and improves the solubility so that it can be administered by injection, alter metabolism and change the excretion.

The compound or pharmaceutically acceptable salt or hydrate disclosed herein may be used effectively for preventing, managing, treating or lessening the severity of tissue or organ fibrosis in a patient, especially in renal interstitial fibrosis, glomerulosclerosis, liver fibrosis, pulmonary fibrosis, peritoneum fibrosis, myocardial fibrosis, dermatofibrosis, postsurgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

General Synthetic Procedures

Generally, the compounds disclosed herein may be prepared by methods described herein, wherein the substituents are as defined for Formulas (I), (V), (VI), (VII) or (IV), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra were recorded with a Bruker 400 MHz spectrometer at ambient temperature. $^1H$ NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis, An ESI source was used on the LC-MS spectrometer.

Low-resolution mass spectral (MS) data were also determined on an Agilent 6120 series LC-MS spectrometer equipped with G1311A Quaternary pump, a G1316A TCC (Temperature Control of Column, maintained at 30° C.), a G1329A autosampler and a G1315D DAD detector were used in the analysis, An ESI source was used on the LC-MS spectrometer.

Both LC-MS spectrometers were equipped with an Agilent Zorbax SB-C18, 2.1×30 mm, 5 µm column. Injection volumn was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient condition is shown in Table 1:

TABLE 1

| Time(min) | A (CH$_3$CN, 0.1% HCOOH) | B (H$_2$O, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were also assessed by Agilent 1100 Series high performance liquid chromatography (HPLC) with UV detection at 210 nm and 254 nm (Zorbax SB-C18, 2.1×30 mm, 4 micron, 10 min, 0.6 mL/min flow rate, 5 to 95% (0.1% formic acid in CH$_3$CN) in (0.1% formic acid in H$_2$O). Column was operated at 40° C.

The following abbreviations are used throughout the specification:

BPO benzoyl peroxide
NH$_4$Cl ammonium chloride
BOC, Boc tert-butyloxycarbonyl
Boc2O Di-tert-butyl dicarbonate
Cs$_2$CO$_3$ cesium carbonate
CHCl$_3$ chloroform
CCl$_{1-4}$ carbon tetrachloride
CDCl$_3$ chloroform deuterated
CuI copper (I) iodide
DMAC N,N-Dimethylacetamide
DMF dimethylformamide
DMAP 4-dimethylaminopyridine
DMSO dimethylsulfoxide
EtOAc ethyl acetate
g gram
h hour(s)
min minute(s)
HCl hydrochloric acid
H$_2$ hydrogen
MeOH, CH$_3$OH methanol
EtOH ethanol
CH$_2$Cl$_2$, DCM dichloromethane
mL, ml milliliter
N$_2$ nitrogen
Pd/C palladium on carbon
PE petroleum ether (60-90° C.)
K$_2$CO$_3$ potassium carbonate
RT, rt, room temperature
NaHCO$_3$ sodium bicarbonate
NaCl sodium chloride
Na$_2$SO$_4$ sodium sulfate
NaOH sodium hydroxide
THF tetrahydrofuran
Et$_3$N, TEA triethylamine
NBS N-bromosuccinimide
H$_2$O water
AlMe$_3$ trimethylaluminium
Lawesson's Reagent 1,3,2,4-dithiadiphosphetane, 2,4-bis(4-methoxyphenyl)-,2,4-disulfide
TBAB tetrabutyl ammonium bromide
Rh$_2$(OAc)$_2$ Rhodium (II) acetate
PFD pirfenidone

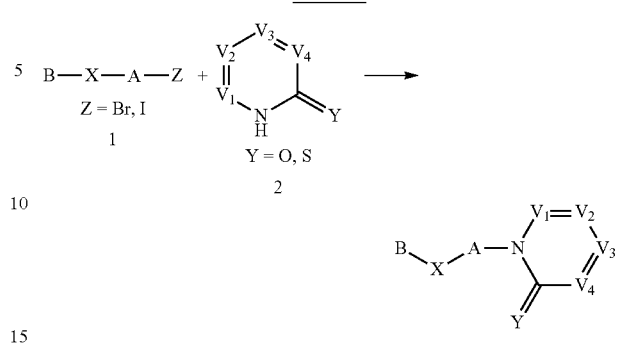

Scheme 1

Compound 3, wherein each of V$_1$, V$_2$, V$_3$, V$_4$, A, B and X is as defined above, can be prepared by the process illustrated in Scheme 1. A mixture of compound 1, compound 2, a base (such as potassium carbonate, cesium carbonate, potassium phosphate, etc.) and a ligand (such as 8-hydroxyquinoline, ethyl 2-oxocyclohexanecarboxylate, N,N'-dimethylethane-1,2-diamine, etc.) dissolved in a solvent (such as dioxane, N,N-dimethyl formamide or dimethyl sulfoxide) is heated at an appropriate temperature (such as 50-140 C.) under a nitrogen atmosphere to give the target compound 3.

Scheme 2

Compound 6, wherein each of R$^2$, R$^4$, X and B is as defined above, can be prepared by the process illustrated in Scheme 2. A mixture of iodine-containing derivative 4, pyridone derivative 5, a base (such as potassium carbonate, cesium carbonate, potassium phosphate, etc.) and a ligand (such as 8-hydroxyquinoline, ethyl 2-oxocyclohexanecarboxylate, N,N'-dimethyl ethane-1,2-diamine, etc.) dissolved in a solvent (such as dioxane, N,N-dimethyl formamide or dimethyl sulfoxide) is heated at an appropriate temperature (such as 50-140° C.) under a nitrogen atmosphere to give the compound 6.

135

Scheme 3

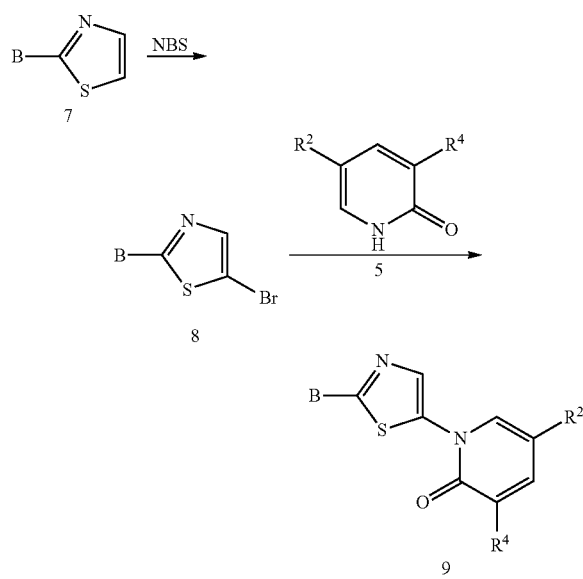

Compound 9, wherein each of R², R⁴ and B is as defined above, can be prepared by the process illustrated in Scheme 3. Thiazole derivative 7 is reacted with NBS to afford a bromine-containing derivative 8. A mixture of bromine-containing derivative 8, pyridone derivatives 5, a base (such as potassium carbonate, cesium carbonate, potassium phosphate, etc.), a ligand (such as 8-hydroxyquinolinemorpholine, ethyl 2-oxocyclohexanecarboxylate, N,N'-dimethyl ethane-1,2-diamine, etc.) dissolved in a solvent (such as dioxane, N,N-dimethyl formamide or dimethyl sulfoxide) is heated at an appropriate temperature (such as 50-140° C.) under a nitrogen atmosphere to give the compound 9.

Scheme 4

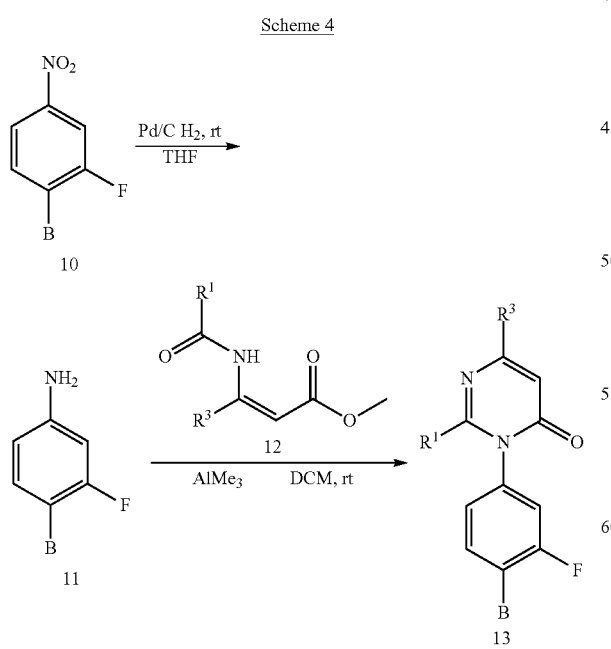

Compound 13, wherein each of R¹, R³ and B is as defined herein, can be prepared by the process illustrated in Scheme

136

4. Amines 11 can be prepared through catalytic hydrogenation of nitro derivative 10. The amines 11 is then reacted with compound 12 under the action of trimethylaluminium in organic solvent (such as dichloromethane, etc.) to give the target compound 13.

Scheme 5

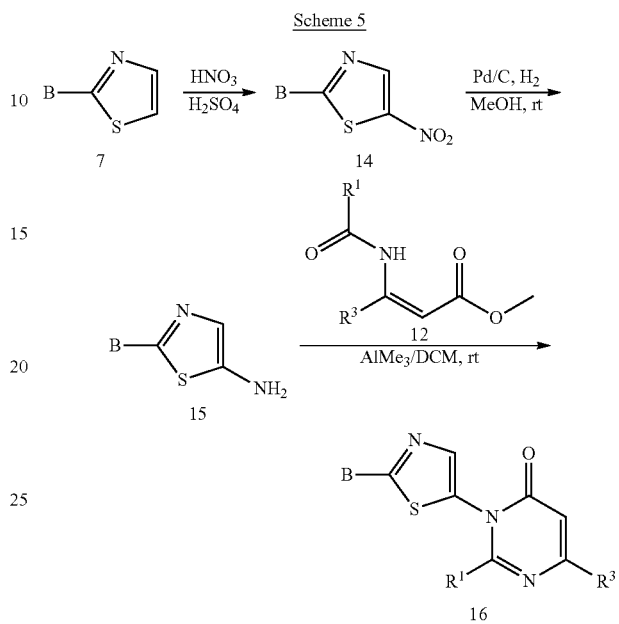

Compound 16, wherein each of R¹, R³ and B is as defined herein, can be prepared by the process illustrated in Scheme 5. Thiazole derivative 7 can be transformed to nitro derivative 14 under the action of strong acid (such as concentrated nitric acid, concentrated sulfuric acid, etc.). The nitro derivative 14 is then reduced through catalytic hydrogenation to afford amine 15 followed by reacting with compound 12 under the action of trimethylaluminum in organic solvent (such as dichloromethane, etc.) to give the target compound 16.

Scheme 6

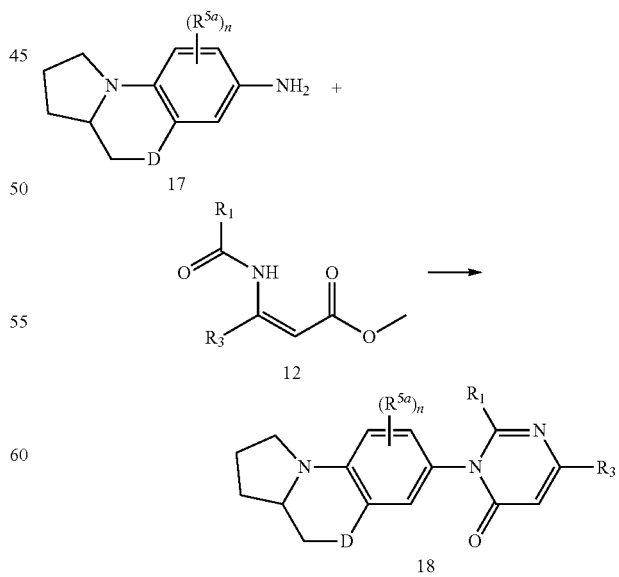

Compound 18, wherein each of R¹, R³, R⁵ᵃ, n and D is as defined herein, can be prepared by the process illustrated in Scheme 6. Fused tricyclic compound 17 is reacted with compound 12 under the action of trimethylaluminium in organic solvent (such as dichloromethane, etc.) to give the target compound 18.

EXAMPLES

Example 1

1-(3-fluoro-4-(morpholinomethyl)phenyl)-5-methyl-pyridin-2(1H)-one

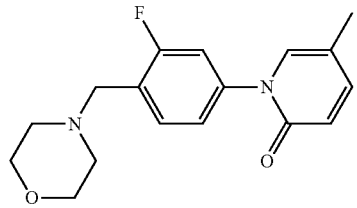 [SMILES: Cc1ccc(=O)n(-c2ccc(CN3CCOCC3)c(F)c2)c1]

Step 1) 4-(2-fluoro-4-iodobenzyl)morpholine

To a solution of 2-fluoro-4-iodotoluene (23.60 g, 0.10 mol) in CHCl$_3$ (1000 mL) was added BPO (0.55 g, 2.27 mmol) and NBS (24.92 g, 0.14 mol) under N$_2$. The reaction mixture was refluxed for 6 h, then cooled and filtered. The filtrate was concentrated in vacuo. The residue was added to a solution of morpholine (43.56 g, 0.50 mol) in EtOH (1000 mL) under N$_2$. The resulting mixture was stirred at rt overnight, and concentrated in vacuo. The residue was purified by a silica gel column chromatography (PE/EtOAc (V/V)=3:1) to give the title compound as a white solid (4.82 g, 15%).

Step 2) 1-(3-fluoro-4-(morpholinomethyl)phenyl)-5-methylpyridin-2(1H)-one

A mixture of CuI (0.19 g, 1 mmol), Cs$_2$CO$_3$ (6.85 g, 20 mmol) and ethyl 2-oxocyclohexanecarboxylate (0.34 g, 2 mmol) in DMSO (10 mL) was stirred at rt for 30 min under N$_2$. Then to the reaction mixture was added a solution of 5-methylpyridone (1.09 g, 10 mmol) and 4-(2-fluoro-4-iodobenzyl) morpholine (3.21 g, 10 mmol) in DMSO (12 mL) via syringe. The reaction mixture was heated at 100° C. overnight, cooled to rt and filtered. The filtrate diluted with H$_2$O (50 mL) was extracted with CH$_2$Cl$_2$ (50 mL×3). The combined organic phases were concentrated in vacuo. The residue was purified by a silica gel column chromatography (PE/EtOAc (V/V)=10:1) to give the title compound as a white solid (0.70 g, 23%). The compound was characterized by the following spectroscopic data:

MS (ESI, pos.ion) m/z: 303.2 (M+1);

$^1$H-NMR (400 MHz, CDCl$_3$): δ 2.06 (s, 3H), 3.16-3.32 (m, 4H), 3.86-3.97 (m, 4H), 4.44 (s, 2H), 6.47 (d, 1H, J=9.6 Hz), 7.39-7.44 (m, 2H), 7.48 (s, 1H), 7.52-7.55 (m, 1H), 7.99 (t, 1H, J=8.2 Hz).

Example 2

1-(3-fluoro-4-(morpholinomethyl)phenyl)-3,5-dimethylpyridin-2(1H)-one

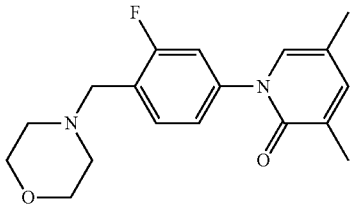

A mixture of 3,5-dimethylpyridin-2(1H)-one (0.22 g, 1.80 mmol), 4-(2-fluoro-4-iodobenzyl)morpholine (0.58 g, 1.80 mmol), K$_2$CO$_3$ (2.48 g, 18 mmol), CuI (0.02 g, 0.1 mmol) and DMF (3 mL) was refluxed under N$_2$. The reaction process was monitored by TLC. The reaction mixture was cooled to rt and filtered. To the filtrate was added H$_2$O (10 mL) and CH$_2$Cl$_2$ (20 mL). The CH$_2$Cl$_2$ layer was separated, and the aqueous layer was extracted with CH$_2$Cl$_2$ (20 mL×2). The combined organic phases were dried over Na$_2$SO$_4$ and concentrated in vacuo. The residue was purified by a silica gel column chromatography (PE/EtOAc (V/V)=1:1) to give the title compound as a white solid (0.28 g, 50%). The compound was characterized by the following spectroscopic data:

MS (ESI, pos.ion) m/z: 317.1 (M+1);

$^1$H-NMR (400 MHz, CDCl$_3$): δ 2.06 (s, 3H), 2.16 (s, 3H), 2.61 (s, 2H), 4.10 (m, 4H), 4.32 (m, 4H), 6.97 (s, 1H), 7.09 (s, 1H), 7.24 (d, 1H), 7.31 (d, 1H), 8.1 (s, 1H).

Example 3

1-(3-fluoro-4-((4-methylpiperazin-1-yl)methyl)phenyl)-3,5-dimethylpyridin-2(1H)-one

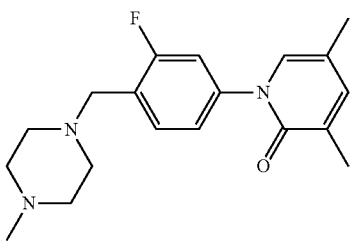 [SMILES: Cc1cc(C)c(=O)n(-c2ccc(CN3CCN(C)CC3)c(F)c2)c1]

Step 1)
1-(2-fluoro-4-iodobenzyl)-4-methylpiperazine

To a mixture of 2-fluoro-4-iodotoluene (0.94 g, 4.0 mmol) in CCl$_4$ (40 mL) were added BPO (0.02 g, 0.08 mmol) and NBS (0.78 g, 4.4 mmol) under N$_2$. The reaction mixture was refluxed for 5 h, then cooled and concentrated in vacuo. To the residue was added a solution of methylpiperazine (2.00 g, 20 mmol) in EtOH (40 mL) under N$_2$. The mixture was stirred at rt overnight and concentrated in vacuo. The resulting residue was purified by a silica gel column chromatography (PE/EtOAc (V/V)=10:1) to give the title compound as a white solid (0.69 g, 52%).

Step 2) 1-(3-fluoro-4-((4-methylpiperazin-1-yl) methyl)phenyl)-3,5-dimethyl pyridin-2(1H)-one A mixture of 3,5-dimethylpyridin-2(1H)-one (0.07 g, 0.57 mmol), 1-(2-fluoro-4-iodobenzyl)-4-methylpiperazine (0.19 g, 0.57 mmol), K$_2$CO$_3$ (0.08 g, 0.58 mmol), CuI (0.005 g, 0.026 mmol) and DMF (1 mL) was refluxed under N$_2$. The reaction process was monitored by TLC. After the reaction was completed, the mixture was cooled to rt. To the resulting mixture was added H$_2$O (5 mL) and CH$_2$Cl$_2$ (10 mL×3). The organic phase was separated, dried over Na$_2$SO$_4$ and concentrated in vacuo. The residue was purified by a silica gel column chromatography (PE/EtOAc (V/V)=1:1) to give the title compound as a pale yellow solid (0.07 g, 37%). The compound was characterized by the following spectroscopic data:

MS (ESI, pos.ion) m/z: 317.1 (M+1);
$^1$H-NMR (400 MHz, CDCl$_3$): δ 2.08 (s, 3H), 2.17 (s, 3H), 2.29 (s, 3H), 2.46-2.54 (m, 8H), 3.61 (s, 2H), 6.97 (s, 1H), 7.11-7.15 (m, 3H), 7.47-7.511 (m, 1H).

Example 4

1-(4-((diethylamino)methyl)-3-fluorophenyl)-3,5-dimethylpyridin-2(1H)-one

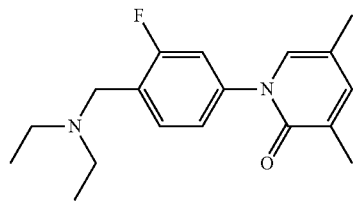 [SMILES: CCN(CC)Cc1ccc(-n2cc(C)cc(C)c2=O)cc1F]

Step 1) 1-(bromomethyl)-2-fluoro-4-iodobenzene

To a solution of 2-fluoro-4-iodotoluene (2.83 g, 12 mmol) in CCl$_4$ (120 mL) were added NBS (2.24 g, 12.6 mmol) and BPO (0.06 g, 0.24 mmol). The reaction mixture was refluxed for 9 h under N$_2$, then cooled to rt and concentrated in vacuo. The residue was purified by a silica gel column chromatography (PE) to give the title compound as a white solid (2.16 g, 57%).

Step 2) N-ethyl-N-(2-fluoro-4-iodobenzyl)ethanamine

A mixture of 1-(bromomethyl)-2-fluoro-4-iodobenzene (1.89 g, 6.0 mmol) and a solution of diethylamine (2.19 g, 30 mmol) in EtOH (60 mL) was stirred at rt overnight under N$_2$, then concentrated in vacuo. The residue was dissolved in EtOAc (100 mL), and washed with water (100 mL×3) followed by brine (100 mL). The organic phase was concentrated in vacuo to give the title compound as colorless oil (1.72 g, 94%).

Step 3) 1-(4-((diethylamino)methyl)-3-fluorophenyl)-3,5-dimethylpyridin-2(1H)-one To a solution of N-ethyl-N-(2-fluoro-4-iodobenzyl)ethanamine (1.72 g, 5.60 mmol) in dioxane (50 mL) was added 3,5-dimethyl-pyridone (0.69 g, 5.60 mmol), N,N'-dimethyl ethane-1,2-diamine (0.20 g, 2.24 mmol), CuI (0.21 g, 1.12 mmol) and potassium phosphate (2.38 g, 11.20 mmol) under N$_2$. The reaction mixture was heated at 110° C. for 9 h, then cooled to rt and poured into CH$_2$Cl$_2$ (200 mL). The mixture was filtered, and the filtrate was washed with water (200 mL×3) and brine (200 mL). The organic phase was concentrated in vacuo. The residue was purified by a silica gel column chromatography (CH$_2$Cl$_2$/MeOH (V/V)=10:1) to give the title compound as a yellow solid (0.23 g, 14%). The compound was characterized by the following spectroscopic data:

MS (ESI, pos.ion) m/z: 303.7 (M+1);
$^1$H-NMR (400 MHz, CDCl$_3$): δ 1.06 (t, 6H, J=7.2 Hz), 2.07 (s, 3H), 2.17 (s, 3H), 2.53-2.58 (m, 4H), 3.65 (s, 2H), 6.98 (s, 1H), 7.15-7.09 (m, 3H), 7.55 (t, 1H, J=8.2 Hz).

Example 5

3-(3-fluoro-4-(morpholinomethyl)phenyl)-2,6-dimethylpyrimidin-4(3H)-one

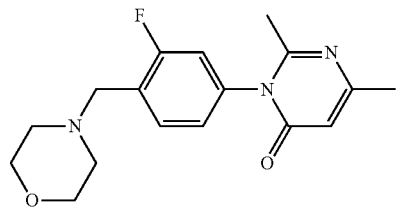

Step 1) 1-(bromomethyl)-2-fluoro-4-nitrobenzene

To a solution of 1-methyl-2-fluoro-4-nitrobenzene (4.96 g, 32 mmol) and NBS (6.05 g, 34 mmol) in CCl$_4$ (80 mL) was added BPO (0.39 g, 1.6 mmol). The mixture was heated at 68° C. for 5 h, then filtered and concentrated in vacuo. The residue was purified by a silica gel column chromatography (PE/EtOAc (V/V)=20:1) to give the title compound as a yellow solid (4.53 g, 60%).

Step 2) 4-(2-fluoro-4-nitrobenzyl)morpholine

To a solution of 1-(bromomethyl)-2-fluoro-4-nitrobenzene (3.04 g, 13 mmol) in CH$_2$Cl$_2$ (50 mL) were added morpholine (1.74 g, 20 mmol) and Et$_3$N (2.63 g, 26 mmol). The reaction was refluxed overnight, and then concentrated in vacuo. The residue was purified by a silica gel column chromatography (PE/EtOAc (V/V)=4:1) to give the title compound as a yellow solid (2.05 g, 65%).

Step 3) 3-fluoro-4-(morpholinomethyl)aniline

To a solution of 4-(2-fluoro-4-nitrobenzyl)morpholine (14.80 g, 62 mmol) in MeOH (100 mL) was added Pd/C (4.0 g). The reaction mixture was stirred at rt under H$_2$ overnight and filtered. The filtrate was concentrated in vacuo. The residue was purified by a silica gel column chromatography (PE/EtOAc (V/V)=1:1) to give the title compound as a claybank solid (11.27 g, 87%).

Step 4) 3-(3-fluoro-4-(morpholinomethyl)phenyl)-2,6-dimethylpyrimidin-4(3H)-one

A mixture of 3-fluoro-4-(morpholinomethyl)aniline (0.21 g, 1.00 mmol), anhydrous CH$_2$Cl$_2$ (10 mL) and trimethylaluminum (4.5 mL, 4.5 mmol, 1.0 M in heptane) was stirred at rt for 20 min under N$_2$, followed by the addition of a solution of methyl 3-acetaminocrotonate (0.19 g, 1.20 mmol) in CH$_2$Cl$_2$ (5 mL). The reaction mixture was stirred at rt for 10 h, then quenched with saturated NH$_4$Cl aqueous solution and extracted with CH$_2$Cl$_2$. The combined organic phases were washed with saturated NaHCO$_3$ aqueous solution and brine, dried over anhydrous Na$_2$SO$_4$ and concentrated in vacuo. The residue was purified by a silica gel column chromatography (PE/EtOAc (V/V)=1:1) to give the title compound as a pale yellow solid (0.105 g, 30%). The compound was characterized by the following spectroscopic data:

MS (ESI, pos.ion) m/z: 318.2 (M+1);
$^1$H-NMR (400 MHz, CDCl$_3$): δ 2.18 (s, 3H), 2.31 (s, 3H), 2.53 (s, 4H), 3.62 (m, 2H), 3.74 (s, 4H), 6.3 (s, 1H), 6.96 (m, 2H), 7.61 (s, 1H).

Example 6

1-(2-(4-ethoxyphenyl)thiazol-5-yl)-3,5-dimethyl-pyridin-2(1H)-one

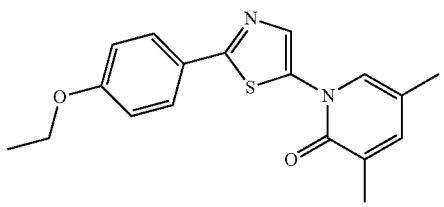 [SMILES: CCOc1ccc(-c2ncc(-n3cc(C)cc(C)c3=O)s2)cc1]

Step 1) 2-(4-hydroxyphenyl)thiazole

To a mixture of 4-hydroxybenzothioamide (30.64 g, 0.20 mol) and 2-bromo-1,1-dimethoxyethane (31.00 g, 0.20 mol) in EtOH (600 mL) was added 4-methylbenzenesulfonic acid (34.44 g, 0.20 mol) with stirring at rt. The reaction mixture was heated at 90° C. for 24 h, then cooled to rt and concentrated in vacuo. The mixture was diluted with H$_2$O (200 mL), adjusted to pH 10 with saturated NaHCO$_3$ aqueous solution and extracted with DCM (200 mL×3). The combined organic phases were concentrated in vacuo to give the title compound as s yellow solid (21.3 g, 60%).

Step 2) 2-(4-ethoxyphenyl)thiazole

To a mixture of 2-(4-hydroxyphenyl)thiazole (21.27 g, 0.12 mol) and K$_2$CO$_3$ (82.93 g, 0.60 mol) in acetone (1000 mL) was added bromoethane (39.24 g, 0.36 mol) with stirring at rt. The reaction mixture was heated at 60° C. for 11 h, then cooled to rt, filtered and concentrated in vacuo to give the title compound as a white solid (24.54 g, 100%).

Step 3) 5-bromo-2-(4-ethoxyphenyl)thiazole

To a solution of 2-(4-ethoxyphenyl)thiazole (1.03 g, 5.00 mmol) in DCM (30 mL) were added NBS (0.98 g, 5.50 mmol) and acetic acid (0.3 mL) with stirring at rt under N$_2$. The reaction was stirred at 48° C. for 3 h, then cooled to rt and concentrated in vacuo. The residue was purified by a silica gel column chromatography (PE/EtOAc (V/V)=1:1) to give the title compound as a white solid (1.34 g, 94%).

Step 4) 1-(2-(4-ethoxyphenyl)thiazol-5-yl)-3,5-dimethylpyridin-2(1H)-one

A mixture of CuI (0.038 g, 0.20 mmol), Cs$_2$CO$_3$ (0.98 g, 3.00 mmol) and 8-hydroxyquinoline ligand (0.029 g, 0.20 mmol) in DMSO (2 mL) was stirred at rt for 30 min under N$_2$. Then to the reaction mixture was added a solution of 3,5-dimethylpyridin-2(1H)-one (0.30 g, 2.40 mmol) and 5-bromo-2-(4-ethoxyphenyl)thiazole (0.57 g, 2.00 mmol) in DMSO (2 mL) via syringe. The reaction mixture was heated at 130° C. for 12 h, then cooled to rt and filtered. The filtrate was diluted with H$_2$O (10 mL) and extracted with CH$_2$Cl$_2$ (20 mL×3). The combined organic phases were concentrated in vacuo. The residue was purified by a silica gel column chromatography (PE/EtOAc (V/V)=1:10) to give the title compound (0.17 g, 26%). The compound was characterized by the following spectroscopic data:

MS (ESI, pos.ion) m/z: 327 (M+1);
$^1$H-NMR (400 MHz, CDCl$_3$): δ 1.44 (t, 3H, J=7.0 Hz), 2.15 (s, 3H), 2.21 (s, 3H), 4.07-4.12 (m, 2H), 6.95 (d, 2H, J=8.8 Hz), 7.16 (s, 1H), 7.36 (s, 1H), 7.82 (s, 1H), 7.88 (d, 2H, J=8.8 Hz).

Example 7

3-(3-fluoro-4-morpholinophenyl)-2,6-dimethylpyrimidin-4(3H)-one

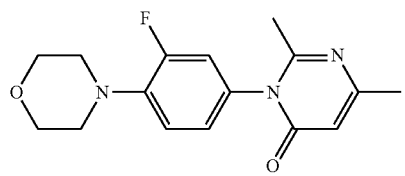

Step 1) 4-(2-fluoro-4-nitrophenyl)morpholine

To a solution of morpholine (12.04 g, 0.14 mol) and Et$_3$N (13.97 g, 0.14 mol) in EtOAc was added 3,4-difluoronitrobenzene (20.0 g, 0.13 mol) dropwise in an ice bath. The reaction mixture was warmed to rt slowly, stirred at rt overnight, and then filtered. The filter cake was washed with water, dried in vacuo to obtain the 1$^{st}$ crop of product. The organic phase was separated from the filtrate, and the water phase was washed with EtOAc. The combined organic phases were dried over anhydrous Na$_2$SO$_4$ and concentrated in vacuo to obtain the 2$^{nd}$ crop of product. The solids of 1$^{st}$ crop and 2$^{nd}$ crop were combined to give the title compound as a yellow solid (28.0 g, 99%).

Step 2) 3-fluoro-4-morpholinoaniline

To a solution of 4-(2-fluoro-4-nitrophenyl)morpholine (15.0 g, 66 mmol) in THF (100 mL) was added Pd/C (3.0 g). The reaction mixture was stirred at rt under H$_2$ for 12 h. The mixture was filtered through a celite pad, and the filtrate was concentrated in vacuo to give the title compound as a white solid (11.55 g, 89%).

Step 3) methyl 3-acetaminocrotonate

To acetic anhydride (300 mL, 3.04 mol) was added methyl-2-aminocrotonate (100 g, 0.87 mol). The mixture was stirred at 75° C. for 3 h, cooled to rt and concentrated in vacuo. The crude product was recrystallized from EtOH (150 mL) to give the title compound as a white solid (46 g, 34%).

Step 4) 3-(3-fluoro-4-morpholinophenyl)-2,6-dimethylpyrimidin-4(3H)-one

To a solution of 3-fluoro-4-morpholinoaniline (11.0 g, 56 mmol) in $CH_2Cl_2$ (200 mL) was added trimethylaluminium (168 mL, 168 mmol, 1 M in heptane) dropwise carefully under $N_2$. The mixture was stirred at rt for 20 min, followed by the addition of a solution of methyl 3-acetaminocrotonate (10.57 g, 67 mmol) in $CH_2Cl_2$ (30 mL). The reaction was stirred at rt for 5 h, then quenched with saturated $NH_4Cl$ aqueous solution and extracted with $CH_2Cl_2$. The combined organic phases were washed with water, dried over anhydrous $Na_2SO_4$ and concentrated in vacuo. The residue was recrystallized from EtOAc to give the title compound as a pale yellow solid (11.39 g, 67%). The compound was characterized by the following spectroscopic data:

MS (ESI, pos.ion) m/z: 304.2 (M+1);
$^1$H-NMR (400 MHz, $CDCl_3$): δ 2.19 (s, 3H), 2.30 (s, 3H), 3.09-3.22 (m, 4H), 3.88 (t, 4H, J=4.6 Hz), 6.28 (s, 1H), 6.90-6.94 (m, 2H), 7.01-7.06 (m, 1H).

Example 8

3-(4-(diethylamino)-3-fluorophenyl)-2,6-dimethylpyrimidin-4(3H)-one

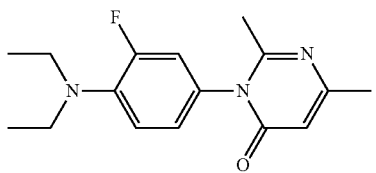 [SMILES: CCN(CC)c1ccc(-n2c(C)nc(C)cc2=O)cc1F]

Step 1) N,N-diethyl-2-fluoro-4-nitroaniline

To a solution of diethylamine (2.53 g, 34.59 mmol) and $Et_3N$ (3.82 g, 37.75 mmol) in EtOAc (40 mL) was added 3,4-difluoronitrobenzene (5.00 g, 31.43 mmol) dropwise over a period of 30 min in an ice bath. Upon the end of addition the reaction was warmed to rt slowly, and solid was precipitated out. The mixture was filtered. The filter cake was washed with an appropriate amount of water, and dried in vacuo to obtain the $1^{st}$ crop of product. The filtrate was extracted with EtOAc. The combined organic phases were dried over anhydrous $Na_2SO_4$ and concentrated in vacuo to obtain the $2^{nd}$ crop of product. The solids of $1^{st}$ crop and $2^{nd}$ crop were combined to give the title compound as a yellow solid (7.20 g, 99%).

Step 2) $N^1,N^1$-diethyl-2-fluorobenzene-1,4-diamine

To a solution of N,N-diethyl-2-fluoro-4-nitroaniline (4.00 g, 18.84 mmol) in THF (50 mL) was added Pd/C (1.50 g). The reaction mixture was stirred at rt under $H_2$ for 12 h. The mixture was filtered, and the filtrate was concentrated in vacuo to give the title compound as an offwhite solid (3.20 g, 93%).

Step 3) 3-(4-(diethylamino)-3-fluorophenyl)-2,6-dimethylpyrimidin-4(3H)-one To a solution of $N^1,N^1$-diethyl-2-fluorobenzene-1,4-diamine (1.50 g, 8.23 mmol) in anhydrous $CH_2Cl_2$ (60 mL) was added trimethylaluminium (33 mL, 33 mmol, 1 M in heptane) dropwise slowly under $N_2$. Upon the end of addition the mixture was stirred at rt for 40 min. To this mixture was added a solution of methyl 3-acetaminocrotonate (2.58 g, 16.40 mmol) in anhydrous $CH_2Cl_2$ (20 mL). The resulting reaction mixture was stirred at rt for another 6 h, then quenched with water. The organic phase was washed with brine, dried over anhydrous $Na_2SO_4$ and concentrated in vacuo. The crude product was recrystallized from EtOAc to give the title compound as a pale yellow solid (1.60 g, 67%). The compound was characterized by the following spectroscopic data:

MS (ESI, pos.ion) m/z: 290.2 (M+1);
$^1$H-NMR (400 MHz, DMSO): δ 1.07 (t, 6H, J=7.04 Hz), 2.08 (s, 3H), 2.19 (s, 3H), 3.22-3.27 (m, 4H), 6.22 (s, 1H), 6.98-7.06 (m, 2H), 7.16-7.20 (m, 1H).

Example 9

3-(3-fluoro-4-thiomorpholinophenyl)-2,6-dimethylpyrimidin-4(3H)-one

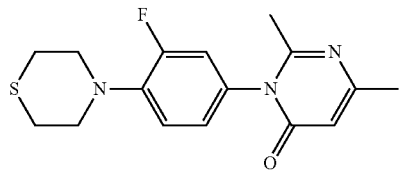

Step 1) 4-(2-fluoro-4-nitrophenyl)thiomorpholine

To a solution of thiomorpholine (3.57 g, 34.56 mmol) and $Et_3N$ (3.50 g, 34.56 mmol) in EtOAc was added 3,4-difluoronitrobenzene (5.00 g, 31.43 mmol) dropwise over a period of 30 min in an ice bath. Upon the end of addition the reaction mixture was warmed to rt slowly, and solid was precipitated out. The mixture was filtered. The filter cake was washed with an appropriate amount of water, dried in vacuo to obtain the $1^{st}$ crop of product. The filtrate was extracted with EtOAc. The combined organic phases were dried over anhydrous $Na_2SO_4$ and concentrated in vacuo to obtain the $2^{nd}$ crop of product. The solids of $1^{st}$ crop and $2^{nd}$ crop were combined to give the title compound as a yellow solid (5.50 g, 72%).

Step 2) 3-fluoro-4-thiomorpholinoaniline

To a solution of 4-(2-fluoro-4-nitrophenyl)thiomorpholine (4.00 g, 16.51 mmol) in THF (50 mL) was added Pd/C (1.30 g). The reaction mixture was stirred at rt under $H_2$ for 12 h. The mixture was filtered, and the filtrate was concentrated in vacuo to give the title compound as an offwhite solid (3.40 g, 97%).

Step 3) 3-(3-fluoro-4-thiomorpholinophenyl)-2,6-dimethylpyrimidin-4(3H)-one To a solution of 3-fluoro-4-thiomorpholinoaniline (1.20 g, 5.65 mmol) in anhydrous $CH_2Cl_2$ (60 mL) was added trimethylaluminium (28.5 mL, 28.5 mmol, 1 M in heptane) carefully dropwise under the protection of N₂. Upon the end of addition the mixture was stirred at rt for 40 min, followed by the addition of a solution of methyl 3-acetaminocrotonate (2.66 g, 16.92 mmol) in anhydrous CH₂Cl₂ (20 mL). Upon the end of addition the reaction mixture was stirred at rt for another 6 h, then quenched with water and extracted with CH₂Cl₂. The combined organic phases were washed with brine, dried over anhydrous Na₂SO₄ and concentrated in vacuo to give the title compound as pale yellow solid (0.91 g, 67%). The compound was characterized by the following spectroscopic data:

MS (ESI, pos.ion) m/z: 320.2 (M+1);
¹H-NMR (400 MHz, CDCl₃): δ 2.07 (s, 3H), 2.19 (s, 3H), 2.77 (t, 4H, J=4.76 Hz), 3.33 (d, 4H, J=4.12 Hz), 6.23 (s, 1H), 7.08-7.11 (m, 1H), 7.16-7.20 (m, 1H), 7.25-7.29 (m, 1H).

Example 10

3-(4-(1,1-dioxidothiomorpholino)-3-fluorophenyl)-2,6-dimethylpyrimidin-4(3H)-one

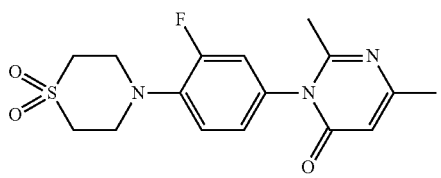 [SMILES: Cc1cc(=O)n(-c2ccc(N3CCS(=O)(=O)CC3)c(F)c2)c(C)n1]

Step 1) 4-(2-fluoro-4-nitrophenyl)1,1-dioxidothiomorpholine

To a suspension of K₂CO₃ (5.53 g, 40 mmol) and 1,1-dioxo-thio-morpholinehydrochloride (3.60 g, 21 mmol) in DMSO (50 mL) was added 3,4-difluoronitrobenzene (3.18 g, 20 mmol). The reaction was heated at 100° C. for 12 h. The mixture was diluted with water (150 mL) and extracted with CH₂Cl₂ (100 mL×2). The combined organic phases were dried over anhydrous Na₂SO₄ and concentrated in vacuo to give the title compound as a yellow solid (6.04 g, 70%).

Step 2) 4-(4-amino-2-fluorophenyl)1,1-dioxidothiomorpholine

To a solution of 4-(2-fluoro-4-nitrophenyl)1,1-dioxidothiomorpholine (4.00 g, 14.58 mmol) in THF (50 mL) was added Pd/C (1.30 g). The reaction mixture was stirred at rt under H₂ for 12 h. The mixture was filtered, and the filtrate was concentrated in vacuo to give the title compound as an offwhite solid (2.40 g, 67%).

Step 3) 3-(4-(1,1-dioxidothiomorpholino)-3-fluorophenyl)-2,6-dimethyl pyrimidin-4(3H)-one To a solution of 4-(4-amino-2-fluorophenyl)1,1-dioxidothiomorpholine (1.20 g, 4.91 mmol) in anhydrous CH₂Cl₂ (100 mL) was added trimethylaluminium (28.5 mL, 28.5 mmol, 1 M in heptane) carefully dropwise under N₂. Upon the end of addition the mixture was stirred at rt for 20 min, followed by the addition of a solution of methyl 3-acetaminocrotonate (2.32 g, 14.76 mmol) in anhydrous CH₂Cl₂ (30 mL). Upon the end of addition the reaction mixture was stirred at rt for another 15 h, then quenched with an appropriate amount of water and extracted with CH₂Cl₂. The combined organic phases were washed with brine, dried and concentrated in vacuo to give the title compound as a yellow solid (0.81 g, 47%). The compound was characterized by the following spectroscopic data:

MS (ESI, pos.ion) m/z: 352.1 (M+1);
¹H-NMR (400 MHz, DMSO-d₆): δ 2.07 (s, 3H), 2.20 (s, 3H), 3.29 (t, 4H, J=4.4 Hz), 3.58 (d, 4H, J=4.4 Hz), 6.23 (s, 1H), 7.13-7.11 (m, 1H), 7.26-7.28 (m, 1H), 7.31-7.35 (m, 1H).

Example 11

3-(3-fluoro-4-(piperidin-1-yl)phenyl)-2,6-dimethyl-pyrimidin-4(3H)-one

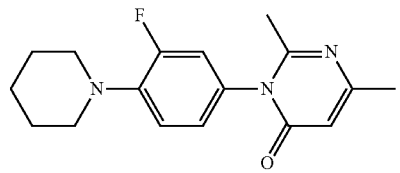 [SMILES: Cc1cc(=O)n(-c2ccc(N3CCCCC3)c(F)c2)c(C)n1]

Step 1) 1-(2-fluoro-4-nitrophenyl)piperidine

To a solution of piperidine (5.88 g, 69 mmol) and Et₃N (6.98 g, 69 mmol) in EtOAc (60 mL) was added 1,2-difluoro-4-nitrobenzene (10.00 g, 63 mmol) dropwise. The mixture was stirred at rt overnight. The resulting mixture was washed with brine, dried over anhydrous Na₂SO₄ and concentrated in vacuo to give the title compound as a yellow solid (14.00 g, 99%).

Step 2) 3-fluoro-4-(piperidin-1-yl)aniline

To a solution of 1-(2-fluoro-4-nitrophenyl)piperidine (14.00 g, 62 mmol) in THF (80 mL) was added Pd/C (3.00 g). The reaction mixture was stirred at rt under H₂ overnight. The mixture was filtered, and the filtrate was concentrated in vacuo to give the title compound as a claybank solid (11.00 g, 87%).

Step 3) 3-(3-fluoro-4-(piperidin-1-yl)phenyl)-2,6-dimethylpyrimidin-4(3H)-one

To a solution of 3-fluoro-4-(piperidin-1-yl)aniline (10.00 g, 51 mmol) in anhydrous CH₂Cl₂ (100 mL) was added trimethylaluminum (155 mL, 155 mmol, 1.0 M in toluene) under N₂. The mixture was stirred at rt for 20 min, followed by the addition of a solution of methyl 3-acetaminocrotonate (9.72 g, 62 mmol) in anhydrous CH₂Cl₂ (20 mL). The reaction mixture was stirred at rt for 5 h, then quenched with saturated NH₄Cl aqueous solution and extracted with CH₂Cl₂. The combined organic phases were washed with brine, dried over anhydrous Na₂SO₄ and concentrated in vacuo. The residue was purified by a silica gel column chromatography (PE/EtOAc (V/V)=2:1) to give the title compound as a pale yellow solid (11.02 g, 71%). The compound was characterized by the following spectroscopic data:

MS (ESI, pos.ion) m/z: 302.2 (M+1);

¹H-NMR (400 MHz, CDCl₃): δ 1.57-1.63 (m, 2H), 1.78-1.72 (m, 4H), 2.18 (s, 3H), 2.29 (s, 3H), 3.07-3.01 (m, 2H), 3.11-3.16 (m, 2H), 6.28 (s, 1H), 6.86-6.88 (m, 1H), 6.89-6.90 (m, 1H), 7.02-7.06 (m, 1H).

Example 12

3-(3-fluoro-4-(4-methylpiperazin-1-yl)phenyl)-2,6-dimethylpyrimidin-4(3H)-one

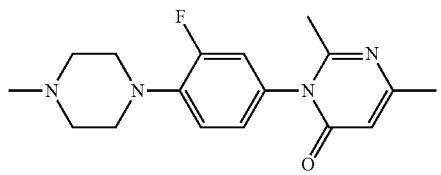

Step 1)
1-(2-fluoro-4-nitrophenyl)-4-methylpiperazine

To a solution of 1-methylpiperazine (6.91 g, 69 mmol) and Et₃N (6.98 g, 69 mmol) in EtOAc (60 mL) was added 1,2-difluoro-4-nitrobenzene (10.02 g, 63 mmol) dropwise with stirring and the mixture was stirred at rt overnight. The reaction mixture was washed with brine, dried over anhydrous Na₂SO₄ and concentrated in vacuo to give the title compound as a yellow solid (14.75 g, 98%).

Step 2) 3-fluoro-4-(4-methylpiperazin-1-yl)aniline

To a solution of 1-(2-fluoro-4-nitrophenyl)-4-methylpiperazine (14.76 g, 61.70 mmol) in THF (80 mL) was added Pd/C (3.00 g). The reaction was stirred at rt under H₂ overnight. The mixture was filtered, and the filtrate was concentrated in vacuo to give the title compound as an offwhite solid (11.99 g, 93%).

Step 3) 3-(3-fluoro-4-(4-methylpiperazin-1-yl)phenyl)-2,6-dimethylpyrimidin-4(3H)-one To a solution of 3-fluoro-4-(4-methylpiperazin-1-yl)aniline (11.01 g, 52.60 mol) in anhydrous CH₂Cl₂ (200 mL) was added trimethylaluminum (158 mL, 158 mmol, 1.0 M in toluene) slowly under N₂. The mixture was stirred at rt for 20 min, followed by the addition of a solution of methyl 3-acetaminocrotonate (9.92 g, 63.10 mmol) in anhydrous CH₂Cl₂ (20 mL). The reaction mixture was stirred at rt for another 5 h, then quenched with saturated NH₄Cl aqueous solution and extracted with CH₂Cl₂. The combined organic phases were washed with brine, dried over anhydrous Na₂SO₄ and concentrated in vacuo. The residue was purified by a silica gel column chromatography (CH₂Cl₂/MeOH (V/V)=5:1) to give the title compound as a white solid (11.31 g, 68%). The compound was characterized by the following spectroscopic data:

MS (ESI, pos.ion) m/z: 317.2 (M+1);

¹H-NMR (400 MHz, CDCl₃): δ 2.19 (s, 3H), 2.29 (s, 3H), 2.37 (s, 3H), 2.61 (s, 4H), 3.14-3.24 (m, 4H), 6.28 (s, 1H), 6.88-6.91 (m, 2H), 7.05 (t, 1H, J=8.8 Hz).

Example 13

3-(9-fluoro-2,3,3a,4-tetrahydro-1H-benzo[b]pyrrolo[1,2-d][1,4]oxazin-7-yl)-2,6-dimethylpyrimidin-4(3H)-one

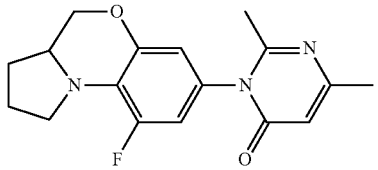 [SMILES: Cc1cc(=O)n(-c2cc(F)c3c(c2)OCC2CCCN32)c(C)n1]

Step 1) 9-fluoro-7-nitro-2,3,3a,4-tetrahydro-1H-benzo[b]pyrrolo[1,2-d][1,4]oxazine To a suspension of prolinol (2.74 g, 27.11 mmol) and KOH (3.17 g, 56.47 mmol) in DMSO (30 mL) was added 1,2,3-trifluoro-5-nitrobenzene (4.00 g, 22.59 mmol) at rt. The reaction mixture was heated at 65° C. for 4 h. The mixture was diluted with water (150 mL) and extracted with CH₂Cl₂ (100 mL×2). The combined organic phases were dried over anhydrous Na₂SO₄ and concentrated in vacuo to give the title compound as a yellow solid (5.00 g, 93%).

Step 2) 9-fluoro-2,3,3a,4-tetrahydro-1H-benzo[b]pyrrolo[1,2-d][1,4]oxazin-7-amine To a solution of 9-fluoro-7-nitro-2,3,3a,4-tetrahydro-1H-benzo[b]pyrrolo[1,2-d][1,4]oxazine (4.00 g, 16.79 mmol) in THF (40 mL) was added Pd/C (1.50 g). The reaction mixture was stirred at rt under H₂ for 12 h. The mixture was filtered through a celite pad, and the filtrate was concentrated in vacuo to give the title compound as an offwhite solid (3.00 g, 85%).

Step 3) 3-(9-fluoro-2,3,3a,4-tetrahydro-1H-benzo[b]pyrrolo[1,2-d][1,4]oxazin-7-yl)-2,6-dimethylpyrimidin-4(3H)-one To a solution of 9-fluoro-2,3,3a,4-tetrahydro-1H-benzo[b]pyrrolo[1,2-d][1,4]oxazin-7-amine (2.00 g, 9.61 mmol) in anhydrous CH₂Cl₂ (50 mL) was added trimethylaluminum (48 mL, 48 mmol, 1 M in heptane) slowly under N₂. Upon the end of addition the mixture was stirred at rt for 40 min, followed by addition of a solution of methyl 3-acetaminocrotonate (2.66 g, 16.92 mmol) in anhydrous CH₂Cl₂ (30 mL) dropwise. The reaction mixture was stirred at rt for another 5 h, then quenched with an appropriate amount of water. The organic phase was washed with brine, dried over anhydrous Na₂SO₄ and concentrated in vacuo to give the title compound as a white solid (1.00 g, 33.0%). The compound was characterized by the following spectroscopic data:

MS (ESI, pos.ion) m/z: 316.2 (M+1);

¹H-NMR (400 MHz, DMSO-d₆): δ 1.52-1.56 (m, 1H), 1.88-1.90 (m, 2H), 2.10 (s, 3H), 2.18 (s, 3H), 2.31 (s, 1H), 3.12-3.18 (q, 1H), 3.37-3.40 (m, 2H), 3.79-3.84 (m, 1H), 4.35 (d, 1H, J=9.5 Hz), 6.20 (s, 1H), 6.71 (s, 1H), 6.82 (d, 1H, J=1.7 Hz).

Example 14

3-(2-(4-(diethylamino)phenyl)thiazol-5-yl)-2,6-dimethylpyrimidin-4(3H)-one

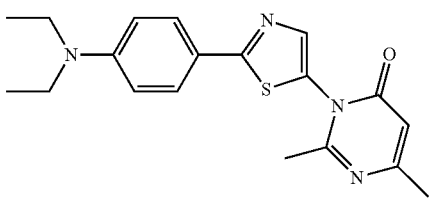 [SMILES: CCN(CC)c1ccc(-c2ncc(-n3c(C)nc(C)cc3=O)s2)cc1]

Step 1) 4-(diethylamino)benzamide

To a solution of 4-aminobenzamide (6.81 g, 50 mmol) in DMF (70 mL) were added NaI (22.48 g, 150 mmol) and $K_2CO_3$ (13.82 g, 100 mmol) followed by bromoethane (13.62 g, 125 mmol) with stirring. The reaction mixture was heated at 110° C. overnight, followed by the addition of bromoethane (13.62 g, 125 mmol). The reaction mixture was stirred further at 110° C. for another 6 h, then cooled to rt. DMF was removed in vacuo. To the residue was added water (100 mL). The mixture was stirred for 10 min, filtered and the filter cake was dried in vacuo to give the title compound as a yellow solid (7.40 g, 77%).

Step 2) 4-(diethylamino)benzothioamide

To a solution of 4-(diethylamino)benzamide (5.66 g, 29.43 mmol) in THF (80 mL) was added $P_2S_5$ (9.81 g, 44.14 mmol) at 50° C. over a period of 1 h. The mixture was heated at 55° C. for 8 h, then cooled to rt, filtered and the filtrate was concentrated in vacuo. The residue was purified by a silica gel column chromatography (PE/EtOAc (V/V)=2:1) to give the title compound as a yellow solid (1.23 g, 20%).

Step 3) N,N-diethyl-4-(thiazol-2-yl)aniline

To a solution of 4-(diethylamino)benzothioamide (2.29 g, 11 mmol) in EtOH (60 mL) were added 2-bromo-1,1-dimethoxyethane (1.86 g, 11 mmol) and p-toluenesulfonic acid (1.89 g, 11 mmol). The reaction mixture was heated at 95° C. overnight, then cooled to rt and concentrated in vacuo. The residue was purified by a silica gel column chromatography (PE/EtOAc/$Et_3N$ (V/V/V)=2:1:0.05) to give the title compound as a white solid (1.40 g, 55%).

Step 4) N,N-diethyl-4-(5-nitrothiazol-2-yl)aniline

To a mixture of N,N-diethyl-4-(thiazol-2-yl)aniline (1.39 g, 6.00 mmol) and concentrated sulfuric acid (10 mL) was added concentrated nitric acid (0.45 mL) at −10° C. The reaction mixture was stirred at 0° C. for 3 h, then poured into ice water and extracted with $CH_2Cl_2$ (30 mL×3). The organic phase was dried over $Na_2SO_4$ and concentrated in vacuo. The residue was purified by a silica gel column chromatography (PE/$CH_2Cl_2$ (V/V)=1:1) to give the title compound as a yellow solid (0.73 g, 44%).

Step 5) 2-(4-(diethylamino)phenyl)thiazol-5-amine

To a solution of N,N-diethyl-4-(5-nitrothiazol-2-yl)aniline (0.73 g, 2.64 mmol) in MeOH (30 mL) was added Pd/C (73 mg). The reaction mixture was stirred at rt under $H_2$ overnight, then filtered. The filtrate was concentrated in vacuo. The residue was purified by a silica gel column chromatography (PE/EtOAc (V/V)=5:1) to give the title compound as a white solid (0.45 g, 69%).

Step 6) 3-(2-(4-(diethylamino)phenyl)thiazol-5-yl)-2,6-dimethylpyrimidin-4(3H)-one To a solution of 2-(4-(diethylamino)phenyl)thiazol-5-amine (0.45 g, 1.82 mmol) in $CH_2Cl_2$ (20 mL) was added trimethylaluminum (4.5 mL, 9.0 mmol, 2 M in toluene) dropwise at rt. The reaction mixture was stirred at rt for 1 h, followed by the addition of a solution of methyl 3-acetaminocrotonate ((315 mg, 2 mmol) in anhydrous $CH_2Cl_2$ (5 mL). The reaction mixture was stirred at rt for 3 days, then quenched with saturated $NH_4Cl$ aqueous solution and extracted with $CH_2Cl_2$ (50 mL×3). The combined organic phases were dried over $Na_2SO_4$ and concentrated in vacuo. The residue was purified by a silica gel column chromatography to give the title compound as a yellow solid (22 mg, 3%). The compound was characterized by the following spectroscopic data:

MS (ESI, pos.ion) m/z: 355.2 (M+1);
$^1$H-NMR (400 MHz, DMSO-$d_6$): δ 0.89 (t, 6H, J=12.0 Hz), 2.08 (s, 3H), 2.23 (s, 3H), 2.95-3.02 (m, 4H), 6.33 (s, 1H), 7.29 (d, 1H, J=12.0 Hz), 7.72-7.74 (m, 2H), 7.87 (d, 1H, J=4.0 Hz), 7.95-7.98 (m, 1H).

Example 15

2,6-dimethyl-3-(2-(4-morpholinophenyl)thiazol-5-yl)pyrimidin-4(3H)-one

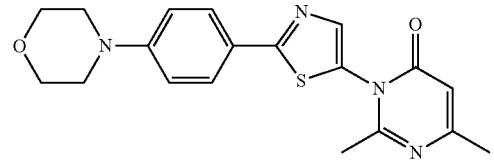 [SMILES: Cc1cc(=O)n(-c2cnc(-c3ccc(N4CCOCC4)cc3)s2)c(C)n1]

Step 1) 4-morpholinobenzamide

To a solution of 4-aminobenzamide (6.81 g, 50 mmol) in DMF (70 mL) were added NaI (22.48 g, 150 mmol) and $K_2CO_3$ (13.82 g, 100 mmol). The mixture was heated to 140° C. and 2,2'-dichlorodiethyl ether (14.30 g, 100 mmol) was added. The reaction mixture was heated at 150° C. for 5 h, and cooled to rt. The mixture was diluted with water (100 mL), stirred for 10 min, and filtered. The filter cake was washed with water and dried to give the title compound as a yellow solid (6.60 g, 64%).

Step 2) 4-morpholinobenzothioamide

To a solution of 4-morpholinobenzamide (4.91 g, 23.80 mmol) in THF (70 mL) was added Lawesson's Reagent (10.60 g, 26.20 mmol) with stirring. The mixture was heated at 70° C. for 4 h, then cooled to rt and concentrated in vacuo. $CH_2Cl_2$ (30 mL) and water (100 mL) was added to the residue. The mixture was then filtered and the filter cake was washed with water and dried to give the title compound as a yellow solid (4.41 g, 83.3%).

Step 3) 4-(4-(thiazol-2-yl)phenyl)morpholine

To a solution of 4-morpholinobenzothioamide (2.22 g, 10 mmol) in EtOH (50 mL) were added 2-bromo-1,1-dimethoxyethane (1.69 g, 10 mmol) and p-toluenesulfonic acid (1.90 g, 10 mmol). The reaction mixture was heated at 95° C. overnight, then cooled to rt and filtered. The filter cake was dried to give the title compound as a yellow solid (2.00 g, 81%).

Step 4) 4-(4-(5-nitrothiazol-2-yl)phenyl)morpholine

To a mixture of 4-(4-(thiazol-2-yl)phenyl)morpholine (2.00 g, 8.13 mmol) and concentrated sulfuric acid (25 mL) was added concentrated nitric acid (0.60 mL) at −10° C. The reaction mixture was stirred at 0° C. for 4.5 h, then poured into ice water, and extracted with $CH_2Cl_2$ (60 mL×3). The organic phase was dried over $Na_2SO_4$ and concentrated in vacuo to give the title compound as a yellow solid (0.70 g, 30%).

Step 5) 2-(4-morpholinophenyl)thiazol-5-amine

To a solution of 4-(4-(5-nitrothiazol-2-yl)phenyl)morpholine (0.70 g, 2.44 mmol) in $CH_2Cl_2$ (20 mL) was added Pd/C (70 mg). The reaction mixture was stirred at rt under $H_2$ overnight, and filtered. The filtrate was concentrated in vacuo to give the title compound as an offwhite solid (0.20 g, 32%).

Step 6) 2,6-dimethyl-3-(2-(4-morpholinophenyl)thiazol-5-yl)pyrimidin-4(3H)-one To a solution of 2-(4-morpholinophenyl)thiazol-5-amine (0.20 g, 0.77 mmol) in $CH_2Cl_2$ (20 mL) was added trimethylaluminum (2.3 mL, 4.6 mmol, 2 M in toluene) dropwise at rt. The reaction mixture was stirred at rt for 1 h, followed by the addition of a solution of methyl 3-acetaminocrotonate (132 mg, 0.84 mmol) in anhydrous $CH_2Cl_2$ (5 mL). The reaction mixture was stirred at rt overnight, then quenched with saturated $NH_4Cl$ aqueous solution and extracted with $CH_2Cl_2$ (50 mL×3). The combined organic phases were dried over anhydrous $Na_2SO_4$ and concentrated in vacuo. The residue was purified by preparative TLC to give the title compound as a pale yellow solid (20 mg, 7%). The compound was characterized by the following spectroscopic data:

MS (ESI, pos.ion) m/z: 369.1 (M+1);

$^1$H-NMR (400 MHz, DMSO-$d_6$): δ 2.20 (s, 3H), 2.34 (s, 3H), 2.62-2.84 (m, 2H), 3.06-3.10 (s, 2H), 3.63-3.66 (m, 4H), 6.32 (s, 1H), 7.26 (d, 1H, J=4.2 Hz), 7.32 (d, 2H, J=3.2 Hz), 7.77 (d, 1H, J=2.4 Hz), 7.84 (d, 1H, J=3.6 Hz), 8.02-8.05 (m, 1H).

Example 16

2,6-dimethyl-3-(3-morpholinophenyl)pyrimidin-4(3H)-one

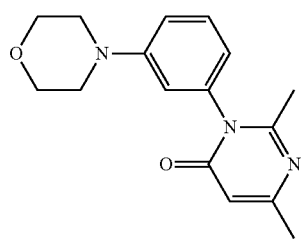 [SMILES: Cc1cc(=O)n(-c2cccc(N3CCOCC3)c2)c(C)n1]

Step 1) tert-butyl (3-nitrophenyl)carbamate

To a solution of 3-nitroaniline (6.91 g, 50 mmol) in THF (150 mL) were added $Boc_2O$ (13.10 g, 60 mmol) and DMAP (1.53 g, 12.5 mmol) with stirring. The reaction mixture was refluxed overnight under $N_2$, then cooled to rt and concentrated in vacuo. The residue was dissolved in $CH_2Cl_2$ (200 mL). The solution was then washed with water (200 mL×3) and brine (200 mL), dried over anhydrous $Na_2SO_4$ and concentrated in vacuo. The crude product was purified by a silica gel column chromatography (PE/EtOAc (V/V)=4:1) to give the title compound as a pale yellow solid (10.75 g, 90%).

Step 2) tert-butyl (3-aminophenyl)carbamate

To a solution of tert-butyl (3-nitrophenyl)carbamate (10.75 g, 45.12 mmol) in MeOH (150 mL) was added catalyst 10% Pd/C (0.48 g). The reaction mixture was stirred at rt under $H_2$ overnight, and filtered. The filtrate was concentrated in vacuo. The residue was purified by a silica gel column chromatography (PE/EtOAc (V/V)=4:1) to give the title compound as a pale yellow solid (7.59 g, 81%).

Step 3) tert-butyl (3-morpholinophenyl)carbamate

To a suspension of tert-butyl (3-aminophenyl)carbamate (7.59 g, 36.40 mmol), $K_2CO_3$ (10.06 g, 72.80 mmol) and NaI (16.37 g, 109.20 mmol) in DMF (300 mL) was added 2,2'-dichlorodiethyl ether (5.73 g, 40.1 mmol) slowly at 150° C. under $N_2$. The reaction mixture was stirred at 150° C. overnight, then cooled to rt, poured into water (700 mL) and extracted with $CH_2Cl_2$ (200 mL×3). The combined organic phases were washed with water (200 mL×3) and brine (200 mL), dried over anhydrous $Na_2SO_4$ and concentrated in vacuo. The residue was purified by a silica gel column chromatography (PE/EtOAc (V/V)=4:1) to give the title compound as a yellow solid (5.91 g, 58%).

Step 4) 3-morpholinoaniline

A solution of tert-butyl (3-morpholinophenyl)carbamate (5.91 g, 21.20 mmol) in a solution of HCl (106 mL, 106.0 mmol, 1 M in MeOH) was stirred at rt overnight, then concentrated in vacuo. The residue was dissolved in water (100 mL). The soltution was basified with saturated $Na_2CO_3$ aqueous solution and extracted with $CH_2Cl_2$ (100 mL×3). The combined organic phases were washed with brine (150 mL), dried over anhydrous $Na_2SO_4$ and concentrated in vacuo to give the title compound as a light brown solid (3.42 g, 91%).

Step 5) 2,6-dimethyl-3-(3-morpholinophenyl)pyrimidin-4(3H)-one

To a solution of 3-morpholinylaniline (3.42 g, 19.20 mmol) in $CH_2Cl_2$ (100 mL) was added trimethylaluminum (96 mL, 96 mmol, 1 M in toluene) carefully under $N_2$. The reaction mixture was stirred at rt for 30 min, followed by the addition of a solution of methyl 3-acetaminocrotonate (3.29 g, 19.20 mmol) in anhydrous $CH_2Cl_2$ (50 mL). The reaction mixture was stirred at rt overnight, then quenched with saturated $NH_4Cl$ aqueous solution (200 mL) and extracted with $CH_2Cl_2$ (200 mL×3). The combined organic phases were washed with brine (300 mL), dried over anhydrous $Na_2SO_4$ and concentrated in vacuo. The residue was purified by a silica gel column chromatography (PE/EtOAc (V/V)=1:1) to give the title compound as a yellow solid (0.73 g, 13%). The compound was characterized by the following spectroscopic data:

MS (ESI, pos.ion) m/z: 286.3 (M+1);

$^1$H-NMR (400 MHz, CDCl$_3$): δ 2.19 (s, 3H), 2.29 (s, 3H), 3.17-3.19 (m, 4H), 3.84 (t, 4H, J=4.8 Hz), 6.28 (s, 1H), 6.66 (d, 2H, J=8.0 Hz), 6.98 (d, 1H, J=9.3 Hz), 7.40 (t, 1H, J=8.2 Hz).

Example 17

3-(2-fluoro-5-morpholinophenyl)-2,6-dimethylpyrimidin-4(3H)-one

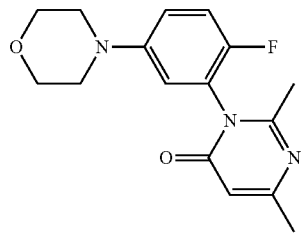 [SMILES: Cc1cc(=O)n(-c2cc(N3CCOCC3)ccc2F)c(C)n1]

Step 1) tert-butyl (2-fluoro-5-nitrophenyl)carbamate

To a solution of 2-fluoro-5-nitroaniline (4.68 g, 30 mmol) in THF (150 mL) were added Boc$_2$O (9.82 g, 45 mmol) and DMAP (7.33 g, 60 mmol). The reaction mixture was refluxed overnight under N$_2$, then cooled to rt and concentrated in vacuo. The residue was dissolved in EtOAc (250 mL), and the organic phase was washed with water (200 mL×3) and brine (200 mL), dried over anhydrous Na$_2$SO$_4$ and concentrated in vacuo. The crude product was purified by a silica gel column chromatography (PE/EtOAc (V/V)=8:1) to give the title compound as a yellowish solid (3.54 g, 40%).

Step 2) tert-butyl (2-fluoro-5-aminophenyl)carbamate

To a solution of tert-butyl (2-fluoro-5-nitrophenyl)carbamate (3.54 g, 13.8 mmol) in MeOH (100 mL) was added catalyst 10% Pd/C (0.15 g). The reaction was stirred at rt under H$_2$ overnight, and filtered. The filtrate was concentrated in vacuo. The residue was purified by a silica gel column chromatography (PE/EtOAc (V/V)=4:1) to give the title compound as a yellowish solid (2.02 g, 65%).

Step 3) tert-butyl (2-fluoro-5-morpholinophenyl)carbamate

To a mixture of tert-butyl (2-fluoro-5-aminophenyl)carbamate (2.02 g, 8.93 mmol), K$_2$CO$_3$ (2.47 g, 17.86 mmoll) and NaI (4.02 g, 26.79 mmol) in DMF (60 mL) was added 2,2'-dichlorodiethyl ether (1.28 g, 8.93 mmol) slowly at 150° C. under N$_2$. The reaction was heated at 150° C. overnight, then cooled to rt, poured into water (200 mL) and extracted with CH$_2$Cl$_2$ (200 mL×2). The combined organic phases were washed with water (200 mL×2) and brine (200 mL), dried over anhydrous Na$_2$SO$_4$ and concentrated in vacuo. The residue was purified by a silica gel column chromatography (PE/EtOAc (V/V)=4:1) to give the title compound as a yellow solid (0.93 g, 35%).

Step 4) 2-fluoro-5-morpholinoaniline

A mixture of tert-butyl (2-fluoro-5-morpholinophenyl)carbamate (0.93 g, 3.14 mmol) and a solution of HCl (31 mL, 31 mmol, 1 M in MeOH) was stirred at rt overnight, then concentrated in vacuo. The residue was dissolved in water (150 mL). The soltution was basified with saturated Na$_2$CO$_3$ aqueous solution and extracted with CH$_2$Cl$_2$ (100 mL×3). The combined organic phases were washed with brine (150 mL), dried over anhydrous Na$_2$SO$_4$ and concentrated in vacuo to give the title compound as a light brown solid (0.35 g, 57%).

Step 5) 3-(2-fluoro-5-morpholinophenyl)-2,6-dimethylpyrimidin-4(3H)-one

To a solution of 2-fluoro-5-morpholinoaniline (0.35 g, 1.78 mmol) in CH$_2$Cl$_2$ (20 mL) was added trimethylaluminum (3.3 mL, 6.6 mmol, 2 M in toluene) dropwise. The reaction mixture was stirred at rt for 20 min, followed by the addition of a solution of methyl 3-acetaminocrotonate (0.30 g, 1.78 mmol) in anhydrous CH$_2$Cl$_2$ (10 mL). The reaction mixture was stirred at rt overnight, then quenched with saturated NH$_4$Cl aqueous solution (80 mL) and extracted with CH$_2$Cl$_2$ (100 mL×3). The combined organic phases were washed with brine (150 mL), dried over anhydrous Na$_2$SO$_4$ and concentrated in vacuo. The residue was purified by a silica gel column chromatography (PE/EtOAc (V/V)=1:2) to give the title compound as a yellow solid (0.37 g, 69%). The compound was characterized by the following spectroscopic data:

MS (ESI, pos.ion) m/z: 304.2 (M+1);

$^1$H-NMR (400 MHz, CDCl$_3$): δ 2.23 (s, 3H), 2.30 (s, 3H), 3.11-3.14 (m, 4H), 3.85 (t, 4H, J=4.8 Hz), 6.29 (s, 1H), 6.70-6.71 (m, 1H), 6.96-7.00 (m, 1H), 7.18 (t, 1H, J=9.0 Hz).

Example 18

3-(3-fluoro-4-(1H-pyrrol-1-yl)phenyl)-2,6-dimethylpyrimidin-4(3H)-one

Step 1) 1-(2-fluoro-4-nitrophenyl)-1H-pyrrole

To a solution of 1,2-difluoro-4-nitrobenzene (1.59 g, 10 mmol) in DMSO (15 mL) were added K$_2$CO$_3$ (3.04 g, 22 mmol) and pyrrole (0.74 g, 11 mmol) with stirring. The reaction mixture was heated at 90° C. for 18 h, and cooled to rt. The mixture was diluted with water (50 mL), filtered and the filter cake was dried to give the title compound as a yellow solid (2.00 g, 97%).

Step 2) 3-fluoro-4-(1H-pyrrol-1-yl)aniline

To a solution of 1-(2-fluoro-4-nitrophenyl)-1H-pyrrole (2.00 g, 9.70 mmol) in CH$_2$Cl$_2$ (35 mL) was added catalyst Pd/C (0.20 g). The reaction mixture was stirred at rt under H$_2$ for 5 h, and filtered. The filtrate was concentrated in vacuo. The residue was purified by a silica gel column chromatography (PE/CH$_2$Cl$_2$ (V/V)=3:1) to give the title compound as a white solid (1.30 g, 76%).

Step 3) 3-(3-fluoro-4-(1H-pyrrol-1-yl)phenyl)-2,6-dimethylpyrimidin-4(3H)-one To a solution of 3-fluoro-4-(1H-pyrrol-1-yl)aniline (0.80 g, 4.55 mmol) in CH$_2$Cl$_2$ (30 mL) was added trimethylaluminum (23 mL, 23 mmol, 1 M in heptane) slowly. The reaction mixture was stirred at rt for 0.5 h, followed by the addition of a solution of methyl 3-acetaminocrotonate (785 mg, 5.0 mmol) in CH$_2$Cl$_2$ (10 mL). The reaction mixture was stirred at rt for 3 days, then quenched with saturated NH$_4$Cl aqueous solution and extracted with CH$_2$Cl$_2$ (100 mL×3). The combined organic phases were dried over anhydrous Na$_2$SO$_4$ and concentrated in vacuo. The residue was purified by a silica gel column chromatography (PE/EtOAc (V/V)=3:2) to give the title compound as a pale yellow solid (450 mg, 35%). The compound was characterized by the following spectroscopic data:

MS (ESI, pos.ion) m/z: 284.2 (M+1);
$^1$H-NMR (400 MHz, CDCl$_3$): δ 2.25 (s, 3H), 2.32 (s, 3H), 6.32 (s, 1H), 6.40 (t, 2H, J=2.2 Hz), 7.08-7.11 (m, 3H), 7.13 (dd, 1H, J$_1$=2.2 Hz, J$_2$=10.8 Hz), 7.54 (t, 1H, J=8.4 Hz).

Example 19

3-(3-fluoro-4-(1H-pyrazol-1-yl)phenyl)-2,6-dimethylpyrimidin-4(3H)-one

Step 1) 1-(2-fluoro-4-nitrophenyl)-1H-pyrazole

To a solution of 1,2-difluoro-4-nitrobenzene (3.18 g, 20 mmol) in DMSO (35 mL) were added K$_2$CO$_3$ (6.08 g, 44 mmol) and pyrazole (1.50 g, 22 mmol) with stirring. The reaction mixture was heated at 90° C. for 18 h, and cooled to rt. The mixture was diluted with water (50 mL) and filtered. The filtrate was extracted with DCM (50 mL×3), the combined organic phases were concentrated in vacuo. The crude product was purified by a silica gel column chromatography (PE/CH$_2$Cl$_2$ (V/V)=1:1) to give the title compound as a yellow solid (3.31 g, 80%).

Step 2) 3-fluoro-4-(1H-pyrazol-1-yl)aniline

To a solution of 1-(2-fluoro-4-nitrophenyl)-1H-pyrazole (3.31 g, 16 mmol) in CH$_2$Cl$_2$ (60 mL) was added catalyst Pd/C (0.33 g). The reaction mixture was stirred at rt under H$_2$ overnight, and filtered. The filtrate was concentrated in vacuo. The residue was purified by a silica gel column chromatography (PE/CH$_2$Cl$_2$ (V/V)=1:1) to give the title compound as a white solid (1.30 g, 46%).

Step 3) 3-(3-fluoro-4-(1H-pyrazol-1-yl)phenyl)-2,6-dimethylpyrimidin-4(3H)-one To a solution of 3-fluoro-4-(1H-pyrazol-1-yl)aniline (0.65 g, 3.68 mmol) in CH$_2$Cl$_2$ (30 mL) was added trimethylaluminum (18.4 mL, 36.8 mmol, 2 M in heptane) slowly. The reaction mixture was stirred at rt for 0.5 h, followed by the addition of a solution of methyl 3-acetaminocrotonate (634 mg, 4.04 mmol) in CH$_2$Cl$_2$ (10 mL). The reaction was stirred at rt for 3 days, then quenched with saturated NH$_4$Cl aqueous solution and extracted with CH$_2$Cl$_2$ (100 mL×3). The combined organic phases were dried over anhydrous Na$_2$SO$_4$ and concentrated in vacuo. The residue was purified by a silica gel column chromatography (PE/EtOAc (V/V)=1:2) to give the title compound as a white solid (400 mg, 38%). The compound was characterized by the following spectroscopic data:

MS (ESI, pos.ion) m/z: 285.2 (M+1);
$^1$H-NMR (400 MHz, CDCl$_3$): δ 2.23 (s, 3H), 2.32 (s, 3H), 6.32 (s, 1H), 6.54 (t, 1H, J=2.0 Hz), 7.13-7.19 (m, 2H), 7.78 (d, 1H, J=4.0 Hz), 8.08 (t, 1H, J=2.0 Hz), 8.12-8.16 (m, 1H).

Example 20

3-(3-fluoro-4-morpholinophenyl)-2-((3-fluorophenoxy)methyl)-6-methylpyrimidin-4(3H)-one

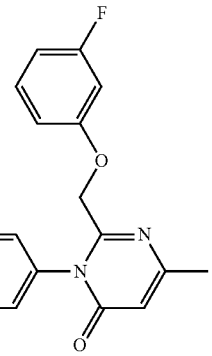

Step 1) methyl 3-(2-bromoacetamido)crotonate

A mixture of methyl 3-aminocrotonate (3.20 g, 27.79 mmol) and pyridine (2.64 g, 33.33 mmol) in CH$_2$Cl$_2$ (60 mL) was stirred at −20° C. for 20 min. To the mixture was added a solution of bromoacetyl bromide (5.61 g, 27.79 mmol) in CH$_2$Cl$_2$ (20 mL) dropwise. The mixture was stirred at rt for 2 h. The organic phase was washed with brine (100 mL×3), dried over anhydrous Na$_2$SO$_4$ and concentrated in vacuo. The residue was purified by a silica gel column chromatography (PE/EtOAc (V/V)=5:1) to give the title compound as a reddish solid (0.99 g, 15%).

Step 2) methyl 3-(2-(3-fluorophenoxy)acetamido)crotonate

To a suspension of K$_2$CO$_3$ (0.37 g, 2.68 mmol) in acetone (10 mL) were added 3-fluorophenol (0.30 g, 2.68 mmol) and methyl 3-(2-bromoacetamido)crotonate (0.76 g, 3.22 mmol), the mixture was refluxed for 5 h and cooled to rt. The mixture was concentrated in vacuo and the residue was dissolved in CH$_2$Cl$_2$ (40 mL), washed with brine (40 mL×3).

The organic phase was dried over anhydrous Na₂SO₄ and concentrated in vacuo. The residue was purified by a silica gel column chromatography (PE/EtOAc (V/V)=10:1) to give the title compound as a yellowish solid (0.50 g, 70%).

Step 3) 3-(3-fluoro-4-morpholinophenyl)-2-((3-fluorophenoxy)methyl)-6-methyl-pyrimidin-4(3H)-one To a solution of 3-fluoro-4-morpholinoaniline (0.55 g, 2.80 mmol) in anhydrous CH₂Cl₂ (40 mL) was added trimethylaluminium (2.0 mL, 4 mmol, 2 M in heptane) carefully under N₂ at rt. The mixture was stirred at rt for 30 min, followed by the addition of a solution of methyl 3-(2-(3-fluorophenoxy)acetamido)crotonate (0.75 g, 2.80 mmol) in anhydrous CH₂Cl₂ (10 mL). The reaction mixture was stirred for another 7 h, then quenched with an appropriate amount of water and washed with brine twice. The organic phase was dried over anhydrous Na₂SO₄ and concentrated in vacuo. The crude product was purified by a silica gel column chromatography (PE/EtOAc (V/V)=1:1) to give the title compound as a white solid (0.24 g, 62%). The compound was characterized by the following spectroscopic data:

MS (ESI, pos.ion) m/z: 414.3 (M+1);
¹H-NMR (400 MHz, CDCl₃): δ 2.34 (s, 3H), 3.03-3.14 (m, 4H), 3.85 (t, 4H, J=4.8 Hz), 4.67 (s, 2H), 6.38 (s, 1H), 6.45-6.49 (m, 1H), 6.53-6.55 (m, 1H), 6.64-6.68 (m, 1H), 6.95-6.98 (m, 3H), 7.13-7.19 (m, 1H).

Example 21

3-(3-fluoro-4-(pyrrolidin-1-yl)phenyl)-2,6-dimethyl-pyrimidin-4(3H)-one

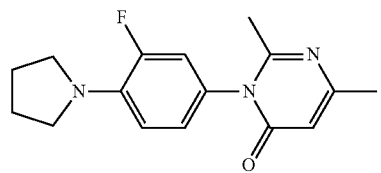 [SMILES: Cc1cc(=O)n(-c2ccc(N3CCCC3)c(F)c2)c(C)n1]

Step 1) 1-(2-fluoro-4-nitrophenyl)pyrrolidine

To a solution of pyrrolidine (0.78 g, 11 mmol) in EtOAc (15 mL) and Et₃N (1.52 g, 15 mmol) was added 1,2-difluoro-4-nitrobenzene (1.59 g, 10 mmol) in an ice bath. The mixture was stirred at rt overnight and filtered. The filter cake was washed with water and dried to give the title compound as a yellow solid (1.60 g, 76%).

Step 2) 3-fluoro-4-(pyrrolidin-1-yl)aniline

To a solution of 1-(2-fluoro-4-nitrophenyl)pyrrolidine (1.60 g, 7.62 mmol) in mixed solvents of CH₂Cl₂ (20 mL) and MeOH (20 mL) was added catalyst Pd/C (0.16 g). The reaction was stirred at rt under H₂ overnight, and filtered. The filtrate was concentrated in vacuo. The residue was purified by a silica gel column chromatography (PE/EtOAc (V/V) 5:1) to give the title compound as a white solid (1.20 g, 88%).

Step 3) 3-(3-fluoro-4-(pyrrolidin-1-yl)phenyl)-2,6-dimethylpyrimidin-4(3H)-one

To a solution of 3-fluoro-4-(pyrrolidin-1-yl)aniline (0.50 g, 2.78 mmol) in CH₂Cl₂ (20 mL) was added trimethylaluminum (14 mL, 14 mmol, 1 M in heptane) slowly at rt. The reaction mixture was stirred at rt for 0.5 h, followed by the addition of a solution of methyl 3-acetaminocrotonate (480 mg, 3.06 mmol) in CH₂Cl₂ (10 mL). The reaction mixture was stirred at rt for 3 days, then quenched with saturated NH₄Cl aqueous solution and extracted with CH₂Cl₂ (100 mL×3). The combined organic phases were dried over anhydrous Na₂SO₄ and concentrated in vacuo. The residue was purified by a silica gel column chromatography (PE/EtOAc (V/V)=1:1) to give the title compound as a pale yellow solid (300 mg, 38%). The compound was characterized by the following spectroscopic data:

MS (ESI, pos.ion) m/z: 288.3 (M+1);
¹H-NMR (400 MHz, CDCl₃): δ 1.96-1.99 (m, 4H), 2.21 (s, 3H), 2.29 (s, 3H), 3.43-3.48 (m, 4H), 6.28 (s, 1H), 6.71 (t, 1H, J=8.8 Hz), 6.78-6.84 (m, 2H).

Example 22

3-(4-(di-n-butylamino)-3-fluorophenyl)-2,6-dimethylpyrimidin-4(3H)-one

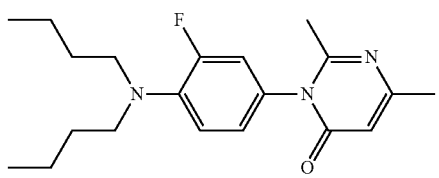 [SMILES: CCCCN(CCCC)c1ccc(-n2c(C)nc(C)cc2=O)cc1F]

Step 1) N,N-di-n-butyl-2-fluoro-4-nitroaniline

To a solution of 3,4-difluoronitrobenzene (3.18 g, 20 mmol) in DMSO (25 mL) were added K₂CO₃ (6.08 g, 44 mmol) and di-n-butylamine (2.84 g, 22 mmol) with stirring. The mixture was heated at 90° C. overnight, then cooled to rt, diluted with water (100 mL) and extracted with CH₂Cl₂ (80 mL×3). The combined organic phases were dried over anhydrous Na₂SO₄ and concentrated in vacuo. The residue was purified by a silica gel column chromatography (PE/CH₂Cl₂ (V/V)=10:1) to give the title compound as yellow oil (4.03 g, 75%).

Step 2) N¹,N¹-di-n-butyl-2-fluorobenzene-1,4-diamine

To a solution of N,N-di-n-butyl-2-fluoro-4-nitroaniline (4.03 g, 15 mmol) in mixed solvents of CH₂Cl₂ (70 mL) and MeOH (20 mL) was added catalyst Pd/C (0.40 g). The reaction mixture was stirred at rt under H₂ overnight, and filtered. The filtrate was concentrated in vacuo. The residue was purified by a silica gel column chromatography (PE/CH₂Cl₂ (V/V)=8:1) to give the title compound as colorless oil (2.32 g, 65%).

Step 3) 3-(4-(di-n-butylamino)-3-fluorophenyl)-2,6-dimethylpyrimidin-4(3H)-one

To a solution of N¹,N¹-di-n-butyl-2-fluorobenzene-1,4-diamine (1.10 g, 4.62 mmol) in CH₂Cl₂ (20 mL) was added trimethylaluminum (23 mL, 23 mmol, 1 M in heptane) slowly at rt. The reaction mixture was stirred at rt for 0.5 h, followed by the addition of a solution of methyl 3-acetaminocrotonate (798 mg, 5.08 mmol) in CH₂Cl₂ (10 mL).

The reaction was stirred at rt for 3 days, then quenched with saturated NH$_4$Cl aqueous solution and extracted with CH$_2$Cl$_2$ (100 mL×3). The combined organic phases were dried over anhydrous Na$_2$SO$_4$ and concentrated in vacuo. The residue was purified by a silica gel column chromatography (PE/EtOAc (V/V)=3:2) to give the title compound as pale yellow oil (800 mg, 50%). The compound was characterized by the following spectroscopic data:

MS (ESI, pos.ion) m/z: 346.3 (M+1);
$^1$H-NMR (400 MHz, CDCl$_3$): δ 0.93 (t, 6H, J=7.4 Hz), 1.26-1.36 (m, 4H), 1.55 (t, 4H, J=8.0 Hz), 2.20 (s, 3H), 2.29 (s, 3H), 3.21 (t, 4H, J=7.6 Hz), 6.28 (s, 1H), 6.80-6.85 (m, 2H), 6.88-6.93 (m, 1H).

Example 23

3-(4-(diisobutylamino)-3-fluorophenyl)-2,6-dimethylpyrimidin-4(3H)-one

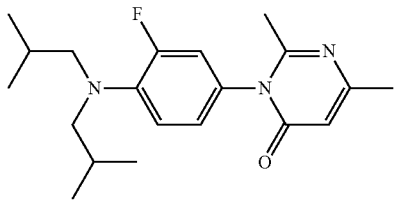 [SMILES: Cc1cc(=O)n(-c2ccc(N(CC(C)C)CC(C)C)c(F)c2)c(C)n1]

Step 1) 2-fluoro-N,N-diisobutyl-4-nitroaniline

To a solution of 3,4-difluoronitrobenzene (1.59 g, 10 mmol) in DMSO (15 mL) were added K$_2$CO$_3$ (3.04 g, 22 mmol) and diisobutylamine (1.42 g, 11 mmol). The mixture was heated at 90° C. overnight, then cooled to rt, diluted with water (50 mL) and extracted with CH$_2$Cl$_2$ (50 mL×3). The combined organic phases were dried over anhydrous Na$_2$SO$_4$ and concentrated in vacuo. The residue was purified by a silica gel column chromatography (PE/EtOAc (V/V)=10:1) to give the title compound as pale yellow oil (0.80 g, 30%).

Step 2) 2-fluoro-N$^1$,N$^1$-diisobutylbenzene-1,4-diamine

To a solution of 2-fluoro-N,N-diisobutyl-4-nitroaniline (0.8 g, 3 mmol) in mixed solvents of CH$_2$Cl$_2$ (15 mL) and MeOH (15 mL) was added catalyst Pd/C (80 mg). The reaction mixture was stirred at rt under H$_2$ overnight, and filtered. The filtrate was concentrated in vacuo. The residue was purified by a silica gel column chromatography (PE/EtOAc (V/V)=8:1) to give the title compound as pale yellow oil (0.40 g, 56%).

Step 3) 3-(4-(diisobutylamino)-3-fluorophenyl)-2,6-dimethylpyrimidin-4(3H)-one

To a solution of 2-fluoro-N$^1$,N$^1$-diisobutylbenzene-1,4-diamine (0.40 g, 1.68 mmol) in CH$_2$Cl$_2$ (20 mL) was added trimethylaluminum (8.4 mL, 8.4 mmol, 1 M in heptane) slowly at rt. The reaction mixture was stirred at rt for 0.5 h, followed by the addition of a solution of methyl 3-acetaminocrotonate (290 mg, 1.85 mmol) in CH$_2$Cl$_2$ (10 mL). The reaction mixture was stirred at rt for 3 days, then quenched with saturated NH$_4$Cl aqueous solution and extracted with CH$_2$Cl$_2$ (100 mL×3). The combined organic phases were dried over anhydrous Na$_2$SO$_4$ and concentrated in vacuo. The residue was purified by a silica gel column chromatography (PE/EtOAc (V/V)=1:1) to give the title compound as pale yellow oil (280 mg, 48%). The compound was characterized by the following spectroscopic data:

MS (ESI, pos.ion) m/z: 346.4 (M+1);
$^1$H-NMR (400 MHz, CDCl$_3$): δ 0.88-0.90 (m, 12H), 1.87-1.94 (m, 2H), 2.20 (s, 3H), 2.29 (s, 3H), 3.00-3.10 (m, 4H), 6.28 (s, 1H), 6.80-6.84 (m, 2H), 6.95 (t, 1H, J=12.9 Hz).

Example 24

3-(4-(di-n-hexylamino)-3-fluorophenyl)-2,6-dimethylpyrimidin-4(3H)-one

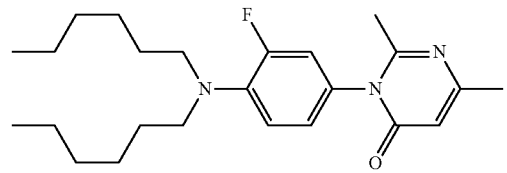

Step 1) 2-fluoro-N,N-di-n-hexyl-4-nitroaniline

To a solution of 3,4-difluoronitrobenzene (1.59 g, 10 mmol) in DMSO (15 mL) were added K$_2$CO$_3$ (3.04 g, 22 mmol) and di-n-hexylamine (2.04 g, 11 mmol). The mixture was heated at 90° C. overnight, then cooled to rt, diluted with water (50 mL) and extracted with CH$_2$Cl$_2$ (50 mL×3). The combined organic phases were dried over anhydrous Na$_2$SO$_4$ and concentrated in vacuo. The residue was purified by a silica gel column chromatography (PE/CH$_2$Cl$_2$ (V/V)=10:1) to give the title compound as pale yellow oil (2.79 g, 86%).

Step 2) 2-fluoro-N$^1$,N$^1$-di-n-hexylbenzene-1,4-diamine

To a solution of 2-fluoro-N,N-di-n-hexyl-4-nitroaniline (2.79 g, 8.64 mmol) in MeOH (50 mL) was added catalyst Pd/C (0.28 g). The reaction mixture was stirred at rt under H$_2$ overnight, and filtered. The filtrate was concentrated in vacuo. The residue was purified by a silica gel column chromatography (PE/EtOAc (V/V)=10:1) to give the title compound as pale yellow oil (1.60 g, 63%).

Step 3) 3-(4-(di-n-hexylamino)-3-fluorophenyl)-2,6-dimethylpyrimidin-4(3H)-one

To a solution of 2-fluoro-N$^1$,N$^1$-di-n-hexyl benzene-1,4-diamine (0.58 g, 1.97 mmol) in CH$_2$Cl$_2$ (20 mL) was added trimethylaluminum (9.9 mL, 19.8 mmol, 2 M in heptane) slowly at rt. The reaction mixture was stirred at rt for 0.5 h, followed by the addition of a solution of methyl 3-acetaminocrotonate (341 mg, 2.17 mmol) in CH$_2$Cl$_2$ (5 mL). The reaction mixture was stirred at rt for 3 days, then quenched with saturated NH$_4$Cl aqueous solution and extracted with CH$_2$Cl$_2$ (100 mL×3). The combined organic phases were dried over anhydrous Na$_2$SO$_4$ and concentrated in vacuo. The residue was purified by a silica gel column chromatography (PE/EtOAc (V/V)=2:1) to give the title compound as pale yellow oil (500 mg, 63%). The compound was characterized by the following spectroscopic data:

MS (ESI, pos.ion) m/z: 402.3 (M+1);

$^1$H-NMR (400 MHz, CDCl$_3$): δ 0.89 (t, 6H, J=7.0 Hz), 1.31 (t, 12H, J=7.8 Hz), 1.55 (t, 4H, J=7.2 Hz), 2.20 (s, 3H), 2.29 (s, 3H), 3.18-3.21 (m, 4H), 6.28 (s, 1H), 6.79-6.82 (m, 2H), 6.84-6.92 (m, 1H).

Example 25

2,6-dimethyl-3-(6-morpholinopyridin-3-yl)pyrimidin-4(3H)-one

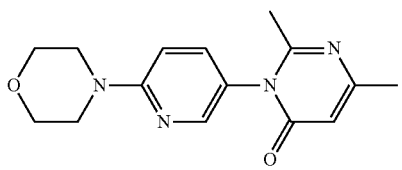

Step 1) 4-(5-nitropyridin-2-yl)morpholine

A mixture of 2-chloro-5-nitropyridine (3.17 g, 20 mmol), morpholine (2.00 g, 23 mmol) and Et$_3$N (2.43 g, 24 mmol) in EtOAc (200 mL) was refluxed for 3 h, then cooled to rt, and washed with water (100 mL×3). The organic phase was dried over anhydrous Na$_2$SO$_4$ and concentrated in vacuo to give the title compound as a yellow solid (3.89 g, 93%).

Step 2) 6-morpholinopyridin-3-amine

To a solution of 4-(5-nitropyridin-2-yl)morpholine (3.89 g, 18.60 mmol) in THF (100 mL) was added catalyst Pd/C (0.5 g). The reaction was stirred at rt under H$_2$ overnight, and filtered. The filtrate was concentrated in vacuo to give the title compound as a brown-red solid (3.30 g, 99%).

Step 3) 2,6-dimethyl-3-(6-morpholinopyridin-3-yl)pyrimidin-4(3H)-one

To a solution of 6-morpholinopyridin-3-amine (1.79 g, 10 mmol) in CH$_2$Cl$_2$ (100 mL) was added trimethylaluminium (40 mL, 40 mmol, 1 M in heptane) carefully under N$_2$. The mixture was stirred at rt for 30 min, followed by the addition of a solution of methyl 3-acetaminocrotonate (1.89 g, 12 mmol) in CH$_2$Cl$_2$ (5 mL). The reaction was stirred at rt for 6 h, then quenched with saturated NH$_4$Cl aqueous solution (100 mL). The organic phase was dried over anhydrous Na$_2$SO$_4$ and concentrated in vacuo. The residue was purified by recrystallized from EtOAc to give the title compound as a pale yellow solid (1.11 g, 39%). The compound was characterized by the following spectroscopic data:

MS (ESI, pos.ion) m/z: 287.2 (M+1);

$^1$H-NMR (400 MHz, CDCl$_3$): δ 2.22 (s, 3H), 2.30 (s, 3H), 3.54-3.60 (m, 4H), 3.83 (t, 4H, J=4.9 Hz), 6.29 (s, 1H), 6.74 (d, 1H, J=8.8 Hz), 7.33 (dd, 1H, J$_1$=2.1 Hz, J$_2$=8.8 Hz), 8.00 (d, 1H, J=2.6 Hz).

Example 26

3-(3-fluoro-4-(4-hydroxypiperidin-1-yl)phenyl)-2,6-dimethylpyrimidin-4(3H)-one

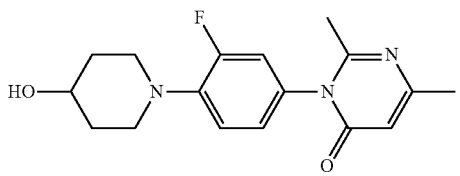 [SMILES: Cc1cc(=O)n(-c2ccc(N3CCC(O)CC3)c(F)c2)c(C)n1]

Step 1) 1-(2-fluoro-4-nitrophenyl)piperidin-4-ol

To a solution of piperidin-4-ol (11.11 g, 0.11 mol) and Et$_3$N (12.14 g, 0.12 mol) in EtOAc (500 mL) was added 1,2-difluoro-4-nitrobenzene (15.91 g, 0.10 mol). The mixture was stirred at rt for 24 h, and washed with water (200 mL×4). The organic phase was dried over anhydrous Na$_2$SO$_4$ and concentrated in vacuo to give the title compound as orange oil (19.35 g, 80%).

Step 2) 1-(4-amino-2-fluorophenyl)piperidin-4-ol

To a solution of 1-(2-fluoro-4-nitrophenyl)piperidin-4-ol (2.67 g, 11 mmol) in MeOH (100 mL) was added catalyst Pd/C (1.00 g). The reaction mixture was stirred at rt under H$_2$ for 6 h, then filtered. The filtrate was concentrated in vacuo to give the crude product (2.50 g) for the next step without further purification.

Step 3) 3-(3-fluoro-4-(4-hydroxypiperidin-1-yl)phenyl)-2,6-dimethylpyrimidin-4(3H)-one To a solution of 1-(4-amino-2-fluorophenyl)piperidin-4-ol (1.68 g, 8.00 mmol) in CH$_2$Cl$_2$ (20 mL) was added trimethylaluminium (32 mL, 64 mmol, 2 M in heptane) carefully under N$_2$. The mixture was stirred at rt for 30 min, followed by the addition of a solution of methyl 3-acetaminocrotonate (1.40 g, 8.90 mol) in CH$_2$Cl$_2$ (5 mL). The reaction mixture was stirred at rt for another 5 h, then quenched with saturated NH$_4$Cl aqueous solution (100 mL). The organic phase was dried over anhydrous Na$_2$SO$_4$ and concentrated in vacuo. The residue was purified by recrystallized from EtOAc to give the title compound as a yellow solid (1.25 g, 50%). The compound was characterized by the following spectroscopic data:

MS (ESI, pos.ion) m/z: 318.2 (M+1);

$^1$H-NMR (400 MHz, CDCl$_3$): δ 1.74-1.77 (m, 2H), 2.02-2.05 (m, 2H), 2.18 (s, 3H), 2.29 (s, 3H), 2.85-2.99 (m, 2H), 3.36-3.48 (m, 2H), 3.84-3.92 (m, 1H), 6.28 (s, 1H), 6.90 (d, 1H, J=1.2 Hz), 7.05 (t, 1H, J=0.8 Hz).

Example 27

3-(3-fluoro-4-((2-morpholinoethyl)amino)phenyl)-2,6-dimethylpyrimidin-4(3H)-one

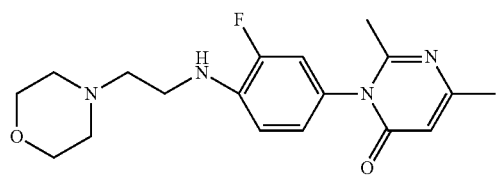 [SMILES: Cc1cc(=O)n(-c2ccc(NCCN3CCOCC3)c(F)c2)c(C)n1]

Step 1) 2-morpholinoacetonitrile

To a suspension of $K_2CO_3$ (6.50 g, 47 mmol) and morpholine (3.75 g, 43 mmol) in acetonitrile (30 mL) was added 2-bromoacetonitrile (5.16 g, 43 mmol) in one portion under the protection of $N_2$ in an ice bath. The mixture was stirred at rt for 2 h, then filtered. The filtrate was concentrated in vacuo to give the title compound as a yellow solid (5.41 g, 100%).

Step 2) 2-morpholinoethanamine

To anhydrous THF (35 mL) was added $LiAlH_4$ (3.19 g, 84 mmol) in one portion in an ice bath. The mixture was stirred at 0° C. for 20 min, and a solution of 2-morpholinoacetonitrile (3.50 g, 28 mmol) in anhydrous THF (10 mL) was added dropwise. Upon the end of addition the mixture was refluxed for 3 h, then cooled to rt, diluted with water (20 mL), filtered and concentrated in vacuo to give the title compound as yellow oil (2.62 g, 72%).

Step 3) 2-fluoro-N-(2-morpholinoethyl)-4-nitroaniline

A solution of 2-morpholinoethanamine (0.90 g, 6.91 mmol), 1,2-difluoro-4-nitrobenzene (1.10 g, 6.91 mmol) and $Et_3N$ (1.40 g, 13.82 mmol) in EtOAc (10 mL) was refluxed under $N_2$ for 24 h, then cooled to rt and concentrated in vacuo. The residue was purified by a silica gel column chromatography (PE/EtOAc (V/V)=4:1) to give the title compound as yellow oil (1.57 g, 84%).

Step 4) 2-fluoro-$N^1$-(2-morpholinoethyl)benzene-1,4-diamine

To a solution of 2-fluoro-N-(2-morpholinoethyl)-4-nitroaniline (0.60 g, 2.23 mmol) in THF (8.0 mL) was added catalyst Pd/C (0.03 g). The reaction mixture was stirred at rt under $H_2$ overnight, then filtered. The filtrate was concentrated in vacuo to give the title compound as yellow oil (0.50 g, 94%).

Step 5) 3-(3-fluoro-4-((2-morpholinoethyl)amino)phenyl)-2,6-dimethyl pyrimidin-4(3H)-one To a solution of 2-fluoro-$N^1$-(2-morpholinoethyl)benzene-1,4-diamine (0.50 g, 2.09 mmol) in $CH_2Cl_2$ (20 mL) was added trimethylaluminum (3.2 mL, 6.40 mmol, 2 M in toluene) slowly at rt. The reaction mixture was stirred at rt for 0.5 h, followed by the addition of a solution of methyl 3-acetaminocrotonate (0.65 g, 4.13 mmol) in $CH_2Cl_2$ (5 mL). The reaction mixture was stirred at rt for 36 h, then quenched with saturated $NH_4Cl$ aqueous solution and extracted with $CH_2Cl_2$ (100 mL×3). The combined organic phases were dried over anhydrous $Na_2SO_4$ and concentrated in vacuo. The residue was purified by a silica gel column chromatography (EtOAc/MeOH (V/V)=30:1) to give the title compound as a white solid (0.50 g, 24%). The compound was characterized by the following spectroscopic data:

MS (ESI, pos.ion) m/z: 347.2 (M+1);

$^1$H-NMR (400 MHz, $CDCl_3$): δ 2.08 (s, 3H), 2.18 (m, 3H), 2.43 (s, 4H), 2.57 (s, 2H), 3.25 (m, 2H), 3.58 (t, 4H, J=4.32 Hz), 5.52 (s, 1H), 6.20 (s, 1H), 6.79-6.83 (m, 1H), 6.91-6.93 (m, 1H), 7.08-7.12 (m, 1H).

Example 28

3-(3-fluoro-4-(methyl(2-morpholinoethyl)amino)phenyl)-2,6-dimethylpyrimidin-4(3H)-one

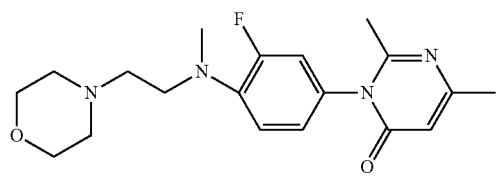 [SMILES: Cc1cc(=O)n(-c2ccc(N(C)CCN3CCOCC3)c(F)c2)c(C)n1]

To a suspension of 3-(3-fluoro-4-((2-morpholinoethyl)amino)phenyl)-2,6-dimethyl pyrimidin-4(3H)-one (0.24 g, 0.69 mmol) and $K_2CO_3$ (0.48 g, 3.47 mmol) in acetonitrile (15 mL) was added $CH_3I$ (0.30 g, 2.11 mmol). The mixture was stirred at rt for 36 h, then filtered and concentrated in vacuo. The residue was purified by a silica gel column chromatography (EtOAc/MeOH (V/V)=50:1) to give the title compound as a white solid (50 mg, 20%). The compound was characterized by the following spectroscopic data:

MS (ESI, pos.ion) m/z: 361.2 (M+1);

$^1$H-NMR (400 MHz, $CDCl_3$): δ 1.26 (s, 3H), 2.16 (s, 3H), 2.26 (s, 3H), 2.62 (m, 4H), 3.48 (m, 2H), 3.69-3.74 (m, 2H), 4.00 (m, 4H), 6.17 (s, 1H), 6.755-6.84 (m, 2H), 7.03 (m, 1H).

Example 29

3-(2-chloro-4-((2-morpholinoethyl)amino)phenyl)-2,6-dimethylpyrimidin-4(3H)-one

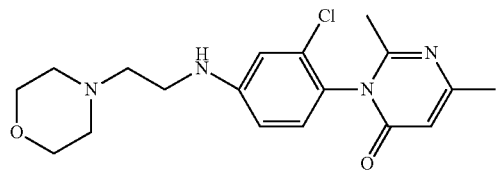 [SMILES: Cc1cc(=O)n(-c2ccc(NCCN3CCOCC3)cc2Cl)c(C)n1]

Step 1) 3-chloro-N-(2-morpholinoethyl)-4-nitroaniline

A suspension of 2-morpholinoethanamine (5.34 g, 41 mmol), 2,4-dichloro-1-nitrobenzene (7.87 g, 41 mmol) and $Cs_2CO_3$ (26.73 g, 82 mmol) in acetonitrile (100 mL) was refluxed for 6 h under $N_2$, then cooled to rt, filtered and concentrated in vacuo. The residue was purified by a silica gel column chromatography (PE/EtOAc (V/V)=4:1) to give the title compound as a yellow solid (5.90 g, 50%).

Step 2) 3-chloro-$N^1$-(2-morpholinoethyl)benzene-1,4-diamine

To a solution of 3-chloro-N-(2-morpholinoethyl)-4-nitroaniline (3.50 g, 12.25 mmol) in EtOAc (60 mL) was added catalyst Pd/C (0.73 g). The reaction was stirred at rt under $H_2$ overnight, then filtered. The filtrate was concentrated in vacuo to give the crude product for the next step without further purification.

Step 3) 3-(3-fluoro-4-((2-morpholinoethyl)amino) phenyl)-2,6-dimethyl pyrimidin-4(3H)-one To a solution of 3-chloro-N$^1$-(2-morpholinoethyl)benzene-1,4-diamine (0.70 g, 1.93 mmol) in CH$_2$Cl$_2$ (20 mL) was added trimethylaluminum (6.8 mL, 13.6 mmol, 2 M in toluene) slowly at rt. The reaction mixture was stirred at rt for 0.5 h, followed by the addition of a solution of methyl 3-acetaminocrotonate (0.43 g, 2.74 mmol) in CH$_2$Cl$_2$ (5 mL). The reaction mixture was stirred at rt for another 72 h, then quenched with saturated NH$_4$Cl aqueous solution and extracted with CH$_2$Cl$_2$ (50 mL×3). The combined organic phases were dried over anhydrous Na$_2$SO$_4$ and concentrated in vacuo. The residue was purified by a silica gel column chromatography (EtOAc/MeOH (V/V)=30:1) to give the title compound as a yellowish solid (0.33 g, 47%). The compound was characterized by the following spectroscopic data:

MS (ESI, pos.ion) m/z: 363.1 (M+1);
$^1$H-NMR (400 MHz, CDCl$_3$): δ 2.17 (s, 3H), 2.33 (s, 3H), 2.42-2.43 (m, 4H), 2.50-2.64 (m, 2H), 3.09-3.13 (m, 2H), 3.59-3.63 (m, 4H), 4.55-4.57 (t, 1H), 6.32 (s, 1H), 6.76-6.81 (m, 1H), 6.80-6.81 (m, 1H), 6.89-6.91 (m, 1H).

Example 30

3-(3-fluoro-4-((3-morpholinopropyl)amino)phenyl)-2,6-dimethylpyrimidin-4(3H)-one

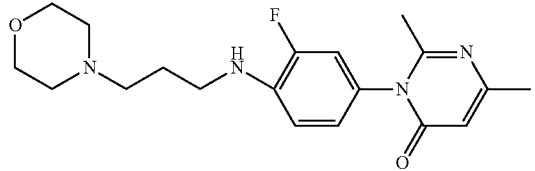 [SMILES: Cc1cc(=O)n(-c2ccc(NCCCN3CCOCC3)c(F)c2)c(C)n1]

Step 1) 4-(3-chloropropyl)morpholine

To a suspension of 1-bromo-3-chloropropane (0.79 g, 5.00 mmol) and K$_2$CO$_3$ (1.38 g, 10.00 mmol) in EtOAc (20 mL) was added a solution of morpholine (0.44 g, 5.05 mmol) in EtOAc (20 mL) dropwise at rt under N$_2$. The mixture was stirred at rt overnight, then filtered and concentrated in vacuo to give the crude product for the next step without further purification.

Step 2) 2-fluoro-N-(3-morpholinopropyl)-4-nitroaniline

To a suspension of 4-(3-chloropropyl)morpholine (1.64 g, 10 mmol) and K$_2$CO$_3$ (4.14 g, 30 mmol) in acetonitrile (20 mL) was added 2-fluoro-4-nitroaniline (1.56 g, 10 mmol) dropwise. The mixture was stirred at rt for 24 h, then filtered and concentrated in vacuo. The residue was purified by a silica gel column chromatography (PE/EtOAc (V/V)=1:1) to give the title compound as yellow oil (1.78 g, 63%).

Step 3) 2-fluoro-N$^1$-(3-morpholinopropyl)benzene-1,4-diamine

To a solution of 2-fluoro-N-(3-morpholinopropyl)-4-nitroaniline (1.78 g, 6.28 mmol) in mixed solvents of EtOAc (15 mL) and MeOH (15 mL) was added catalyst Pd/C (0.30 g). The reaction was stirred at rt under H$_2$ for 2 h, then filtered. The filtrate was concentrated in vacuo to give the crude product for the next step without further purification.

Step 4) 3-(3-fluoro-4-((3-morpholinopropyl)amino) phenyl)-2,6-dimethyl pyrimidin-4(3H)-one To a solution of 2-fluoro-N$^1$-(3-morpholinopropyl)benzene-1,4-diamine (1.60 g, 6.23 mmol) in CH$_2$Cl$_2$ (30 mL) was added trimethylaluminum (22 mL, 44 mmol, 2 M in toluene) slowly at rt. The reaction mixture was stirred at rt for 0.5 h, followed by the addition of a solution of methyl 3-acetaminocrotonate (1.98 g, 12.59 mmol) in CH$_2$Cl$_2$ (10 mL). The reaction was stirred at rt overnight, then quenched with saturated NH$_4$Cl aqueous solution and extracted with CH$_2$Cl$_2$ (50 mL×3). The combined organic phases were dried over anhydrous Na$_2$SO$_4$ and concentrated in vacuo. The residue was purified by a silica gel column chromatography (PE/EtOAc (V/V)=2:1) to give the title compound as a pale yellow solid (0.60 g, 27%). The compound was characterized by the following spectroscopic data:

MS (ESI, pos.ion) m/z: 361.2 (M+1);
$^1$H-NMR (400 MHz, CDCl$_3$): δ 1.85-1.88 (m, 2H), 2.21 (s, 3H), 2.29 (s, 3H), 2.49 (m, 4H), 2.53-2.56 (t, 2H), 3.20-3.31 (m, 2H), 3.75-3.77 (t, 4H), 6.28 (s, 1H), 6.70-6.74 (t, 1H), 6.81-6.84 (m, 2H).

Example 31

3-(3-fluoro-4-((4-morpholinobutyl)amino)phenyl)-2,6-dimethylpyrimidin-4(3H)-one

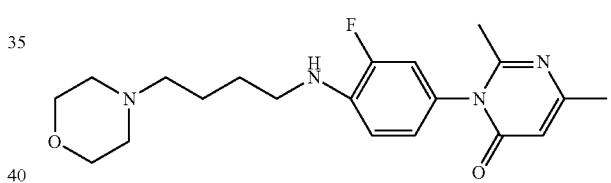

Step 1) 4-morpholinobutanenitrile

To a suspension of K$_2$CO$_3$ (8.28 g, 60 mmol) and morpholine (4.35 g, 50 mmol) in acetonitrile (50 mL) was added 4-bromobutyronitrile (7.40 g, 50 mmol) dropwise at rt under N$_2$. The mixture was stirred at rt for 6 h, filtered and concentrated in vacuo to give the title compound (7.26 g, 94.2%).

Step 2) 4-morpholinobutan-1-amine

To anhydrous THF (70 mL) was added LiAlH$_4$ (5.37 g, 142 mmol) in one portion. The mixture was stirred at 0° C. for 20 min, and a solution of 4-morpholinobutanenitrile (7.26 g, 47 mmol) in anhydrous THF (40 mL) was added dropwise. Upon the end of addition the mixture was refluxed for 4 h, then cooled to 0° C., diluted with water (20 mL) and filtered. The filtrate was concentrated in vacuo to give the crude product for the next step without further purification.

Step 3) 2-fluoro-N-(4-morpholinobutyl)-4-nitroaniline

A suspension of 4-morpholinobutan-1-amine (0.63 g, 4.00 mmol), 1,2-difluoro-4-nitrobenzene (0.64 g, 4.00 mmol) and K₂CO₃ (1.10 g, 8.00 mmol) in acetonitrile (20 mL) was stirred at rt for 19 h under N₂, then filtered. The filtrate was concentrated in vacuo to give the crude product for the next step without further purification.

Step 4) 2-fluoro-N$^1$-(4-morpholinobutyl)benzene-1,4-diamine

To a solution of 2-fluoro-N-(4-morpholinobutyl)-4-nitroaniline (1.19 g, 4.00 mmol) in mixed solvents of EtOAc (20 mL) and MeOH (20 mL) was added catalyst Pd/C (0.30 g). The reaction was stirred at rt under H₂ for 2 h, then filtered. The filtrate was concentrated in vacuo. The residue was purified by a silica gel column chromatography (EtOAc/MeOH (V/V)=10:1) to give the title compound as a white solid (1.07 g, 100%).

Step 5) 3-(3-fluoro-4-((4-morpholinobutyl)amino)phenyl)-2,6-dimethyl pyrimidin-4(3H)-one To a solution of 2-fluoro-N$^1$-(4-morpholinobutyl)benzene-1,4-diamine (1.07 g, 4.00 mmol) in CH₂Cl₂ (30 mL) was added trimethylaluminum (14 mL, 28 mmol, 2 M in toluene) slowly at rt. The reaction mixture was stirred at rt for 0.5 h, followed by the addition of a solution of methyl 3-acetaminocrotonate (1.30 g, 8.27 mmol) in CH₂Cl₂ (5 mL). The reaction mixture was stirred at rt overnight, then quenched with saturated NH₄Cl aqueous solution and extracted with CH₂Cl₂ (50 mL×3). The combined organic phases were dried over anhydrous Na₂SO₄ and concentrated in vacuo. The residue was purified by a silica gel column chromatography (PE/EtOAc (V/V)=2:1) to give the title compound as a yellowish solid (0.26 g, 17%). The compound was characterized by the following spectroscopic data:

MS (ESI, pos.ion) m/z: 375.2 (M+1);
$^1$H-NMR (400 MHz, CDCl₃): δ 1.63-1.74 (m, 4H), 2.20 (s, 3H), 2.29 (s, 3H), 2.39-2.43 (t, 2H), 2.47 (t, 4H), 3.19-3.22 (m, 2H), 3.73-3.75 (t, 4H), 6.28 (s, 1H), 6.72-6.76 (t, 1H), 6.81-6.83 (d, 2H).

Example 32

3-(4-(bis(2-propoxyethyl)amino)-3-fluorophenyl)-2,6-dimethylpyrimidin-4(3H)-one

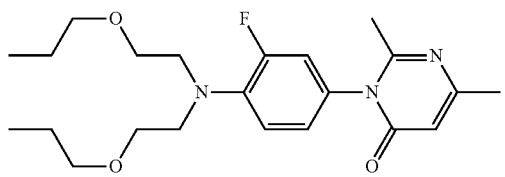

Step 1) tert-butyl bis(2-hydroxyethyl)carbamate

To a solution of 2,2'-azanediyldiethanol (4.21 g, 40 mmol) in acetonitrile (50 mL) was added a solution of Boc₂O (9.60 g, 44 mmol) in acetonitrile (50 mL) under N₂. The reaction mixture was stirred at rt for 3.5 h, and concentrated in vacuo to give the title compound as colorless oil (8.20 g, 100%).

Step 2) tert-butyl bis(2-propoxyethyl)carbamate

To a solution of tert-butyl bis(2-hydroxyethyl)carbamate (8.20 g, 40 mmol) in hexane (30 mL) was added a solution of NaOH (8.00 g, 200 mmol) in water (30 mL), 1-bromopropane (9.84 g, 80 mmol) and TBAB (1.00 g) under N₂. The reaction mixture was refluxed overnight, then cooled to rt and poured into CH₂Cl₂ (100 mL). The organic phase was washed with water (100 mL×3), dried over anhydrous Na₂SO₄ and concentrated in vacuo. The residue was purified by a silica gel column chromatography (PE/EtOAc (V/V)=4:1) to give the title compound as colorless oil (1.78 g, 15%).

Step 3) bis(2-propoxyethyl)amine

To a solution of HCl in EtOAc (15 mL, 30 mmol, 2 M) was added tert-butyl bis(2-propoxyethyl)carbamate (1.78 g, 6.15 mmol). The reaction mixture was stirred at rt overnight, then concentrated in vacuo to give the title compound as colorless oil (1.16 g, 100%).

Step 4) 2-fluoro-4-nitro-N,N-bis(2-propoxyethyl)aniline

To a solution of 1,2-difluoro-4-nitrobenzene (2.94 g, 18.45 mmol) in DMF (30 mL) were added Et₃N (3.11 g, 30.75 mmol) and bis(2-propoxyethyl)amine (1.16 g, 6.15 mmol) with stirring. The reaction mixture was heated at 90° C. overnight, then cooled to rt and poured into CH₂Cl₂ (100 mL). The organic phase was washed with water (100 mL×3), dried over anhydrous Na₂SO₄ and concentrated in vacuo. The residue was purified by a silica gel column chromatography (PE/EtOAc (V/V)=10:1) to give the title compound as yellow oil (1.47 g, 73%).

Step 5) 2-fluoro-N$^1$,N$^1$-bis(2-propoxyethyl)benzene-1,4-diamine

To a solution of 2-fluoro-4-nitro-N,N-bis(2-propoxyethyl)aniline (1.47 g, 4.48 mmol) in MeOH (50 mL) was added catalyst Pd/C (0.15 g). The reaction was stirred at rt under H₂ overnight, then filtered. The filtrate was concentrated in vacuo. The residue was purified by a silica gel column chromatography (PE/EtOAc (V/V)=4:1) to give the title compound as blackish oil (0.50 g, 34%).

Step 6) 3-(4-(bis(2-propoxyethyl)amino)-3-fluorophenyl)-2,6-dimethyl pyrimidin-4(3H)-one To a solution of 2-fluoro-N$^1$,N$^1$-bis(2-propoxyethyl)benzene-1,4-diamine (0.50 g, 1.68 mmol) in CH₂Cl₂ (10 mL) was added trimethylaluminum (3.4 mL, 6.8 mmol, 2 M in toluene) slowly. The reaction mixture was stirred at rt for 0.5 h, followed by the addition of a solution of methyl 3-acetaminocrotonate (0.32 g, 2.02 mmol) in CH₂Cl₂ (2 mL). The reaction mixture was stirred at rt for 72 h, then quenched with saturated NH₄Cl aqueous solution and extracted with CH₂Cl₂ (50 mL×3). The combined organic phases were dried over anhydrous Na₂SO₄ and concentrated in vacuo. The residue was purified by a silica gel column chromatography (PE/EtOAc (V/V)=2:1) to give the title compound as pale yellow oil (0.53 g, 78%). The compound was characterized by the following spectroscopic data:

MS (ESI, pos.ion) m/z: 406.2 (M+1);
$^1$H-NMR (400 MHz, DMSO-d₆): δ 0.83 (t, 6H, J=7.4 Hz), 1.42-1.51 (m, 4H), 2.38 (t, 3H, J=4.4 Hz), 2.50-2.51 (m, 3H), 3.32 (t, 4H, J=6.5 Hz), 3.50-3.54 (m, 8H), 6.53 (s, 1H), 7.07-7.09 (m, 1H), 7.15 (t, 1H, J=9.2 Hz), 7.20-7.24 (m, 1H).

Example 33

3-(3-fluoro-4-(hexylamino)phenyl)-2,6-dimethylpyrimidin-4(3H)-one

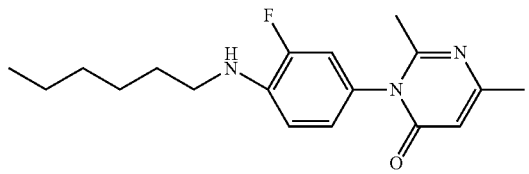 [SMILES: CCCCCCNc1ccc(-n2c(C)nc(C)cc2=O)cc1F]

Step 1) 2-fluoro-N-hexyl-4-nitroaniline

To a solution of 3,4-difluoronitrobenzene (3.18 g, 20 mmol) in EtOAc (50 mL) were added Et$_3$N (2.43 g, 24 mmol) and hexan-1-amine (2.02 g, 20 mmol). The reaction mixture was refluxed overnight, then cooled to rt and concentrated in vacuo to give the title compound as yellow oil (4.37 g, 91%).

Step 2) 2-fluoro-N$^1$-hexylbenzene-1,4-diamine

To a solution of 2-fluoro-N-hexyl-4-nitroaniline (4.37 g, 18.2 mmol) in MeOH (50 mL) was added catalyst Pd/C (0.50 g). The reaction mixture was stirred at rt under H$_2$ overnight. The mixture was filtered, and the filtrate was concentrated in vacuo. The residue was purified by a silica gel column chromatography (PE/EtOAc (V/V)=4:1) to give the title compound as blackish oil (3.36 g, 88%).

Step 3) 3-(3-fluoro-4-(hexylamino)phenyl)-2,6-dimethylpyrimidin-4(3H)-one

To a solution of 2-fluoro-N$^1$-hexylbenzene-1,4-diamine (3.36 g, 16 mmol) in CH$_2$Cl$_2$ (20 mL) was added trimethylaluminium (40 mL, 80 mmol, 2 M in toluene) slowly. The mixture was stirred at rt for 0.5 h, followed by the addition of a solution of methyl 3-acetaminocrotonate (3.02 g, 19.2 mmol) in CH$_2$Cl$_2$ (5 mL). The reaction mixture was stirred at rt for 72 h, then quenched with saturated NH$_4$Cl aqueous solution and extracted with CH$_2$Cl$_2$ (150 mL×3). The combined organic phases were washed with brine, dried over anhydrous Na$_2$SO$_4$ and concentrated in vacuo. The residue was purified by a silica gel column chromatography (PE/EtOAc (V/V)=4:1) to give the title compound as pale yellow oil (1.57 g, 31%). The compound was characterized by the following spectroscopic data:

MS (ESI, pos.ion) m/z: 318.2 (M+1);

$^1$H-NMR (400 MHz, MeOD): δ 0.92 (t, 3H, J=7.0 Hz), 1.17 (t, 1H, J=7.1 Hz), 1.35-1.37 (m, 4H), 1.63-1.70 (m, 2H), 2.45 (s, 3H), 2.49 (s, 3H), 3.22 (t, 2H, J=7.2 Hz), 3.30-3.31 (m, 3H), 3.58-3.63 (m, 1H), 6.54 (s, 1H), 6.89 (t, 1H, J=8.7 Hz), 7.00-7.07 (m, 2H).

Example 34

3-(4-((3-ethoxypropyl)amino)-3-fluorophenyl)-2,6-dimethylpyrimidin-4(3H)-one

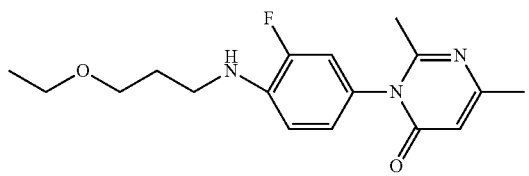 [SMILES: CCOCCCNc1ccc(-n2c(C)nc(C)cc2=O)cc1F]

Step 1) N-(3-ethoxypropyl)-2-fluoro-4-nitroaniline

To a solution of 3,4-difluoronitrobenzene (6.36 g, 40 mmol) in EtOAc (60 mL) were added Et$_3$N (12.14 g, 120 mmol) and 3-ethoxypropan-1-amine (4.54 g, 44 mmol). The reaction mixture was refluxed overnight, then cooled to rt and concentrated in vacuo to give the title compound as yellow oil (8.68 g, 90%).

Step 2) N$^1$-(3-ethoxypropyl)-2-fluorobenzene-1,4-diamine

To a solution of N-(3-ethoxypropyl)-2-fluoro-4-nitroaniline (8.68 g, 36 mmol) in MeOH (50 mL) was added catalyst Pd/C (0.87 g). The reaction mixture was stirred at rt under H$_2$ overnight. The mixture was filtered, and the filtrate was concentrated in vacuo. The residue was purified by a silica gel column chromatography (PE/EtOAc (V/V)=1:1) to give the title compound as blackish oil (5.52 g, 72%).

Step 3) 3-(4-((3-ethoxypropyl)amino)-3-fluorophenyl)-2,6-dimethyl pyrimidin-4(3H)-one To a solution of N$^1$-(3-ethoxypropyl)-2-fluorobenzene-1,4-diamine (5.52 g, 26 mmol) in CH$_2$Cl$_2$ (40 mL) was added trimethylaluminium (52 mL, 104 mmol, 2 M in toluene) slowly. The mixture was stirred at rt for 0.5 h, followed by the addition of a solution of methyl 3-acetaminocrotonate (4.87 g, 31 mmol) in CH$_2$Cl$_2$ (10 mL). The reaction mixture was stirred at rt for 72 h, then quenched with saturated NH$_4$Cl aqueous solution and extracted with CH$_2$Cl$_2$ (150 mL×3). The combined organic phases were washed with brine, dried over anhydrous Na$_2$SO$_4$ and concentrated in vacuo. The residue was purified by a silica gel column chromatography (PE/EtOAc (V/V)=1:1) to give the title compound as pale yellow oil (2.22 g, 27%). The compound was characterized by the following spectroscopic data:

MS (ESI, pos.ion) m/z: 320.2 (M+1);

$^1$H-NMR (400 MHz, CDCl$_3$): δ 1.23 (t, 3H, J=7.0 Hz), 1.91-1.97 (m, 2H), 2.20 (s, 3H), 2.28 (s, 3H), 3.26-3.33 (m, 2H), 3.47-3.52 (m, 2H), 3.55-3.61 (m, 2H), 4.74 (brs, 1H), 6.27 (s, 1H), 6.75 (t, 1H, J=8.5 Hz), 6.82 (d, 2H, J=9.3 Hz).

Example 35

3-(4-((3-(1H-imidazol-1-yl)propyl)amino)-3-fluorophenyl)-2,6-dimethylpyrimidin-4(3H)-one

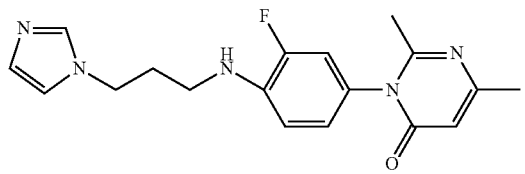 [SMILES: Cc1cc(=O)n(-c2ccc(NCCCn3ccnc3)c(F)c2)c(C)n1]

Step 1) 1-(3-chloropropyl)-1H-imidazole

Anhydrous THF (25 mL) was cooled in an ice bath. After NaH (1.40 g, 35 mmol, 60%) was added to the THF in one portion, the mixture was stirred at rt for 30 min and cooled in an ice bath. Then a solution of 1H-imidazole (2.00 g, 30 mmol) in anhydrous THF (6 mL) was added dropwise. The reaction mixture was then warmed to rt and stirred at rt for 1.5 h. To the mixture was added 1-bromo-3-chloropropane (4.60 g, 30 mmol) dropwise, and stirred at rt overnight. To the resulting mixture was added MeOH (5 mL) in one portion. The resulting mixture was filtered and the filtrate was concentrated in vacuo. The residue was purified by a silica gel column chromatography (DCM/MeOH (V/V)=30:1) to give the title compound as pale yellow oil (3.10 g, 73%).

Step 2) N-(3-(1H-imidazol-1-yl)propyl)-2-fluoro-4-nitroaniline

To a solution of 1-(3-chloropropyl)-1H-imidazole (1.90 g, 13.14 mmol), cesium carbonate (4.28 g, 13.14 mmol) and a catalytic amount of KI in DMF (30 mL) cooled in an ice-bath was added 2-fluoro-4-nitroaniline (1.38 g, 8.84 mmol) in one portion. At the end of addition, the mixture was refluxed and stirred further for 36 h. The reaction mixture was cooled to rt and filtered. The filtrate was concentrated in vacuo. To the residue was added water (50 mL) and the resulting mixture was extracted with DCM (20 mL×2). The combined organic layers were washed with brine (20 mL×2) and concentrated in vacuo. The residue was purified by a silica gel column chromatography (DCM/MeOH (V/V)=15:1) to give the title compound as yellow oil (2.85 g, 82%).

Step 3) $N^1$-(3-(1H-imidazol-1-yl)propyl)-2-fluorobenzene-1,4-diamine

To a solution of N-(3-(1H-imidazol-1-yl)propyl)-2-fluoro-4-nitroaniline (1.20 g, 4.54 mmol) in THF (20 mL) was added catalyst Pd/C (0.30 g). The reaction mixture was stirred at rt under $H_2$ overnight. The mixture was filtered, and the filtrate was concentrated in vacuo to give the title compound as yellow oil (1.00 g, 94%).

Step 4) 3-(4-((3-(1H-imidazol-1-yl)propyl)amino)-3-fluorophenyl)-2,6-dimethyl-pyrimidin-4(3H)-one To a solution of $N^1$-(3-(1H-imidazol-1-yl)propyl)-2-fluorobenzene-1,4-diamine (1.00 g, 4.27 mmol) in $CH_2Cl_2$ (30 mL) was added trimethylaluminium (16.4 mL, 32.8 mmol, 2 M in toluene) slowly. The mixture was stirred at rt for 0.5 h, followed by the addition of a solution of methyl 3-acetaminocrotonate (1.00 g, 6.36 mmol) in $CH_2Cl_2$ (8 mL). The reaction mixture was stirred at rt for 24 h, then quenched with saturated $NH_4Cl$ aqueous solution and extracted with $CH_2Cl_2$ (50 mL×3). The combined organic phases were washed with brine, dried over anhydrous $Na_2SO_4$ and concentrated in vacuo. The residue was purified by a silica gel column chromatography (DCM/MeOH (V/V)=20:1) to give the title compound as pale yellow oil (0.22 g, 15%). The compound was characterized by the following spectroscopic data:

MS (ESI, pos.ion) m/z: 342.2 (M+1);
$^1$H-NMR (400 MHz, DMSO-$d_6$): δ 2.01 (m, 2H), 2.07 (s, 3H), 2.18 (s, 3H), 3.07 (t, 2H, J=6.6 Hz), 4.07 (t, 2H, J=7.0 Hz), 6.19 (s, 1H), 6.69-6.74 (m, 1H), 6.89-6.91 (m, 2H), 7.07-7.11 (m, 1H), 7.20-7.21 (m, 1H), 7.65 (s, 1H).

Example 36

3-(3-fluoro-4-((2-(piperidin-1-yl)ethyl)amino)phenyl)-2,6-dimethylpyrimidin-4(3H)-one

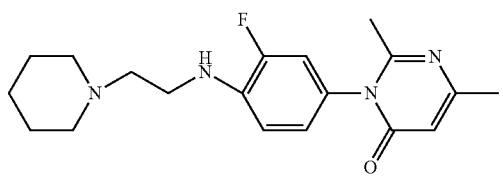 [SMILES: Cc1cc(=O)n(-c2ccc(NCCN3CCCCC3)c(F)c2)c(C)n1]

Step 1) 2-fluoro-4-nitro-N-(2-(piperidin-1-yl)ethyl)aniline

To a suspension of 2-(piperidin-1-yl)ethanamine (0.90 g, 7.02 mmol) and $K_2CO_3$ (0.97 g, 7.02 mmol) in acetone (30 mL) was added 1,2-difluoro-4-nitrobenzene (1.11 g, 6.98 mmol) in one portion in an ice bath and the mixture was refluxed overnight, cooled to rt and filtered. The filtrate was concentrated in vacuo to give the crude product, which was used for next step without further purification.

Step 2) 2-fluoro-$N^1$-(2-(piperidin-1-yl)ethyl)benzene-1,4-diamine

To a solution of 2-fluoro-4-nitro-N-(2-(piperidin-1-yl)ethyl)aniline (1.87 g, 7.00 mmol) in THF (20 mL) was added catalyst Pd/C (0.50 g). The reaction mixture was stirred at rt under $H_2$ overnight. The mixture was filtered, and the filtrate was concentrated in vacuo. The residue was purified by a silica gel column chromatography (DCM/MeOH (V/V)=15:1) to give the title compound as yellow oil (1.50 g, 90%).

Step 3) 3-(3-fluoro-4-((2-(piperidin-1-yl)ethyl)amino)phenyl)-2,6-dimethyl-pyrimidin-4(3H)-one To a solution of 2-fluoro-$N^1$-(2-(piperidin-1-yl)ethyl)benzene-1,4-diamine (1.00 g, 4.21 mmol) in $CH_2Cl_2$ (30 mL) was added trimethylaluminium (6.3 mL, 12.6 mmol, 2 M in toluene) slowly. The mixture was stirred at rt for 0.5 h, followed by the addition of a solution of methyl 3-acetaminocrotonate (1.6 g, 10.18 mmol) in $CH_2Cl_2$ (8 mL). The reaction mixture was stirred at rt for 24 h, then quenched with saturated $NH_4Cl$ aqueous solution and extracted with $CH_2Cl_2$ (50 mL×3). The combined organic phases were washed with brine, dried over anhydrous $Na_2SO_4$ and concentrated in vacuo. The residue was purified by a silica gel column chromatography (DCM/MeOH (V/V)=20:1) to give the title compound as a pale yellow solid (0.07 g, 5%). The compound was characterized by the following spectroscopic data:

MS (ESI, pos.ion) m/z: 345.3 (M+1);
$^1$H-NMR (400 MHz, DMSO-$d_6$): δ 1.43 (s, 2H), 1.57 (s, 4H), 2.08 (s, 3H), 2.19 (s, 3H), 2.45 (m, 4H), 2.60 (m, 2H), 3.35 (m, 2H), 6.20 (s, 1H), 6.81-6.86 (m, 1H), 6.92-6.95 (m, 1H), 7.10-7.13 (m, 1H).

Example 37

3-(4-((3-(1H-tetrazol-1-yl)propyl)amino)-3-fluorophenyl)-2,6-dimethylpyrimidin-4(3H)-one

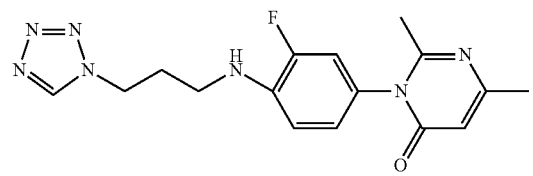 [SMILES: Cc1cc(=O)n(-c2ccc(NCCCn3cnnn3)c(F)c2)c(C)n1]

Step 1) 1-(3-chloropropyl)-1H-tetrazole

To anhydrous DMF (25 mL) was added NaH (0.70 g, 17.50 mmol, 60%) in one portion in an ice bath, and the mixture was warmed to rt and stirred at rt for 30 min. Then a solution of 1H-tetrazole (1.00 g, 14.28 mmol) in anhydrous DMF (6 mL) was added dropwise to the mixture cooled in an ice bath. The reaction mixture was then warmed to rt and stirred for 1.5 h followed by dropwise addition of 1-bromo-3-chloropropane (2.35 g, 14.93 mmol) to the mixture. The reaction mixture was stirred further at rt overnight. MeOH (1 mL) was added in one portion, and the mixture was filtered. The filtrate was concentrated in vacuo to give the crude product, which was used for next step without further purification.

Step 2) N-(3-(1H-tetrazol-1-yl)propyl)-2-fluoro-4-nitroaniline

To a mixture of 1-(3-chloropropyl)-1H-tetrazole (2.10 g, 14.33 mmol), cesium carbonate (4.66 g, 14.33 mmol) and a catalytic amount of KI in DMF (30 mL) in an ice bath was added 2-fluoro-4-nitroaniline (1.50 g, 9.61 mmol) in one portion. After the mixture was refluxed for 35 h, the mixture was cooled to rt and filtered. The filtrate was concentrated in vacuo. To the residue was added water (50 mL) and the resulting mixture was extracted with DCM (20 mL 2). The combined organic layers were washed with brine (20 mL×2) and concentrated in vacuo. The residue was purified by a silica gel column chromatography (PE/EtOAc (V/V)=2:1) to give the title compound as oil (0.36 g, 10%).

Step 3) $N^1$-(3-(1H-tetrazol-1-yl)propyl)-2-fluorobenzene-1,4-diamine

To a solution of N-(3-(1H-tetrazol-1-yl)propyl)-2-fluoro-4-nitroaniline (0.36 g, 1.35 mmol) in THF (10 mL) was added catalyst Pd/C (0.12 g). The reaction mixture was stirred at rt under $H_2$ overnight. The mixture was filtered, and the filtrate was concentrated in vacuo. The residue was purified by a silica gel column chromatography (PE/EtOAc (V/V)=2:1) to give the title compound as red oil (0.20 g, 63%).

Step 4) 3-(4-((3-(1H-tetrazol-1-yl)propyl)amino)-3-fluorophenyl)-2,6-dimethyl-pyrimidin-4(3H)-one To a solution of $N^1$-(3-(1H-imidazol-1-yl)propyl)-2-fluorobenzene-1,4-diamine (0.20 g, 0.85 mmol) in $CH_2Cl_2$ (20 mL) was added trimethylaluminium (1.3 mL, 2.6 mmol, 2 M in toluene) slowly. The mixture was stirred at rt for 0.5 h, followed by the addition of a solution of methyl 3-acetaminocrotonate (0.20 g, 1.27 mmol) in $CH_2Cl_2$ (5 mL). The reaction mixture was stirred further at rt for 24 h, then quenched with saturated $NH_4Cl$ aqueous solution and extracted with $CH_2Cl_2$ (20 mL×2). The combined organic phases were washed with brine (20 mL×3), dried over anhydrous $Na_2SO_4$ and concentrated in vacuo. The residue was purified by a silica gel column chromatography (PE/EtOAc (V/V)=1:1) to give the title compound as a pale yellow solid (0.16 g, 55%). The compound was characterized by the following spectroscopic data:

MS (ESI, pos.ion) m/z: 344.1 (M+1);

$^1$H-NMR (400 MHz, DMSO-$d_6$): δ 2.08 (s, 3H), 2.18 (s, 3H), 2.24 (m, 2H), 3.18 (t, 2H, J=6.60 Hz), 4.83 (t, 2H, J=6.96 Hz), 6.20 (s, 1H), 6.74-6.78 (m, 1H), 6.89-6.91 (m, 1H), 7.08-7.12 (m, 1H), 8.97 (s, 1H).

Example 38

3-(4-((2-(1H-indol-2-yl)ethyl)amino)-3-fluorophenyl)-2,6-dimethylpyrimidin-4(3H)-one

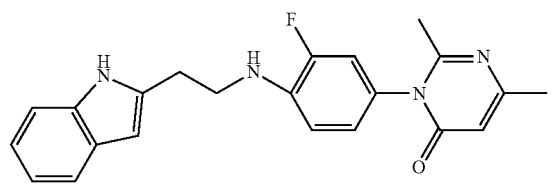 [SMILES: Cc1cc(=O)n(-c2ccc(NCCc3cc4ccccc4[nH]3)c(F)c2)c(C)n1]

Step 1) N-(2-(1H-indol-2-yl)ethyl)-2-fluoro-4-nitroaniline

To a suspension of 1,2-difluoro-4-nitrobenzene (1.59 g, 10 mmol) and $K_2CO_3$ (6.90 g, 50 mmol) in DCM (40 mL) was added 2-(1H-indol-2-yl)ethanamine (1.96 g, 10 mmol) in one portion under $N_2$ and the mixture was stirred at rt for 24 h. The mixture was then filtered, and the filtrate was concentrated in vacuo. The residue was purified by a silica gel column chromatography (PE/EtOAc (V/V)=10:1) to give the title compound as a yellow solid (2.32 g, 78%).

Step 2) $N^1$-(2-(1H-indol-2-yl)ethyl)-2-fluorobenzene-1,4-diamine

A mixture of N-(2-(1H-indol-2-yl)ethyl)-2-fluoro-4-nitroaniline (2.32 g, 7.75 mmol) and Pd/C (0.60 g) in mixed solvents of EtOAc (25 mL) and MeOH (25 mL) was stirred at rt under $H_2$ overnight. The mixture was then filtered, and the filtrate was concentrated in vacuo to give the crude product, which was used for next step without further purification.

Step 3) 3-(4-((2-(1H-indol-2-yl)ethyl)amino)-3-fluorophenyl)-2,6-dimethyl-pyrimidin-4(3H)-one To a solution of $N^1$-(2-(1H-indol-2-yl)ethyl)-2-fluorobenzene-1,4-diamine (2.09 g, 7.76 mmol) in $CH_2Cl_2$ (30 mL) was added trimethylaluminium (19.4 mL, 38.8 mmol, 2 M in toluene) slowly. The mixture was stirred at rt for 1 h, followed by the addition of a solution of methyl 3-acetaminocrotonate (2.44 g, 15.52 mmol) in $CH_2Cl_2$ (10 mL). The reaction mixture was stirred further at rt for 72 h, then quenched with saturated $NH_4Cl$ aqueous solution and extracted with $CH_2Cl_2$ (50 mL×2). The combined organic phases were washed with brine (50 mL×3), dried over anhydrous $Na_2SO_4$ and concentrated in vacuo. The residue was purified by a silica gel column chromatography (PE/EtOAc (V/V)=1:1) to give the title compound as a pale yellow solid (0.95 g, 33%). The compound was characterized by the following spectroscopic data:

MS (ESI, pos.ion) m/z: 377.2 (M+1);

$^1$H-NMR (400 MHz, CDCl$_3$): δ 2.18 (s, 3H), 2.28 (s, 3H), 3.10-3.14 (m, 2H), 3.48-3.53 (m, 2H), 4.21-4.22 (m, 1H), 6.28 (s, 1H), 6.74-6.81 (m, 3H), 7.03-7.04 (d, 1H), 7.11-7.15 (m, 1H), 7.18-7.23 (m, 1H), 7.35-7.37 (m, 1H), 7.60-7.62 (d, 1H).

Example 39

3-(3-fluoro-4-(4-(prop-2-yn-1-yl)piperazin-1-yl)phenyl)-2,6-dimethylpyrimidin-4(3H)-one

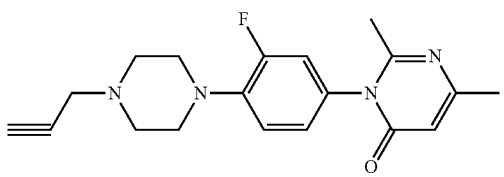 [SMILES: C#CCN1CCN(c2ccc(-n3c(C)nc(C)cc3=O)cc2F)CC1]

To a suspension of 3-(3-fluoro-4-(piperazin-1-yl)phenyl)-2,6-dimethylpyrimidin-4(3H)-one (0.30 g, 1.00 mmol) and K$_2$CO$_3$ (0.69 g, 5.00 mmol) in CH$_3$CN (15 mL) was added 3-bromoprop-1-yne (0.12 g, 1.01 mmol) and the mixture was stirred at rt for 36 h. The mixture was then filtered, and the filtrate was concentrated in vacuo. The residue was purified by a silica gel column chromatography (PE/EtOAc (V/V)=1:1) to give the title compound as a white solid (0.15 g, 44%). The compound was characterized by the following spectroscopic data:

MS (ESI, pos.ion) m/z: 341.3 (M+1);
$^1$H-NMR (400 MHz, CDCl$_3$): δ 2.18 (s, 3H), 2.29 (s, 3H), 2.29 (s, 1H), 2.76-2.78 (t, 4H), 3.17-3.38 (m, 4H), 3.38 (s, 2H), 6.28 (s, 1H), 6.89-6.92 (m, 2H), 7.03-7.05 (m, 1H).

Example 40

3-(3-chloro-4-(dihexylamino)phenyl)-2,6-dimethyl-pyrimidin-4(3H)-one

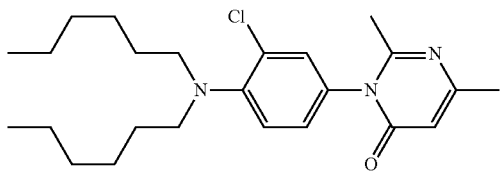 [SMILES: CCCCCCN(CCCCCC)c1ccc(-n2c(C)nc(C)cc2=O)cc1C#N]

Step 1) 2-chloro-N,N-dihexyl-4-nitroaniline

To a solution of 2-chloro-4-fluoro-1-nitrobenzene (17.55 g, 0.10 mol) in DMF (100 mL) were added K$_2$CO$_3$ (27.64 g, 0.20 mol) and dihexylamine (18.54 g, 0.10 mol) and the mixture was stirred at 90° C. for 72 h. The mixture was cooled to rt and filtered. The filtrate was concentrated to 50 mL. The resulting solution was poured into 150 mL of DCM and washed with water (150 mL×3), brine (150 mL), dried over anhydrous Na$_2$SO$_4$ and concentrated in vacuo. The residue was purified by a silica gel column chromatography (PE/EtOAc (V/V)=10:1) to give the title compound as yellow oil (23.64 g, 69%).

Step 2) 2-chloro-N$^1$,N$^1$-dihexylbenzene-1,4-diamine

A mixture of concentrated hydrochloric acid (1.0 mL), water (50 mL) and iron powder (5.58 g, 100 mmol) was stirred at 65° C. for 15 min. The aqueous layer of the mixture was poured out, and a solution of 2-chloro-N,N-dihexyl-4-nitroaniline (3.41 g, 10 mmol) in MeOH (100 mL) was added to the above processed iron powder. The mixture was acidified to pH 3 with hydrochloric acid and stirred at 65° C. for 45 min. The mixture was then cooled to rt, adjusted to pH 10 with Et$_3$N and filtered. The filtrate was concentrated in vacuo and the residue was dissolved in 150 mL of DCM. The solution was washed with water (100 mL×3) and brine (100 mL), dried over anhydrous Na$_2$SO$_4$ and concentrated in vacuo to give the title compound as colorless oil (3.00 g, 97%).

Step 3) N-(3-chloro-4-(dihexylamino)phenyl)-3-oxobutanamide

To a solution of 2-chloro-N$^1$,N$^1$-dihexylbenzene-1,4-diamine (3.11 g, 10 mmol) in toluene (50 mL) was added acetyl ketene (1.68 g, 20 mmol) and the mixture was stirred at 80° C. overnight. The mixture was cooled to rt and concentrated in vacuo to give the title compound as blackish oil (3.94 g, 100%).

Step 4) (Z)-3-amino-N-(3-chloro-4-(dihexylamino)phenyl)but-2-enamide

A mixture of N-(3-chloro-4-(dihexylamino)phenyl)-3-oxobutanamide (3.94 g, 10 mmol), MeOH (50 mL) and ammonia (50 mL) was stirred at rt overnight. The mixture was then concentrated in vacuo to give the title compound as black oil (3.94 g, 100%).

Step 5) 3-(3-chloro-4-(dihexylamino)phenyl)-2,6-dimethylpyrimidin-4(3H)-one

A mixture of (Z)-3-amino-N-(3-chloro-4-(dihexylamino)phenyl)but-2-enamide (3.94 g, 10 mmol) and triethyl orthoacetate (80 mL) was stirred at 150° C. overnight. The mixture was then cooled to rt and concentrated in vacuo. The residue was purified by a silica gel column chromatography (PE/EtOAc (V/V)=2:1) to give the title compound as pale yellow oil (1.36 g, 33%). The compound was characterized by the following spectroscopic data:

MS (ESI, pos.ion) m/z: 418.3 (M+1);
$^1$H-NMR (400 MHz, DMSO-d$_6$): δ 0.83-0.89 (m, 6H), 1.24-1.31 (m, 12H), 1.46-1.51 (m, 4H), 2.19 (s, 3H), 2.29 (s, 3H), 3.08-3.12 (m, 4H), 6.28 (s, 1H), 6.98-7.01 (m, 1H), 7.14-7.19 (m, 1H), 7.19 (d, 1H, J=2.5 Hz).

Example 41

3-(3-bromo-4-(dihexylamino)phenyl)-2,6-dimethyl-pyrimidin-4(3H)-one

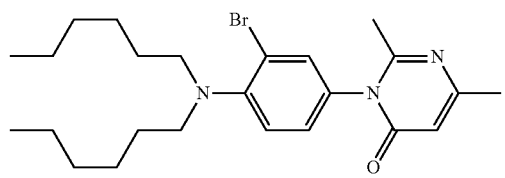

Step 1) 2-bromo-4-fluoro-1-nitrobenzene

To a mixture of 2-fluoro-5-nitroaniline (9.45 g, 60.5 mmol) and CuBr$_2$ (16.22 g, 72.6 mmol) in CH$_3$CN (200 mL) was added tert-Butyl nitrite (10.8 mL, 90.1 mmol) dropwise and the mixture was refluxed for 3.5 h. The mixture was then cooled to rt and poured into 200 mL of EtOAc. The resulting mixture was washed with diluted hydrochloric acid (150 mL×2, 2 M), water (150 mL) and brine (150 mL×2), dried over anhydrous $Na_2SO_4$ and concentrated in vacuo to give the title compound, which was used for next step without further purification.

Step 2) 2-bromo-N,N-dihexyl-4-nitroaniline

To a solution of 2-bromo-4-fluoro-1-nitrobenzene (13.30 g, 60.5 mmol) in DMF (100 mL) were added $K_2CO_3$ (16.78 g, 121 mmol) and dihexylamine (11.22 g, 60.5 mmol), and the mixture was stirred at 90° C. for 48 h. The mixture was cooled to rt and filtered and the filtrate was concentrated to 30 mL. The resulting solution was poured into 150 mL of DCM and washed with water (150 mL×3), brine (150 mL), dried over anhydrous $Na_2SO_4$ and concentrated in vacuo. The residue was purified by a silica gel column chromatography (PE/EtOAc (V/V)=10:1) to give the title compound as yellow oil (9.28 g, 40%).

Step 3) 2-bromo-$N^1$,$N^1$-dihexylbenzene-1,4-diamine

A mixture of concentrated hydrochloric acid (4.0 mL), water (100 mL) and iron powder (13.44 g, 241 mmol) was stirred at 65° C. for 15 min. The aqueous layer of the mixture was poured out, and a solution of 2-bromo-N,N-dihexyl-4-nitroaniline (9.28 g, 24.1 mmol) in MeOH (150 mL) was added to the above processed iron powder. The mixture was acidified to pH 3 with hydrochloric acid and stirred at 65° C. for 30 min. The mixture was then cooled to rt, adjusted to pH 10 with $Et_3N$ and filtered and the filtrate was concentrated. The residue was dissolved in 150 mL of DCM and the solution was washed with water (100 mL×3) and brine (100 mL), dried over anhydrous $Na_2SO_4$ and concentrated in vacuo. The residue was purified by a silica gel column chromatography (PE/EtOAc (V/V)=20:1) to give the title compound as colorless oil (4.40 g, 51%).

Step 4) N-(3-bromo-4-(dihexylamino)phenyl)-3-oxobutanamide

To a solution of 2-bromo-$N^1$,$N^1$-dihexylbenzene-1,4-diamine (4.40 g, 12.4 mmol) in EtOAc (120 mL) was added acetyl ketene (1.57 g, 18.7 mmol), and the mixture was stirred at 80° C. overnight. The mixture was cooled to rt and concentrated in vacuo. The residue was purified by a silica gel column chromatography (PE/EtOAc (V/V)=10:1) to give the title compound as colorless oil (5.10 g, 94%).

Step 5) (Z)-3-amino-N-(3-bromo-4-(dihexylamino)phenyl)but-2-enamide

A mixture of N-(3-bromo-4-(dihexylamino)phenyl)-3-oxobutanamide (5.10 g, 11.6 mmol), MeOH (60 mL) and ammonia (60 mL) was stirred at rt overnight. The mixture was then concentrated in vacuo to give the title compound as black oil (5.10 g, 100%).

Step 6) 3-(3-bromo-4-(dihexylamino)phenyl)-2,6-dimethylpyrimidin-4(3H)-one

A mixture of (Z)-3-amino-N-(3-bromo-4-(dihexylamino)phenyl)but-2-enamide (5.10 g, 11.6 mmol) and triethyl orthoacetate (100 mL) was stirred at 150° C. overnight. The mixture was then cooled to rt and concentrated in vacuo. The residue was purified by a silica gel column chromatography (PE/EtOAc (V/V)=2:1) to give the title compound as pale yellow oil (1.74 g, 33%). The compound was characterized by the following spectroscopic data:

MS (ESI, pos.ion) m/z: 464.3 (M+1);
$^1$H-NMR (400 MHz, DMSO-$d_6$): δ 0.81-0.84 (m, 6H), 1.22-1.25 (m, 12H), 1.40-1.42 (m, 4H), 2.01 (s, 3H), 2.19 (s, 3H), 3.02-3.07 (m, 4H), 6.23 (s, 1H), 7.26-7.33 (m, 2H), 7.61 (d, 1H, J=2.32 Hz).

Example 42

2-(dihexylamino)-5-(2,4-dimethyl-6-oxopyrimidin-1(6H)-yl)benzonitrile

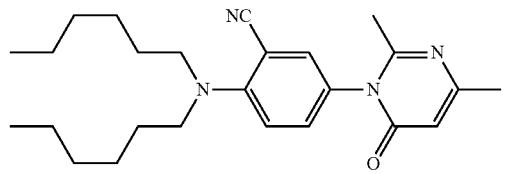

Step 1) 2-cyano-N,N-dihexyl-4-nitroaniline

To a solution of 2-fluoro-5-nitrobenzonitrile (1.83 g, 10.0 mmol) in $CH_3CN$ (20 mL) were added $K_2CO_3$ (2.76 g, 20.0 mmol) and dihexylamine (1.85 g, 9.98 mmol) and the mixture was stirred at 80° C. for 40 h. The mixture was cooled to rt, poured into 100 mL of DCM and washed with water (100 mL×3), brine (100 mL), dried over anhydrous $Na_2SO_4$ and concentrated in vacuo. The residue was purified by a silica gel column chromatography (PE/EtOAc (V/V)=125:2) to give the title compound as yellow oil (2.89 g, 87%).

Step 2) 2-cyano-$N^1$,$N^1$-dihexylbenzene-1,4-diamine

A mixture of 2-cyano-N,N-dihexyl-4-nitroaniline (2.89 g, 8.72 mmol) and Pd/C (0.30 g) in MeOH (30 mL) under $H_2$ was stirred at rt overnight. The mixture was filtered, and the filtrate was concentrated in vacuo. The residue was purified by a silica gel column chromatography (PE/EtOAc (V/V)=5:1) to give the title compound as colorless oil (1.55 g, 59%).

Step 3) N-(3-cyano-4-(dihexylamino)phenyl)-3-oxobutanamide

To a solution of 2-cyano-$N^1$,$N^1$-dihexylbenzene-1,4-diamine (1.55 g, 5.14 mmol) in EtOAc (30 mL) was added acetyl ketene (0.52 g, 6.19 mmol) with stirring and the mixture was stirred at 80° C. overnight. The mixture was then cooled to rt and concentrated in vacuo. The residue was purified by a silica gel column chromatography (PE/EtOAc (V/V)=2:1) to give the title compound as yellow oil (1.47 g, 74%).

Step 4) (Z)-3-amino-N-(3-cyano-4-(dihexylamino)phenyl)but-2-enamide

A mixture of N-(3-cyano-4-(dihexylamino)phenyl)-3-oxobutanamide (1.47 g, 3.81 mmol), MeOH (15 mL) and ammonia (15 mL) was stirred at rt overnight. The mixture was concentrated in vacuo to give the title compound as black oil (1.30 g, 88%).

Step 5) 2-(dihexylamino)-5-(2,4-dimethyl-6-oxopyrimidin-1(6H)-yl)benzonitrile

A mixture of (Z)-3-amino-N-(3-cyano-4-(dihexylamino)phenyl)but-2-enamide (1.30 g, 3.38 mmol) and triethyl orthoacetate (30 mL) was stirred at 150° C. overnight. The mixture was then cooled to rt and concentrated in vacuo. The residue was purified by a silica gel column chromatography (PE/EtOAc (V/V)=50:1) to give the title compound as pale yellow oil (60 mg, 4%). The compound was characterized by the following spectroscopic data:

MS (ESI, pos.ion) m/z: 409.3 (M+1);
$^1$H-NMR (400 MHz, DMSO-$d_6$): δ 0.88-0.91 (m, 6H), 1.26-1.36 (m, 12H), 1.63-1.67 (m, 4H), 2.20 (s, 3H), 2.29 (s, 3H), 3.43 (t, 4H, J=7.8 Hz), 6.28 (s, 1H), 6.90 (d, 1H, J=9.16 Hz), 7.14 (dd, 1H, $J_1$=2.68 Hz, $J_2$=9.12 Hz), 7.29 (d, 1H, J=2.64 Hz).

Example 43

3-(4-((2-(adamantan-1-yl)ethyl)amino)-3-fluorophenyl)-2,6-dimethylpyrimidin-4(3H)-one

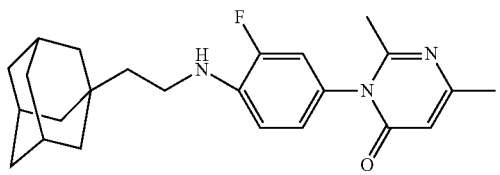 [SMILES: Cc1cc(=O)n(-c2ccc(NCCC34CC5CC(CC(C5)C3)C4)c(F)c2)c(C)n1]

Step 1) N-(2-(adamantan-1-yl)ethyl)-2-fluoro-4-nitroaniline

To a solution of 2-fluoro-4-nitroaniline (2.34 g, 15.0 mmol) in DMF (30 mL) were added $K_2CO_3$ (4.2 g, 30.4 mmol), KI (0.5 g, 3.01 mmol) and 1-(2-bromoethyl)adamantane (3.65 g, 15.0 mmol) and the mixture was stirred at 140° C. for 12 h. The mixture was then cooled to rt and filtered. The filtrate was diluted with 150 mL of DCM and washed with water (50 mL×3), brine (150 mL), dried over anhydrous $Na_2SO_4$ and concentrated in vacuo. The residue was purified by a silica gel column chromatography (PE/EtOAc (V/V)=8:1) to give the title compound as a yellow solid (477 mg, 10%).

Step 2) $N^1$-(2-(adamantan-1-yl)ethyl)-2-fluorobenzene-1,4-diamine

To a mixture of water (50 mL) and iron powder (0.88 g, 15.8 mmol) at 65° C. was added concentrated hydrochloric acid (1 mL) dropwise and the mixture was stirred for 15 min. The aqueous layer of the mixture was poured out, and a solution of N-(2-(adamantan-1-yl)ethyl)-2-fluoro-4-nitroaniline (0.5 g, 1.57 mmol) in MeOH (50 mL) was added to the above processed iron powder. The mixture was further stirred at 65° C. for 30 min. The mixture was then cooled to rt and filtered. The filtrate was concentrated and the residue was purified by a silica gel column chromatography (PE/EtOAc (V/V)=4:1) to give the title compound as a white solid (382 mg, 84%).

Step 3) N-(4-((2-(adamantan-1-yl)ethyl)amino)-3-fluorophenyl)-3-oxobutan amide

To a solution of $N^1$-(2-(adamantan-1-yl)ethyl)-2-fluorobenzene-1,4-diamine (0.38 g, 1.32 mmol) in EtOAc (20 mL) was added acetyl ketene (0.22 g, 2.62 mmol) and the mixture was stirred at 90° C. overnight. The mixture was then cooled to rt and concentrated in vacuo. The residue was purified by a silica gel column chromatography (PE/EtOAc (V/V)=4:1) to give the title compound as a white solid (317 mg, 64%).

Step 4) (Z)—N-(4-((2-(-adamantan-1-yl)ethyl)amino)-3-fluorophenyl)-3-amino but-2-enamide A mixture of N-(4-((2-(-adamantan-1-yl)ethyl)amino)-3-fluorophenyl)-3-oxobutanamide (0.31 g, 0.83 mmol), MeOH (10 mL) and ammonia (10 mL) was stirred at rt overnight. The mixture was then concentrated in vacuo to give the title compound, which was used for next step without further purification.

Step 5) 3-(4-((2-(adamantan-1-yl)ethyl)amino)-3-fluorophenyl)-2,6-dimethyl-pyrimidin-4(3H)-one A mixture of (Z)—N-(4-((2-(adamantan-1-yl)ethyl)amino)-3-fluorophenyl)-3-aminobut-2-enamide (0.31 g, 0.83 mmol) and triethyl orthoacetate (20 mL) was stirred at 150° C. for 12 h. The mixture was cooled to rt and concentrated in vacuo. The residue was purified by a silica gel column chromatography (PE/EtOAc (V/V)=4:1) to give the title compound as a red brown solid (10 mg, 3%). The compound was characterized by the following spectroscopic data:

MS (ESI, pos.ion) m/z: 396.2 (M+1);
$^1$H-NMR (400 MHz, DMSO-$d_6$): δ 1.57 (d, 2H), 1.58 (m, 6H), 1.98 (m, 6H), 2.22 (m, 6H), 2.28 (s, 3H), 3.17 (d, 2H), 3.97 (s, 1H), 6.28 (s, 1H), 6.74-6.83 (m, 3H).

Example 44

3-(3-fluoro-4-((3-(tetrahydrofuran-2-yl)propyl)amino)phenyl)-2,6-dimethylpyrimidin-4(3H)-one

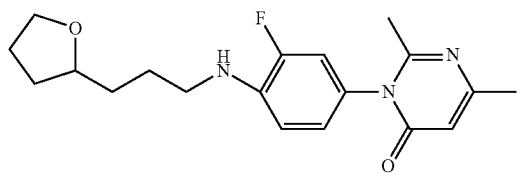 [SMILES: Cc1cc(=O)n(-c2ccc(NCCCC3CCCO3)c(F)c2)c(C)n1]

Step 1) 3-(tetrahydrofuran-2-yl)propanoic acid

A mixture of 3-(furan-2-yl)propanoic acid (11.0 g, 80.0 mmol) and Pd/C (1.1 g, 10%) in MeOH (110 mL) was stirred at 60° C. under 30 bar of $H_2$ overnight. The mixture was then filtered and the filtrate was concentrated in vacuo to give the title compound, which was used for next step without further purification.

Step 2) 3-(tetrahydrofuran-2-yl)propan-1-ol

To a solution of 3-(tetrahydrofuran-2-yl)propanoic acid (11.5 g, 80.0 mmol) in anhydrous THF (200 mL) was added borane (160 mL, 160 mmol, 1 mol/L in THF) dropwise under $N_2$ and the mixture was stirred at rt overnight. The reaction mixture was quenched with MeOH and concentrated in vacuo to give the title compound, which was used for next step without further purification.

Step 3) 2-(3-chloropropyl)tetrahydrofuran

To 3-(tetrahydrofuran-2-yl)propan-1-ol (3.90 g, 30.0 mmol) was added dichlorosulfoxide (15 mL) dropwise under $N_2$ and the mixture was refluxed for 3.5 h. It was then cooled to rt and concentrated in vacuo. To the residue was added water (30 mL) and the resulting mixture was extracted with DCM (30 mL×4). The combined organic layers were washed with brine (40 mL×2), dried over anhydrous $Na_2SO_4$ and concentrated in vacuo to give the title compound as yellow liquid, which was used for next step without further purification.

Step 4) 2-fluoro-4-nitro-N-(3-(tetrahydrofuran-2-yl)propyl)aniline

To a mixture of 2-fluoro-4-nitroaniline (7.02 g, 45.0 mmol), $Cs_2CO_3$ (29.3 g, 90.0 mmol), KI (16.6 g, 100 mmol) and DMF (100 mL) was added 2-(3-chloropropyl)tetrahydrofuran (7.43 g, 50.0 mmol) dropwise under $N_2$ and the mixture was stirred at 140° C. for 48 h. The mixture was cooled to rt and filtered and the filtrate was concentrated in vacuo. To the residue was added water (30 mL) and the mixture was extracted with DCM (30 mL×4). The combined organic layers were washed with brine (40 mL×2), dried over anhydrous $Na_2SO_4$ and concentrated in vacuo. The residue was purified by a silica gel column chromatography (PE/EtOAc (V/V)=20:1) to give the title compound as a yellow solid (3.74 g, 31%).

Step 5) 2-fluoro-$N^1$-(3-(tetrahydrofuran-2-yl)propyl)benzene-1,4-diamine

A mixture of 2-fluoro-4-nitro-N-(3-(tetrahydrofuran-2-yl)propyl)aniline (480 mg, 1.79 mmol), MeOH (40 mL), water (20 mL), iron powder (504 mg, 9.03 mmol) and $NH_4Cl$ (193 mg, 3.61 mmol) was stirred at 60° C. overnight. The mixture was then cooled to rt and saturated $NaHCO_3$ aqueous solution was added. The resulting mixture was filtered and the filtrate was extracted with DCM (30 mL×4). The combined organic layers were washed with brine (40 mL×3), dried over anhydrous $Na_2SO_4$ and concentrated in vacuo. The residue was purified by a silica gel column chromatography (PE/EtOAc (V/V)=2:1) to give the title compound as red liquid (260 mg, 61%).

Step 6) N-(3-fluoro-4-((3-(tetrahydrofuran-2-yl)propyl)amino)phenyl)-3-oxobutan-amide To a solution of 2-fluoro-$N^1$-(3-(tetrahydrofuran-2-yl)propyl)benzene-1,4-diamine (260 mg, 1.09 mmol) in EtOAc (10 mL) was added acetyl ketene (110 mg, 1.31 mmol) and the mixture was stirred at 80° C. overnight. The mixture was cooled to rt and concentrated in vacuo. The residue was purified by a silica gel column chromatography (PE/EtOAc (V/V)=2:1) to give the title compound as yellow liquid (83 mg, 24%).

Step 7) 3-(3-fluoro-4-((3-(tetrahydrofuran-2-yl)propyl)amino)phenyl)-2,6-dimethyl-pyrimidin-4(3H)-one A mixture of N-(3-fluoro-4-((3-(tetrahydrofuran-2-yl)propyl)amino)phenyl)-3-oxobutanamide (250 mg, 0.78 mmol), acetamide (92 mg, 1.56 mmol), titanium tetraisopropanolate (1.9 mL) and xylene (10 mL) was stirred at 165° C. for 24 h. The mixture was then cooled to rt. 60 mL of toluene and 60 mL of saturated $NH_4Cl$ aqueous solution were added and the resulting mixture was stirred further at rt overnight. The mixture was then filtered and the filtrate was extracted with DCM (15 mL×3). The combined organic layers were washed with brine (15 mL×2), dried over anhydrous $Na_2SO_4$ and concentrated in vacuo. The residue was purified by a silica gel column chromatography (PE/EtOAc (V/V)=1:2) to give the title compound as a yellow solid (80 mg, 29%). The compound was characterized by the following spectroscopic data:

MS (ESI, pos.ion) m/z: 346.2 (M+1);
$^1$H-NMR (400 MHz, $CDCl_3$): δ 1.52-1.43 (m, 2H), 1.81-1.75 (m, 2H), 1.94-1.87 (m, 2H), 2.04-2.09 (m, 2H), 2.20 (s, 3H), 2.28 (s, 3H), 3.23-3.19 (t, 2H, J=6.6 Hz), 3.76-3.73 (m, 1H), 3.89-3.83 (m, 2H), 4.29 (brs, 1H), 6.27 (s, 1H), 6.76-6.72 (t, 1H, J=8.7 Hz), 6.82-6.80 (d, 2H, J=9.1 Hz).

Example 45

3-(3-chloro-4-((2-methyl-1-(naphthalen-2-yl)propan-2-yl)amino)phenyl)-2,6-dimethylpyrimidin-4(3H)-one

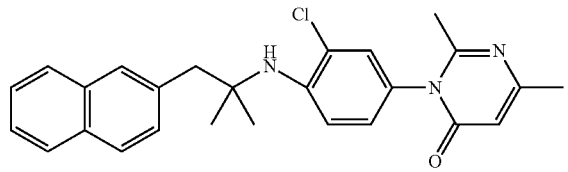

Step 1) 2-chloro-N-(2-methyl-1-(naphthalen-2-yl)propan-2-yl)-4-nitroaniline

A mixture of 2-methyl-1-(naphthalen-2-yl)propan-2-amine hydrochloride (5.9 g, 25.0 mmol), 3-chloro-4-fluoro-1-nitrobenzene (5.27 g, 30.0 mmol) and $K_2CO_3$ (6.9 g, 50.0 mmol) in DMSO (50 mL) was stirred at 140° C. overnight. The mixture was cooled to rt and poured into 150 mL of water. The mixture was then extracted with EtOAc (50 mL×3). The combined organic layers were dried over anhydrous $Na_2SO_4$ and concentrated in vacuo. The residue was purified by a silica gel column chromatography (PE/DCM (V/V)=10:1) to give the title compound as yellow foam (3.78 g, 43%).

Step 2) 2-chloro-$N^1$-(2-methyl-1-(naphthalen-2-yl)propan-2-yl)benzene-1,4-diamine To a mixture of water (50 mL) and iron powder (3.78 g, 67.7 mmol) at 65° C. was added concentrated hydrochloric acid (1.0 mL) dropwise and the mixture was stirred for 15 min. The aqueous layer of the mixture was poured out and a solution of 2-chloro-N-(2-methyl-1-(naphthalen-2-yl)propan-2-yl)-4-nitroaniline (2.4 g, 6.76 mmol) in THF (50 mL) was added to the above processed iron powder. The mixture was stirred further at 65° C. for 30 min. The mixture was then cooled to rt and filtered, and the filtrate was concentrated in vacuo. The residue was purified by a silica gel column chromatography (PE/EtOAc (V/V)=8:1) to give the title compound as a white solid (1.86 g, 84%).

Step 3) N-(3-chloro-4-((2-methyl-1-(naphthalen-2-yl)propan-2-yl)amino)phenyl)-3-oxobutanamide To a solution of 2-chloro-$N^1$-(2-methyl-1-(naphthalen-2-yl)propan-2-yl)benzene-1,4-diamine (2.0 g, 6.16 mmol) in EtOAc (30 mL) was added acetyl ketene (1.55 g, 1.84 mmol) and the mixture was stirred at 90° C. overnight. The mixture was cooled to rt and concentrated in vacuo. The residue was purified by a silica gel column chromatography (PE/EtOAc (V/V)=1:1) to give the title compound as a white solid (2.00 g, 79%).

Step 4) (Z)-3-amino-N-(3-chloro-4-((2-methyl-1-(naphthalen-2-yl)propan-2-yl)amino)phenyl)but-2-enamide A mixture of N-(3-chloro-4-((2-methyl-1-(naphthalen-2-yl)propan-2-yl)amino) phenyl)-3-oxobutanamide (2.0 g, 4.89 mmol), MeOH (15 mL) and ammonia (15 mL) was stirred at rt overnight. The mixture was then concentrated in vacuo to give the title compound, which was used for next step without further purification.

Step 5) 3-(3-chloro-4-((2-methyl-1-(naphthalen-2-yl)propan-2-yl)amino)phenyl)-2,6-dimethylpyrimidin-4(3H)-one A mixture of (Z)-3-amino-N-(3-chloro-4-((2-methyl-1-(naphthalen-2-yl)propan-2-yl)amino)phenyl)but-2-enamide and (2.0 g, 4.90 mmol) and triethyl orthoacetate (20 mL) was stirred at 150° C. for 12 h. The mixture was cooled to rt and concentrated in vacuo. The residue was purified by a silica gel column chromatography (PE/EtOAc (V/V)=1:1) to give the title compound as a pale yellow solid (1.59 g, 76%). The compound was characterized by the following spectroscopic data:
MS (ESI, pos.ion) m/z: 432.3 (M+1);
$^1$H-NMR (400 MHz, CDCl$_3$): δ 1.43 (s, 6H), 2.11 (s, 3H), 2.19 (s, 3H), 3.20 (d, 2H), 4.63 (s, 1H), 6.23 (s, 1H), 7.11-7.83 (m, 10H).

Example 46

3-(3-chloro-4-morpholinophenyl)-2,6-dimethylpyrimidin-4(3H)-one

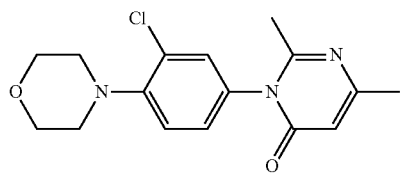

Step 1) 4-(2-chloro-4-nitrophenyl)morpholine

To a solution of morpholine (1.1 mL, 12.6 mmol) in DMF (30 mL) were added 2-chloro-1-fluoro-4-nitrobenzene (1.76 g, 10.0 mmol) and Et$_3$N (4.2 mL, 30.1 mmol) with stirring and the mixture was stirred at rt overnight. The mixture was then filtered and the organic phase was poured into 150 mL of DCM, washed with water (150 mL×3) and brine (150 mL), dried over anhydrous Na$_2$SO$_4$ and concentrated in vacuo. The residue was purified by a silica gel column chromatography (PE/DCM (V/V)=10:1) to give the title compound as a yellow solid (1.53 g, 63%).

Step 2) 3-chloro-4-morpholinoaniline

To a mixture of concentrated hydrochloric acid (1.0 mL) and water (50 mL) was added iron powder (7.55 g, 135 mmol) in one portion and the mixture was stirred at 65° C. for 15 min. The aqueous layer of the mixture was poured out and a solution of 4-(2-chloro-4-nitrophenyl)morpholine (3.28 g, 13.5 mmol) in MeOH (50 mL) was added to the above processed iron powder. The mixture was acidified to pH 3 with hydrochloric acid and stirred further at 65° C. for 45 min. The mixture was then cooled to rt, adjusted to pH 10 with Et$_3$N and filtered and the filtrate was concentrated in vacuo. The residue was dissolved in DCM (150 mL) and the solution was washed with water (100 mL×3) and brine (100 mL), dried over anhydrous Na$_2$SO$_4$ and concentrated in vacuo to give the title compound as a white solid (2.05 g, 71%).

Step 3) N-(3-chloro-4-morpholinophenyl)-3-oxobutanamide

To a solution of 3-chloro-4-morpholinoaniline (2.05 g, 9.64 mmol) in EtOAc (30 mL) was added acetyl ketene (1.62 g, 19.3 mmol) with stirring and the mixture was stirred at 80° C. overnight. The mixture was cooled to rt and concentrated in vacuo. The residue was purified by a silica gel column chromatography (PE/EtOAc (V/V)=3:1) to give the title compound as a pale yellow solid (2.59 g, 91%).

Step 4) (Z)-3-amino-N-(3-chloro-4-morpholinophenyl)but-2-enamide

A mixture of N-(3-chloro-4-morpholinophenyl)-3-oxobutanamide (2.0 g, 6.74 mmol), MeOH (15 mL) and ammonia (15 mL) was stirred at rt overnight. The mixture was then concentrated in vacuo to give the title compound, which was used for next step without further purification.

Step 5) 3-(3-chloro-4-morpholinophenyl)-2,6-dimethylpyrimidin-4(3H)-one

A mixture of (Z)-3-amino-N-(3-chloro-4-morpholinophenyl)but-2-enamide (2.0 g, 6.76 mmol) and triethyl orthoacetate (20 mL) was stirred at 150° C. for 12 h. The mixture was cooled to rt and concentrated in vacuo. The residue was purified by a silica gel column chromatography (PE/EtOAc (V/V)=1:1) to give the title compound as a pale yellow solid (1.63 g, 76%). The compound was characterized by the following spectroscopic data:
MS (ESI, pos.ion) m/z: 320.1 (M+1);
$^1$H-NMR (400 MHz, CDCl$_3$): δ 2.19 (s, 3H), 2.30 (s, 3H), 3.06 (m, 4H), 3.88 (t, 4H), 6.28 (s, 1H), 7.07-7.28 (m, 3H).

Example 47

2,6-dimethyl-3-(4-morpholino-3-(trifluoromethyl) phenyl)pyrimidin-4(3H)-one

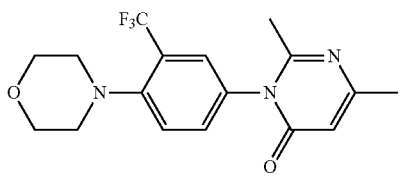 [SMILES: Cc1cc(=O)n(-c2ccc(N3CCOCC3)c(C(F)(F)F)c2)c(C)n1]

Step 1) 4-(4-nitro-2-(trifluoromethyl)phenyl)morpholine

A mixture of 1-fluoro-4-nitro-2-(trifluoromethyl)benzene (4.18 g, 20.0 mmol), morpholine (2.09 g, 24.0 mmol), $Et_3N$ (6.07 g, 60.0 mmol) and EtOAc (30 mL) was stirred at rt for 5 h. The mixture was then concentrated in vacuo. The residue was purified by a silica gel column chromatography (PE/EtOAc (V/V)=1:1) to give the title compound as a yellow solid (5.0 g, 91%).

Step 2) 3-trifluoromethyl-4-morpholinoaniline

A mixture of 4-(4-nitro-2-(trifluoromethyl)phenyl)morpholine (5.0 g, 18.1 mmol), MeOH (20 mL) and Pd/C (500 mg, 10%) under $H_2$ was stirred at rt overnight. The mixture was then filtered and the filtrate was concentrated in vacuo. The residue was purified by a silica gel column chromatography (PE/EtOAc (V/V)=2:1) to give the title compound as a pale yellow solid (4.01 g, 90%).

Step 3) N-(3-trifluoromethyl-4-morpholinophenyl)-3-oxobutanamide

A mixture of 3-trifluoromethyl-4-morpholinoaniline (4.0 g, 16.2 mmol), EtOAc (30 mL) and acetyl ketene (2.73 g, 32.5 mmol) was stirred at 90° C. overnight. The mixture was cooled to rt and concentrated in vacuo. The residue was purified by a silica gel column chromatography (PE/EtOAc (V/V)=1:1) to give the title compound as a yellow solid (4.0 g, 75%).

Step 4) (Z)-3-amino-N-(3-trifluoromethyl-4-morpholinophenyl)but-2-enamide

A mixture of N-(3-trifluoromethyl-4-morpholinophenyl)-3-oxobutanamide (4.0 g, 12.1 mmol), MeOH (20 mL) and ammonia (20 mL) was stirred at rt overnight. The mixture was then concentrated in vacuo to give the title compound, which was used for next step without further purification.

Step 5) 3-(3-trifluoromethyl-4-morpholinophenyl)-2,6-dimethylpyrimidin-4(3H)-one A mixture of (Z)-3-amino-N-(3-trifluoromethyl-4-morpholinophenyl)but-2-enamide (4.0 g, 12.1 mmol) and triethyl orthoacetate (10 mL) was stirred at 150° C. overnight. The mixture was cooled to rt and concentrated in vacuo. The residue was purified by a silica gel column chromatography (PE/EtOAc (V/V)=1:1) to give the title compound as a pale yellow solid (3.00 g, 70%). The compound was characterized by the following spectroscopic data:

MS (ESI, pos.ion) m/z: 354.2 (M+1);
$^1$H-NMR (400 MHz, $CDCl_3$): δ 2.05 (s, 3H), 2.21 (s, 3H), 2.92 (t, 4H), 3.72 (m, 4H), 6.26 (s, 1H), 7.66-7.77 (m, 3H).

Example 48

3-((6-(2,4-dimethyl-6-oxopyrimidin-1(6H)-yl)-1H-indol-1-yl)methoxy)benzonitrile

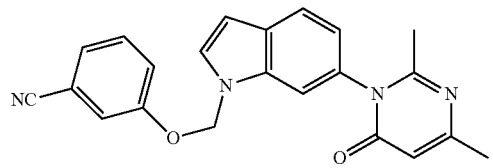 [SMILES: Cc1cc(=O)n(-c2ccc3ccn(COc4cccc(C#N)c4)c3c2)c(C)n1]

Step 1) 3-((6-nitro-1H-indol-1-yl)methoxy)benzonitrile

To a mixture of NaH (3.0 g, 75.0 mmol, 60%) in DMF (20 mL) were added a solution of 6-nitro-1H-indole (4.86 g, 30.0 mmol) in DMF (10 mL) and a solution of 3-hydroxybenzonitrile (3.57 g, 30.0 mmol) in DMF (10 mL) at 0° C. and the mixture was stirred at rt for 2 h. To the reaction mixture was added a solution of diiodomethane (7.5 mL, 90.0 mmol) in DMF (10 mL) slowly without light and the mixture was stirred at rt for 20 h. The mixture was then quenched with water and filtered. The filtrate was extracted with DCM (30 mL×6) and the combined organic layers were washed with brine (50 mL×3), dried over anhydrous $Na_2SO_4$ and concentrated in vacuo. The residue was purified by a silica gel column chromatography (PE/EtOAc (V/V)=1:1) to give the title compound as a yellow solid (4.47 g, 51%).

Step 2) 3-((6-amino-1H-indol-1-yl)methoxy)benzonitrile

To a mixture of 3-((6-nitro-1H-indol-1-yl)methoxy)benzonitrile (3.0 g, 10.2 mmol), THF (80 mL) and water (40 mL) were added iron powder (2.86 g, 51.2 mmol) and $NH_4Cl$ (1.09 g, 20.4 mmol) and the mixture was stirred at 64° C. overnight. The mixture was then cooled to rt and to the resulting mixture was added saturated $NaHCO_3$ aqueous solution. The mixture was filtered and the filtrate was extracted with EtOAc (30 mL×4). The combined organic layers were washed with brine (40 mL×3), dried over anhydrous $Na_2SO_4$ and concentrated in vacuo. The residue was purified by a silica gel column chromatography (PE/EtOAc (V/V)=2:1) to give the title compound as a yellow solid (1.76 g, 65%).

Step 3) N-(1-((3-cyanophenoxy)methyl)-1H-indol-6-yl)-3-oxobutanamide

To a solution of 3-((6-amino-1H-indol-1-yl)methoxy)benzonitrile (2.62 g, 9.95 mmol) in EtOAc (20 mL) was added acetyl ketene (1.0 g, 11.9 mmol) and the mixture was stirred at 80° C. overnight. The mixture was cooled to rt and concentrated in vacuo. The residue was purified by a silica gel column chromatography (PE/EtOAc (V/V)=1:1) to give the title compound as a yellow solid (2.70 g, 78%).

Step 4) (Z)-3-amino-N-(1-((3-cyanophenoxy)methyl)-1H-indol-6-yl)but-2-enamide A mixture of N-(1-((3-cyanophenoxy)methyl)-1H-indol-6-yl)-3-oxobutanamide (1.04 g, 2.99 mmol), MeOH (20 mL) and ammonia (20 mL) was stirred at rt overnight. The mixture was concentrated in vacuo to give the title compound, which was used for next step without further purification.

Step 5) 3-((6-(2,4-dimethyl-6-oxopyrimidin-1(6H)-yl)-1H-indol-1-yl)methoxy)benzonitrile A mixture of (Z)-3-amino-N-(1-((3-cyanophenoxy)methyl)-1H-indol-6-yl)but-2-enamide (1.04 g, 3.00 mmol) and triethyl orthoacetate (20 mL) was stirred at 130° C. overnight. The mixture was cooled to rt and concentrated in vacuo. The residue was purified by a silica gel column chromatography (PE/EtOAc (V/V)=1:1) to give the title compound as a yellow solid (272 mg, 25%). The compound was characterized by the following spectroscopic data:
MS (ESI, pos.ion) m/z: 371.1 (M+1);
$^1$H-NMR (400 MHz, DMSO-d$_6$): δ 2.05 (s, 3H), 2.21 (s, 3H), 6.25 (s, 1H), 6.29 (s, 2H), 6.64-6.63 (d, 1H, J=3.2 Hz), 7.01-6.99 (dd, 1H, J$_1$=1.4 Hz, J$_2$=8.3 Hz), 7.39-7.37 (m, 1H), 7.51-7.44 (m, 2H), 7.63 (s, 1H), 7.72-7.68 (m, 3H).

Example 49

2-((3,4-difluorophenoxy)methyl)-3-(3-fluoro-4-morpholinophenyl)-6-methylpyrimidin-4(3H)-one

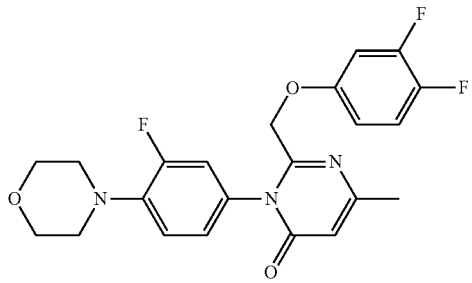 [SMILES: Cc1cc(=O)n(-c2ccc(N3CCOCC3)c(F)c2)c(COc2ccc(F)c(F)c2)n1]

Step 1) (Z)-methyl 3-(2-(3,4-difluorophenoxy)acetamido)but-2-enoate

To a suspension of K$_2$CO$_3$ (1.38 g, 10.0 mmol) in acetone (50 mL) were added 3,4-difluorophenol (0.78 g, 6.00 mmol) and (Z)-methyl-3-(2-bromoacetamido)but-2-enoate (1.18 g, 5.00 mmol) and the mixture was refluxed for 5 h. The mixture was cooled to rt and filtered and the filtrate was concentrated in vacuo. To the residue was added DCM (100 mL) and the mixture was washed with water (100 mL×2) and brine (100 mL), dried over anhydrous Na$_2$SO$_4$ and concentrated in vacuo. The residue was purified by a silica gel column chromatography (PE/EtOAc (V/V)=5:1) to give the title compound as a white solid (0.85 g, 59%).

Step 2) 2-((3,4-difluorophenoxy)methyl)-3-(3-fluoro-4-morpholinophenyl)-6-methyl-pyrimidin-4(3H)-one To a solution of 3-fluoro-4-morpholinoaniline (0.39 g, 2.00 mmol) in DCM (15 mL) was added trimethylaluminium (3.5 mL, 7.0 mmol, 2 M in toluene) and the mixture was stirred at rt for 0.5 h. A solution of (Z)-methyl-3-(2-(3,4-difluorophenoxy)acetamido)but-2-enoate (0.57 g, 2.00 mmol) in DCM (5 mL) was added slowly and the resulting mixture was stirred further at rt for 12 h. The mixture was then quenched with saturated NH$_4$Cl aqueous solution and extracted with CH$_2$Cl$_2$ (50 mL×2). The combined organic phases were washed with brine (100 mL), dried over anhydrous Na$_2$SO$_4$ and concentrated in vacuo. The residue was purified by a silica gel column chromatography (PE/EtOAc (V/V)=1:1) to give the title compound as a pale brown solid (0.50 g, 58%). The compound was characterized by the following spectroscopic data:
MS (ESI, pos.ion) m/z: 432.1 (M+1);
$^1$H-NMR (400 MHz, CDCl$_3$): δ 2.35 (s, 3H), 3.04-3.17 (m, 4H), 3.86 (t, 4H, J=4.7 Hz), 4.65 (s, 2H), 6.39 (s, 1H), 6.46-6.51 (m, 1H), 6.58-6.64 (m, 1H), 6.95-6.98 (m, 3H), 7.03 (t, 1H, J=9.4 Hz).

Example 50

2-((3,5-difluorophenoxy)methyl)-3-(3-fluoro-4-morpholinophenyl)-6-methylpyrimidin-4(3H)-one

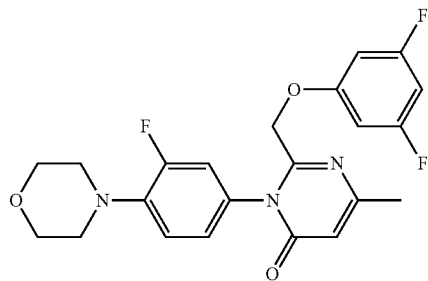 [SMILES: Cc1cc(=O)n(-c2ccc(N3CCOCC3)c(F)c2)c(COc2cc(F)cc(F)c2)n1]

Step 1) (Z)-methyl-3-(2-(3,5-difluorophenoxy)acetamido)but-2-enoate

To a suspension of K$_2$CO$_3$ (1.38 g, 10.0 mmol) in acetone (50 mL) were added 3,5-difluorophenol (0.78 g, 6.00 mmol) and (Z)-methyl-3-(2-bromoacetamido)but-2-enoate (1.18 g, 5.00 mmol) and the mixture was refluxed for 5 h. The mixture was cooled to rt and filtered and the filtrate was concentrated in vacuo. To the residue was added DCM (100 mL) and the mixture was washed with water (100 mL×2) and brine (100 mL), dried over anhydrous Na$_2$SO$_4$ and concentrated in vacuo. The residue was purified by a silica gel column chromatography (PE/EtOAc (V/V)=5:1) to give the title compound as a white solid (1.18 g, 83%).

Step 2) 2-((3,5-difluorophenoxy)methyl)-3-(3-fluoro-4-morpholinophenyl)-6-methyl-pyrimidin-4(3H)-one To a solution of 3-fluoro-4-morpholinoaniline (0.81 g, 4.13 mmol) in DCM (15 mL) was added trimethylaluminium (6.2 mL, 12.4 mmol, 2 M in toluene) and the mixture was stirred at rt for 0.5 h. A solution of (Z)-methyl-3-(2-(3,5-difluorophenoxy)acetamido)but-2-enoate (1.18 g, 4.14 mmol) in DCM (5 mL) was added slowly and the resulting mixture was stirred at rt for 12 h. The mixture was quenched with saturated NH$_4$Cl aqueous solution and extracted with CH$_2$Cl$_2$ (50 mL×2). The combined organic phases were washed with brine (100 mL), dried over anhydrous Na$_2$SO$_4$ and concentrated in vacuo. The residue was purified by a silica gel column chromatography (PE/EtOAc (V/V)=1:1) to give the title compound as a pale brown solid (1.08 g, 61%). The compound was characterized by the following spectroscopic data:

MS (ESI, pos.ion) m/z: 432.0 (M+1);

$^1$H-NMR (400 MHz, CDCl$_3$): δ 2.35 (s, 3H), 3.05-3.16 (m, 4H), 3.86 (t, 4H, J=4.6 Hz), 4.67 (s, 2H), 6.30-6.33 (m, 2H), 6.39 (s, 1H), 6.39-6.45 (m, 1H), 6.95-6.98 (m, 3H).

Example 51

3-(3-fluoro-4-morpholinophenyl)-2-(((3-fluorophenyl)thio)methyl)-6-methylpyrimidin-4(3H)-one

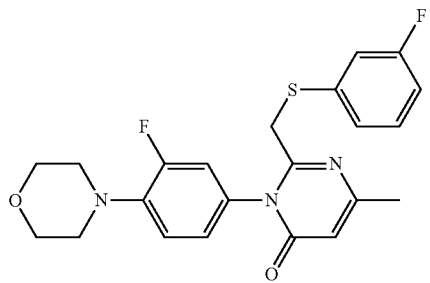 [SMILES: Cc1cc(=O)n(-c2ccc(N3CCOCC3)c(F)c2)c(CSc2cccc(F)c2)n1]

Step 1) (Z)-methyl 3-(2-(3-fluorophenyl)thio)acetamido)but-2-enoate

To a suspension of K$_2$CO$_3$ (1.38 g, 10.0 mmol) in acetone (50 mL) were added 3-fluorobenzenethiol (0.77 g, 6.01 mmol) and (Z)-methyl-3-(2-bromoacetamido)but-2-enoate (1.18 g, 5.00 mmol) and the mixture was refluxed for 5 h. The mixture was cooled to rt and filtered and the filtrate was concentrated in vacuo. To the residue was added DCM (100 mL) and the mixture was washed with water (100 mL×2) and brine (100 mL), dried over anhydrous Na$_2$SO$_4$ and concentrated in vacuo. The residue was purified by a silica gel column chromatography (PE/EtOAc (V/V)=5:1) to give the title compound as a white solid (0.78 g, 55%).

Step 2) 2-(((3-fluorophenyl)thio)methyl)-3-(3-fluoro-4-morpholinophenyl)-6-methyl-pyrimidin-4(3H)-one To a solution of 3-fluoro-4-morpholinoaniline (0.54 g, 2.75 mmol) in DCM (15 mL) was added trimethylaluminium (4.8 mL, 9.60 mmol, 2 M in toluene) and the mixture was stirred at rt for 0.5 h. A solution of (Z)-methyl-3-(2-((3-fluorophenyl)thio)acetamido)but-2-enoate (0.78 g, 2.75 mmol) in DCM (5 mL) was added slowly and the resulting mixture was stirred at rt for 12 h. The mixture was quenched with saturated NH$_4$Cl aqueous solution and extracted with CH$_2$Cl$_2$ (50 mL×2). The combined organic phases were washed with brine (100 mL), dried over anhydrous Na$_2$SO$_4$ and concentrated in vacuo. The residue was purified by a silica gel column chromatography (PE/EtOAc (V/V)=1:1) to give the title compound as a pale brown solid (0.79 g, 67%). The compound was characterized by the following spectroscopic data:

MS (ESI, pos.ion) m/z: 430.3 (M+1);

$^1$H-NMR (400 MHz, CDCl$_3$): δ 2.26 (s, 3H), 3.09-3.21 (m, 4H), 3.81 (s, 2H), 3.89 (t, 4H, J=4.7 Hz), 6.30 (s, 1H), 6.91-7.03 (m, 4H), 7.06-7.10 (m, 2H), 7.20-7.24 (m, 1H).

Example 52

3-(3-fluoro-4-morpholinophenyl)-2-(3-fluorophenethyl)-6-methylpyrimidin-4(3H)-one

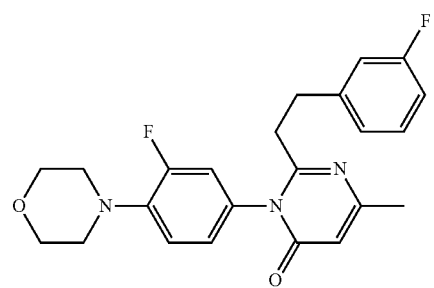 [SMILES: Cc1cc(=O)n(-c2ccc(N3CCOCC3)c(F)c2)c(CCc2cccc(F)c2)n1]

Step 1) 3-(3-fluorophenyl)propanoyl chloride

A mixture of 3-(3-fluorophenyl)propanoic acid (2.50 g, 14.9 mmol) and dichlorosulfane (10 mL) under N$_2$ was refluxed for 3 h. The mixture was cooled to rt and concentrated in vacuo to give the title compound, which was used for next step without further purification.

Step 2) (Z)-methyl 3-(3-(3-fluorophenyl)propanamido)but-2-enoate

To a solution of (Z)-methyl 3-aminobut-2-enoate (1.70 g, 14.8 mmol) and pyridine (1.30 g, 16.4 mmol) in DCM (25 mL) was added a solution of 3-(3-fluorophenyl)propanoyl chloride (2.77 g, 14.8 mmol) in DCM (5 mL) dropwise with stirring. At the end of addition, the mixture was stirred further at rt for 1 h. It was then washed with brine (50 mL×3), dried over anhydrous Na$_2$SO$_4$ and concentrated in vacuo. The residue was purified by a silica gel column chromatography (PE/EtOAc (V/V)=3:1) to give the title compound as a white solid (2.00 g, 51%).

Step 3) 3-(3-fluoro-4-morpholinophenyl)-2-(3-fluorophenethyl)-6-methyl-pyrimidin-4(3H)-one To a solution of 3-fluoro-4-morpholinoaniline (1.10 g, 5.61 mmol) in DCM (20 mL) was added trimethylaluminium (5.7 mL, 11.4 mmol, 2 M in toluene) and the mixture was stirred at rt for 0.5 h. A solution of (Z)-methyl-3-(3-(3-fluorophenyl)propanamido)but-2-enoate (1.00 g, 3.77 mmol) in DCM (8 mL) was added slowly and the resulting mixture was stirred at rt for 24 h. The mixture was then quenched with saturated NH$_4$Cl aqueous solution and extracted with CH$_2$Cl$_2$ (50 mL×2). The combined organic phases were washed with brine (100 mL), dried over anhydrous Na$_2$SO$_4$ and concentrated in vacuo. The residue was purified by a silica gel column chromatography (EtOAc) to give the title compound as an orange solid (1.10 g, 71%). The compound was characterized by the following spectroscopic data:

MS (ESI, pos.ion) m/z: 412.3 (M+1);

$^1$H-NMR (400 MHz, CDCl$_3$): δ 2.25 (s, 3H), 2.57 (t, 3H, J=7.5 Hz), 2.91 (t, 3H, J=7.8 Hz), 3.02-3.06 (m, 4H), 3.75

(t, 4H, J=4.6 Hz), 6.26 (s, 1H), 6.88-6.91 (m, 2H), 6.96-7.01 (m, 1H), 7.04-7.06 (m, 1H), 7.10-7.14 (m, 1H), 7.17-7.21 (m, 1H), 7.24-7.29 (m, 1H).

Example 53

3-(3-fluoro-4-morpholinophenyl)-2-(3-(3-fluorophenoxy)propyl)-6-methylpyrimidin-4(3H)-one

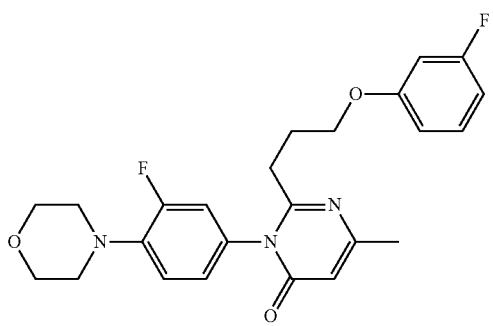 [SMILES: Cc1cc(=O)n(-c2ccc(N3CCOCC3)c(F)c2)c(CCCOc2cccc(F)c2)n1]

Step 1) ethyl 4-(3-fluorophenoxy)butanoate

A mixture of 3-fluorophenol (6.00 g, 53.5 mmol), ethyl 4-bromobutanoate (15.70 g, 80.5 mmol) and Cs$_2$CO$_3$ (26.20 g, 80.4 mmol) in DMF (25 mL) under N$_2$ was refluxed overnight. The mixture was then cooled to rt and 150 mL of water was added. The resulting mixture was extracted with DCM (100 mL×2) and the combined organic phases were washed with brine (100 mL×2), dried over anhydrous Na$_2$SO$_4$ and concentrated in vacuo. The residue was purified by a silica gel column chromatography (PE/EtOAc (V/V)=10:1) to give the title compound as colorless oil (12.0 g, 99%).

Step 2) 4-(3-fluorophenoxy)butanoic acid

To a solution of KOH (0.24 g, 4.28 mmol) in mixed solvents of water (3 mL) and ethanol (3 mL) under N$_2$ was added ethyl 4-(3-fluorophenoxy)butanoate (0.30 g, 1.33 mmol) in one portion and the mixture was stirred at 40° C. for 4 h. It was then cooled to rt and 20 mL of DCM was added. The organic layer was washed with brine (20 mL×2), dried over anhydrous Na$_2$SO$_4$ and concentrated in vacuo to give the title compound as a white solid (0.25 g, 96%).

Step 3) 4-(3-fluorophenoxy)butanoyl chloride

A solution of 4-(3-fluorophenoxy)butanoic acid (3.00 g, 15.1 mmol) in dichlorosulfane (15 mL) under N$_2$ was refluxed for 3 h. The mixture was cooled to rt and concentrated in vacuo to give the title compound, which was used for next step without further purification.

Step 4) (Z)-methyl 3-(4-(3-fluorophenoxy)butanamido)but-2-enoate

To a solution of (Z)-methyl-3-aminobut-2-enoate (1.70 g, 14.8 mmol) and pyridine (1.20 g, 15.2 mmol) in DCM (25 mL) was added a solution of 4-(3-fluorophenoxy)butanoyl chloride (3.28 g, 15.1 mmol) in DCM (5 mL) with stirring and the mixture was stirred for 1 h. It was then washed with brine (50 mL×3), dried over anhydrous Na$_2$SO$_4$ and concentrated in vacuo. The residue was purified by a silica gel column chromatography (PE/EtOAc (V/V)=3:1) to give the title compound as a white solid (1.20 g, 28%).

Step 5) 3-(3-fluoro-4-morpholinophenyl)-2-(3-(3-fluorophenoxy)propyl)-6-methyl-pyrimidin-4(3H)-one To a solution of 3-fluoro-4-morpholinoaniline (0.36 g, 1.83 mmol) in DCM (20 mL) was added trimethylaluminium (2.7 mL, 5.40 mmol, 2 M in toluene) and the mixture was stirred at rt for 0.5 h. A solution of (Z)-methyl-3-(4-(3-fluorophenoxy)butanamido)but-2-enoate (0.80 g, 2.71 mmol) in DCM (4 mL) was added slowly and the resulting mixture was stirred at rt for 24 h. The mixture was quenched with saturated NH$_4$Cl aqueous solution and extracted with CH$_2$Cl$_2$ (50 mL×2). The combined organic phases were washed with brine (100 mL), dried over anhydrous Na$_2$SO$_4$ and concentrated in vacuo. The residue was purified by a silica gel column chromatography (EtOAc) to give the title compound as a pale yellow solid (0.40 g, 49%). The compound was characterized by the following spectroscopic data:

MS (ESI, pos.ion) m/z: 442.3 (M+1);

$^1$H-NMR (400 MHz, CDCl$_3$): δ 2.00 (m, 2H), 2.22 (s, 3H), 2.44 (m, 2H), 3.07 (m, 4H), 3.76 (t, 4H, J=4.6 Hz), 3.95 (t, 2H, J=6.4 Hz), 6.22 (s, 1H), 6.73-6.74 (m, 3H), 7.07-7.08 (m, 2H), 7.12-7.28 (m, 2H).

Example 54

3-(3-fluoro-4-morpholinophenyl)-6-((3-fluorophenoxy)methyl)-2-methylpyrimidin-4(3H)-one

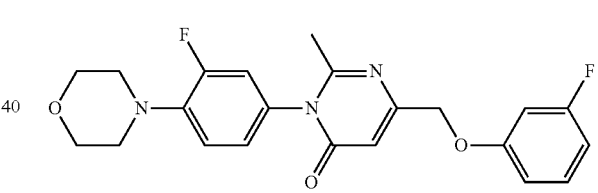

Step 1) 4-bromo-N-(3-fluoro-4-morpholinophenyl)-3-oxobutanamide

To a solution of N-(3-fluoro-4-morpholinophenyl)-3-oxobutanamide (11.2 g, 40.0 mmol) and AcOH (100 mL) under N$_2$ was added Br$_2$ (2.4 mL) at rt. At end of addition, the mixture was stirred further at rt for 24 h. The mixture was then concentrated in vacuo and 40 mL of water was added. The resulting mixture was extracted with EtOAc (30 mL×4). The combined organic phases were washed with brine (40 mL×3), dried over anhydrous Na$_2$SO$_4$ and concentrated in vacuo. The residue was purified by a silica gel column chromatography (PE/EtOAc (V/V)=2:1) to give the title compound as a yellow solid (6.80 g, 47%).

Step 2) N-(3-fluoro-4-morpholinophenyl)-4-(3-fluorophenoxy)-3-oxobutan amide

To a solution of 3-fluorophenol (2.33 g, 20.8 mmol) in anhydrous THF (20 mL) was added NaH (909 mg, 22.7 mmol, 60%) and the mixture was stirred at rt for 3 h. A solution of 4-bromo-N-(3-fluoro-4-morpholinophenyl)-3- oxobutanamide (6.8 g, 18.9 mmol) in THF (40 mL) was added. The resulting mixture was stirred at rt overnight. The reaction mixture was then poured into 100 mL of water and the mixture was extracted with EtOAc (30 mL×5). The combined organic phases were washed with brine (50 mL×2), dried over anhydrous $Na_2SO_4$ and concentrated in vacuo. The residue was purified by a silica gel column chromatography (PE/EtOAc (V/V)=2:1) to give the title compound as a yellow solid (0.16 g, 2%).

Step 3) 3-(3-fluoro-4-morpholinophenyl)-6-((3-fluorophenoxy)methyl)-2-methyl-pyrimidin-4(3H)-one A mixture of N-(3-fluoro-4-morpholinophenyl)-4-(3-fluorophenoxy)-3-oxobutanamide (510 mg, 1.31 mmol), acetamide (154 mg, 2.61 mmol) and titanium tetraisopropanolate (3.2 mL) in xylene (10 mL) was stirred at 165° C. for 24 h. The mixture was cooled to rt and 60 mL of toluene and 60 mL of saturated $NH_4Cl$ aqueous solution were added. The resulting mixture was stirred at rt overnight. The mixture was then filtered and the filtrate was extracted with DCM (20 mL×4). The combined organic phases were washed with brine (30 mL×2), dried over anhydrous $Na_2SO_4$ and concentrated in vacuo. The residue was purified by a silica gel column chromatography (PE/EtOAc (V/V)=1:1) to give the title compound as a yellow solid (0.09 g, 17%). The compound was characterized by the following spectroscopic data:

MS (ESI, pos.ion) m/z: 414.1 (M+1);
$^1$H-NMR (400 MHz, DMSO-$d_6$): δ 2.12 (s, 3H), 3.07 (d, 4H, J=5.4 Hz), 3.76 (t, 4H, J=4.5 Hz), 4.97 (s, 2H), 6.41 (s, 1H), 6.84-6.80 (m, 1H), 6.99-6.91 (m, 2H), 7.16-7.14 (m, 2H), 7.38-7.31 (m, 2H).

Example 55

3-(3-fluoro-4-(4-methylpiperazin-1-yl)phenyl)-2-((3-fluorophenoxy)methyl)-6-methylpyrimidin-4(3H)-one

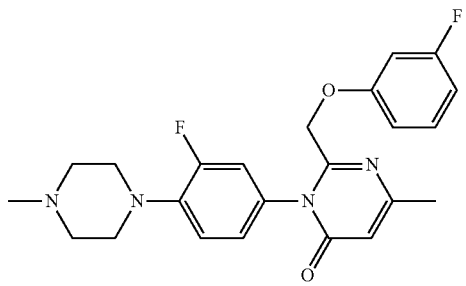 [SMILES: Cc1cc(=O)n(-c2ccc(N3CCN(C)CC3)c(F)c2)c(COc2cccc(F)c2)n1]

To a solution of 3-fluoro-4-(4-methylpiperazin-1-yl)aniline (0.63 g, 3.01 mmol) in DCM (15 mL) was added trimethylaluminium (5.3 mL, 10.6 mmol, 2 M in toluene) and the mixture was stirred at rt for 0.5 h. A solution of (Z)-methyl-3-(2-(3-fluorophenoxy)acetamido)but-2-enoate (0.80 g, 2.99 mmol) in DCM (5 mL) was added slowly and the resulting mixture was stirred at rt for 12 h. The mixture was then quenched with saturated $NH_4Cl$ aqueous solution and extracted with $CH_2Cl_2$ (50 mL×2). The combined organic phases were washed with brine (100 mL), dried over anhydrous $Na_2SO_4$ and concentrated in vacuo. The residue was purified by a silica gel column chromatography (PE/EtOAc (V/V)=1:1) to give the title compound as a pale yellow solid (0.94 g, 73%). The compound was characterized by the following spectroscopic data:

MS (ESI, pos.ion) m/z: 427.2 (M+1);
$^1$H-NMR (400 MHz, CDCl$_3$): δ 2.34 (s, 3H), 2.35 (s, 3H), 2.58 (t, 4H, J=4.8 Hz), 3.08-3.16 (m, 4H), 4.68 (s, 2H), 6.38 (d, 1H, J=0.8 Hz), 6.49 (tt, 1H, $J_1$=2.4 Hz, $J_2$=10.6 Hz), 6.54 (dd, 1H, $J_1$=2.3 Hz, $J_2$=5.3 Hz), 6.64-6.60 (m, 1H), 6.94-6.98 (m, 3H), 7.14-7.20 (m, 1H).

Example 56

3-(3-fluoro-4-(2-morpholinoethoxy)phenyl)-2-((3-fluorophenoxy)methyl)-6-methylpyrimidin-4(3H)-one

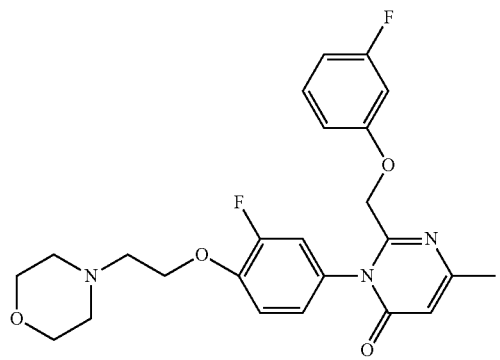 [SMILES: Cc1cc(=O)n(-c2ccc(OCCN3CCOCC3)c(F)c2)c(COc2cccc(F)c2)n1]

Step 1) 2-morpholinoethanol

A mixture of 2-bromoethanol (27.9 g, 223 mmol), morpholine (40 g, 459 mmol) and $K_2CO_3$ (48.4 g, 350 mmol) in $CH_3CN$ (30 mL) was refluxed for 3 h. The mixture was then cooled to rt and filtered. The filtrate was concentrated in vacuo to give the title compound as a yellow solid (24.40 g, 83%), which was used for next step without further purification.

Step 2)
4-(2-(2-fluoro-4-nitrophenoxy)ethyl)morpholine

A mixture of 1,2-difluoro-4-nitrobenzene (1.0 g, 6.29 mmol), 2-morpholinoethanol (1.0 g, 7.62 mmol) and $Cs_2CO_3$ in DMF (10 mL) was stirred at 75° C. for 12 h. 30 mL of water was then added and the resulting mixture was extracted with DCM (30 mL×2). The combined organic phases were washed with brine (30 mL×3), dried over anhydrous $Na_2SO_4$ and concentrated in vacuo. The residue was purified by a silica gel column chromatography (PE/EtOAc (V/V)=4:1) to give the title compound as yellow oil (1.30 g, 76%).

Step 3) 3-fluoro-4-(2-morpholinoethoxy)aniline

A mixture of 4-(2-(2-fluoro-4-nitrophenoxy)ethyl)morpholine (1.3 g, 4.81 mmol) and Pd/C (0.4 g, 10%) in THF (12 mL) under $H_2$ was stirred at rt overnight. The mixture was then filtered and the filtrate was concentrated in vacuo to give the title compound as yellow oil (1.00 g, 86%), the crude product was used for next step without further purification.

Step 4) 3-(3-fluoro-4-(2-morpholinoethoxy)phenyl)-2-((3-fluorophenoxy)methyl)-6-methyl-pyrimidin-4(3H)-one To a solution of 3-fluoro-4-(2-morpholinoethoxy)aniline (0.33 g, 1.37 mmol) in DCM (20 mL) was added trimethylaluminium (2.7 mL, 5.40 mmol, 2 M in toluene) and the mixture was stirred at rt for 0.5 h. A solution of (Z)-methyl-3-(2-(3-fluorophenoxy)acetamido)but-2-enoate (0.37 g, 1.38 mmol) in DCM (5 mL) was added slowly and the resulting mixture was stirred at rt for 24 h. The mixture was quenched with saturated NH$_4$Cl aqueous solution and extracted with CH$_2$Cl$_2$ (50 mL×2). The combined organic phases were washed with brine (100 mL), dried over anhydrous Na$_2$SO$_4$ and concentrated in vacuo. The residue was purified by a silica gel column chromatography (PE/EtOAc (V/V)=30:1) to give the title compound as a pale yellow solid (0.19 g, 30%). The compound was characterized by the following spectroscopic data:

MS (ESI, pos.ion) m/z: 458.1 (M+1);

$^1$H-NMR (400 MHz, CDCl$_3$): δ 2.24 (s, 3H), 2.45 (t, 4H, J=4.34 Hz), 2.66 (t, 2H, J=5.58 Hz), 3.55 (t, 4H, J=4.56 Hz), 4.15 (m, 2H), 4.72 (s, 2H), 6.37 (s, 1H), 6.63-6.75 (m, 3H), 7.17-7.27 (m, 3H), 7.38-7.41 (m, 1H).

Example 57

3-(3-fluoro-4-((2-morpholinoethyl)amino)phenyl)-2-((3-fluorophenoxy)methyl)-6-methylpyrimidin-4(3H)-one

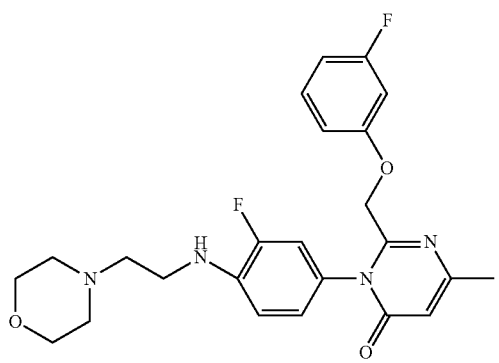 [SMILES: Cc1cc(=O)n(-c2ccc(NCCN3CCOCC3)c(F)c2)c(COc2cccc(F)c2)n1]

To a solution of 2-fluoro-N$^1$-(2-morpholinoethyl)benzene-1,4-diamine (0.33 g, 1.38 mmol) in DCM (20 mL) was added trimethylaluminium (2.1 mL, 4.2 mmol, 2 M in toluene) slowly and the mixture was stirred at rt for 0.5 h. A solution of (Z)-methyl-3-(2-(3-fluorophenoxy)acetamido)but-2-enoate (0.37 g, 1.38 mmol) in DCM (5 mL) was added slowly and the resulting mixture was stirred at rt for 24 h. 50 mL of water was then added to the mixture slowly and the mixture was extracted with CH$_2$Cl$_2$ (50 mL×2). The combined organic phases were washed with brine (100 mL×3), dried over anhydrous Na$_2$SO$_4$ and concentrated in vacuo. The residue was purified by a silica gel column chromatography (EtOAc) to give the title compound as a pale yellow solid (0.5 g, 79%). The compound was characterized by the following spectroscopic data:

MS (ESI, pos.ion) m/z: 457.2 (M+1);

$^1$H-NMR (400 MHz, CDCl$_3$): δ 2.22 (s, 3H), 2.44 (m, 4H), 3.19 (t, 2H, J=3.19 Hz), 3.76 (t, 4H, J=2.24 Hz), 4.70 (s, 2H), 6.34 (s, 1H), 6.52-6.64 (m, 2H), 6.53-6.56 (m, 1H), 6.69-6.81 (m, 3H), 6.98-7.01 (m, 1H), 7.14-7.21 (m, 1H), 7.21-7.28 (m, 1H).

Example 58

2-((cyclohexyloxy)methyl)-3-(3-fluoro-4-morpholinophenyl)-6-methylpyrimidin-4(3H)-one

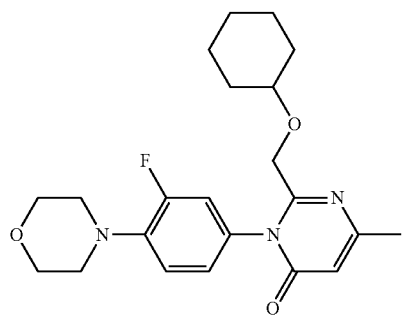 [SMILES: Cc1cc(=O)n(-c2ccc(N3CCOCC3)c(F)c2)c(COC2CCCCC2)n1]

Step 1) ethyl 2-(cyclohexyloxy)acetate

To a mixture of cyclohexanol (2.40 g, 24.0 mmol) and Rh$_2$(OAc)$_4$ (50 mg, 0.11 mmol) in DCM (50 mL) was added ethyl 2-diazoacetate (2.73 g, 23.9 mmol) and the mixture was stirred at rt for 5 min. It was then filtered and the filtrate was concentrated in vacuo. The residue was purified by a silica gel column chromatography (PE/EtOAc (V/V)=15:1) to give the title compound as colorless oil (3.8 g, 85%).

Step 2) 2-(cyclohexyloxy)acetic acid

To a solution of NaOH (4.89 g, 122 mmol) in a mixture of water (20 mL) and MeOH (20 mL) in an ice bath was added a solution of ethyl 2-(cyclohexyloxy)acetate (3.8 g, 20.4 mmol) in MeOH (10 mL) slowly and the mixture was stirred at rt for 2 h. It was then acidified to pH 4 with concentrated hydrochloric acid and extracted with DCM (20 mL×2). The combined organic layers were washed with brine (40 mL×2), dried over anhydrous Na$_2$SO$_4$ and concentrated in vacuo. The residue was purified by a silica gel column chromatography (EtOAc) to give the title compound as pale yellow oil (2.7 g, 84%).

Step 3) 2-(cyclohexyloxy)acetyl chloride

A mixture of 2-(cyclohexyloxy)acetic acid (0.90 g, 5.69 mmol) and dichlorosulfane (10 mL) was refluxed for 2 h. The mixture was cooled to rt and concentrated in vacuo to give the title compound as yellow oil, which was used for next step without further purification.

Step 4) 2-(cyclohexyloxy)acetamide

To 15 mL of NH$_4$OH (25-28%) was added a solution of 2-(cyclohexyloxy)acetyl chloride (1.01 g, 5.72 mmol) in DCM (2 mL) in an ice bath and the mixture was stirred at rt for 5 min and extracted with DCM (20 mL×3). The combined organic layers were washed with brine (20 mL×2), dried over anhydrous Na$_2$SO$_4$ and concentrated in vacuo to give the title compound as a white solid (0.5 g, 56%).

Step 5) 3-(3-fluoro-4-morpholinophenyl)-2-(3-(3-fluorophenoxy)propyl)-6-methyl-pyrimidin-4(3H)-one A mixture of 2-(cyclohexyloxy)acetamide (0.4 g, 2.54 mmol), N-(3-fluoro-4-morpholinophenyl)-3-oxobutanamide (0.7 g, 2.50 mmol) and titanium tetraisopropanolate (5.8 g, 20.4 mmol) in xylene (16 mL) was stirred at 165° C. for 30 h. The mixture was then cooled to rt and 60 mL of EtOAc and 60 mL of water were added. The resulting mixture was filtered and the filtrate was concentrated in vacuo. The residue was purified by a silica gel column chromatography (PE/EtOAc (V/V)=2:1) to give the title compound as yellow oil (0.16 g, 16%). The compound was characterized by the following spectroscopic data:

MS (ESI, pos.ion) m/z: 402.2 (M+1);
$^1$H-NMR (400 MHz, CDCl$_3$): δ 1.04 (m, 6H), 1.23 (m, 4H), 2.21 (s, 3H), 2.9 (m, 1H), 3.05 (m, 4H), 3.76 (t, 4H, J=4.60 Hz), 4.07 (s, 2H), 6.32 (s, 1H), 7.08-7.15 (m, 2H), 7.21-7.24 (m, 1H).

Example 59

3-(3-fluoro-4-morpholinophenyl)-6-methyl-2-((pyridin-3-yloxy)methyl)pyrimidin-4(3H)-one

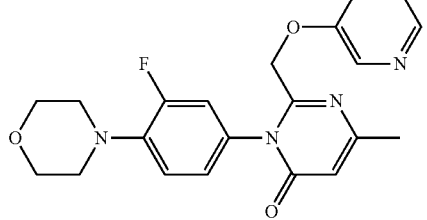

Step 1) 2-(pyridin-3-yloxy)acetonitrile

To a mixture of pyridin-3-ol (4.0 g, 42.1 mmol) and K$_2$CO$_3$ (6.96 g, 50.4 mmol) in CH$_3$CN (6 mL) was added dropwise 2-bromoacetonitrile (2.52 g, 21.0 mmol) at rt and the mixture was stirred at rt for 40 h. The mixture was filtered and the filtrate was concentrated in vacuo. The residue was purified by a silica gel column chromatography (PE/EtOAc (V/V)=2:1) to give the title compound as a yellow solid (0.45 g, 16%).

Step 2) 2-(pyridin-3-yloxy)acetamide

To a mixture of 2-(pyridin-3-yloxy)acetonitrile (100 mg, 0.75 mmol), K$_2$CO$_3$ (103 mg, 0.75 mmol) and DMSO (0.1 mL) in H$_2$O (2 mL) was added H$_2$O$_2$ (0.1 mL, 30%) dropwise in an ice bath and the mixture was stirred at rt for 5 min. It was then concentrated in vacuo and the residue was purified by a silica gel column chromatography (EtOAc) to give the title compound as a white solid (62.2 mg, 55%).

Step 3) 3-(3-fluoro-4-morpholinophenyl)-6-methyl-2-((pyridin-3-yloxy)methyl)pyrimidin-4(3H)-one A mixture of 2-(pyridin-3-yloxy)acetamide (120 mg, 0.79 mmol), N-(3-fluoro-4-morpholinophenyl)-3-oxobutanamide (221.1 mg, 0.79 mmol) and titanium tetraisopropanolate (1.79 g, 6.30 mmol) in xylene (16 mL) was stirred at 165° C. for 50 h. The mixture was then cooled to rt and 30 mL of EtOAc and 5 mL of water were added. The resulting mixture was filtered and the filtrate was concentrated in vacuo. The residue was purified by a silica gel column chromatography (EtOAc) to give the title compound as a yellow solid (0.90 g, 29%). The compound was characterized by the following spectroscopic data:

MS (ESI, pos.ion) m/z: 397.2 (M+1);
$^1$H-NMR (400 MHz, CDCl$_3$): δ 2.21 (s, 3H), 2.97 (m, 4H), 3.72 (t, 4H, J=4.62 Hz), 4.79 (s, 2H), 6.37 (s, 1H), 7.04-7.08 (m, 1H), 7.17-7.20 (m, 1H), 7.23-7.27 (m, 2H), 7.32-7.35 (m, 1H), 7.67-7.74 (m, 1H), 8.14-8.15 (m, 2H).

Example 60

3-(3-fluoro-4-morpholinophenyl)-2-(((5-fluoropyridin-3-yl)oxy)methyl)-6-methylpyrimidin-4(3H)-one

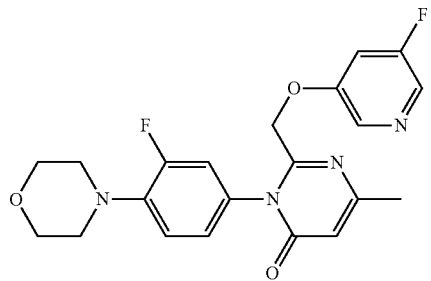

Step 1) 2-((5-fluoropyridin-3-yl)oxy)acetonitrile

To a mixture of 5-fluoropyridin-3-ol (0.95 g, 8.40 mmol) and K$_2$CO$_3$ (1.16 g, 8.40 mmol) in CH$_3$CN (6 mL) was added dropwise 2-bromoacetonitrile (1.01 g, 8.42 mmol) at rt and upon the end of addition the mixture was stirred at rt for 40 h. The mixture was filtered and the filtrate was concentrated in vacuo. The residue was purified by a silica gel column chromatography (PE/EtOAc (V/V)=3:1) to give the title compound as a yellow solid (0.55 g, 43%).

Step 2) 2-((5-fluoropyridin-3-yl)oxy)acetamide

To a mixture of 2-((5-fluoropyridin-3-yl)oxy)acetonitrile (0.55 g, 3.62 mmol), K$_2$CO$_3$ (0.60 g, 4.34 mmol) and DMSO (0.55 mL) in H$_2$O (8 mL) was added H$_2$O$_2$ (0.55 mL, 30%) dropwise in an ice bath and the mixture was stirred at rt for 5 min. It was then concentrated in vacuo and the residue was purified by a silica gel column chromatography (EtOAc) to give the title compound as a white solid (0.37 g, 60%).

Step 3) 3-(3-fluoro-4-morpholinophenyl)-2-(((5-fluoropyridin-3-yl)oxy)methyl)-6-methyl-pyrimidin-4(3H)-one To a mixture of 2-((5-fluoropyridin-3-yl)oxy)acetamide (200 mg, 1.18 mmol) and N-(3-fluoro-4-morpholinophenyl)-3-oxobutanamide (330 mg, 1.18 mmol) in xylene (10 mL) was added titanium tetraisopropanolate (2.7 mg, 9.5 mmol) and the mixture was refluxed for 50 h. The mixture was cooled to rt and 60 mL of EtOAc and 10 mL of water were added. The resulting mixture was filtered and the filtrate was concentrated in vacuo. The residue was purified by a silica gel column chromatography (PE/EtOAc (V/V)=1:1) to give the title compound as a yellow solid (130 mg, 27%). The compound was characterized by the following spectroscopic data:

MS (ESI, pos.ion) m/z: 415.2 (M+1);

$^1$H-NMR (400 MHz, DMSO-$d_6$): δ 2.21 (s, 3H), 2.98 (m, 4H), 3.73 (t, 4H, J=4.62 Hz), 4.84 (s, 2H), 6.37 (s, 1H), 7.04-7.08 (m, 1H), 7.18-7.21 (m, 1H), 7.32-7.37 (m, 2H), 8.07-8.08 (m, 1H), 8.16 (m, 1H).

Example 61

3-(3-fluoro-4-morpholinophenyl)-2-(2-(3-fluorophenoxy)propan-2-yl)-6-methylpyrimidin-4(3H)-one

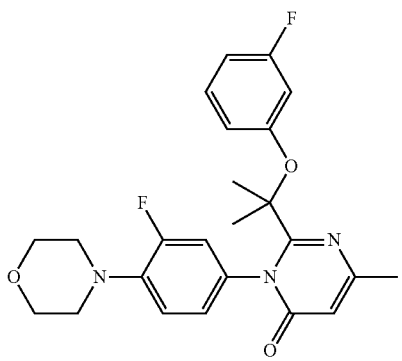 [SMILES: Cc1cc(=O)n(-c2ccc(N3CCOCC3)c(F)c2)c(C(C)(C)Oc2cccc(F)c2)n1]

Step 1) ethyl 2-(3-fluorophenoxy)-2-methylpropanoate

A mixture of 3-fluorophenol (3.36 g, 30.0 mmol), ethyl 2-bromo-2-methylpropanoate (8.78 g, 45.0 mmol) and $K_2CO_3$ (6.22 g, 45.0 mmol) in acetone (50 mL) was refluxed overnight. The mixture was cooled to rt and 60 mL of water was added. The resulting mixture was extracted with DCM (40 mL×2). The combined organic phases were washed with brine (40 mL×2), dried over anhydrous $Na_2SO_4$ and concentrated in vacuo. The residue was purified by a silica gel column chromatography (PE/EtOAc (V/V)=4:1) to give the title compound as colorless liquid (3.20 g, 47%).

Step 2) 2-(3-fluorophenoxy)-2-methylpropanoic acid

To a solution of KOH (2.38 g, 42.4 mmol) in mixed solvents of water (50 mL) and ethanol (70 mL) was added ethyl-2-(3-fluorophenoxy)-2-methylpropanoate (3.20 g, 14.1 mmol) in one portion and the mixture was stirred at 40° C. for 2 h. The mixture was cooled to 0° C., acidified to pH 3 with concentrated hydrochloric acid and extracted with DCM (20 mL×2). The combined organic layers were washed with brine (20 mL×2), dried over anhydrous $Na_2SO_4$ and concentrated in vacuo to give the title compound as a white solid (1.70 g, 61%).

Step 3) 2-(3-fluorophenoxy)-2-methylpropanoyl chloride

To 2-(3-fluorophenoxy)-2-methylpropanoic acid (1.70 g, 8.58 mmol) was added dichlorosulfane (15 mL) dropwise under $N_2$ and the mixture was refluxed for 3 h. The mixture was cooled to rt and concentrated in vacuo to give the title compound as yellow oil, which was used for next step without further purification.

Step 4) (Z)-methyl 3-(2-(3-fluorophenoxy)-2-methylpropanamido)but-2-enoate

To a solution of (Z)-methyl-3-aminobut-2-enoate (0.90 g, 7.82 mmol) and pyridine (0.80 g, 10.1 mmol) in DCM (20 mL) was added a solution of 2-bromo-2-methylpropanoyl chloride (1.86 g, 8.59 mmol) in DCM (5 mL) under $N_2$ and the mixture was stirred at rt overnight. It was then washed with brine (20 mL×3), dried over anhydrous $Na_2SO_4$ and concentrated in vacuo. The residue was purified by a silica gel column chromatography (PE/EtOAc (V/V)=20:1) to give the title compound as a yellow solid (1.13 g, 49%).

Step 5) 3-(3-fluoro-4-morpholinophenyl)-2-(3-(3-fluorophenoxy)propyl)-6-methyl-pyrimidin-4(3H)-one To a solution of 3-fluoro-4-morpholinoaniline (0.50 g, 2.55 mmol) in anhydrous DCM (40 mL) was added trimethylaluminium (3.9 mL, 7.8 mmol, 2 M in toluene) under $N_2$ and the mixture was stirred at rt for 0.5 h. A solution of (Z)-methyl-3-(2-(3-fluorophenoxy)-2-methylpropanamido)but-2-enoate (1.13 g, 3.83 mmol) in DCM (5 mL) was added dropwise slowly and the resulting mixture was stirred at rt for 3 days. The mixture was then quenched with saturated $NH_4Cl$ aqueous solution (50 mL) and extracted with $CH_2Cl_2$ (30 mL×3). The combined organic phases were washed with brine (30 mL×3), dried over anhydrous $Na_2SO_4$ and concentrated in vacuo. The residue was purified by a silica gel column chromatography (PE/EtOAc (V/V)=3:1) to give the title compound as a pale yellow solid (0.17 g, 15%). The compound was characterized by the following spectroscopic data:

MS (ESI, pos.ion) m/z: 442.2 (M+1);

$^1$H-NMR (400 MHz, CDCl$_3$): δ 1.55 (s, 3H), 1.68-1.65 (d, 3H, J=12.8 Hz), 2.35 (s, 3H), 3.17-3.06 (m, 4H), 3.88-3.85 (m, 4H), 6.24-6.20 (dt, 1H, $J_1$=10.8 Hz, $J_2$=2.4 Hz), 6.31-6.28 (dd, 1H, $J_1$=8.2 Hz, $J_2$=2.2 Hz), 6.35 (s, 1H), 6.60-6.56 (dd, 1H, $J_1$=12.9 Hz, $J_2$=2.4 Hz), 6.71-6.65 (m, 2H), 6.85-6.80 (t, 1H, J=8.8 Hz), 7.17-7.11 (m, 1H).

Example 62

3-(4-(dihexylamino)-3-fluorophenyl)-2-((3-fluorophenoxy)methyl)-6-methylpyrimidin-4(3H)-one

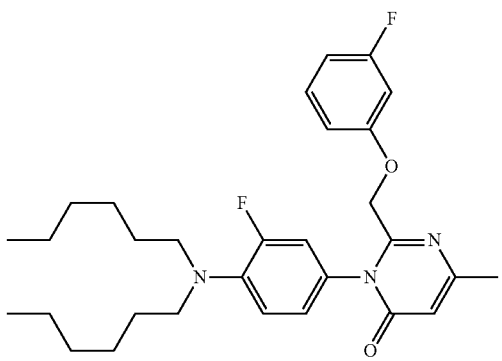 [SMILES: CCCCCCN(CCCCCC)c1ccc(-n2c(COc3cccc(F)c3)nc(C)cc2=O)cc1F]

Step 1) N-(4-(dihexylamino)-3-fluorophenyl)-3-oxobutanamide

To a solution of 2-fluoro-N$^1$,N$^1$-dihexylbenzene-1,4-diamine (2.94 g, 10.0 mmol) in toluene (50 mL) was added acetyl ketene (0.84 g, 10.0 mmol) and the mixture was stirred at 80° C. overnight. The mixture was cooled to rt and concentrated in vacuo. The residue was purified by a silica gel column chromatography (PE/EtOAc (V/V)=1:4) to give the title compound as yellow oil (2.67 g, 70%).

Step 2) 2-(3-fluorophenoxy)acetamide

A mixture of 3-fluorophenol (11.2 g, 100 mmol), 2-bromoacetamide (13.8 g, 100 mmol), K$_2$CO$_3$ (13.82 g, 100 mmol) and Cs$_2$CO$_3$ (32.58 g, 100 mmol) in acetone (150 mL) was refluxed overnight. The mixture was cooled to rt and filtered and the filtrate was concentrated in vacuo. The residue was purified by a silica gel column chromatography (PE/EtOAc (V/V)=1:1) to give the title compound as a white solid (5.06 g, 30%).

Step 3) 3-(4-(dihexylamino)-3-fluorophenyl)-2-((3-fluorophenoxy)methyl)-6-methyl-pyrimidin-4(3H)-one To a mixture of N-(4-(dihexylamino)-3-fluorophenyl)-3-oxobutanamide (2.67 g, 7.05 mmol), and 2-(3-fluorophenoxy)acetamide (2.37 g, 14.0 mmol) in xylene (20 mL) was added titanium tetraisopropanolate (5.97 g, 21.0 mmol) and the mixture was stirred at 165° C. for 24 h. The mixture was cooled to rt and 120 mL of toluene and 150 mL of saturated NH$_4$Cl aqueous solution were added. The resulting mixture stirred at rt overnight and filtered and the filtrate was extracted with DCM (150 mL×3). The combined organic layers were dried over anhydrous Na$_2$SO$_4$ and concentrated in vacuo. The residue was purified by a silica gel column chromatography (PE/EtOAc (V/V)=2:1) to give the title compound as a yellow solid (0.95 g, 26%). The compound was characterized by the following spectroscopic data:

MS (ESI, pos.ion) m/z: 512.3 (M+1);
$^1$H-NMR (400 MHz, DMSO-d$_6$): δ 0.88 (t, 6H, J=7.2 Hz), 1.25-1.30 (m, 16H), 2.42 (s, 3H), 3.62 (t, 4H, J=7.8 Hz), 4.84 (s, 2H), 6.54 (s, 1H), 6.54 (s, 1H), 6.58-6.60 (m, 1H), 6.64-6.66 (m, 1H), 6.68-6.73 (m, 1H), 7.21-7.27 (m, 1H), 7.60 (d, 1H, J=8.6 Hz), 7.74-7.77 (m, 1H), 7.96 (t, 1H, J=8.3 Hz).

Example 63

3-(3-chloro-4-morpholinophenyl)-2-((3-fluorophenoxy)methyl)-6-methylpyrimidin-4(3H)-one

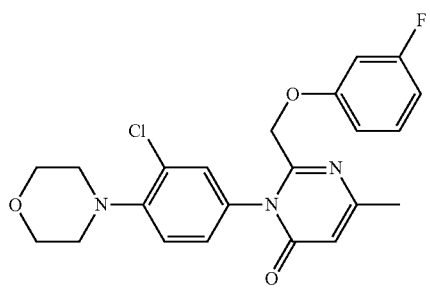 [SMILES: Cc1cc(=O)n(-c2ccc(N3CCOCC3)c(Cl)c2)c(COc2cccc(F)c2)n1]

A mixture of N-(3-chloro-4-morpholinophenyl)-3-oxobutanamide (0.89 g, 3.00 mmol), 2-(3-fluorophenoxy)acetamide (1.01 g, 5.97 mmol) and titanium tetraisopropanolate (7.2 mL) in xylene (20 mL) was stirred at 165° C. for 24 h. The mixture was cooled to rt and 45 mL of toluene and 60 mL of saturated NH$_4$Cl aqueous solution were added. The resulting mixture stirred at rt overnight and filtered and the filtrate was extracted with DCM (60 mL×3). The combined organic layers were washed with brine, dried over anhydrous Na$_2$SO$_4$ and concentrated in vacuo. The residue was purified by a silica gel column chromatography (PE/EtOAc (V/V)=1:1) to give the title compound as a yellow solid (0.29 g, 23%). The compound was characterized by the following spectroscopic data:

MS (ESI, pos.ion) m/z: 430.1 (M+1);
$^1$H-NMR (400 MHz, DMSO-d$_6$): δ 2.35 (s, 3H), 3.00-3.06 (m, 4H), 3.85-3.87 (m, 4H), 4.68 (d, 2H, J=5.12 Hz), 6.39 (s, 1H), 6.45-6.49 (m, 1H), 6.54 (dd, 1H, J$_1$=2.32 Hz, J$_2$=8.34 Hz), 6.64-6.68 (m, 1H), 7.07 (s, 1H), 7.11-7.19 (m, 2H), 7.29 (d, 1H, J=2.4 Hz).

Example 64

3-(3-chloro-4-morpholinophenyl)-2-((3-chlorophenoxy)methyl)-6-methylpyrimidin-4(3H)-one

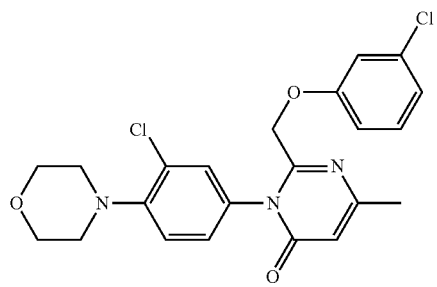 [SMILES: Cc1cc(=O)n(-c2ccc(N3CCOCC3)c(Cl)c2)c(COc2cccc(Cl)c2)n1]

Step 1) 2-(3-chlorophenoxy)acetamide

A mixture of 3-chlorophenol (2.57 g, 20.0 mmol), 2-bromoacetamide (2.76 g, 20.0 mmol) and K$_2$CO$_3$ (5.53 g, 40.0 mmol) in acetone (40 mL) was stirred at 70° C. overnight. The mixture was then cooled to rt and filtered and the filtrate was concentrated in vacuo. The residue was purified by a silica gel column chromatography (PE/EtOAc (V/V)=1:1) to give the title compound as a white solid (3.22 g, 87%).

Step 2) 3-(3-chloro-4-morpholinophenyl)-2-((3-chlorophenoxy)methyl)-6-methyl-pyrimidin-4(3H)-one A mixture of N-(3-chloro-4-morpholinophenyl)-3-oxobutanamide (0.48 g, 1.62 mmol), 2-(3-chlorophenoxy)acetamide (0.60 g, 3.24 mmol) and titanium tetraisopropanolate (2.4 mL) in xylene (10 mL) was stirred at 165° C. for 24 h. The mixture was cooled to rt and 60 mL of toluene and 60 mL of saturated NH$_4$Cl aqueous solution were added. The resulting mixture was stirred at rt overnight and filtered and the filtrate was extracted with DCM (20 mL×4). The combined organic layers were washed with brine (30 mL×2), dried over anhydrous Na$_2$SO$_4$ and concentrated in vacuo. The residue was purified by a silica gel column chromatography (PE/EtOAc (V/V)=1:1) to give the title compound as a yellow solid (0.46 g, 64%). The compound was characterized by the following spectroscopic data:

MS (ESI, pos.ion) m/z: 446.1 (M+1);

$^1$H-NMR (400 MHz, CDCl$_3$): δ 2.35 (s, 3H), 3.08-2.99 (m, 4H), 3.87-3.85 (t, 4H, J=4.6 Hz), 4.69-4.68 (d, 2H, J=6.2 Hz), 6.39 (s, 1H), 6.67-6.64 (m, 1H), 6.75-6.74 (t, 1H, J=2.2 Hz), 6.95-6.92 (m, 1H), 7.07-7.05 (d, 1H, J=8.5 Hz), 7.16-7.11 (m, 2H), 7.29 (s, 1H).

Example 65

3-((1-(3-chloro-4-morpholinophenyl)-4-methyl-6-oxo-1,6-dihydropyrimidin-2-yl)methoxy)benzonitrile

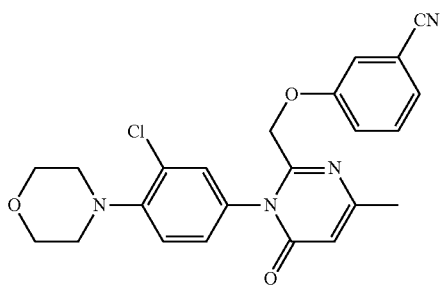 [SMILES: Cc1cc(=O)n(-c2ccc(N3CCOCC3)c(Cl)c2)c(COc2cccc(C#N)c2)n1]

Step 1) 2-(3-cyanophenoxy)acetamide

A mixture of 3-hydroxybenzonitrile (2.38 g, 20.0 mmol), 2-bromoacetamide (3.04 g, 22.0 mmol) and K$_2$CO$_3$ (5.53 g, 40.0 mmol) in acetone (20 mL) was stirred at 70° C. for 17.5 h. The mixture was cooled to rt and filtered and the filtrate was concentrated in vacuo. The residue was purified by a silica gel column chromatography (PE/EtOAc (V/V)=1:1) to give the title compound as a white solid (2.70 g, 77%).

Step 2) 3-((1-(3-chloro-4-morpholinophenyl)-4-methyl-6-oxo-1,6-dihydro pyrimidin-2-yl)methoxy)benzonitrile A mixture of N-(3-chloro-4-morpholinophenyl)-3-oxobutanamide (0.59 g, 2.00 mmol), 2-(3-cyanophenoxy)acetamide (0.71 g, 4.03 mmol) and titanium tetraisopropanolate (4.8 mL) in xylene (20 mL) was stirred at 165° C. for 24 h. The mixture was cooled to rt and 30 mL of toluene and 40 mL of saturated NH$_4$Cl aqueous solution were added. The resulting mixture was stirred at rt overnight and filtered and the filtrate was extracted with DCM (50 mL×3). The combined organic layers were dried over anhydrous Na$_2$SO$_4$ and concentrated in vacuo. The residue was purified by a silica gel column chromatography (PE/EtOAc (V/V)=1:1) to give the title compound as a yellow solid (0.51 g, 59%). The compound was characterized by the following spectroscopic data:

MS (ESI, pos.ion) m/z: 437.1 (M+1);

$^1$H-NMR (400 MHz, CDCl$_3$): δ 2.35 (s, 3H), 2.98-3.11 (m, 4H), 3.85-3.87 (m, 4H), 4.68-4.76 (m, 2H), 6.39 (d, 1H, J=0.84 Hz), 7.02-7.05 (m, 3H), 7.13 (dd, 1H, J$_1$=2.36 Hz, J$_2$=8.52 Hz), 7.25-7.34 (m, 3H).

Example 66

4-(2-fluoro-4-(2-((3-fluorophenoxy)methyl)-4-methyl-6-oxopyrimidin-1(6H)-yl)phenyl) morpholin-3-one

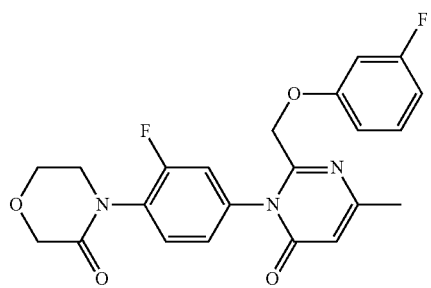 [SMILES: Cc1cc(=O)n(-c2ccc(N3CCOCC3=O)c(F)c2)c(COc2cccc(F)c2)n1]

Step 1) 2-(3-fluorophenoxy)acetamide

A mixture of 3-fluorophenol (5.61 g, 50.0 mmol), 2-bromoacetamide (7.59 g, 55.0 mmol) and K$_2$CO$_3$ (13.82 g, 100 mmol) in acetone (80 mL) was stirred at 70° C. overnight. The mixture was cooled to rt and filtered and the filtrate was concentrated in vacuo. The residue was purified by a silica gel column chromatography (PE/EtOAc (V/V)=1:1) to give the title compound as a white solid. (7.89 g, 93%)

Step 2) 4-(2-fluoro-4-nitrophenyl)morpholin-3-one

A mixture of 1,2-difluoro-4-nitrobenzene (7.95 g, 50.0 mmol), morpholin-3-one (5.06 g, 50.0 mmol) and K$_2$CO$_3$ (13.82 g, 100 mmol) in DMF (80 mL) was stirred at 140° C. overnight. The mixture was cooled to rt and filtered and the filtrate was concentrated in vacuo. The residue was purified by a silica gel column chromatography (PE/EtOAc (V/V)=3:1) to give the title compound as a yellow solid (5.00 g, 42%).

Step 3) 4-(4-amino-2-fluorophenyl)morpholin-3-one

A mixture of iron powder (8.8 g, 158 mmol), water (60 mL) and hydrochloric acid (2 mL) was stirred at 65° C. for 20 min. It was then cooled to rt and the aqenous layer was poured out. A solution of 4-(2-fluoro-4-nitrophenyl)morpholin-3-one (3.8 g, 15.8 mmol) in MeOH (100 mL) was added and the resuting mixture was acidified to pH 2 with hydrochloric acid and stirred at 65° C. for 4 h. The mixture was cooled to rt, adjusted to pH 8 with saturated NaHCO$_3$ aqueous solution and filtered. The MeOH was removed in vacuo and the mixture was extracted with EtOAc (20 mL×3). The combined organic layers were washed with brine (20 mL×4), dried over anhydrous Na$_2$SO$_4$ and concentrated in vacuo. The residue was purified by a silica gel column chromatography (PE/EtOAc (V/V)=1:2) to give the title compound as a white solid (1.89 g, 57%).

Step 4) N-(3-fluoro-4-(3-oxomorpholino)phenyl)-3-oxobutanamide

A mixture of 4-(4-amino-2-fluorophenyl)morpholin-3-one (2.51 g, 11.9 mmol) and acetyl ketene (2.51 g, 29.9 mmol) in EtOAc (40 mL) was stirred at 80° C. for 24 h. The mixture was cooled to rt and concentrated in vacuo. The residue was purified by a silica gel column chromatography (PE/EtOAc (V/V)=1:4) to give the title compound as a yellow solid (2.15 g, 61%).

Step 5) 4-(2-fluoro-4-(2-((3-fluorophenoxy)methyl)-4-methyl-6-oxopyrimidin-1(6H)-yl)phenyl)morpholin-3-one A mixture of N-(3-fluoro-4-(3-oxomorpholino)phenyl)-3-oxobutanamide (0.59 g, 2.00 mmol), 2-(3-fluorophenoxy) acetamide (0.94 g, 5.56 mmol) and titanium tetraisopropanolate (4.8 mL) in xylene (10 mL) was stirred at 165° C. for 24 h. The mixture was cooled to rt and 60 mL of toluene and 60 mL of saturated NH$_4$Cl aqueous solution were added. The resulting mixture was stirred at rt overnight and filtered and the filtrate was extracted with DCM (20 mL×4). The combined organic layers were washed with brine (30 mL×2), dried over anhydrous Na$_2$SO$_4$ and concentrated in vacuo. The residue was purified by a silica gel column chromatography (PE/EtOAc (V/V)=1:2) to give the title compound as a yellow solid (0.06 g, 7%). The compound was characterized by the following spectroscopic data:

MS (ESI, pos.ion) m/z: 428.1 (M+1);
$^1$H-NMR (400 MHz, CDCl$_3$): δ 2.36 (s, 3H), 3.70 (d, 2H, J=3.12 Hz), 4.03 (t, 2H, J=4.6 Hz), 4.35 (s, 2H), 4.73 (s, 2H), 6.38 (s, 1H), 6.55-6.53 (m, 2H), 6.67 (t, 1H, J=7.3 Hz), 7.21-7.11 (m, 3H), 7.44 (t, 1H, J=8.2 Hz).

Example 67

3-(3-chloro-4-morpholinophenyl)-2-((4-chloronaphthalen-1-yl)oxy)methyl)-6-methyl pyrimidin-4(3H)-one

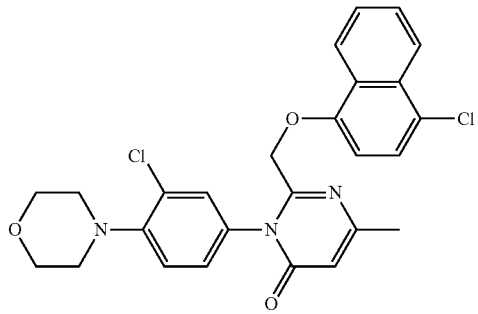 [SMILES: Cc1cc(=O)n(-c2ccc(N3CCOCC3)c(Cl)c2)c(COc2ccc(Cl)c3ccccc23)n1]

Step 1) 2-((4-chloronaphthalen-1-yl)oxy)acetamide

A mixture of 4-chloronaphthalen-1-ol (3.57 g, 20.0 mmol), 2-bromoacetamide (2.76 g, 20.0 mmol) and K$_2$CO$_3$ (5.53 g, 40.0 mmol) in acetone (40 mL) was stirred at 70° C. overnight. The mixture was cooled to rt and filtered and the filtrate was concentrated in vacuo. The residue was purified by a silica gel column chromatography (PE/EtOAc (V/V)=1:1) to give the title compound as a white solid (2.32 g, 49%).

Step 2) 3-(3-chloro-4-morpholinophenyl)-2-(((4-chloronaphthalen-1-yl)oxy)methyl)-6-methylpyrimidin-4(3H)-one A mixture of N-(3-chloro-4-morpholinophenyl)-3-oxobutanamide (0.59 g, 2.0 mmol), 2-((4-chloronaphthalen-1-yl) oxy)acetamide (0.94 g, 4.0 mmol) and titanium tetraisopropanolate (4.8 mL) in xylene (10 mL) was stirred at 165° C. for 24 h. The mixture was cooled to rt and 60 mL of toluene and 60 mL of saturated NH$_4$Cl aqueous solution were added. The resulting mixture was stirred at rt overnight and filtered and the filtrate was extracted with DCM (20 mL×4). The combined organic layers were washed with brine (30 mL×2), dried over anhydrous Na$_2$SO$_4$ and concentrated in vacuo. The residue was purified by a silica gel column chromatography (PE/EtOAc (V/V)=1:1) to give the title compound as a yellow solid (0.56 g, 56%). The compound was characterized by the following spectroscopic data:

MS (ESI, pos.ion) m/z: 496.1 (M+1);
$^1$H-NMR (400 MHz, CDCl$_3$): δ 2.37 (s, 3H), 2.96-2.86 (m, 4H), 3.83-3.80 (t, 4H, J=4.6 Hz), 4.93-4.92 (d, 2H, J=4.9 Hz), 6.41 (s, 1H), 6.62-6.60 (d, 1H, J=8.3 Hz), 6.89-6.87 (d, 1H, J=8.5 Hz), 7.09-7.07 (dd, 1H, J$_1$=2.5 Hz, J$_2$=8.5 Hz), 7.27-7.26 (m, 1H), 7.35-7.33 (d, 1H, J=8.2 Hz), 7.55-7.51 (m, 1H), 7.64-7.60 (m, 1H), 8.04-8.02 (d, 1H, J=8.3 Hz), 8.18-8.16 (d, 1H, J=8.2 Hz).

Example 68

3-(3-chloro-4-morpholinophenyl)-2-((3-ethynylphenoxy)methyl)-6-methylpyrimidin-4(3H)-one

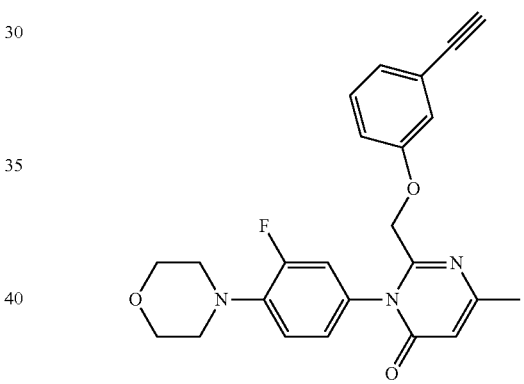

Step 1) 2-(3-ethynylphenoxy)acetamide

A mixture of 3-ethynylphenol (3.31 g, 28.0 mmol), 2-bromoacetamide (2.36 g, 17.1 mmol) and K$_2$CO$_3$ (5.53 g, 40.0 mmol) in acetone (50 mL) was stirred at 70° C. for 7 h. The mixture was cooled to rt and filtered and the filtrate was concentrated in vacuo. The residue was purified by a silica gel column chromatography (PE/EtOAc (V/V)=1:1) to give the title compound as a white solid (2.70 g, 90%).

Step 2) 3-(3-chloro-4-morpholinophenyl)-2-((3-ethynylphenoxy)methyl)-6-methyl-pyrimidin-4(3H)-one A mixture of N-(3-chloro-4-morpholinophenyl)-3-oxobutanamide (0.80 g, 2.85 mmol), 2-(3-ethynylphenoxy)acetamide (1.0 g, 5.71 mmol) and titanium tetraisopropanolate (6.76 mL) in xylene (20 mL) was stirred at 165° C. for 24 h. The mixture was cooled to rt and 50 mL of toluene and 60 mL of saturated NH$_4$Cl aqueous solution were added. The resulting mixture was stirred at rt overnight and filtered and the filtrate was extracted with DCM (150 mL×3). The combined organic layers were dried over anhydrous Na₂SO₄ and concentrated in vacuo. The residue was purified by a silica gel column chromatography (PE/EtOAc (V/V)=1:1) to give the title compound as a yellow solid (0.60 g, 50%). The compound was characterized by the following spectroscopic data:

MS (ESI, pos.ion) m/z: 420.1 (M+1);
¹H-NMR (400 MHz, CDCl₃): δ 2.34 (s, 3H), 3.03-3.11 (m, 5H), 3.83 (t, 4H), 4.68 (s, 2H), 6.38 (s, 1H), 6.76-7.19 (m, 7H).

Example 69

2-(difluoro(3-fluorophenoxy)methyl)-3-(3-fluoro-4-morpholinophenyl)-6-methylpyrimidin-4(3H)-one

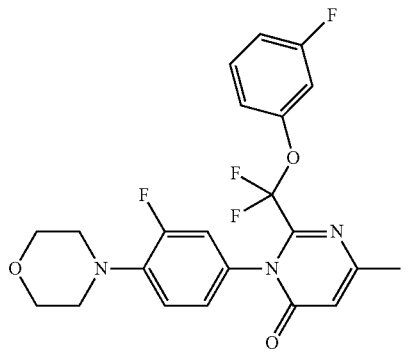 [SMILES: Cc1cc(=O)n(-c2ccc(N3CCOCC3)c(F)c2)c(C(F)(F)Oc2cccc(F)c2)n1]

Step 1) ethyl 2,2-difluoro-2-(3-fluorophenoxy)acetate

A mixture of 3-fluorophenol (2.24 g, 20.0 mmol), ethyl 2-bromo-2,2-difluoroacetate (8.12 g, 40.0 mmol) and K₂CO₃ (6.91 g, 50.0 mmol) in MeOH (20 mL) was stirred at 70° C. overnight. It was then cooled to rt and filtered and the filtrate was concentrated in vacuo to give the title compound, which was used for next step without further purification.

Step 2) 2,2-difluoro-2-(3-fluorophenoxy)acetamide

A mixture of ethyl 2,2-difluoro-2-(3-fluorophenoxy)acetate (3.5 g, 14.9 mmol), MeOH (10 mL) and ammonia (5.09 g) in a 20 mL of sealing tube was stirred at 100° C. for 24 h. The mixture was cooled to rt and concentrated in vacuo to give the title compound, which was used for next step without further purification.

Step 3) 2-(difluoro(3-fluorophenoxy)methyl)-3-(3-fluoro-4-morpholinophenyl)-6-methyl-pyrimidin-4(3H)-one A mixture of N-(3-fluoro-4-morpholinophenyl)-3-oxobutanamide (0.60 g, 2.14 mmol), 2,2-difluoro-2-(3-fluorophenoxy)acetamide (0.88 g, 4.29 mmol) and titanium tetraisopropanolate (4.87 g, 17.1 mmol) in xylene (20 mL) was stirred at 165° C. for 24 h. The mixture was cooled to rt and 60 mL of toluene and 80 mL of saturated NH₄Cl aqueous solution were added. The resulting mixture was stirred at rt overnight and filtered and the filtrate was extracted with DCM (150 mL×3). The combined organic layers were dried over anhydrous Na₂SO₄ and concentrated in vacuo. The residue was purified by a silica gel column chromatography (PE/EtOAc (V/V)=1:1) to give the title compound as a yellow solid (0.38 g, 40%). The compound was characterized by the following spectroscopic data:

MS (ESI, pos.ion) m/z: 450.1 (M+1);
¹H-NMR (400 MHz, CDCl₃): δ 2.43 (s, 3H), 3.15 (t, 4H), 3.85 (m, 4H), 6.36-7.27 (m, 8H).

Example 70

3-((1-(3,5-difluoro-4-morpholinophenyl)-4-methyl-6-oxo-1,6-dihydropyrimidin-2-yl)methoxy)benzonitrile

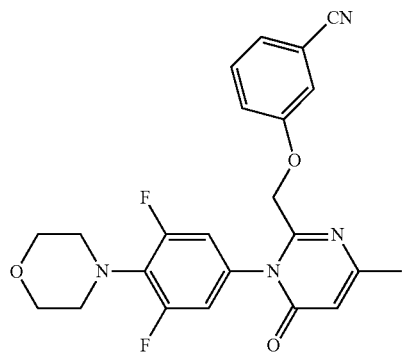 [SMILES: Cc1cc(=O)n(-c2cc(F)c(N3CCOCC3)c(F)c2)c(COc2cccc(C#N)c2)n1]

Step 1) 4-(2,6-difluoro-4-nitrophenyl)morpholine

A mixture of 1,2,3-trifluoro-5-nitrobenzene (3.54 g, 20.0 mmol), morpholine (2.0 mL, 23.0 mmol) and Et₃N (8.5 mL, 61.0 mmol) in EtOAc (30 mL) was stirred at rt for 5 h. The mixture was concentrated in vacuo, and the residue was purified by a silica gel column chromatography (PE/EtOAc (V/V)=8:1) to give the title compound as a yellow solid (4.76 g, 98%).

Step 2) 3,5-difluoro-4-morpholinoaniline

A mixture of 4-(2,6-difluoro-4-nitrophenyl)morpholine (4.71 g, 19.3 mmol), THF (30 mL), ethanol (30 mL) and Pd/C (2.0 g, 10%) was stirred at rt under H₂ overnight. The mixture was filtered and concentrated in vacuo and the residue was purified by a silica gel column chromatography (PE/EtOAc (V/V)=8:1) to give the title compound as a yellow solid (3.62 g, 88%).

Step 3) N-(3,5-difluoro-4-morpholinophenyl)-3-oxobutanamide

A mixture of 3,5-difluoro-4-morpholinoaniline (3.42 g, 16.0 mmol) and acetyl ketene (1.61 g, 19.2 mmol) in EtOAc (20 mL) was stirred at 83° C. overnight. The mixture was cooled to rt and concentrated in vacuo. The residue was purified by a silica gel column chromatography (PE/EtOAc (V/V)=1:1) to give the title compound as a yellow solid (3.10 g, 65%).

Step 4) 2-(3-cyanophenoxy)acetamide

A mixture of 3-hydroxybenzonitrile (2.38 g, 20.0 mmol), 2-bromoacetamide (3.04 g, 22.0 mmol) and K₂CO₃ (5.53 g, 40.0 mmol) in acetone (30 mL) was stirred at 75° C. overnight. It was then cooled to rt and filtered and the filtrate was concentrated in vacuo. The residue was purified by a silica gel column chromatography (PE/EtOAc (V/V)=1:1) to give the title compound as a white solid (1.00 g, 28%).

Step 5) 3-((1-(3,5-difluoro-4-morpholinophenyl)-4-methyl-6-oxo-1,6-dihydropyrimidin-2-yl)methoxy) benzonitrile A mixture of N-(3,5-difluoro-4-morpholinophenyl)-3-oxobutanamide (0.79 g, 2.65 mmol), 2-(3-cyanophenoxy) acetamide (0.93 g, 5.28 mmol) and titanium tetraisopropanolate (6.3 mL) in xylene (25 mL) was stirred at 165° C. for 24 h. The mixture was cooled to rt and 60 mL of toluene and 60 mL of saturated NH₄Cl aqueous solution were added. The resulting mixture was stirred at rt overnight and filtered and the filtrate was extracted with DCM (20 mL×4). The combined organic layers were washed with brine (30 mL×2), dried over anhydrous Na₂SO₄ and concentrated in vacuo. The residue was purified by a silica gel column chromatography (PE/EtOAc (V/V)=1:2) to give the title compound as a yellow solid (0.29 g, 25%). The compound was characterized by the following spectroscopic data:

MS (ESI, pos.ion) m/z: 439.1 (M+1);
$^1$H-NMR (400 MHz, CDCl₃): δ 2.34 (s, 3H), 3.20 (s, 4H), 3.80-3.77 (t, 4H, J=4.4 Hz), 4.77 (s, 2H), 6.37 (s, 1H), 6.83-6.81 (d, 2H, J=8.9 Hz), 7.08-7.06 (dd, 2H, J₁=7.5 Hz, J₂=1.0 Hz), 7.29-7.27 (d, 1H, J=6.4 Hz), 7.39-7.35 (m, 1H).

Example 71

3-(3-fluoro-4-morpholinophenyl)-2-((3-methoxyphenoxy)methyl)-6-methylpyrimidin-4(3H)-one

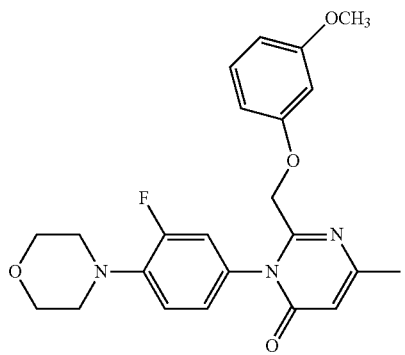 [SMILES: COc1cccc(OCc2nc(C)cc(=O)n2-c2ccc(N3CCOCC3)c(F)c2)c1]

Step 1) 2-(3-methoxyphenoxy)acetamide

A mixture of 3-methoxyphenol (2.48 g, 20.0 mmol), 2-bromoacetamide (3.31 g, 24.0 mmol) and K₂CO₃ (5.53 g, 40.0 mmol) in acetone (30 mL) was stirred at 70° C. for 9 h. The mixture was cooled to rt and filtered and the filtrate was concentrated in vacuo. The residue was purified by a silica gel column chromatography (PE/EtOAc (V/V)=1:1) to give the title compound as a white solid (3.0 g, 83%).

Step 2) 3-(3-fluoro-4-morpholinophenyl)-2-((3-methoxyphenoxy)methyl)-6-methyl-pyrimidin-4 (3H)-one A mixture of N-(3-fluoro-4-morpholinophenyl)-3-oxobutanamide (1.0 g, 3.57 mmol), 2-(3-methoxyphenoxy)acet-amide (1.29 g, 7.12 mmol) and titanium tetraisopropanolate (8.11 g, 28.5 mmol) in xylene (30 mL) was stirred at 165° C. for 24 h. The mixture was cooled to rt and 80 mL of toluene and 100 mL of saturated NH₄Cl aqueous solution were added. The resulting mixture was stirred at rt overnight and filtered and the filtrate was extracted with DCM (150 mL×3). The combined organic layers were dried over anhydrous Na₂SO₄ and concentrated in vacuo. The residue was purified by a silica gel column chromatography (PE/EtOAc (V/V)=1:1) to give the title compound as a yellow solid (0.61 g, 40%). The compound was characterized by the following spectroscopic data:

MS (ESI, pos.ion) m/z: 426.1 (M+1);
$^1$H-NMR (400 MHz, CDCl₃): δ 2.25 (s, 3H), 2.97 (t, 4H), 3.69 (s, 3H), 3.71 (m, 4H), 4.69 (s, 2H), 6.33-7.31 (m, 8H).

Example 72

3-(3-chloro-4-((1-(4-chloro-3-fluorophenyl)-2-methylpropan-2-yl)amino)phenyl)-2,6-dimethylpyrimidin-4(3H)-one

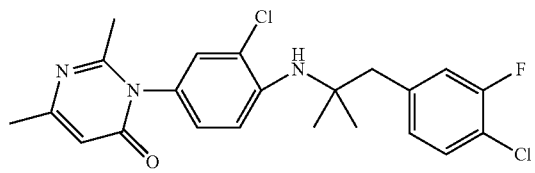 [SMILES: Cc1cc(=O)n(-c2ccc(NC(C)(C)Cc3ccc(Cl)c(F)c3)c(Cl)c2)c(C)n1]

Step 1) 1-(4-chloro-3-fluorophenyl)propan-2-one

To a mixture of 4-bromo-1-chloro-2-fluorobenzene (20.90 g, 100.0 mmol) and acetylacetone (30 mL, 300.0 mmol) in DMSO (100 mL) were added tripotassium phosphate (63.70 g, 300.0 mmol) and CuI (3.00 g, 15.80 mmol) under N₂ and the mixture was stirred at 110° C. for 23 h. The mixture was cooled to rt and hydrochloric acid (300 mL, 2 M) was added. The resulting mixture was extracted with EtOAc (100 mL×3) and the combined organic phases were washed with brine (100 mL×2), dried over anhydrous Na₂SO₄ (50 g), and filtered. The filtrate was concentrated in vacuo. The residue was purified by a silica gel column chromatography (PE/EtOAc (V/V)=10:1) to give the title compound as yellow liquid (9.02 g, 48.2%).

Step 2) 1-(4-chloro-3-fluorophenyl)-2-methylpropan-2-ol

To a solution of methylmagnesium bromide (100 mL, 100.0 mmol, 1.0 M in THF) was added a solution of 1-(4-chloro-3-fluorophenyl)propan-2-one (9.00 g, 48.20 mmol) in THF (20 mL) dropwise at 0° C. under N₂ and the reaction mixture was heated at 76° C. for 12 h. It was then cooled to rt and quenched with saturated NH₄Cl aqueous solution (50 mL) and the mixture was poured into water (200 mL). The resulting mixture was extracted with EtOAc (100 mL×4) and the combined organic phases were washed with brine (100 mL×2), dried over anhydrous Na₂SO₄ (50 g) and concentrated in vacuo. The residue was purified by a silica gel column chromatography (PE/EtOAc (V/V)=8:1) to give the title compound as yellow liquid (8.61 g, 88.2%).

Step 3) N-(1-(4-chloro-3-fluorophenyl)-2-methyl-propan-2-yl)acetamide

To a mixture of 1-(4-chloro-3-fluorophenyl)-2-methylpropan-2-ol (8.61 g, 42.50 mmol), acetonitrile (13 mL, 255.0 mmol) and acetic acid (80 mL) was added sulfuric acid (13 mL) dropwise and the mixture was heated at 65° C. for 5 h. The mixture was cooled to rt and poured into ice water (400 mL) and the resulting mixture was adjusted to pH>11 with NaOH, and extracted with EtOAc (150 mL×3). The combined organic phases were washed with brine (150 mL×2), dried over anhydrous $Na_2SO_4$ (40 g) and filtered. The filtrate was concentrated in vacuo. The residue was purified by a silica gel column chromatography (PE/EtOAc (V/V)=2:1) to give the title compound as a yellow solid (4.38 g, 42.1%). The compound was characterized by the following spectroscopic data:

MS (ESI, pos.ion) m/z: 244.2 (M+1);
$^1$H NMR (400 MHz, $CDCl_3$) δ 7.29 (dd, 1H, $J_1$=10.7 Hz, $J_2$=5.2 Hz), 6.94 (dd, 1H, $J_1$=10.2 Hz, $J_2$=1.9 Hz), 6.87 (dd, 1H, $J_1$=8.1 Hz, $J_2$=1.5 Hz), 5.21 (s, 1H), 3.08 (s, 2H), 1.95 (s, 3H), 1.32 (s, 6H).

Step 4) 1-(4-chloro-3-fluorophenyl)-2-methylpropan-2-amine

A mixture of N-(1-(4-chloro-3-fluorophenyl)-2-methylpropan-2-yl)acetamide (3.36 g, 13.80 mmol) and concentrated hydrochloric acid (60 mL) was heated at 120° C. for 16.5 h. The mixture was cooled to rt and poured into ice water and the resulting mixture was adjusted to pH>12 with NaOH and extracted with EtOAc (80 mL×5). The combined organic phases were washed with brine (100 mL×2), dried over anhydrous $Na_2SO_4$ and filtered. The filtrate was concentrated in vacuo. The residue was dissolved in concentrated hydrochloric acid (60 mL) and the mixture was stirred at 120° C. for 20 h. The reaction mixture was cooled to rt and 100 mL of water was added. The resulting mixture was washed with EtOAc (50 mL×3). The aqueous phase was adjusted to pH>11 with NaOH and extracted with EtOAc (50 mL×3). The combined organic phases were washed with brine (80 mL×2), dried over anhydrous $Na_2SO_4$ (20 g) and concentrated in vacuo to give the tile compound as a yellow solid (0.484 g, 17.4%). The compound was characterized by the following spectroscopic data:

MS (ESI, pos.ion) m/z: 202.1 (M+1).

Step 5) 2-chloro-N-(1-(4-chloro-3-fluorophenyl)-2-methylpropan-2-yl)-4-nitroaniline A mixture of 3-chloro-4-fluoro-1-nitrobenzene (421 mg, 2.40 mmol) and 1-(4-chloro-3-fluorophenyl)-2-methylpropan-2-amine (484 mg, 2.40 mmol) in DMSO (10 mL) was heated at 90° C. under $N_2$ for 3 h. The mixture was cooled to rt and stirred at rt for 38.5 h. It was then heated and stirred further at 90° C. for 81.5 h. The mixture was cooled to rt and 80 mL of water was added. The resulting mixture was extracted with EtOAc (30 mL×3). The combined organic layers were dried over anhydrous $Na_2SO_4$ (10 g) and concentrated in vacuo. The residue was purified by a silica gel column chromatography (PE/DCM (V/V)=20:1) to give the title compound as yellow oil (490 mg, 57.2%). The compound was characterized by the following spectroscopic data:

MS (ESI, pos.ion) m/z: 357.2 (M+1);
$^1$H NMR (400 MHz, $CDCl_3$) δ 8.24 (d, 1H, J=2.6 Hz), 8.10 (dd, 1H, $J_1$=9.2 Hz, $J_2$=2.6 Hz), 7.34-7.26 (m, 1H), 7.04-6.98 (m, 1H), 6.86 (dd, 1H, $J_1$=9.9 Hz, $J_2$=2.0 Hz), 6.77 (dd, 1H, $J_1$=8.2 Hz, $J_2$=1.5 Hz), 5.00 (s, 1H), 3.04 (s, 2H), 1.48 (s, 6H).

Step 6) 2-chloro-$N^1$-(1-(4-chloro-3-fluorophenyl)-2-methylpropan-2-yl)benzene-1,4-diamine To a mixture of water (20 mL) and iron powder (697 mg, 12.50 mmol) at 65° C. was added concentrated hydrochloric acid (0.2 mL) dropwise and the mixture was stirred for 15 min. The aqueous layer of the mixture was poured out and a solution of 2-chloro-N-(1-(4-chloro-3-fluorophenyl)-2-methylpropan-2-yl)-4-nitroaniline (446 mg, 1.25 mmol) in MeOH (20 mL) was added to the above processed iron powder. The mixture was adjusted to pH 2-3 and stirred at 65° C. for 20 min. The mixture was then cooled to rt, adjusted to pH 11 with $Et_3N$, and filtered and the filtrate was concentrated in vacuo. The residue was dissolved in EtOAc (100 mL) and the solution was washed with water (30 mL×3) and brine (30 mL×2), dried over anhydrous $Na_2SO_4$ (10 g) and concentrated in vacuo to give the crude product, which was used for next step with out further purification. The compound was characterized by the following spectroscopic data:

MS (ESI, pos.ion) m/z: 327.1 (M+1).

Step 7) 3-(3-chloro-4-((1-(4-chloro-3-fluorophenyl)-2-methylpropan-2-yl)amino)phenyl)-2,6-dimethylpyrimidin-4(3H)-one To a solution of 2-chloro-$N^1$-(1-(4-chloro-3-fluorophenyl)-2-methylpropan-2-yl)benzene-1,4-diamine (408 mg, 1.25 mmol) in toluene (15 mL) was added trimethylaluminium (2.5 mL, 5.00 mmol, 2.0 M in toluene) dropwise under $N_2$ and the mixture was stirred at rt for 30 min after addition was completed. A solution of (Z)-methyl 3-(2-(3-fluorophenoxy)acetamido)but-2-enoate (295 mg, 1.88 mmol) in toluene (5 mL) was added slowly and the resulting mixture was stirred at rt for 22 h. Trimethylaluminium (2.0 mL, 4.00 mmol, 2 M in toluene) was then added dropwise and the mixture was stirred at rt for 30 min. A solution of (Z)-methyl 3-(2-(3-fluorophenoxy)acetamido)but-2-enoate (295 mg, 1.88 mmol) in toluene (3 mL) was added and the mixture was stirred further for 18 h. The mixture was quenched with saturated $NH_4Cl$ aqueous solution (50 mL) and filtered and the organic phase was separated from the filtrate. The aqueous phase was extracted with EtOAc (30 mL×3). The combined organic layers were washed with brine (30 mL×2), dried over anhydrous $Na_2SO_4$ (15 g) and concentrated in vacuo. The residue was purified by a silica gel column chromatography (PE/EtOAc (V/V)=2:3) to give the title compound as a yellow solid (183 mg, 33.7%). The compound was characterized by the following spectroscopic data:

MS (ESI, pos.ion) m/z: 434.2 (M+1);
$^1$H NMR (400 MHz, $CDCl_3$) δ 7.31 (t, 1H, J=8.0 Hz), 7.16 (d, 1H, J=2.5 Hz), 7.11 (d, 1H, J=8.7 Hz), 6.98 (dd, 1H, $J_1$=8.7 Hz, $J_2$=2.5 Hz), 6.90 (dd, 1H, $J_1$=10.1 Hz, $J_2$=1.9 Hz), 6.83 (dd, 1H, $J_1$=8.2 Hz, $J_2$=1.5 Hz), 6.30 (d, 1H, J=9.9 Hz), 4.48 (s, 1H), 3.01 (dd, 2H, $J_1$=32.3 Hz, $J_2$=13.6 Hz), 2.33 (s, 3H), 2.27 (s, 3H), 1.44 (s, 3H), 1.42 (s, 3H).

The Experiment Method of Cells

1. Cell Seeding

Taking BHK-21 cells which in exponential growth phase, collecting and counting the cells which had digestive transfer culture after fusion growth 85-95%, adjusting the cell density to $2\times10^4$ cells per milliliter, seeding the cells into 96-well plates, 100 μl/well, the cells were incubated in a 5% $CO_2$ incubator at 37° C.

2. Doses of the Cells

The upper clear liquid of the 96-well plates was removed after the cells adhering to the wall 24 hours. The above compounds were confected into solutions of different concentration and the solutions were added to the wells, 100 μl/well. Each concentration solution in 3 replicates, the cells were subcultured 48 hours after dosing.

3. Testing the Optical Density

10 μl of CCK-8 solution was added to each well 48 hours after dosing, and incubated for 2 hours. The optical density (A) of each well was determined by a microplate reader at 450 nm wavelength. Calculating the inhibition ratio of cell proliferation of each compound is based on A and the inhibition ratio of cell proliferation (inhibition ratio, IR)= (1−value of experimental group $(A_i)$/value of control group $(A_o)$)×100% and the $IC_{50}$ of each compound at 48 hours was calculated by data processing software.

TABLE 2

Activity Data

| example | $IC_{50}$(mM) | The ratio with PFD (multiple) |
|---|---|---|
| 1 | 0.4 | 16.6 |
| 7 | 0.74 | 1.35 |
| 8 | 1.66 | 2.31 |
| 10 | 5.55 | 0.72 |
| 11 | 1.32 | 2.91 |
| 12 | 1.40 | 2.74 |
| 13 | 1.98 | 2.01 |
| 15 | 0.97 | 3.97 |
| 18 | 0.56 | 8.10 |
| 19 | 1.19 | 3.21 |
| 20 | 0.04 | 95.70 |
| 21 | 1.30 | 5.57 |
| 22 | 0.19 | 39.47 |
| 23 | 0.11 | 30.31 |
| 24 | 0.04 | 60.63 |
| 27 | N/A | N/A |
| 28 | 4.99 | 1.60 |
| 29 | 1.05 | 6.82 |
| 30 | 0.54 | 13.18 |
| 31 | 2.22 | 3.50 |
| 32 | 0.81 | 9.60 |
| 33 | 0.30 | 25.70 |
| 34 | 2.49 | 3.10 |
| 35 | 3.01 | 2.60 |
| 36 | 2.70 | 2.90 |
| 37 | 4.31 | 1.80 |
| 38 | 0.49 | 15.80 |
| 39 | N/A | N/A |
| 40 | 0.06 | 127.50 |
| 41 | 0.06 | 32.65 |
| 42 | 0.07 | 27.39 |
| 45 | 0.07 | 42.60 |
| 46 | 1.07 | 2.80 |
| 47 | 0.93 | 3.92 |
| 48 | 0.35 | 10.60 |
| 49 | 0.07 | 35.52 |
| 50 | 0.06 | 42.93 |
| 51 | 0.10 | 25.14 |
| 52 | 0.18 | 14.15 |
| 53 | 0.50 | 15.49 |
| 55 | 0.05 | 46.92 |
| 56 | 0.10 | 54.14 |
| 57 | 0.10 | 84.22 |
| 58 | 0.29 | 26.37 |
| 59 | 0.30 | 25.50 |
| 60 | 0.54 | 13.72 |

TABLE 2-continued

Activity Data

| example | $IC_{50}$(mM) | The ratio with PFD (multiple) |
|---|---|---|
| 62 | 0.31 | 24.68 |
| 63 | 0.04 | 47.43 |
| 64 | 0.19 | 10.69 |
| 65 | 0.02 | 119.61 |
| 66 | 0.23 | 14.95 |
| 67 | 0.14 | 25.09 |
| 68 | 0.11 | 26.80 |
| 69 | 0.09 | 42.03 |
| 70 | N/A | N/A |
| 71 | 0.08 | 48.76 |

N/A: There is no inhibitory activity in the range of testing concentration of the compound and the inhibitory activity does not increase with the testing concentration.

The ratio with PFD (multiple): There is the ratio of Pirfenidone $IC_{50}$ from the compound $IC_{50}$; the bigger the multiple, the better the vitro inhibitory activity of the compound.

Common characteristic of organic fibrosis is expanding of extracellular matrix (ECM) and structural remodeling of organs and tissues, where many cytokines (CK) participate in the process. It showed that in experimental screening in vitro, compounds disclosed herein are more active than Pirfenidone, and a part of the compounds are more than 20 times as active as Pirfenidone. Compounds disclosed herein can avoid the phototoxic reaction produced by Pirfenidone, which are effective in anti-fibrosis.

The invention claimed is:

1. A compound of Formula (I):

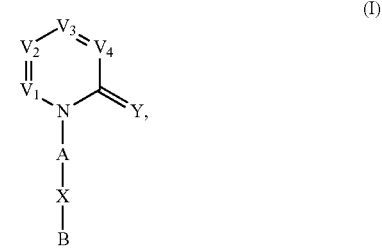

or a stereoisomer, a geometric isomer, a tautomer, an N-oxide, a hydrate, a solvate, or a pharmaceutically acceptable salt thereof, wherein:

$V_1$ is $CR^1$, $V_2$ is N, $V_3$ is $CR^3$, and $V_4$ is $CR^4$;

X is a bond, $NR^5$, or $C_{1-10}$alkylene;

Y is O or S;

A is

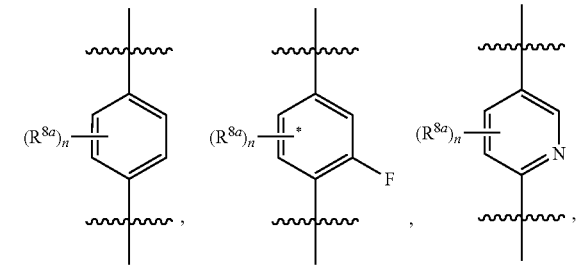

-continued

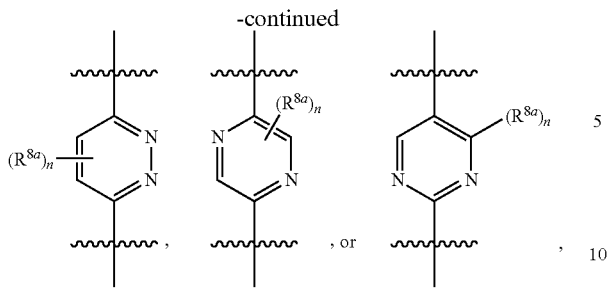

wherein each n is independently 0, 1, 2 or 3;
each $R^{8a}$ is independently H, hydroxy, amino, F, Cl, Br, I, $R^{7a}R^7N—$, cyano, nitro, mercapto, $C_{1-4}$ alkyl, $C_{1-4}$haloalkyl, $C_{1-4}$ alkoxy, $C_{1-4}$ alkylamino, $C_{1-4}$ alkylthio, $C_{6-10}$ aryl, or $C_{1-9}$ heteroaryl;
B is $—NR^7R^{7a}$, $C_{4-12}$ carbocyclyl, $C_{4-12}$ cycloalkyl, heterocyclyl, aryl, heteroaryl, fused bicyclyl, fused heterobicyclyl, spiro bicyclyl, or spiro heterobicyclyl; wherein each of the $C_{4-12}$ carbocyclyl, $C_{4-12}$ cycloalkyl, heterocyclyl, aryl, heteroaryl, fused bicyclyl, fused heterobicyclyl, spiro bicyclyl, and spiro heterobicyclyl is unsubstituted or substituted with at least one substituent wherein the substituent is haloalkyl, oxo (=O), hydroxy, amino, F, Cl, Br, I, cyano, $C_{1-10}$ alkoxy, $C_{1-10}$ alkylamino, $C_{1-10}$ alkylthio, $C_{1-10}$ alkyl, $C_{2-10}$ alkenyl, $C_{2-10}$alkynyl, mercapto, nitro, $C_{6-10}$ aryl, $C_{1-9}$ heteroaryl, $C_{2-10}$ heterocyclyl, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy$C_{1-6}$ alkoxy; wherein each of the $—NR^7R^{7a}$ is unsubstituted or substituted with at least one substituent wherein the substituent is haloalkyl, hydroxy, amino, F, Cl, Br, I, cyano, $C_{1-10}$ alkoxy, $C_{1-10}$ alkylamino, $C_{1-10}$ alkylthio, $C_{1-10}$ alkyl, $C_{2-10}$ alkenyl, $C_{2-10}$alkynyl, mercapto, nitro, $C_{6-10}$ aryl, $C_{1-9}$ heteroaryl, $C_{2-10}$ heterocyclyl, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy$C_{1-6}$ alkoxy;
$R^1$ is H, F, Cl, Br, I, cyano, aliphatic, haloalkyl, alkoxy, hydroxyalkoxy, aminoalkoxy, haloalkoxy, alkylaminohaloalkoxy, alkylaminoalkoxy, alkoxyalkoxy, cycloalkyloxy, arylalkoxy, arylalkylamino, heteroarylalkoxy, heteroarylalkylamino, heterocyclylalkylamino, cycloalkylamino, heterocyclylalkoxy, carbocyclylalkoxy, carbocyclylalkylamino, aryloxy, heteroaryloxy, heteroaryloxyalkoxy, heterocyclyloxyalkoxy, carbocyclyloxyalkoxy, heterocyclyloxy, azidoalkoxy, heterocyclyl, cycloalkyl, aryl, heteroaryl, heterocyclyl aliphatic, cycloalkyl aliphatic, aryl aliphatic, heteroaryl aliphatic, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, or cycloalkyl-$(CH_2)_p$-G-$(CH_2)_m$—, wherein each G is O, S, $NR^5$, S(=O), S(=O)$_2$, C(=O), —C(=O)N($R^7$)—, —OC(=O)N($R^7$)—, —OC(=O)—, —N($R^7$)C(=O)N($R^7$)—, —($R^7$)N—S(=O)$_t$—, —OS(=O)$_t$—, or —OS(=O)$_t$N($R^7$)—; each t is 1 or 2; each p and m is independently 0, 1, 2, 3 or 4; or wherein each of the aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$— is optionally substituted by one or more haloalkyl, oxo (=O), hydroxy, amino, F, Cl, Br, I, cyano, $C_{1-10}$ alkoxy, $C_{1-10}$ alkylamino, $C_{1-10}$ alkylthio, $C_{1-10}$ alkyl, $C_{2-10}$ alkenyl, $C_{2-10}$alkynyl, mercapto, nitro, $C_{6-10}$ aryl, $C_{1-9}$ heteroaryl, $C_{2-10}$ heterocyclyl, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy$C_{1-6}$ alkoxy;
$R^3$ is H, F, Cl, I, cyano, aliphatic, $C_{2-10}$haloalkyl, aryl-$C_{2-10}$ alkoxy, heretoaryl-$C_{3-10}$ alkoxy, cycloalkyl-$C_{2-10}$ alkoxy, $C_{1-4}$ heteroaryl, substituted aryl, heterocyclyl, cycloalkyl, heterocyclyl aliphatic, cycloalkyl aliphatic, $C_{1-4}$ heteroaryl aliphatic, heterocyclylalkyl, alkoxy, hydroxyalkoxy, aminoalkoxy, haloalkoxy, alkylaminohaloalkoxy, alkylaminoalkoxy, alkoxyalkoxy, aryl-$C_{2-10}$alkoxy, heterocyclylalkoxy, carbocyclylalkoxy, aryloxyalkoxy, arylaminoalkoxy, aryloxy, heteroaryloxyalkoxy, heterocyclyloxyalkoxy, carbocyclyloxyalkoxy, heterocyclyloxy, cycloalkyloxy, azidoalkoxy, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, or cycloalkyl-$(CH_2)_p$-G-$(CH_2)_m$—, wherein each G is O, S, $NR^5$, S(=O), S(=O)$_2$, C(=O), —C(=O)N($R^7$)—, —OC(=O)N($R^7$)—, —OC(=O)—, —N($R^7$)C(=O)N($R^7$)—, —($R^7$)N—S(=O)$_t$—, —OS(=O)$_t$—, or —OS(=O)$_t$N($R^7$)—; each t is 1 or 2; each p and m is independently 0, 1, 2, 3 or 4; or wherein each of the aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$— is optionally substituted by one haloalkyl, oxo (=O), hydroxy, amino, F, Cl, Br, I, cyano, $C_{1-10}$ alkoxy, $C_{1-10}$ alkylamino, $C_{1-10}$ alkylthio, $C_{1-10}$ alkyl, $C_{2-10}$ alkenyl, $C_{2-10}$alkynyl, mercapto, nitro, $C_{6-10}$ aryl, $C_{1-9}$ heteroaryl, $C_{2-10}$ heterocyclyl, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy$C_{1-6}$ alkoxy;
$R^4$ is H;
each $R^5$ is independently H, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;
each $R^7$ is independently H, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; and
each $R^{7a}$ is independently aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring or a substituted or unsubstituted spiro bicyclic or fused bicyclic ring.

2. The compound according to claim 1, wherein B is —$NR^7R^{7a}$, $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl, or $C_{5-12}$ spiro heterobicyclyl.

3. The compound according to claim 1, wherein:

$R^1$ is H, F, Cl, Br, I, cyano, $C_{1-6}$ aliphatic, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{2-10}$ heterocyclyl-$C_{1-6}$-alkoxy, $C_{2-10}$ heterocyclyl-$C_{1-6}$-alkylamino, $C_{3-10}$ cycloalkylamino, $C_{3-10}$ carbocyclyl-$C_{1-6}$-alkoxy, $C_{3-10}$ carbocyclyl-$C_{1-6}$-alkylamino, $C_{6-10}$ aryloxy-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{1-6}$ azidoalkoxy, $C_{2-10}$ heterocyclyl, $C_{3-10}$ cycloalkyl, $C_{6-10}$ aryl, $C_{1-9}$ heteroaryl, $C_{2-10}$ heterocyclyl-$C_{1-6}$-aliphatic, $C_{3-10}$ cycloalkyl-$C_{1-6}$-aliphatic, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$, —OS(=O)$_t$, or —OS(=O)$_t$NH—; each t is 1 or 2; each p and m is independently 0, 1, 2, 3 or 4; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-$(CH_2)_m$— is optionally substituted by one or more F, Cl, Br, I, $C_{1-6}$ alkyl, $C_{2-6}$ alkynyl, $C_{1-6}$ alkoxy or cyano;

$R^3$ is H, F, Cl, I, cyano, $C_{1-6}$ aliphatic, $C_{2-10}$ haloalkyl, $C_{6-10}$ aryl-$C_{2-10}$-alkoxy, $C_{1-9}$ heteroaryl-$C_{3-6}$-alkoxy, $C_{3-10}$ cycloalkyl-$C_{2-10}$-alkoxy, $C_{2-10}$ heterocyclyl, $C_{3-10}$ cycloalkyl, $C_{1-4}$ heteroaryl, substituted $C_{6-10}$ aryl, $C_{2-10}$ heterocyclyl-$C_{1-6}$-aliphatic, $C_{3-10}$ cycloalkyl-$C_{1-6}$-aliphatic, $C_{1-4}$ heteroaryl-$C_{1-6}$-aliphatic, $C_{1-9}$ heteroaryloxy-$C_{1-6}$-alkoxy, $C_{2-10}$ hetrerocyclyl-$C_{1-6}$-alkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-haloalkoxy, $C_{1-6}$ alkylamino-$C_{1-6}$-alkoxy, $C_{1-6}$ alkoxy-$C_{1-6}$-alkoxy, $C_{6-10}$ aryl-$C_{2-10}$-alkoxy, $C_{2-10}$ heterocyclyl-$C_{1-6}$-alkoxy, $C_{3-10}$ carbocyclyl-$C_{1-6}$-alkoxy, $C_{6-10}$ aryloxy-$C_{1-6}$-alkoxy, $C_{6-10}$ arylamino-$C_{1-6}$-alkoxy, $C_{6-10}$aryloxy, $C_{2-10}$ heterocyclyloxy-$C_{1-6}$-alkoxy, $C_{3-10}$ carbocyclyloxy-$C_{1-6}$-alkoxy, $C_{2-10}$ heterocyclyloxy, $C_{3-10}$ cycloalkyloxy, $C_{1-6}$ azidoalkoxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$, —OS(=O)$_t$, or —OS(=O)$_t$NH—; each t is 1 or 2; each p and m is independently 0, 1, 2, 3 or 4; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-$(CH_2)_m$— is optionally substituted by one F, Cl, Br, I, $C_{1-6}$ alkyl, $C_{2-6}$ alkynyl, methoxy, ethoxy, propoxy, butoxy or cyano;

$R^4$ is H;

wherein each $R^5$ is independently H, $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryloxy-$C_{1-6}$-aliphatic, $C_{2-10}$ heterocyclyloxy-$C_{1-6}$-aliphatic, $C_{3-10}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-10}$ cycloalkylamino-$C_{1-6}$-aliphatic, $C_{6-10}$ aryl, $C_{1-9}$ heteroaryl, $C_{2-10}$ heterocyclyl or $C_{3-10}$ carbocyclyl;

wherein each $R^7$ is independently H, $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryloxy-$C_{1-6}$-aliphatic, $C_{2-10}$ heterocyclyloxy-$C_{1-6}$-aliphatic, $C_{3-10}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-10}$ cycloalkylamino-$C_{1-6}$-aliphatic, $C_{6-10}$ aryl, $C_{1-9}$ heteroaryl, $C_{2-10}$ heterocyclyl or $C_{3-10}$ carbocyclyl; and each $R^{7a}$ is independently $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$ alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryloxy-$C_{1-6}$-aliphatic, $C_{2-10}$ heterocyclyloxy-$C_{1-6}$-aliphatic, $C_{3-10}$ cycloalkyloxy-$C_{1-6}$-aliphatic, $C_{6-10}$ arylamino-$C_{1-6}$-aliphatic, $C_{2-10}$ heterocyclylamino-$C_{1-6}$-aliphatic, $C_{3-10}$ cycloalkylamino-$C_{1-6}$-aliphatic, $C_{6-10}$ aryl, $C_{1-9}$ heteroaryl, $C_{2-10}$ heterocyclyl or $C_{3-10}$ carbocyclyl; with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring, or a substituted or unsubstituted $C_{5-12}$ spiro bicyclic or $C_{5-12}$ fused bicyclic ring.

4. The compound according to claim 1, wherein each $R^1$ is H, F, Cl, Br, I, cyano, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$aryloxy, $C_{1-9}$ heteroaryloxy, $C_{1-9}$ heteroaryloxy-$C_{1-6}$-alkoxy, $C_{2-10}$ heterocyclyl, $C_{3-10}$cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$, —OS(=O)$_t$, or —OS(=O)$_t$NH—; each t is 1 or 2; each p and m is independently 0, 1, 2, 3 or 4; or wherein each of the $C_{6-10}$aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-

(CH₂)ₘ— is optionally substituted by one or more F, Cl, Br, I, C₁₋₆ alkyl, C₂₋₆ alkynyl, C₁₋₆ alkoxy or cyano; each R³ is H, F, Cl, I, cyano, C₁₋₆ aliphatic, C₂₋₆ haloalkyl, C₆₋₁₀ aryl-C₂₋₆-alkoxy, C₁₋₉ heteroaryl-C₃₋₆-alkoxy, C₁₋₉ heteroaryloxy-C₁₋₆-alkoxy, C₃₋₁₀ cycloalkyl-C₂₋₆-alkoxy, C₂₋₁₀ heterocyclyl, C₃₋₁₀ cycloalkyl, C₂₋₁₀ heterocyclyl-C₁₋₆-aliphatic, C₃₋₁₀ cycloalkyl-C₁₋₆-aliphatic, C₁₋₄ heteroaryl, substituted C₆₋₁₀ aryl, C₁₋₄ heteroaryl-C₁₋₆-aliphatic, C₂₋₁₀ hetrerocyclyl-C₁₋₆-alkyl, C₁₋₆ alkoxy, C₁₋₆ hydroxyalkoxy, C₁₋₆ aminoalkoxy, C₁₋₆haloalkoxy, C₁₋₆ alkylamino-C₁₋₆-haloalkoxy, C₁₋₆alkylamino-C₁₋₆-alkoxy, C₁₋₆ alkoxy-C₁₋₆-alkoxy, C₆₋₁₀ aryl-C₂₋₁₀-alkoxy, C₂₋₁₀ heterocyclyl-C₁₋₆-alkoxy, C₃₋₁₀ carbocyclyl-C₁₋₆-alkoxy, C₂₋₁₀ heterocyclyloxy, C₃₋₁₀ cycloalkyloxy, C₆₋₁₀ aryl-(CH₂)ₚ-G-(CH₂)ₘ—, C₁₋₉ heteroaryl-(CH₂)ₚ-G-(CH₂)ₘ—, C₂₋₁₀ heterocyclyl-(CH₂)ₚ-G-(CH₂)ₘ—, or C₃₋₁₀ cycloalkyl-(CH₂)ₚ-G-(CH₂)ₘ—, wherein each G is O, S, NR⁵, S(=O), S(=O)₂, C(=O), —C(=O)NH—, —OC(=O)NH—, —OC(=O)—, —NHC(=O)NH—, —HN—S(=O)ₜ, —OS(=O)ₜ, or —OS(=O)ₜNH—; each t is 1 or 2; each p and m is independently 0, 1, 2, 3 or 4; and each R⁴ is H.

5. The compound according to claim 1, wherein

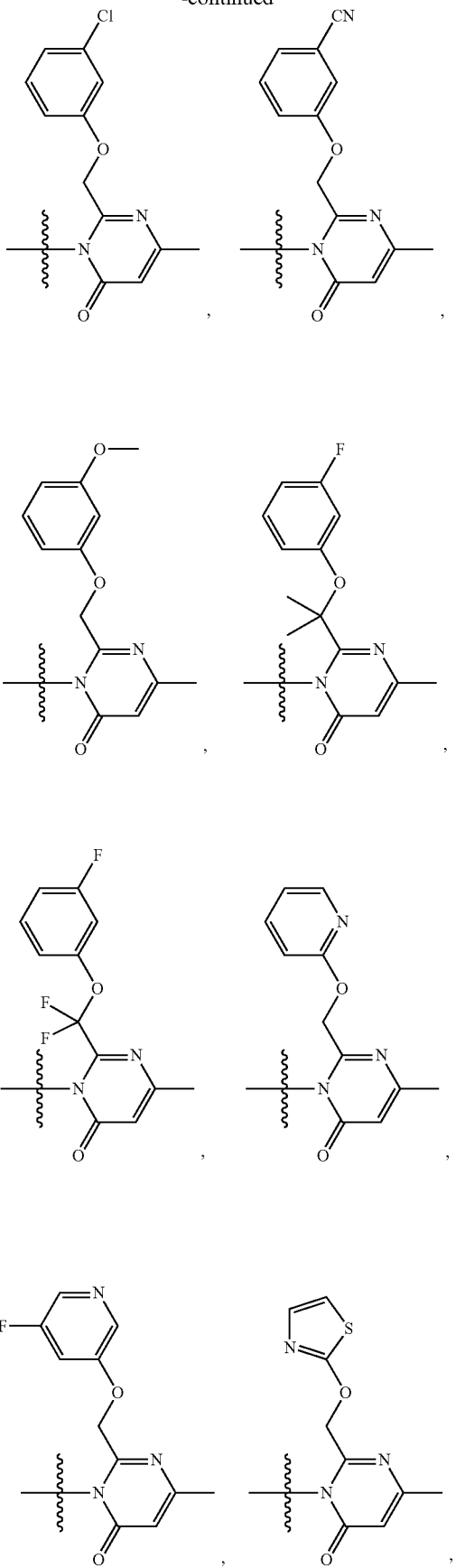

221
-continued

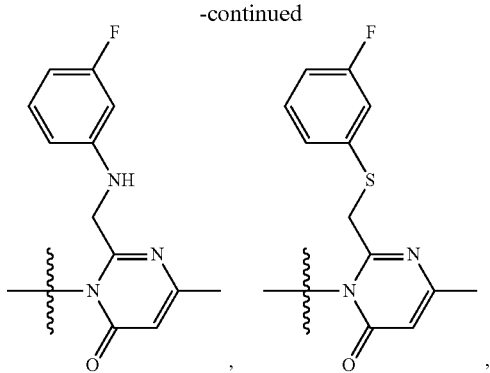

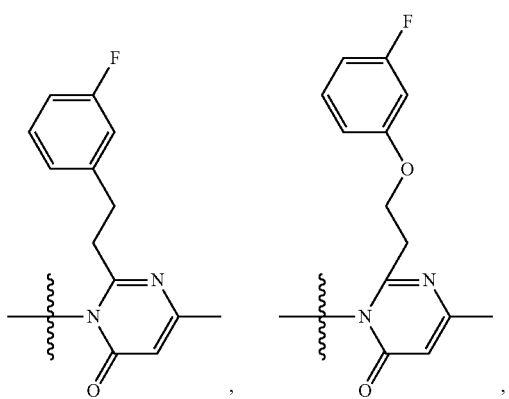

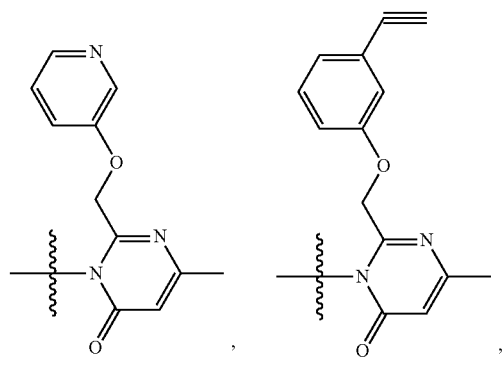

222
-continued

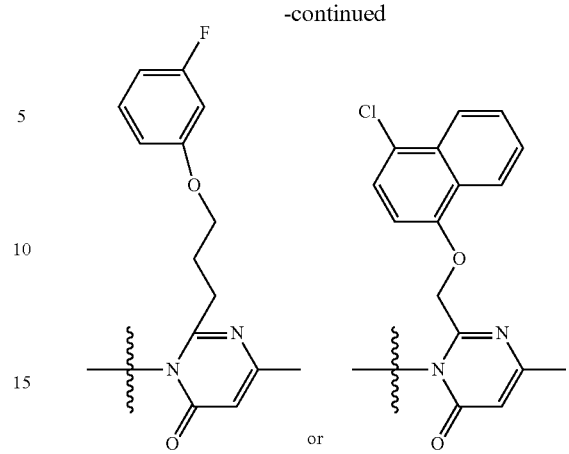

6. The compound according to claim 1 having Formula (IV):

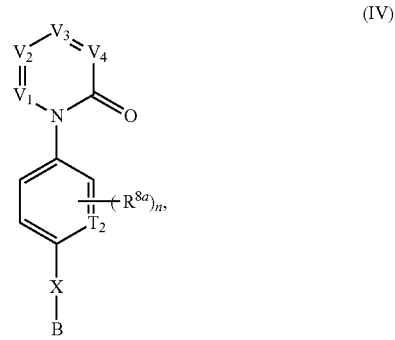

(IV)

wherein $V_1$ is $CR^1$, $V_2$ is N, $V_3$ is $CR^3$, and $V_4$ is $CR^4$; $T_2$ is N or $CR^{10}$;
X is a bond, $NR^5$, or —$(CH_2)_m$—, wherein each m is independently 0, 1, 2 or 3;
B is —$NR^7R^{7a}$, $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl, or $C_{5-12}$ spiro heterobicyclyl; wherein each of the $C_{4-12}$ carbocyclyl, $C_{4-12}$ cycloalkyl, $C_{2-10}$ heterocyclyl, $C_{6-10}$ aryl, $C_{1-9}$ heteroaryl, $C_{5-12}$ fused bicyclyl, $C_{5-12}$ fused heterobicyclyl, $C_{5-12}$ spiro bicyclyl and $C_{5-12}$ spiro heterobicyclyl is optionally substituted by oxo (=O), hydroxy, amino, F, Cl, Br, I, cyano, $C_{6-10}$ aryl, $C_{1-9}$ heteroaryl, $C_{1-6}$ alkoxy, $C_{1-6}$ alkylamino, $C_{1-6}$ alkyl, $C_{2-6}$ alkenyl, $C_{2-6}$ alkynyl, $C_{2-10}$ heterocyclyl, mercapto, nitro, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy $C_{1-6}$ alkoxy; wherein each of the —$NR^7R^{7a}$ is optionally substituted by hydroxy, amino, F, Cl, Br, I, cyano, $C_{6-10}$ aryl, $C_{1-9}$ heteroaryl, $C_{1-6}$ alkoxy, $C_{1-6}$ alkylamino, $C_{1-6}$ alkyl, $C_{2-6}$ alkenyl, $C_{2-6}$ alkynyl, $C_{2-10}$ heterocyclyl, mercapto, nitro, $C_{6-10}$ aryloxy, carboxy, hydroxy-substituted $C_{1-6}$ alkoxy, hydroxy-substituted $C_{1-6}$ alkyl-C(=O)—, $C_{1-6}$ alkyl-C(=O)—, $C_{1-6}$ alkyl-S(=O)—, $C_{1-6}$ alkyl-S(=O)$_2$—, hydroxy-substituted $C_{1-6}$ alkyl-S(=O)—, hydroxy-substituted $C_{1-6}$ alkyl-S(=O)$_2$—, or carboxy $C_{1-6}$ alkoxy;

R¹ is H, F, Cl, Br, I, cyano, $C_{1-6}$ aliphatic, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-alkoxy, $C_{1-6}$ alkoxy-$C_{1-6}$-alkoxy, $C_{3-10}$ cycloalkyloxy, $C_{6-10}$ aryl-$C_{1-6}$-alkoxy, $C_{6-10}$ aryl-$C_{1-6}$-alkylamino, $C_{1-9}$ heteroaryl-$C_{1-6}$-alkoxy, $C_{1-9}$ heteroaryl-$C_{1-6}$-alkylamino, $C_{3-10}$ cycloalkylamino, $C_{2-10}$ heterocyclyl-$C_{1-6}$-alkoxy, $C_{6-10}$ aryloxy, $C_{1-9}$ heteroaryloxy, $C_{1-9}$ heteroaryloxy-$C_{1-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{6-10}$ aryl-$C_{1-6}$-aliphatic, $C_{1-9}$ heteroaryl-$C_{1-6}$-aliphatic, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, $S(=O)$, $S(=O)_2$, $C(=O)$, —C(=O)NH—, —OC(=O)NH—, —OC(=O)—, —NHC(=O)NH—, —HN—S(=O)$_t$, —OS(=O)$_t$, or —OS(=O)$_t$NH—; each t is 1 or 2; each p and m is independently 0, 1, 2, 3 or 4; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-$(CH_2)_m$— is optionally substituted by one or more F, Cl, Br, I, methyl, ethyl, propyl, ethynyl, propynyl, butynyl, methoxy, ethoxy or cyano;

R³ is H, F, Cl, I, cyano, $C_{1-6}$ aliphatic, $C_{2-6}$ haloalkyl, $C_{6-10}$ aryl-$C_{2-6}$-alkoxy, $C_{1-9}$ heteroaryl-$C_{3-6}$-alkoxy, $C_{1-9}$ heteroaryloxy-$C_{1-6}$-alkoxy, $C_{3-10}$ cycloalkyl-$C_{2-6}$-alkoxy, $C_{2-10}$ heterocyclyl, $C_{3-10}$ cycloalkyl, $C_{2-10}$ heterocyclyl-$C_{1-6}$-aliphatic, $C_{3-10}$ cycloalkyl-$C_{1-6}$-aliphatic, $C_{1-4}$ heteroaryl, substituted $C_{6-10}$ aryl, $C_{1-4}$ heteroaryl-$C_{1-6}$-aliphatic, $C_{2-10}$ heterocyclyl-$C_{1-6}$-alkyl, $C_{1-6}$ alkoxy, $C_{1-6}$ hydroxyalkoxy, $C_{1-6}$ aminoalkoxy, $C_{1-6}$ haloalkoxy, $C_{1-6}$ alkylamino-$C_{1-6}$-haloalkoxy, $C_{1-6}$ alkylamino-$C_{1-6}$-alkoxy, $C_{1-6}$ alkoxy-$C_{1-6}$-alkoxy, $C_{6-10}$ aryl-$C_{2-10}$-alkoxy, $C_{2-10}$ heterocyclyl-$C_{1-6}$-alkoxy, $C_{3-10}$ carbocyclyl-$C_{1-6}$-alkoxy, $C_{2-10}$ heterocyclyloxy, $C_{3-10}$ cycloalkyloxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, $S(=O)$, $S(=O)_2$, $C(=O)$, —C(=O)NH—, —OC(=O)NH—, —OC(=O)—, —NHC(=O)NH—, —HN—S(=O)$_t$, —OS(=O)$_t$, or —OS(=O)$_t$NH—; each t is 1 or 2; each p and m is independently 0, 1, 2, 3 or 4; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$cycloalkyl-$(CH_2)_p$-G-$(CH_2)_m$— is optionally substituted by one F, Cl, Br, I, methyl, ethyl, propyl, ethynyl, propynyl, butynyl, methoxy, ethoxy or cyano;

R⁴ is H;

each R⁵ is independently H, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl-$C_{1-3}$-alkyl, $C_{2-10}$ heterocyclyl-$C_{1-3}$-alkyl, $C_{3-10}$ cycloalkyl-$C_{1-3}$-alkyl, $C_{6-10}$ aryl, $C_{1-9}$ heteroaryl, $C_{2-10}$ heterocyclyl or $C_{3-10}$ carbocyclyl;

each R⁷ is independently H, $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$- aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

each $R^{7a}$ is independently $C_{1-6}$ aliphatic, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$cycloalkyl-$C_{1-6}$-aliphatic, $C_{6-10}$aryl, $C_{1-9}$ heteroaryl, $C_{2-10}$heterocyclyl or $C_{3-10}$carbocyclyl; with the proviso that where R⁷ and $R^{7a}$ are bonded to the same nitrogen atom, R⁷ and $R^{7a}$, together with the nitrogen atom they are attached to, optionally form a substituted or unsubstituted 3-8 membered ring;

each $R^{8a}$ is independently H, hydroxy, amino, F, Cl, Br, I, —N(CH₃)₂, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl or $C_{1-9}$ heteroaryl;

n is 0, 1, 2 or 3; and each $R^{10}$ is independently H or F.

7. The compound according to claim 6, wherein:

B is —N(CH₃)₂, —N(CH₂CH₃)₂, —N(CH₂CH₂CH₃)₂, —N(CH₂CH₂CH₂CH₃)₂,

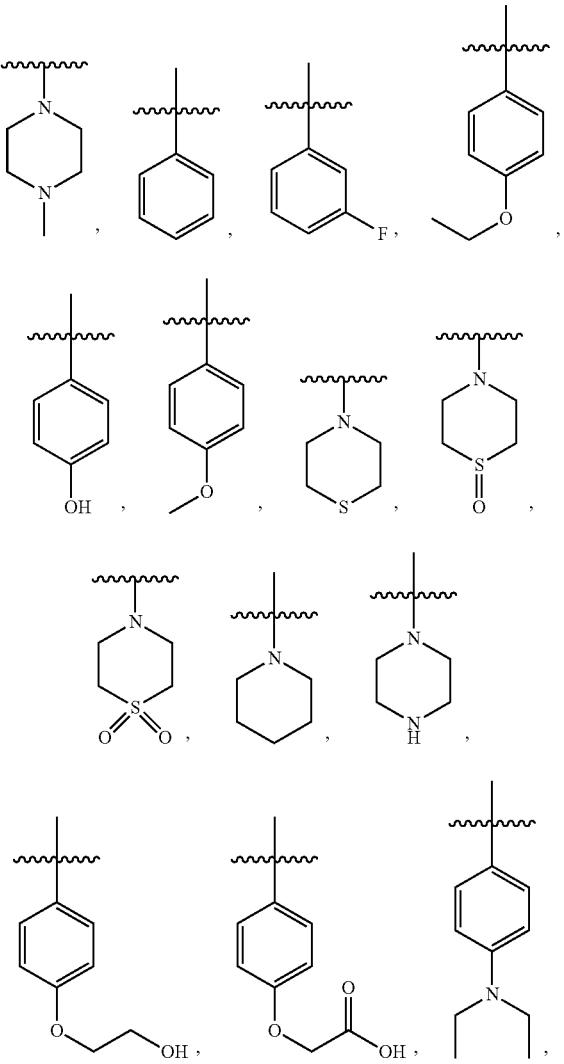

225
-continued
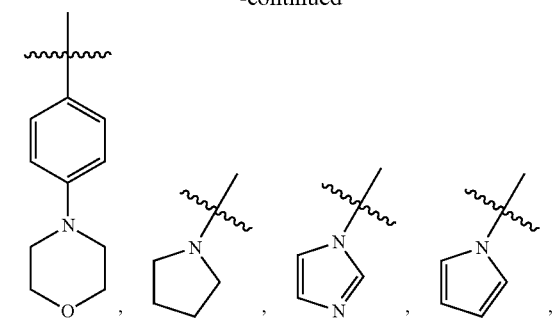
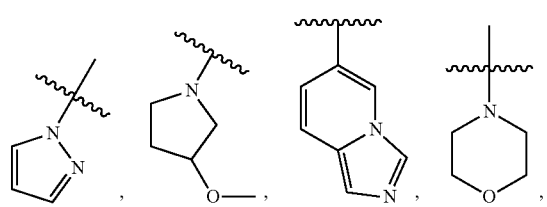
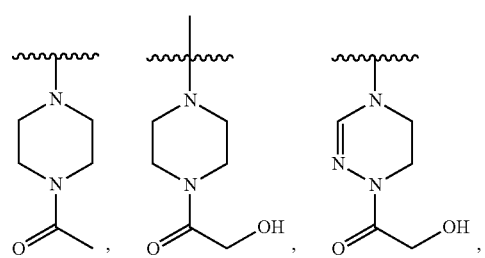
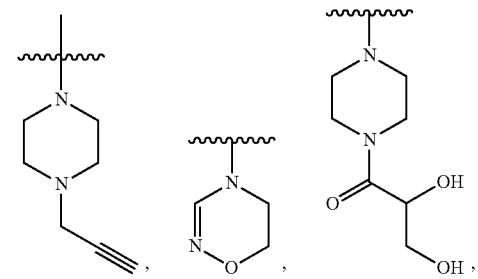
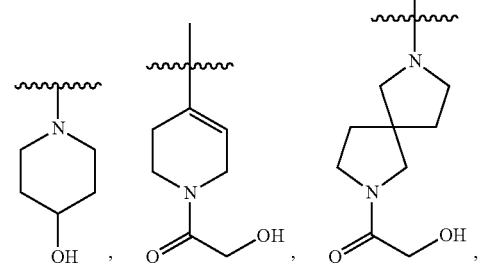
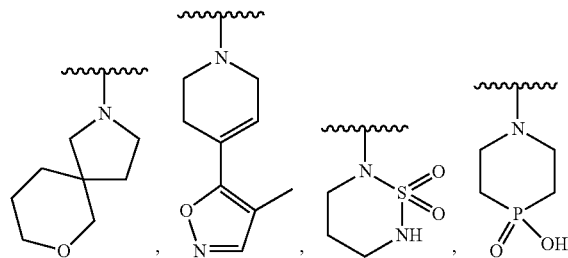
226
-continued
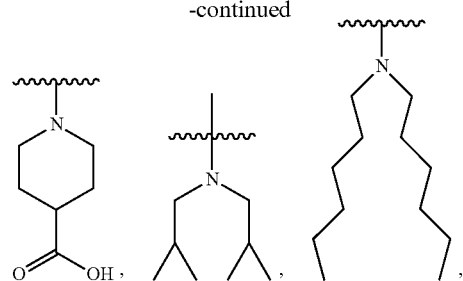
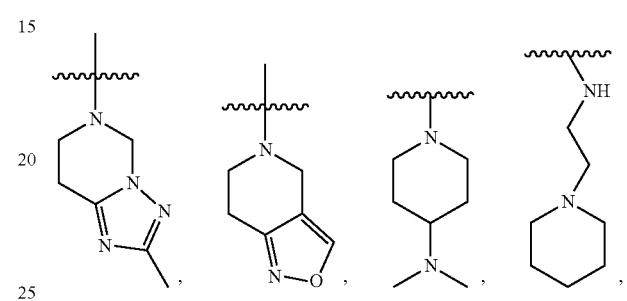
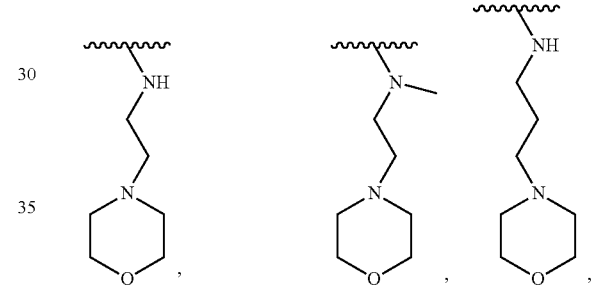
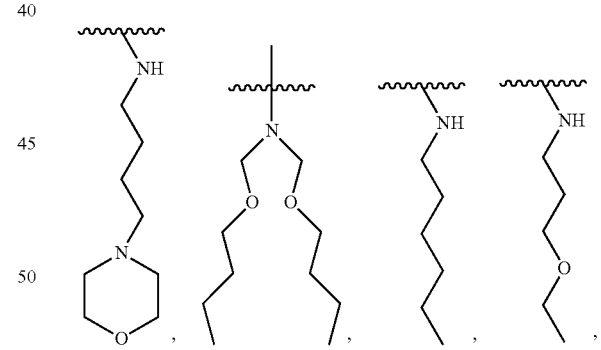
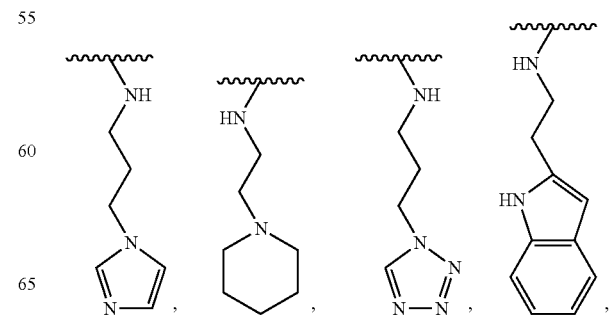

-continued

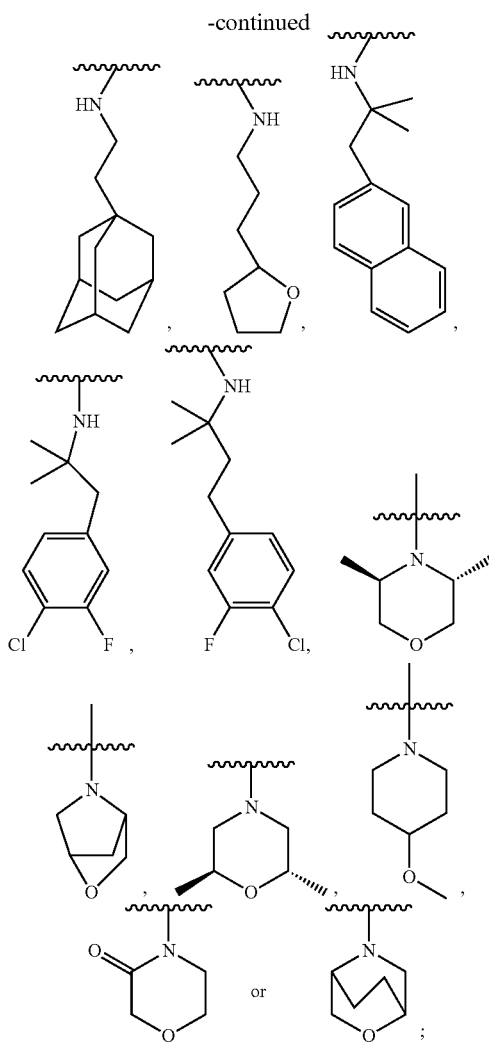

or

R¹ is H, F, Cl, Br, I, cyano, methyl, ethyl, propyl, isopropyl, butyl, tert-butyl, trifluoromethyl, phenyl-$(CH_2)_p$-G-$(CH_2)_m$—, (fluoro-substituted phenyl)-$(CH_2)_p$-G-$(CH_2)_m$—, thiazolyl-$(CH_2)_p$-G-$(CH_2)_m$—, pyridyl-$(CH_2)_p$-G-$(CH_2)_m$—, phenylethyl, cyclohexyl-$(CH_2)_p$-G-$(CH_2)_m$—, naphthyl-$(CH_2)_p$-G-$(CH_2)_m$—, or morpholinyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$, —OS(=O)$_t$, or —OS(=O)$_t$NH—; each t is 1 or 2; each p and m is independently 0, 1, 2, 3 or 4; or wherein each of the phenyl-$(CH_2)_p$-G-$(CH_2)_m$—, (fluoro-substituted phenyl)-$(CH_2)_p$-G-$(CH_2)_m$—, thiazolyl-$(CH_2)_p$-G-$(CH_2)_m$—, pyridyl-$(CH_2)_p$-G-$(CH_2)_m$—, phenylethyl, cyclohexyl-$(CH_2)_p$-G-$(CH_2)_m$—, naphthyl-$(CH_2)_p$-G-$(CH_2)_m$—, or andmorpholinyl-$(CH_2)_p$-G-$(CH_2)_m$— is optionally substituted by one or more F, Cl, Br, I, methyl, ethyl, propyl, ethynyl, propynyl, butynyl, methoxy, ethoxy or cyano;

R³ is H, F, Cl, I, cyano, methyl, ethyl, propyl, isopropyl, butyl, tert-butyl, phenyl-$(CH_2)_p$-G-$(CH_2)_m$—, (fluoro-substituted phenyl)-$(CH_2)_p$-G-$(CH_2)_m$—, thiazolyl-$(CH_2)_p$-G-$(CH_2)_m$—, or morpholinyl-$(CH_2)_p$-G-$(CH_2)_m$—, wherein each G is O, S, $NR^5$, S(=O), S(=O)$_2$, C(=O), —C(=O)NH—, —OC(=O)NH—, —OC(=O)—, —NHC(=O)NH—, —HN—S(=O)$_t$, —OS(=O)$_t$, or —OS(=O)$_t$NH—; each t is 1 or 2;

each p and m is independently 0, 1, 2, 3 or 4; or wherein each of the phenyl-$(CH_2)_p$-G-$(CH_2)_m$—, (fluoro-substituted phenyl)-$(CH_2)_p$-G-$(CH_2)_m$—, thiazolyl-$(CH_2)_p$-G-$(CH_2)_m$—, or morpholinyl-$(CH_2)_p$-G-$(CH_2)_m$— is optionally substituted by one F, Cl, Br, I, methyl, ethyl, propyl, ethynyl, propynyl, butynyl, methoxy, ethoxy or cyano;

R⁴ is H;

each R⁵ is independently H, $C_{1-4}$ alkyl, phenyl, benzyl, pyridyl or morpholino methyl;

each $R^{8a}$ is independently H, hydroxy, amino, F, Cl, Br, I, —N(CH$_3$)$_2$, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl or $C_{1-9}$ heteroaryl;

n is 0, 1, 2, or 3; and each $R^{10}$ is independently H or F.

8. The compound according to claim 1 having Formula (VI):

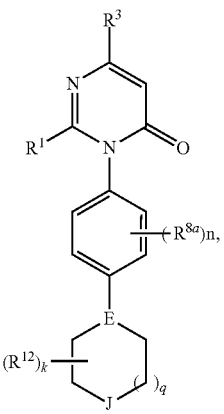

(VI)

wherein E is N or $CR^{10}$;

J is O, S, S(=O), S(=O)$_2$, $NR^{13}$ or $CR^{14}R^{14a}$;

k is 0, 1, 2, 3 or 4;

q is 0, 1 or 2;

R¹ is H, F, Cl, Br, I, cyano, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$C_{1-6}$ alkyl, $C_{6-10}$aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O)NH—, —OC(=O)— or —NHC(=O)NH—; each p and m is independently 0, 1, 2 or 3; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$heterocyclyl-$(CH_2)_p$-G-$(CH_2)_m$—, $C_{6-10}$ aryl-$C_{1-6}$ alkyl, and $C_{3-10}$ cycloalkyl-$(CH_2)_p$-G-$(CH_2)_m$— is optionally substituted by one or more F, Cl, Br, I, methyl, ethyl, propyl, ethynyl, propynyl, butynyl, methoxy, ethoxy, or cyano;

R³ is H, F, Cl, I, cyano, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, or $C_{3-10}$ cycloalkyl-$(CH_2)_p$-G-$(CH_2)_m$—, wherein each G is O, S, $NR^5$, C(=O), —C(=O)NH—, —OC(=O)NH—, —OC(=O)— or —NHC(=O)NH—; each p and m is independently 0, 1, 2 or 3; or wherein each of the $C_{6-10}$ aryl-$(CH_2)_p$-G-$(CH_2)_m$—, $C_{1-9}$ heteroaryl-$(CH_2)_p$-G-$(CH_2)_m$—, $C_{2-10}$ heterocyclyl-$(CH_2)_p$-G-$(CH_2)_m$—, and $C_{3-10}$ cycloalkyl-$(CH_2)_p$-G-$(CH_2)_m$— is optionally substituted by one F, Cl, Br, I, methyl, ethyl, propyl, ethynyl, propynyl, butynyl, methoxy, ethoxy, or cyano;

each $R^5$ is independently H, $R^7R^{7a}NC(=O)-$, $R^7OC(=O)-$, $R^7C(=O)-$, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl-$C_{1-3}$-alkyl, $C_{2-10}$ heterocyclyl-$C_{1-3}$-alkyl, $C_{3-10}$ cycloalkyl-$C_{1-3}$-alkyl, $C_{6-10}$ aryl, $C_{1-9}$ heteroaryl, $C_{2-10}$ heterocyclyl or $C_{3-10}$ carbocyclyl;

each $R^{8a}$ is independently H, hydroxy, amino, F, Cl, Br, I, $-N(CH_3)_2$, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl or $C_{1-9}$ heteroaryl;

n is 0, 1, 2 or 3;

$R^{10}$ is independently H or F;

each $R^{12}$ is oxo (=O), hydroxy, amino, halo, cyano, $C_{1-10}$ alkoxy, $C_{1-10}$ alkylamino, $C_{1-10}$ alkylthio, $C_{1-10}$ alkyl, $C_{2-10}$ alkenyl, $C_{2-10}$ alkynyl, mercapto, nitro, $C_{6-10}$ aryl, $C_{1-9}$ heteroaryl, $C_{2-10}$ heterocyclyl, $C_{6-10}$ aryloxy, carboxy, hydroxy-substituted $C_{1-6}$ alkoxy, hydroxy-substituted $C_{1-6}$ alkyl-$C(=O)-$, $C_{1-6}$ alkyl-$C(=O)-$, $C_{1-6}$ alkyl-$S(=O)-$, $C_{1-6}$ alkyl-$S(=O)_2-$, hydroxy-substituted $C_{1-6}$ alkyl-$S(=O)-$, hydroxy-substituted $C_{1-6}$ alkyl-$S(=O)_2-$, or carboxy $C_{1-6}$alkoxy;

$R^{13}$ is H, $C_{1-4}$ alkyl, $C_{2-4}$ alkynyl, $C_{1-4}$ alkoxy, hydroxy-substituted $C_{1-4}$ alkoxy, $C_{1-4}$carboxyalkoxy, $C_{1-4}$ alkylcarbonyl or hydroxy-substituted $C_{1-4}$ alkylcarbony; and each $R^{14}$ and $R^{14a}$ is independently H, hydroxy, carboxy, $C_{1-4}$ alkyl, $C_{1-4}$ alkoxy or $C_{1-4}$ alkylamino.

9. The compound according to claim 1, wherein:

$R^1$ is independently H, F, Cl, Br, I, cyano, methyl, ethyl, propyl, isopropyl, butyl, tert-butyl, $C_{6-8}$ aryl-$(CH_2)_p$-G-$(CH_2)_m-$ or $C_{4-6}$ heteroaryl-$(CH_2)_p$-G-$(CH_2)_m-$, wherein each G is $NR^5$, O or S, each p and m is independently 0, 1, 2 or 3; or wherein each of the $C_{6-8}$ aryl-$(CH_2)_p$-G-$(CH_2)_m-$ and $C_{4-6}$ heteroaryl-$(CH_2)_p$-G-$(CH_2)_m-$ is optionally substituted by one or more F, Cl, Br, methyl, ethyl, propyl, ethynyl, propynyl, butynyl, methoxy, or cyano; and $R^3$ is independently H, F, Cl, I, cyano, methyl, ethyl, propyl, isopropyl, butyl, tert-butyl, $C_{6-8}$ aryl-$(CH_2)_p$-G-$(CH_2)_m-$ or $C_{4-6}$ heteroaryl-$(CH_2)_p$-G-$(CH_2)_m-$, wherein each G is O or S, each p and m is independently 0, 1, 2 or 3; or wherein each of the $C_{6-8}$ aryl-$(CH_2)_p$-G-$(CH_2)_m-$ and $C_{4-6}$ heteroaryl-$(CH_2)_p$-G-$(CH_2)_m-$ is optionally substituted by one F, Cl, Br, methyl, ethyl, propyl, ethynyl, propynyl, butynyl, or cyano.

10. The compound according to claim 1 having Formula (VII):

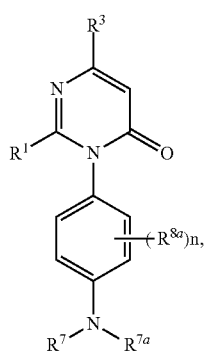

(VII)

wherein $R^1$ is H, F, Cl, Br, I, cyano, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, or $C_{3-10}$ cycloalkyl-$(CH_2)_p$-G-$(CH_2)_m-$, wherein each G is O, S, $NR^5$, $C(=O)$, $-C(=O)NH-$, $-OC(=O)NH-$, $-OC(=O)-$ or $-NHC(=O)NH-$; each p and m is independently 0, 1, 2 or 3; or wherein each of the $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, and $C_{3-10}$ cycloalkyl-$(CH_2)_p$-G-$(CH_2)_m-$ is optionally substituted by one or more F, Cl, Br, I, methyl, ethyl, propyl, cyano, ethynyl, methoxy, ethoxy, or propynyl;

$R^3$ is H, F, Cl, I, cyano, $C_{1-6}$ alkyl, $C_{1-6}$ haloalkyl, $C_{1-6}$ alkoxy, $C_{1-6}$ hydroxyalkoxy, $C_{1-6}$ aminoalkoxy, $C_{1-6}$ haloalkoxy, $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, or $C_{3-10}$ cycloalkyl-$(CH_2)_p$-G-$(CH_2)_m-$, wherein each G is O, S, $NR^5$, $C(=O)$, $-C(=O)NH-$, $-OC(=O)NH-$, $-OC(=O)-$ or $-NHC(=O)NH-$; each p and m is independently 0, 1, 2 or 3; or wherein each of the $C_{6-10}$ aryl-$(CH_2)_p$-G-$(CH_2)_m-$, $C_{1-9}$ heteroaryl-$(CH_2)_p$-G-$(CH_2)_m-$, $C_{2-10}$ heterocyclyl-$(CH_2)_p$-G-$(CH_2)_m-$, and $C_{3-10}$ cycloalkyl-$(CH_2)_p$-G-$(CH_2)_m-$ is optionally substituted by one F, Cl, Br, I, methyl, ethyl, propyl, cyano, ethynyl, methoxy, ethoxy, or propynyl;

each $R^5$ is independently H, $R^7R^{7a}NC(=O)-$, $R^7OC(=O)-$, $R^7C(=O)-$, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl-$C_{1-3}$-alkyl, $C_{2-10}$ heterocyclyl-$C_{1-3}$-alkyl, $C_{3-10}$ cycloalkyl-$C_{1-3}$-alkyl, $C_{6-10}$ aryl, $C_{1-9}$ heteroaryl, $C_{2-10}$ heterocyclyl or $C_{3-10}$ carbocyclyl;

each $R^7$ is independently H, $C_{1-6}$ alkyl, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

each $R^{7a}$ is independently $C_{1-6}$ alkyl, $C_{1-6}$ haloaliphatic, $C_{1-6}$ hydroxyaliphatic, $C_{1-6}$ aminoaliphatic, $C_{1-6}$ alkoxy-$C_{1-6}$-aliphatic, $C_{1-6}$alkylamino-$C_{1-6}$-aliphatic, $C_{1-6}$ alkylthio-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl;

with the proviso that where $R^7$ and $R^{7a}$ are bonded to the same nitrogen atom, $R^7$ and $R^{7a}$, together with the nitrogen atom they are attached to, optionally form a substituted or unsubstituted 3-8 membered ring;

each $R^{8a}$ is independently H, hydroxy, amino, F, Cl, Br, I, $-N(CH_3)_2$, cyano, nitro, mercapto, $C_{1-4}$ alkyl, trifluoromethyl, $C_{1-4}$ alkoxy, $C_{1-4}$ alkylamino, $C_{1-4}$ alkylthio, $C_{6-10}$ aryl or $C_{1-9}$ heteroaryl; and n is 0, 1, 2 or 3.

11. The compound according to claim 10, wherein each $R^7$ is independently H, $C_{1-6}$ alkyl, $C_{1-4}$ alkoxy-$C_{1-6}$-alkyl,

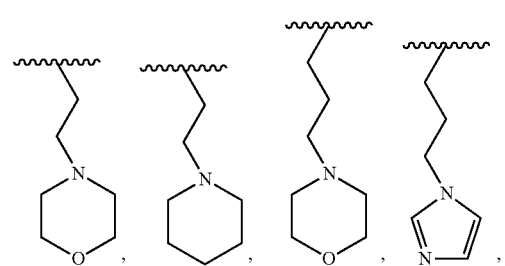
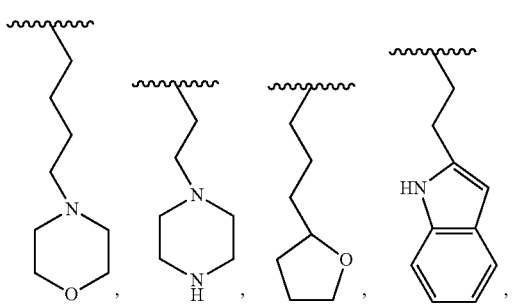
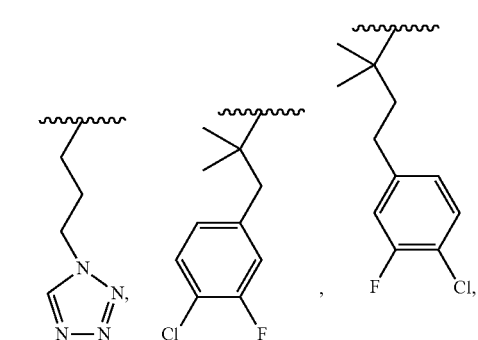
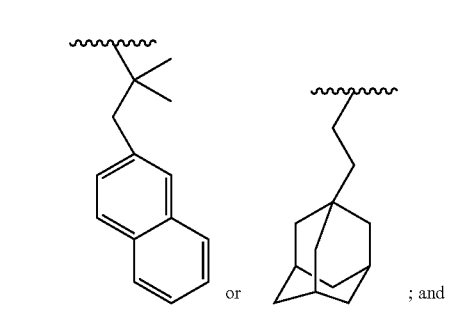
each $R^{7a}$ is independently $C_{1-6}$ alkyl, $C_{1-4}$ alkoxy-$C_{1-6}$-alkyl,
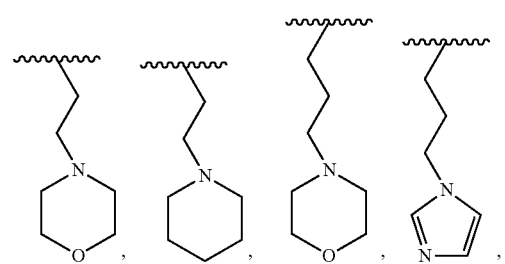
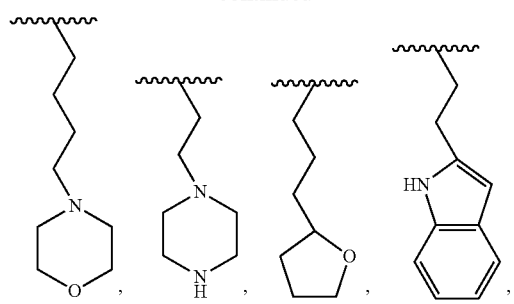
12. The compound according to claim 1 having one of the following structures:
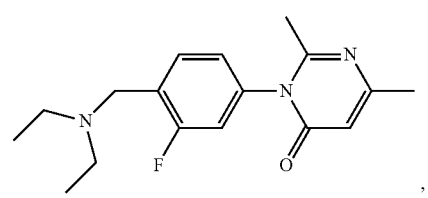
(6)
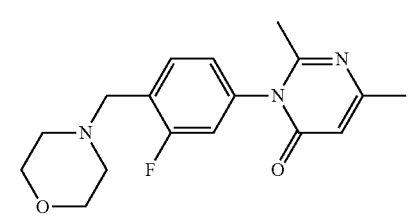
(7)
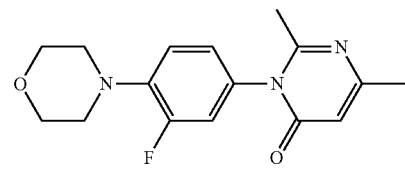
(14)

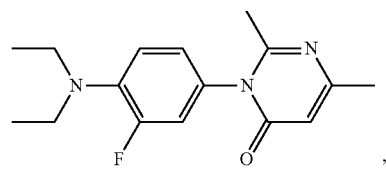 (15)
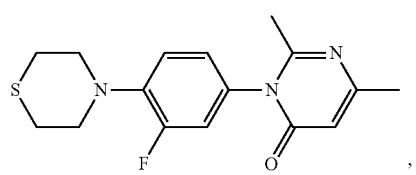 (16)
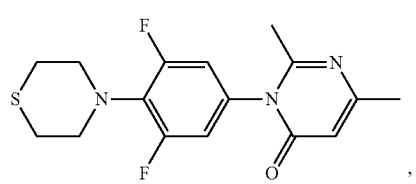 (17)
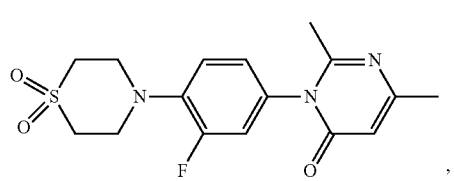 (18)
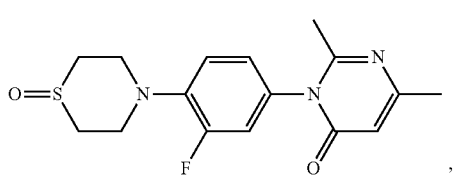 (19)
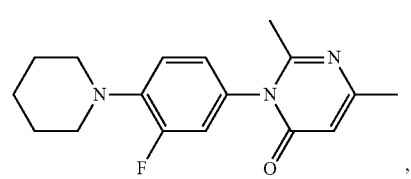 (20)
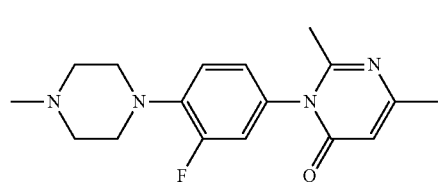 (21)
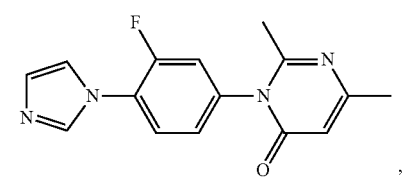 (29)
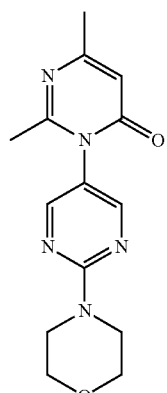 (36)
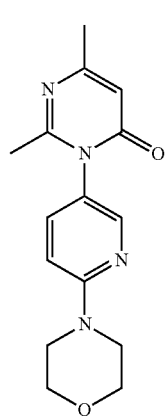 (37)
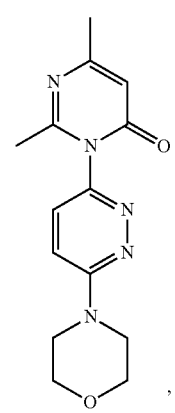 (38)
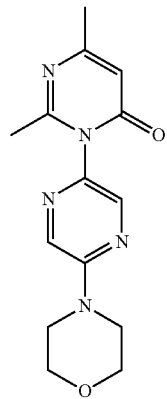 (39)

(44) 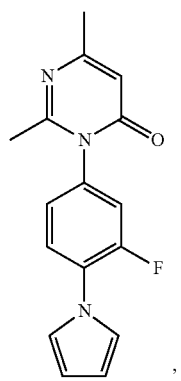
(45) 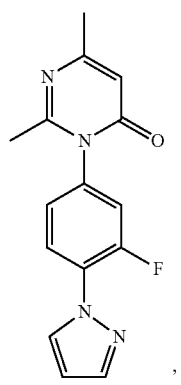
(46) 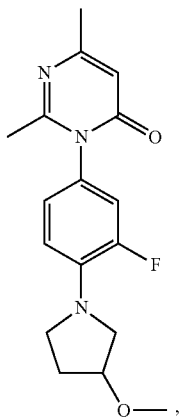
(47) 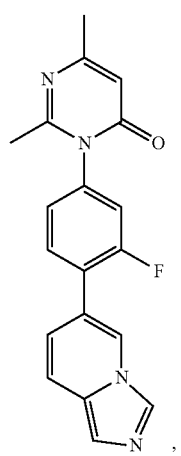
(48) 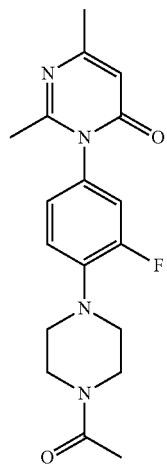
(49) 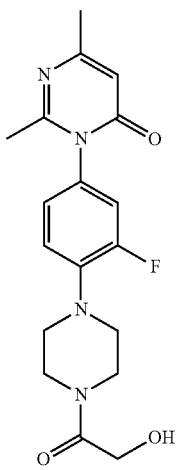
(50) 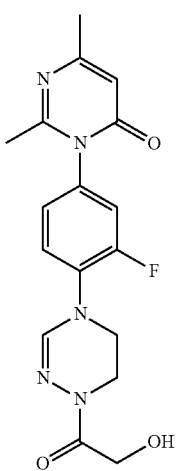

(51) 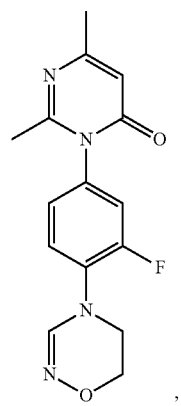
(52) 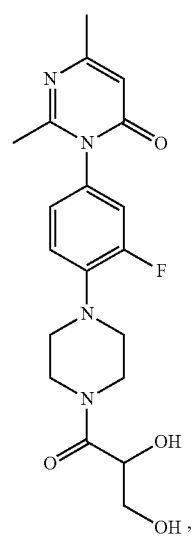
(53) 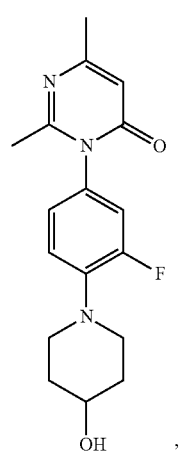
(54) 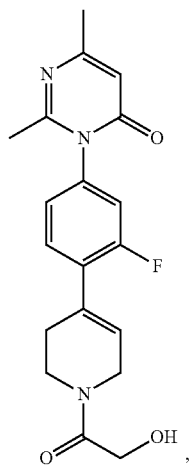
(55) 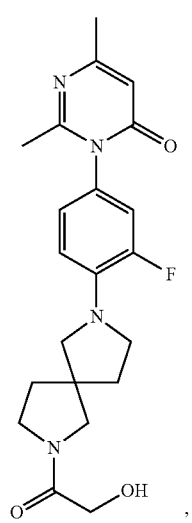
(56) 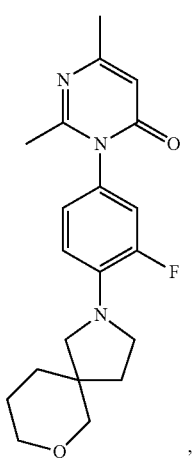

(57) 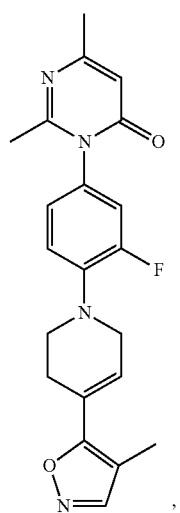
(58) 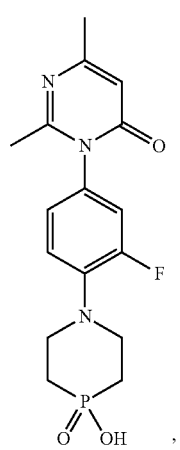
(59)
(60) 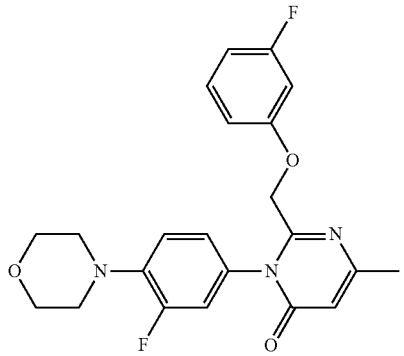
(61) 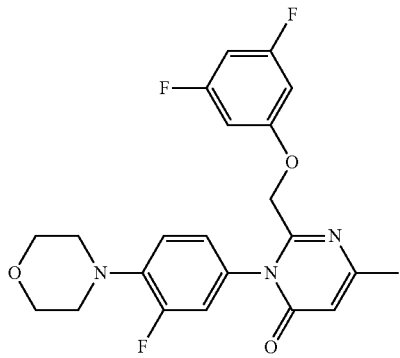
(62) 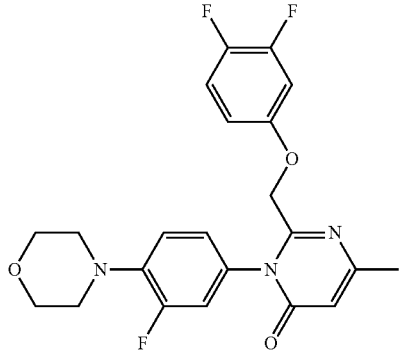
(63) 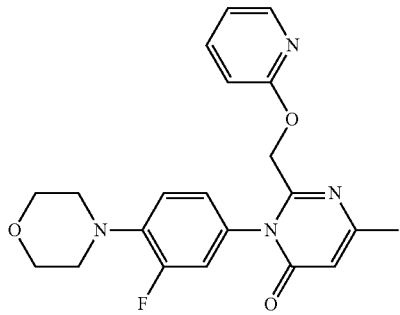

-continued (64), (65), (66), (67), (68), (69), (70), (71), (72), (73)

-continued
(74)
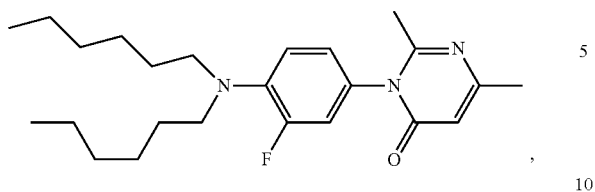
(75)
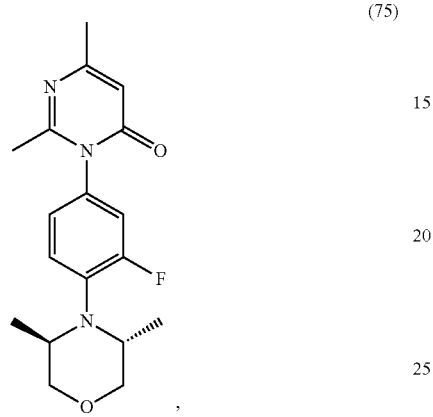
(76)
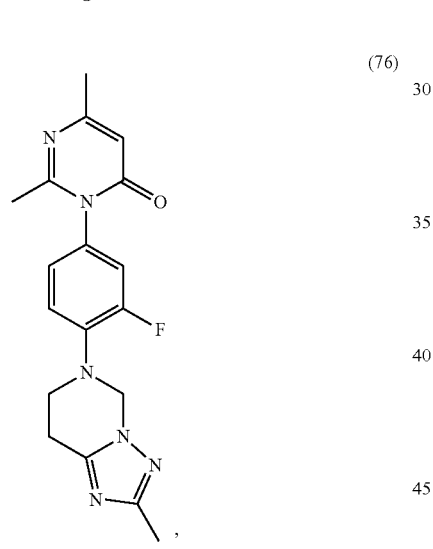
(77)
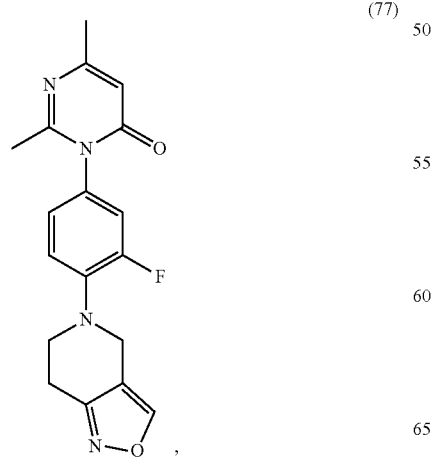
-continued
(78)
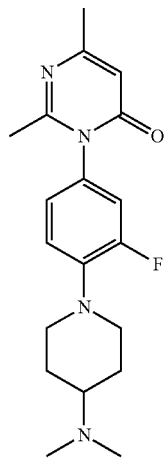
(79)
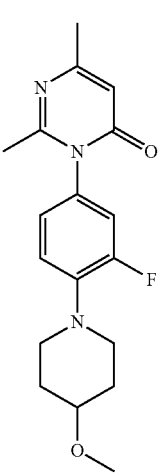
(80)
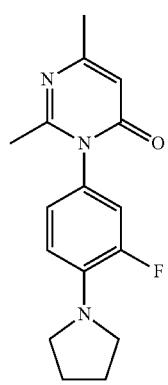

(81)
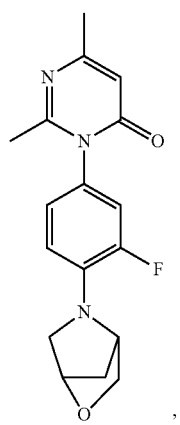
(82)
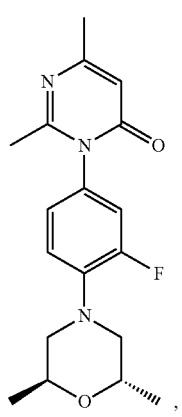
(83)
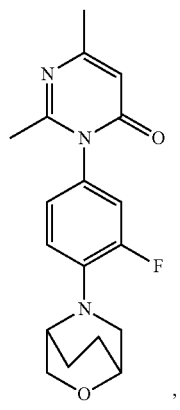
(84)
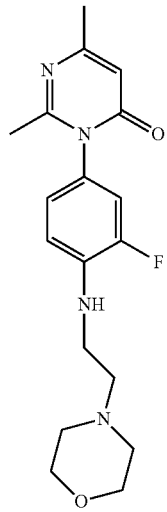
(85)
(86)
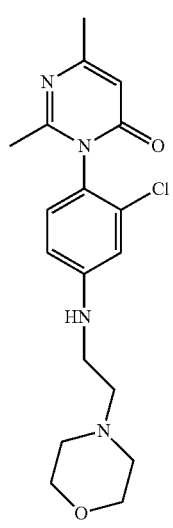

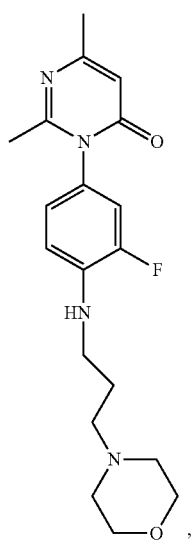 (87)
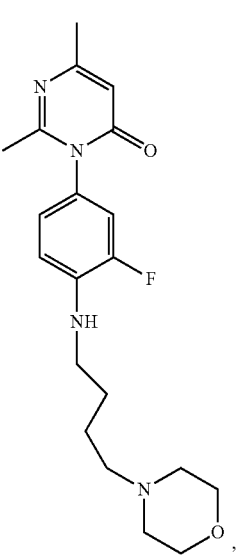 (88)
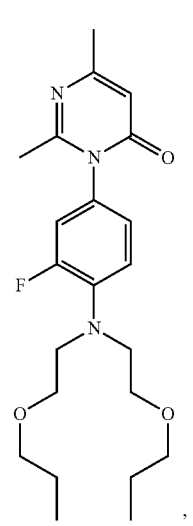 (89)
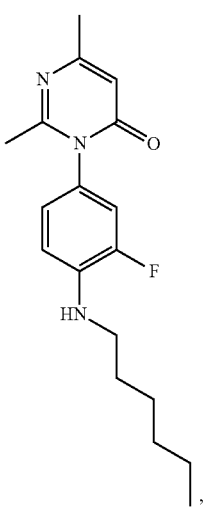 (90)
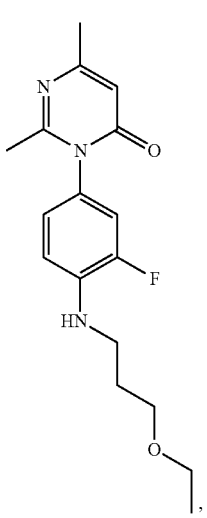 (91)
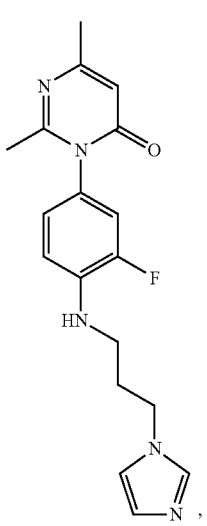 (92)

(93)
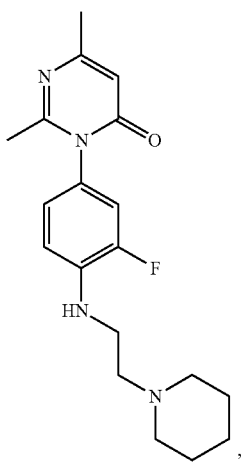
(94)
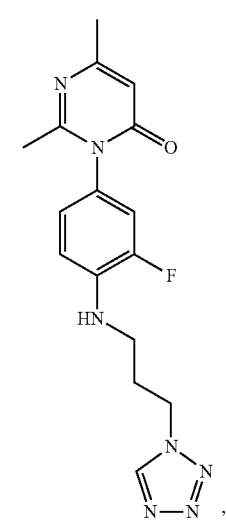
(95)
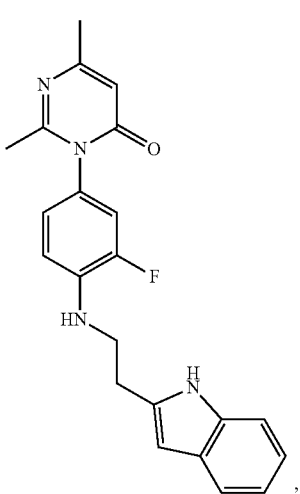
(96)
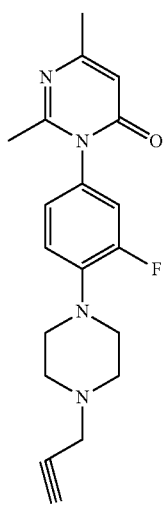
(97)
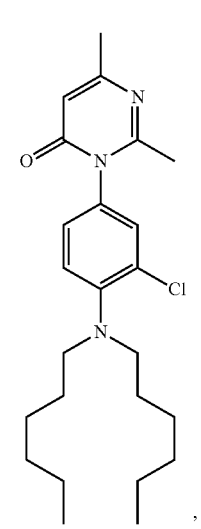
(98)
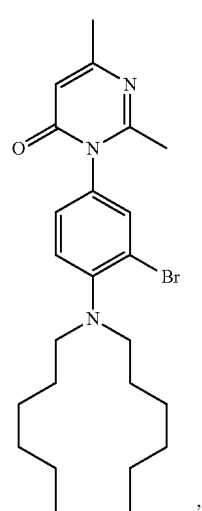

(99)
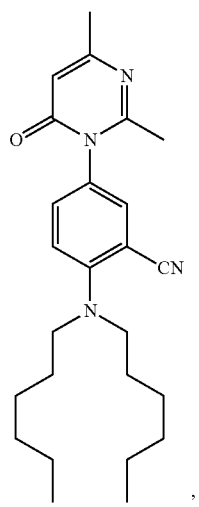
(100)
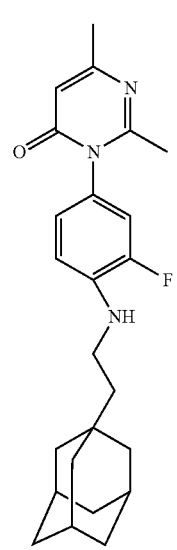
(101)
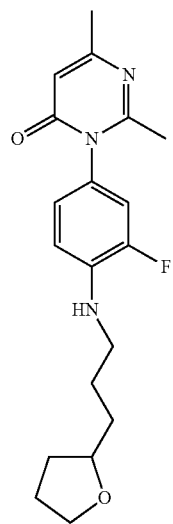
(102)
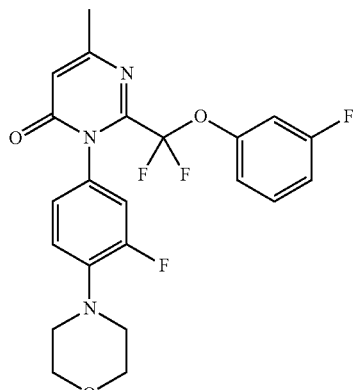
(103)
(104)

(105), (106), (107), (109), (110), (111)

(112) 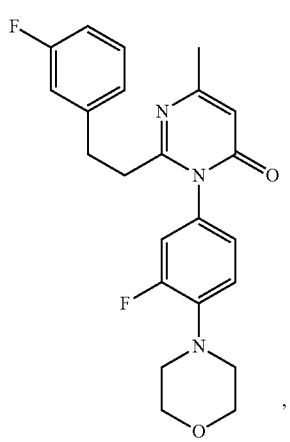
(115) 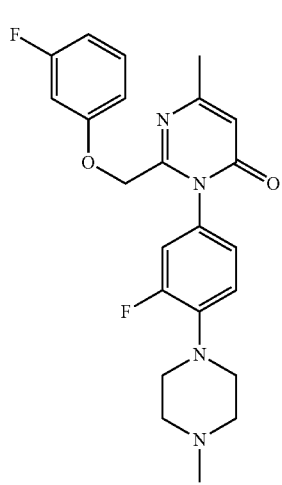
(113) 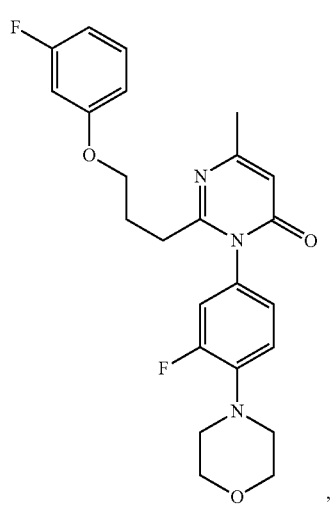
(117) 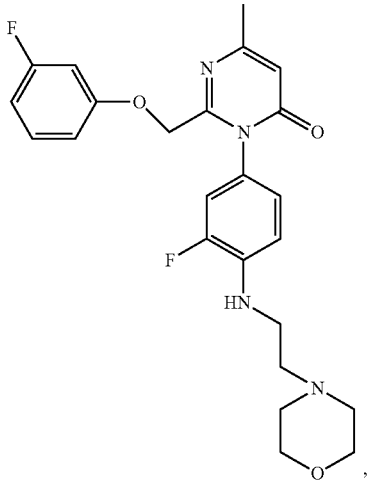
(114) 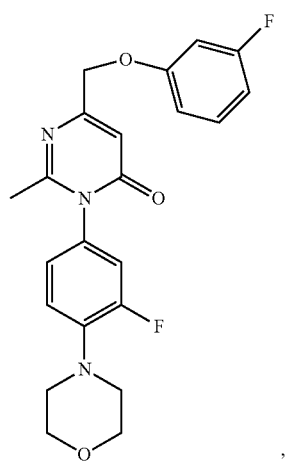
(118) 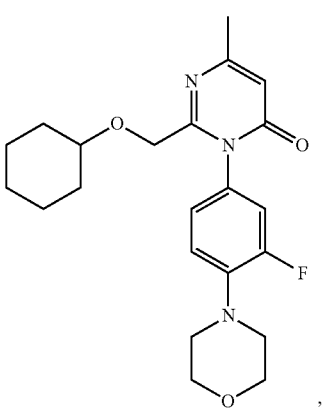

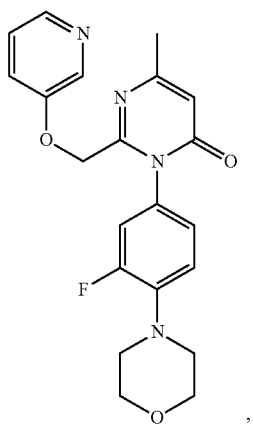
(119)
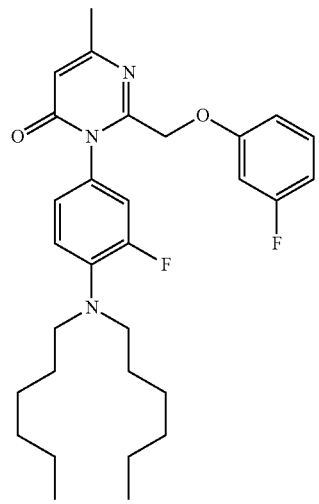
(122)
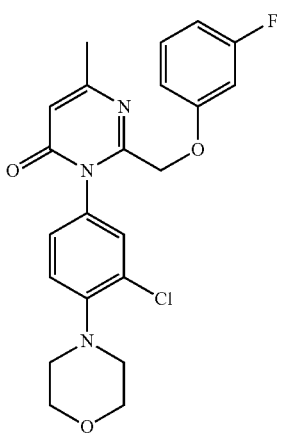
(120)
(123)
(121)
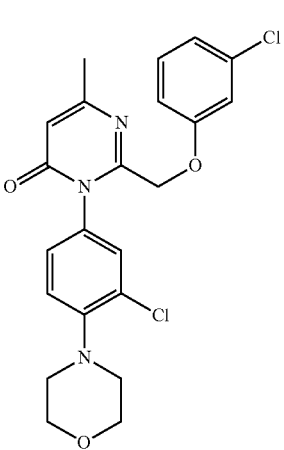
(124)

(125) 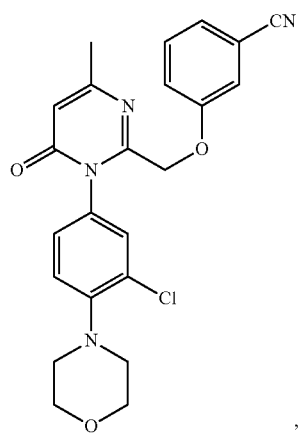
(126) 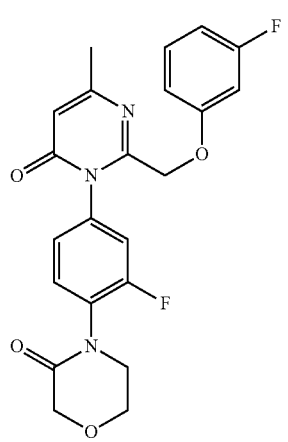
(127) 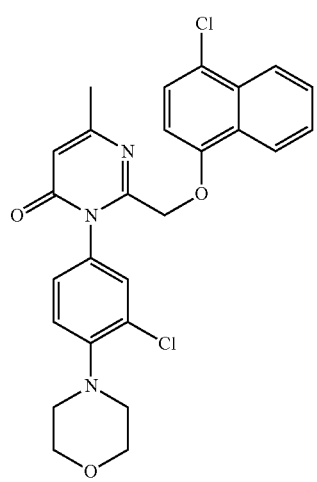
(128) 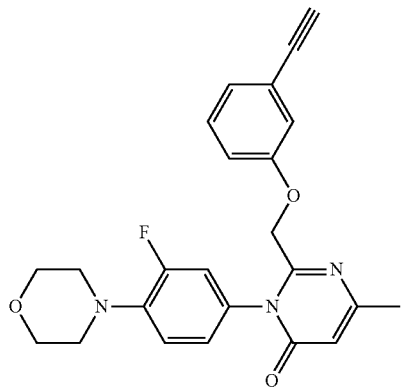
(131) 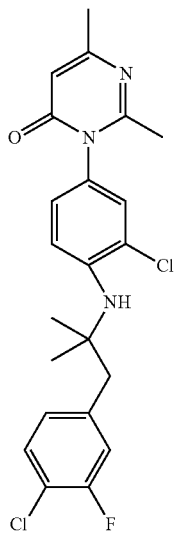
, or
(132) 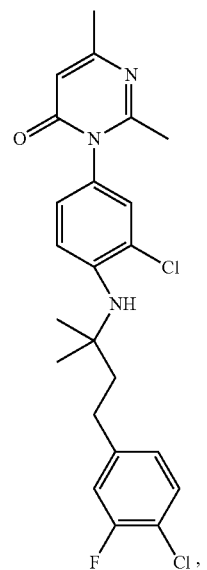
,
or a stereoisomer, a geometric isomer, a tautomer, an N-oxide, a hydrate, a solvate, or a pharmaceutically acceptable salt thereof.

13. A pharmaceutical composition comprising the compound according to claim 1; and a pharmaceutically acceptable carrier, excipient, diluent, adjuvant, vehicle or a combination thereof.

14. A method of managing, treating or lessening the severity of tissue or organ fibrosis in a patient comprising administering to the patient with a therapeutically effective amount of the compound according to claim 1;
   wherein the tissue or organ fibrosis disorder is renal interstitial fibrosis, glomerulosclerosis, liver fibrosis, pulmonary fibrosis, peritoneum fibrosis, myocardial fibrosis, dermatofibrosis, skeletal muscle fibrosis, dermatosclerosis, pancreatic fibrosis, liver cirrhosis, neurofibroma, pulmonary interstitial fibrosis, or vascular fibrosis.

15. A method of managing, treating or lessening the severity of tissue or organ fibrosis in a patient comprising administering to the patient with a therapeutically effective amount of the composition according to claim 13;
   wherein the tissue or organ fibrosis disorder is renal interstitial fibrosis, glomerulosclerosis, liver fibrosis, pulmonary fibrosis, peritoneum fibrosis, myocardial fibrosis, dermatofibrosis, skeletal muscle fibrosis, dermatosclerosis, pancreatic fibrosis, liver cirrhosis, neurofibroma, pulmonary interstitial fibrosis, or vascular fibrosis.

\* \* \* \* \*